US010106530B2

(12) United States Patent
Schunk et al.

(10) Patent No.: US 10,106,530 B2
(45) Date of Patent: *Oct. 23, 2018

(54) PYRAZOLYL SUBSTITUTED TETRAHYDROPYRANYLSULFONES

(71) Applicant: GRÜNENTHAL GMBH, Aachen (DE)

(72) Inventors: Stefan Schunk, Aachen (DE); Melanie Reich, Aachen (DE); René Michael Koenigs, Erkelenz (DE)

(73) Assignee: GRÜNENTHAL GMBH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/287,947

(22) Filed: Oct. 7, 2016

(65) Prior Publication Data

US 2017/0101397 A1     Apr. 13, 2017

(30) Foreign Application Priority Data

Oct. 8, 2015   (EP) ..................................... 15002879

(51) Int. Cl.
    *C07D 405/04*     (2006.01)
    *C07D 405/14*     (2006.01)

(52) U.S. Cl.
    CPC ......... *C07D 405/04* (2013.01); *C07D 405/14* (2013.01)

(58) Field of Classification Search
    None
    See application file for complete search history.

(56) References Cited

U.S. PATENT DOCUMENTS

2015/0291572 A1   10/2015  Schunk et al.
2015/0291573 A1   10/2015  Schunk et al.
2017/0101398 A1    4/2017  Schunk et al.

FOREIGN PATENT DOCUMENTS

WO    2007 125398 A2   11/2007
WO    2010 007072 A1    1/2010
WO    2011 035159 A1    3/2011

OTHER PUBLICATIONS

Yamamoto, et al; "Recent Updates of N-Type Calcium Channel Blockers with Therapeutic Potential for Neuropathic Pain . . . " Current Topics in Medicinal Chemistry, 2009, 9, 377-395.
Barbasiewicz, et al., "New reactions of γ-halocarbanions: underestimated reactive intermediates in organic synthesis"; Russian Chemical Bulletin, International Edition, vol. 53, No. 9, pp. 1846-1858, Sep. 2004.
Bennett et al., "A Peripheral Mononeuropathy in rat that produces disorders of pain sensation like those seen in man": Pain, Elsevier Sciences Publishers B.V., No. 33, pp. 87-107, 1998.
Brandt, et al., "Synthesis of substituted tetrahydrofurans via intermolecular reactions of γ-chlorocarbanions of 3-substituted 3-chloropropylphenyl sulfones with aldehydes", Tetrahedron 66, pp. 3378-3385, 2010.
Craig et al., "Stereoselective Synthesis of 3-(Phenylsulphonyl)-2,5 Disubstituted Tetrahydrofurans via 5-Endo-trig Ring-Closure Reactions"; Tetrahedron Letters, vol. 33, No. 5, pp. 695-698, 1992.
Craig et al., "Stereoselective Synthesis of 2,5-Dialky-3-(phenylsulfonyl) Tetrahydrofurans via Cyclisation of Z-Sulfonyl-substituted Homoallylic Alcohols", Tetrahedron Letters, vol. 36, No. 4, pp. 7531-7534, 1995.
Craig, et al., "Stereoselective Synthesis of Substituted Tetrahydrofurans Using 5-Endo-trig Cyclisation Reactions"; Tetrahedron 55, pp. 13471-13494, 1999.
D'Amour et al., "A Method for Determining Loss of Pain Sensation", The Biologic Research Laboratory, University of Denver, pp. 74-79, Jan. 27, 1941.
Dubuisson et al., "The Formalin Test: A Quantitative Study of the Analgesic Effects of Morphine, Meperidine, and Brain Stem Stimulation in Rats and Cat"; Elsevier/North-Holland Biomedical Press, Pain, No. 4 pp. 161-174, 1977.
Kim et al., "An Experimental Model for Peripheral Neuropathy Produced by Segmental Spinal Nerve Ligation in the Rat", Pain, Elsevier Sciences Publishers by., No. 50, pp. 355-363, 1992.
Mąkosza et al., "New Reactions of γ-Halocarbanions: Simple Synthesis of Substituted Tetrahydrofurans"; Chem. Eur. J., vol. 8, No. 18, pp. 4234-4240, 2002.
Mąkosza et al., "Diastereoselective Synthesis of Tetrahydrofurans via Reaction of γ,δ-Eposycarbanions with Aldehydes", Organic Letters, vol. 7, No. 14, pp. 2945-2948, 2005.
Mąkosza et al. (2009): STN International HCAPLUS database, Columbus (OH) Accession No. 2009:371746.
Makoszaet al., "γ-Diphenylphosphinoxy Carbanions: Slow Reacting Analogues of γ-Halocarbanions", Phosphorus, Sulfur, and Silicon, No. 184, pp. 857-864, 2009.
G.P. Miljanich,"Ziconotide: Neuronal Calcium Channel Blocker for Treating Severe Chronic Pain", Current Medicinal Chemistry, No. 11, pp. 3029-3040, 2004.
Rauck et al., "Intrathecal Ziconotide for Neuropathic Pain: A Review", Pain Practice, vol. 9, Issue 5, pp. 327-337, 2009.
Staats et al., "Intrathecal Ziconotide in the Treatment of Refractory Pain in Patients With Cancer or AIDS a Randomized Controlled Trial", American Medical Association, vol. 291, No. 1, pp. 63-70, 2004.

*Primary Examiner* — Jeffrey S Lundgren
*Assistant Examiner* — Meghan Finn
(74) *Attorney, Agent, or Firm* — Norris McLaughlin & Marcus, P.A.

(57) ABSTRACT

The invention relates to pyrazolyl substituted tetrahydropyranylsulfones as voltage gated calcium channel blockers, to pharmaceutical compositions containing these compounds and also to these compounds for use in the treatment and/or prophylaxis of pain and further diseases and/or disorders.

13 Claims, No Drawings

PYRAZOLYL SUBSTITUTED TETRAHYDROPYRANYLSULFONES

PRIORITY CLAIM

This application claims priority of European Patent Application No. 15002879.3, filed on Oct. 8, 2015, the disclosure of which is incorporated herein by reference.

FIELD OF THE INVENTION

The invention relates to pyrazolyl substituted tetrahydropyranylsulfones as voltage gated Ca-channel (CaV) blockers, to pharmaceutical compositions containing these compounds and also to these compounds for use in the treatment and/or prophylaxis of pain and further diseases and/or disorders.

BACKGROUND OF THE INVENTION

Ion channels are proteins that form pores in membranes of biological cells and control the flow of ions down their electrochemical gradient. They are involved in the regulation of a wide range of cellular functions in both excitable and nonexcitable cells and provide attractive therapeutic targets for the treatment of various diseases.

In the somatosensory context, CaV2.2 channels, specific cellular plasma membrane calcium channels that belong to a diverse superfamily of voltage-gated calcium channels (VGCCs), were demonstrated to play an important role in spinal nociceptive processing.

The critical role of CaV2.2 in pain processing was underlined by the clinical efficacy of the intrathecally delivered, selective CaV2.2 channel antagonist Ziconotide (SNX-111; Prialt™), a synthetic peptide derived from a ω-(omega)-conotoxin peptide (Miljanich, 2004, Curr. Med. Chem., 11(23), p. 3029-40; Staats et al., 2004, JAMA, 291(1), p. 63-70). Inthrathecal administration of Ziconotide is required in order to reach the ion channel in presynaptic terminals of sensory neurons in the spinal cord. Common side effects of Ziconotide include memory impairment, dizziness, nystagmus, speech disorder, nervousness, somnolence and abnormal gait (Rauck et al., 2009, Pain Pract., 9, p. 327-37), which have been attributed to the inhibition of CaV2.2 channels in the brain by Ziconotide.

Therefore, a demand remains for the development of orally available CaV2.2 calcium channel blockers that show the desired qualities and effectively block CaV2.2 calcium channels in the nociceptive signaling pathway.

SUMMARY OF THE INVENTION

The present invention describes small molecule CaV2.2 channel blockers. Sulfonamide based CaV2.2 channel modulators are known from WO 2007/125398.

It was therefore an object of the invention to provide novel compounds, preferably having advantages over the prior-art compounds. The compounds should be suitable in particular as pharmacological active ingredients in pharmaceutical compositions, preferably in pharmaceutical compositions for the treatment and/or prophylaxis of disorders or diseases which are at least partially mediated by CaV2.2 calcium channels.

This object is achieved by the subject matter described herein.

The present invention therefore relates to a compound of general formula (I),

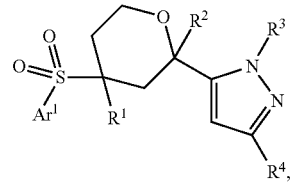

wherein $R^1$ is selected from the group consisting of H or $C_{1-6}$-alkyl;
$R^2$ is selected from the group consisting of H or $C_{1-6}$-alkyl;
$R^3$ is H;
$R^4$ represents L-$R^5$,
  wherein L is bond, $CH_2$, $C(CH_3)_2$, O or $S(=O)_2$ and
  $R^5$ is selected from the group consisting of $C_{1-6}$-alkyl, $C_{3-6}$-cycloalkyl or 3 to 7 membered heterocyclyl,
  wherein said 3 to 7 membered heterocyclyl is characterized that it contains one heteroatom or heteroatom group, selected from O, NH, N($CH_3$), S(=O) and $S(=O)_2$;
  wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
and
  wherein said $C_{3-6}$-cycloalkyl or said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;
$Ar^1$ represents aryl or heteroaryl, wherein said aryl or said heteroaryl is substituted by zero or one or two or three substituents $R^7$,
  wherein each $R^7$ is independently selected from the group consisting of F; Cl; Br; I; $NO_2$; CN; $C_{1-6}$-alkyl; $CF_3$; $CF_2H$; $CFH_2$; $CF_2Cl$; $CFCl_2$; C(O)—H; C(O)—$C_{1-6}$-alkyl; C(O)—OH; C(O)—O—$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—$S(O)_2$—$C_{1-6}$-alkyl; O—$S(O)_2$—OH; O—$S(O)_2$—O—$C_{1-6}$-alkyl; O—$S(O)_2$—$NH_2$; O—$S(O)_2$—N(H)($C_{1-6}$-alkyl); O—$S(O)_2$—N($C_{1-6}$-alkyl)$_2$; $NH_2$; N(H)($C_{1-6}$-alkyl); N($C_{1-6}$-alkyl)$_2$; N($R^{13}$)—C(O)—$C_{1-6}$-alkyl; N($R^{13}$)—C(O)—O—$C_{1-6}$-alkyl; N($R^{13}$)—C(O)—$NH_2$; N($R^{13}$)—C(O)—N(H)($C_{1-6}$-alkyl); N($R^{13}$)—C(O)—N($C_{1-6}$-alkyl)$_2$; N($R^{13}$)—$S(O)_2$OH; N($R^{13}$)—$S(O)_2$—$C_{1-6}$-alkyl; N($R^{13}$)—$S(O)_2$—O—$C_{1-6}$-alkyl; N($R^{13}$)—$S(O)_2$—$NH_2$; N($R^{13}$)—$S(O)_2$—N(H)($C_{1-6}$-alkyl); N($R^{13}$)—$S(O)_2$N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(O)—$C_{1-6}$-alkyl; $S(O)_2$—$C_{1-6}$-alkyl; $S(O)_2$—OH; $S(O)_2$—O—$C_{1-6}$-alkyl; $S(O)_2$—$NH_2$; $S(O)_2$—N(H)($C_{1-6}$-alkyl);

S(O)$_2$—N(C$_{1-6}$-alkyl)$_2$; C$_{3-6}$-cycloalkyl; 3 to 7 membered heterocyclyl; aryl; heteroaryl; O—C$_{3-6}$-cycloalkyl; O-(3 to 7 membered heterocyclyl); O-aryl; O-heteroaryl; N(R$^{13}$)—C$_{3-6}$-cycloalkyl; N(R$^{13}$)-(3 to 7 membered heterocyclyl); N(R$^{13}$)-aryl; N(R$^{13}$)-heteroaryl; C(O)—C$_{3-6}$-cycloalkyl; C(O)-(3 to 7 membered heterocyclyl); C(O)-aryl; C(O)-heteroaryl; S(O)$_2$—C$_{3-6}$-cycloalkyl; S(O)$_2$-(3 to 7 membered heterocyclyl); S(O)$_2$-aryl; S(O)$_2$-heteroaryl; S(O)N(R$^{13}$)—C$_{3-6}$-cycloalkyl; S(O)N(R$^{13}$)-(3 to 7 membered heterocyclyl); S(O)N(R$^{13}$)-aryl and S(O)N(R$^{13}$)-heteroaryl, wherein R$^{13}$ represents H or C$_{1-6}$-alkyl;

with the proviso that the compound of general formula (I) is not 5-(Trifluoro-methyl)-3-[4-methyl-4-[[3-(trifluoromethyl)phenyl]sulfonyl]-tetrahydro-pyran-2-yl]-1H-pyrazole [R$^1$=CH$_3$, R$^2$=H, R$^4$=CF$_3$, Ar$^1$=3-trifluoromethyl-phenyl];

optionally in the form of an individual stereoisomer or a mixture of stereoisomers, in the form of the free compound and/or a physiologically acceptable salt and/or a physiologically acceptable solvate thereof.

DETAILED DESCRIPTION

The term "single stereoisomer" preferably means in the sense of the present invention an individual enantiomer or diastereomer. The term "mixture of stereoisomers" means in the sense of this invention the racemate and mixtures of enantiomers and/or diastereomers in any mixing ratio.

The compounds according to general formula (I) comprise a pyrazole subunit wherein the pyrazole is unsubstituted at the N-pyrazole. Hence, the compound according to general formula (I) may be represented in 2 tautomeric forms:

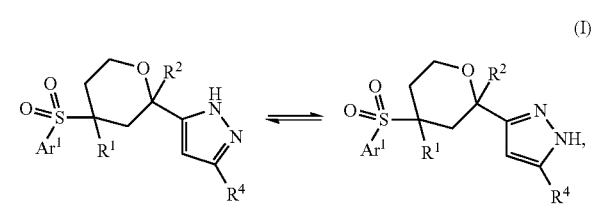

(I)

For the sake of clarity, only one tautomeric form is given within the present invention. It is, however, understood within the scope of the present invention that one given tautomeric form represents both tautomeric forms. Such tautomers may interconvert rapidly, for instance in solubilized form.

As an example, the compound
3-(methylsulfonyl)-5-[4-methyl-4-[[3-(trifluoromethyl)phenyl]sulfonyl]-tetrahydro-pyran-2-yl]-1H-pyrazole
is understood to represent both
3-(methylsulfonyl)-5-[4-methyl-4-[[3-(trifluoromethyl)phenyl]sulfonyl]-tetrahydro-pyran-2-yl]-1H-pyrazole and
5-(methylsulfonyl)-3-[4-methyl-4-[[3-(trifluoromethyl)phenyl]sulfonyl]-tetrahydro-pyran-2-yl]-1H-pyrazole.

The compounds according to general formula (I) possess at least 2 stereogenic carbon atoms: the carbon atom bearing R$^1$ and the carbon atom bearing R$^2$.

The compounds according to formula (I) may be stereochemically differentiated according to their relative structural orientation. The compounds wherein the residues R$^1$ and R$^2$ have the same relative orientation, for instance both up ("bold wedge") or both down ("broken wedge") are referred within the scope of the present invention as the "cis" diastereomer (scheme 1). The compounds wherein the residues R$^1$ and R$^2$ have a differented relative orientation, for instance R$^1$ up ("bold wedge") and R$^2$ down ("broken wedge") or vice versa are referred within the scope of the present invention as the "trans" diastereomer (scheme 2).

Diastereoisomers differ with respect to their physical and chemical properties. Methods to determine the diastereomeric ratio (dr) are well known to the person skilled in the art and include, but are not limited to, NMR-methods.

A diastereomerically pure compound or a diastereomer according to the present invention refers to a stereoisomer, having a diastereomeric ratio of >90:10, particularity >92:8, preferably >95:5, more preferably >98:2 and even more preferably >99:1.

For both diastereomers, two enantiomers are possible. An enantiomerically pure compound or an enantionmer according to the present invention refers to a stereoisomer, having an enatiomeric excess of >90% ee, particularity >92% ee, preferably >95% ee, more preferably >98% ee and even more preferably >98% ee. A racemic mixture or a racemate refers to an equal mixture of two corresponding enantiomers.

Methods to determine the enatiomeric excess are well known to the person skilled in the art and include, but are not limited to, optical rotary dispersion, circular dichroism, NMR-methods using chiral auxiliaries ("shift reagents") or separation via chiral HPLC (high performance liquid chromatography, using a chiral stationary phase), chiral GLC (gas-liquid chromatography, using a chiral stationary phase phase) or chiral SFC (supercritical fluid chromatography using a chiral stationary phase).

Determination of the absolute stereochemical structure is well known to the person skilled in the art and includes, but are not limited to, x-ray diffractometry.

The stereogenic information of the compounds of the present invention is described according to their relative chemical structure as as detailed below:

1) A cis racemic compound (cis-rac) refers to a racemic mixture of two enantiomers as depicted in scheme 1.

(Scheme 1)

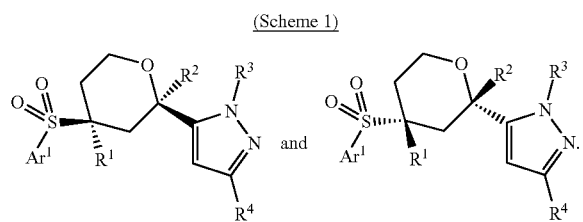

2) A trans racemic compound (trans-rac) refers to a racemic mixture of two enantiomers as depicted in scheme 2.

(Scheme 2)

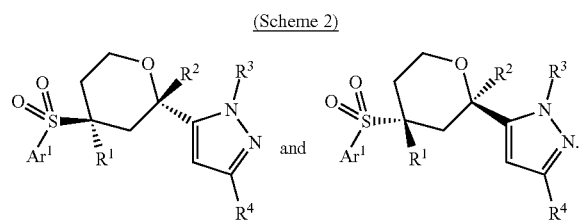

3) A cis enantiomer 1 compound (cis-EN1) refers to one single enantiomer as depicted in scheme 3.

(Scheme 3)

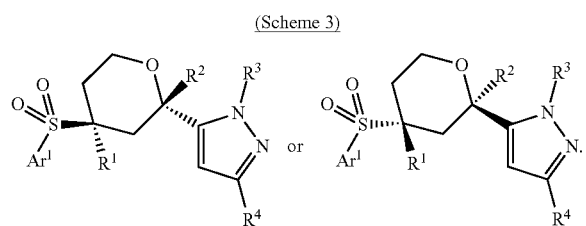

4) A cis enantiomer 2 compound (cis-EN2) refers to the other single enantiomer, which is not cis-EN1 as depicted in scheme 3.

(Scheme 3)

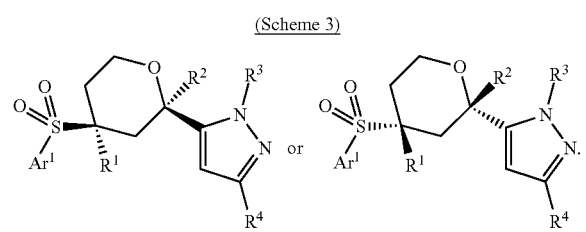

5) A trans enantiomer 1 compound (trans-EN1) refers to one single enantiomer as depicted in scheme 4.

(Scheme 4)

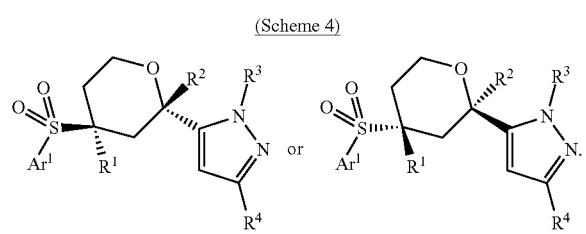

6) A trans enantiomer 2 compound (trans-EN2) refers to the other single enantiomer, which is not trans-EN1 as depicted in scheme 4.

(Scheme 4)

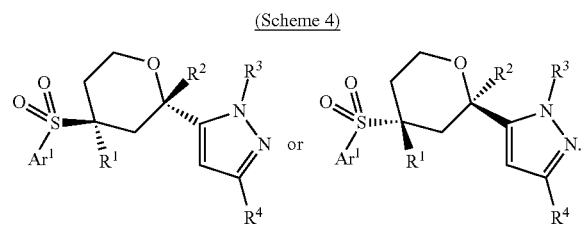

The term "physiologically acceptable salt" preferably comprises in the sense of this invention a salt of at least one compound according to the present invention and at least one physiologically acceptable acid or base.

The term "physiologically acceptable solvate" preferably comprises in the sense of this invention an adduct of one compound according to the present invention and/or a physiologically acceptable salt of at least one compound according to the present invention with distinct molecular equivalents of one solvent or more solvents.

The invention also includes all suitable isotopic variations of a compound of the invention, wherein at least one random or specific atom of the compound is partly or fully replaced by one or more certain isotopes of the respective element, being different from the naturally occurring isotopic distribution for this element. Preferred isotopes are $^2H$ (deuterium), $^3H$ (tritium), $^{13}C$ and $^{14}C$. Isotopic variations of a compound of the invention can be prepared by conventional procedures known by a person skilled in the art.

The term "$C_{1-6}$-alkyl" comprise in the sense of this invention acyclic saturated aliphatic hydrocarbon residues, which can be respectively branched or unbranched and which contain 1 to 6 carbon atoms, i.e. 1, 2, 3, 4, 5 or 6 carbon atoms. Preferred $C_{1-6}$-alkyl groups are selected from the group consisting of methyl, ethyl, n-propyl, 2-propyl, n-butyl, isobutyl, sec.-butyl, tert.-butyl, n-pentyl, isopentyl, neopentyl and n-hexyl.

In relation to the term "$C_{1-6}$-alkyl" the term "monosubstituted" or "polysubstituted" such as di- or tri-substituted refers in the sense of this invention, with respect to the corresponding groups, to the single substitution or multiple substitution, e.g. disubstitution or trisubstitution, of one or more hydrogen atoms each independently of one another by at least one substituent. The term "polysubstituted" such as di- or tri-substituted with respect to polysubstituted groups such as di- or tri-substituted groups includes the polysubstitution of these groups either on different or on the same atoms, for example trisubstituted on the same carbon atom, as in the case of $CF_3$ or $CH_2CF_3$ or at various points, as in the case of $CH(OH)CHF_2$. The multiple substitution can be carried out using the same or using different substituents.

The term "$C_{3-6}$-cycloalkyl" mean for the purposes of this invention cyclic aliphatic hydrocarbons containing 3, 4, 5 or 6 carbon atoms, respectively, wherein the hydrocarbons in each case can be saturated or unsaturated (but not aromatic). The cycloalkyl group can be bound to the respective superordinate general structure via any desired and possible ring member of the cycloalkyl group. The $C_{3-6}$-cycloalkyl can also be condensed with further saturated, (partially) unsaturated, (hetero)cyclic, aromatic or heteroaromatic ring systems, i.e. with cycloalkyl, heterocyclyl, aryl or heteroaryl residues. $C_{3-6}$-cycloalkyls can furthermore be singly or multiply bridged such as, for example, in the case of adamantyl, bicyclo[2.2.1]heptyl or bicyclo[2.2.2]octyl. Preferred $C_{3-6}$-cycloalkyl groups are selected from the group consisting of cyclopropyl, cyclobutyl, cyclopentyl, cyclohexyl, adamantly, cyclopentenyl, cyclohexenyl, cycloheptenyl, cyclooctenyl,

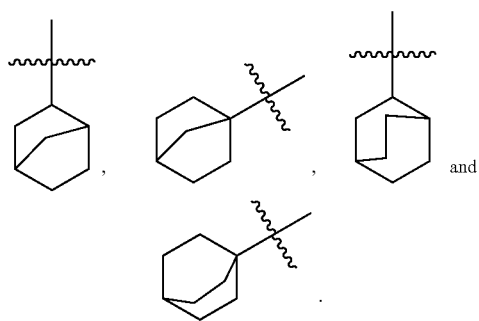

and

Particularly preferred $C_{3-6}$-cycloalkyl groups are $C_{3-6}$-cycloalkyl groups such as cyclopropyl, cyclobutyl, cyclopentyl, cyclohexyl, cyclopentenyl and cyclohexenyl, in particular cyclopropyl.

The terms "3 to 7-membered heterocyclyl" mean for the purposes of this invention heterocycloaliphatic saturated or unsaturated (but not aromatic) residues having 3 to 7, i.e. 3, 4, 5, 6 or 7 ring members, respectively, in which in each case at least one, if appropriate also two or three carbon atoms are replaced by a heteroatom or a heteroatom group each selected independently of one another from the group consisting of O, S, S(=O), S(=O)$_2$, N, NH and N($C_{1-6}$-alkyl) such as N(CH$_3$). The cycloalkyl groups can also be condensed with further saturated or partially) unsaturated cycloalkyl or heterocyclyl, aromatic or heteroaromatic ring systems. The heterocyclyl group can be bound to the superordinate general structure via any desired and possible ring member of the heterocycloaliphatic residue if not indicated otherwise.

The term "aryl" means for the purpose of this invention aromatic hydrocarbons having 6 to 14, i.e. 6, 7, 8, 9, 10, 11, 12, 13 or 14 ring members, preferably having 6 to 10, i.e. 6, 7, 8, 9 or 10 ring members, including phenyls and naphthyls. Each aryl residue can be unsubstituted or mono- or polysubstituted. The aryl can be bound to the superordinate general structure via any desired and possible ring member of the aryl residue. The aryl residues can also be condensed with further sat. or (partially) unsat. cycloalkyl or heterocyclyl, aromatic or heteroaromatic ring systems, which can in turn be unsubstituted or mono- or polysubstituted. Examples of condensed aryl residues are benzodioxolanyl and benzodioxanyl. Preferably, aryl is selected from the group consisting of phenyl, 1-naphthyl, 2-naphthyl, fluorenyl and anthracenyl, each of which can be respectively unsubstituted or mono- or polysubstituted. A particularly preferred aryl is phenyl, unsubstituted or mono- or polysubstituted.

The term "heteroaryl" for the purpose of this invention represents a 5-, 6-, 8-, 9- or 10-membered cyclic aromatic residue containing at least 1, if appropriate also 2, 3, 4 or 5 heteroatoms, wherein the heteroatoms are each selected independently of one another from the group S, N and O and the heteroaryl residue can be unsubstituted or mono- or polysubstituted; in the case of substitution on the heteroaryl, the substituents can be the same or different and be in any desired and possible position of the heteroaryl. The binding to the superordinate general structure can be carried out via any desired and possible ring member of the heteroaryl residue if not indicated otherwise. The heteroaryl can also be part of a bi- or polycyclic system having up to 10 ring members, wherein the ring system can be formed with further sat. or (partially) unsat. cycloalkyl or heterocyclyl, aromatic or heteroaromatic ring systems, which can in turn be unsubstituted or mono- or polysubstituted. It is preferable for the heteroaryl residue to be selected from the group consisting of benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, ind-azolyl, indolizinyl, indolyl, isoquinolinyl, isoxazoyl, isothiazolyl, indolyl, naphthyridinyl, oxazolyl, oxadiazolyl, phenazinyl, phenothiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl.

Within the scope of the present invention, the symbols

used in the formulae denotes a link of a corresponding residue to the respective superordinate general structure.

In one embodiment of the first aspect of the invention, the compound according to general formula (I) is characterized in that $R^2$ represents H, CH$_3$, C$_2$H$_5$, CH$_2$CH$_2$CH$_3$ or CH(CH$_3$)$_2$. Preferably, $R^2$ represents H.

In another embodiment of the first aspect of the invention, the compound according to general formula (I) is characterized in that $R^1$ represents H, CH$_3$, C$_2$H$_5$, CH$_2$CH$_2$CH$_3$ or CH(CH$_3$)$_2$. Preferably, $R^1$ represents CH$_3$.

In another preferred embodiment of the first aspect of the invention, the compound according to general formula (I) is characterized in $R^1$ represents CH$_3$ and $R^2$ represents H, so the compound is represented by general formula (II),

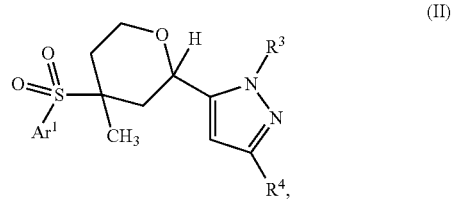

(II)

wherein $Ar^1$, $R^3$ and $R^4$ are defined as herein.

In another embodiment of the first aspect of the invention, the compound according to the invention is one diastereomer. Preferably, the compound according to the invention is the cis-diastereomer. Still preferably, the compound according to the invention is the trans-diastereomer.

Thus, one preferred embodiment of the first aspect of the invention is characterized in that the compound of general formula (I) or (II) is one diastereomer.

The cis-diastereomer or the trans-diastereomer may be in the form of a single enantiomer or in the form of an enantiomeric mixture, preferably of a racemate.

In yet another embodiment of the first aspect of the invention, the compound according to the invention is in only one enantiomeric form. Preferably, the compound according to the invention is the racemate of the cis-diastereomer (cis-rac) or a single enantiomer of the cis-diastereomer (cis-EN1 or cis-EN2). Still preferably, the compound according to the invention is the racemate of the trans-diastereomer (trans-rac) or a single enantiomer of the trans-diastereomer (trans-EN1 or trans-EN2).

Thus, one preferred embodiment of the first aspect of the invention is characterized in that the compound of general formula (I) or (II) is one enantiomer.

In one preferred embodiment of the first aspect of the invention is characterized in that the compound of general formula (I) or (II), (IIa) is the enantiomer, which exhibits at room temperature and a wavelength of 589 nm (Na-D-line) a positive optical rotation in dichloromethane or methanol.

In another preferred embodiment of the first aspect of the invention is characterized in that the compound of general formula (I) or (II) is the enantiomer, which exhibits at room temperature and a wavelength of 589 nm (Na-D-line) a negative optical rotation in dichloromethane or methanol.

In another embodiment of the first aspect of the invention, the compound according to general formula (I) is characterized in that $Ar^1$ represents phenyl or pyridinyl, substituted by zero or one or two or three substituents $R^7$.

In preferred embodiment of the first aspect of the invention, the compound according to general formula (I) is characterized in that $Ar^1$ represents phenyl or pyridinyl, substituted by zero, one or two substituents $R^7$, wherein each $R^7$ is independently selected from the group consisting of F; Cl; CN; $C_{1-6}$-alkyl; $CF_3$; $CF_2H$; $CFH_2$; C(O)—$C_{1-6}$-alkyl; C(O) OH; C(O)—O—$C_{1-6}$-alkyl; C(O)—N(H)(OH); C(O)—$NH_2$; C(O)—N(Fl)($C_{1-6}$-alkyl); C(O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N($C_{1-6}$-alkyl)-C(O)—$C_{1-6}$-alkyl; N(H)—S(O)$_2$—$C_{1-6}$-alkyl; $SCF_3$; S—$C_{1-6}$-alkyl; S(O)—$C_{1-6}$-alkyl; S(O)$_2$—$C_{1-6}$-alkyl; S(O)$_2$—$NH_2$; S(O)$_2$—N(H)($C_{1-6}$-alkyl); S(O)$_2$—N($C_{1-6}$-alkyl)$_2$; $C_{3-6}$-cycloalkyl; 3 to 7 membered heterocyclyl; O—$C_{3-6}$-cycloalkyl and O-(3 to 7 membered heterocyclyl).

Preferably, $R^7$ is independently selected from the group consisting of F; Cl; CN; $C_{1-6}$-alkyl; $CF_3$; $CF_2H$; $CFH_2$; C(=O)—$C_{1-6}$-alkyl; C(=O)—OH; C(=O)—O—$C_{1-6}$-alkyl; C(=O)—N(H)(OH); C(=O)—$NH_2$; C(=O)—N(H)($C_{1-6}$-alkyl); C(=O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N($C_{1-6}$-alkyl)-C(=O)—$C_{1-6}$-alkyl; N(H)—S(=O)$_2$—$C_{1-6}$-alkyl; $SCF_3$; S—$C_{1-6}$-alkyl; S(=O)—$C_{1-6}$-alkyl; S(=O)$_2$—$C_{1-6}$-alkyl; S(=O)$_2$—$NH_2$; S(=O)$_2$—N(H)($C_{1-6}$-alkyl); S(=O)$_2$—N($C_{1-6}$-alkyl)$_2$; $C_{3-6}$-cycloalkyl; 3 to 7 membered heterocyclyl; O—$C_{3-6}$-cycloalkyl and O-(3 to 7 membered heterocyclyl).

In yet another embodiment of the first aspect of the invention, the compound according to general formula (I) or (II) is characterized in that $Ar^1$ is selected from the group consisting of 3-trifluoromethyl-phenyl; 3-difluoromethyl-phenyl; 3-fluoromethyl-phenyl; 3-trifluoromethoxy-phenyl; 3-difluoromethoxy-phenyl; 3-fluoromethoxy-phenyl; 3-fluoro-phenyl; 3-cyanophenyl; 6-trifluoromethyl-pyridin-2-yl; 3-difluoromethyl-pyridin-2-yl; 3-fluoromethyl-pyridin-2-yl; 3-trifluoromethoxy-pyridin-2-yl; 3-difluoromethoxy-pyridin-2-yl; 3-fluoromethoxy-pyridin-2-yl; 3-fluoro-pyridin-2-yl or 3-cyano-pyridin-2-yl. Particularly preferred compounds according to the present invention are characterized in that $Ar^1$ represents of 3-trifluoromethyl-phenyl.

In yet another embodiment of the first aspect of the invention, the compound according to general formula (I) or (II) is characterized in that $R^4$ represents L-$R^5$, wherein L is bond, $CH_2$, $C(CH_3)_2$, O or S(=O)$_2$. Preferably, L is bond or $CH_2$ or $SO_2$ or $C(CH_3)_2$.

In yet another embodiment of the first aspect of the invention, the compound according to general formula (I) or (II) is characterized in that $R^5$ is $C_{1-6}$-alkyl,
wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, S(=O)$_2CH_3$, S(=O)$_2CHF_2$, S(=O)$_2CF_3$, S(=O)$_2CH(CH_3)_2$, S(=O)$_2$(c-propyl), $NH_2$, $NH(CH_3)$, $N(CH_3)_2$, C(=O)$NH_2$, C(=O)$NH(CH_3)$ and C(=O)$N(CH_3)_2$.

In yet another embodiment of the first aspect of the invention, the compound according to general formula (I) or (II) is characterized in that wherein said $C_{3-6}$-cycloalkyl is unsubstituted or substituted by one or two or three or four substituents independently selected from the group consisting of F, Cl, CN, $CH_3$, $CFH_2$, $CHF_2$, $CF_3$, OH, $OCH_3$, $CH_2OH$, $CH_2OCH_3$, $OCFH_2$, $OCHF_2$, $OCF_3$, S(=O)$_2CH_3$, S(=O)$_2CHF_2$, S(=O)$_2CF_3$, S(=O)$_2CH(CH_3)_2$, S(=O)$_2$(c-propyl), $NH_2$, $NH(CH_3)$, $N(CH_3)_2$, C(=O)$NH_2$, C(=O)$NH(CH_3)$ and C(=O)$N(CH_3)_2$.

Preferably, $R^5$ is $C_{3-6}$-cycloalkyl,
wherein said $C_{3-6}$-cycloalkyl is cyclopropyl or cyclobutyl,
wherein said cyclopropyl or said cyclobutyl is unsubstituted or substituted by one or two or three or four substituents independently selected from the group consisting of F, Cl, CN, $CH_3$, $CFH_2$, $CHF_2$, $CF_3$, OH, $OCH_3$, $OCFH_2$, $OCHF_2$, $OCF_3$, S(=O)$_2CH_3$, S(=O)$_2CHF_2$, S(=O)$_2CF_3$, S(=O)$_2CH(CH_3)_2$, S(=O)$_2$(c-propyl), $NH_2$, $NH(CH_3)$, $N(CH_3)_2$, C(=O)$NH_2$, C(=O)$NH(CH_3)$ and C(=O)$N(CH_3)_2$.

More preferably, $R^5$ is selected from the group consisting of

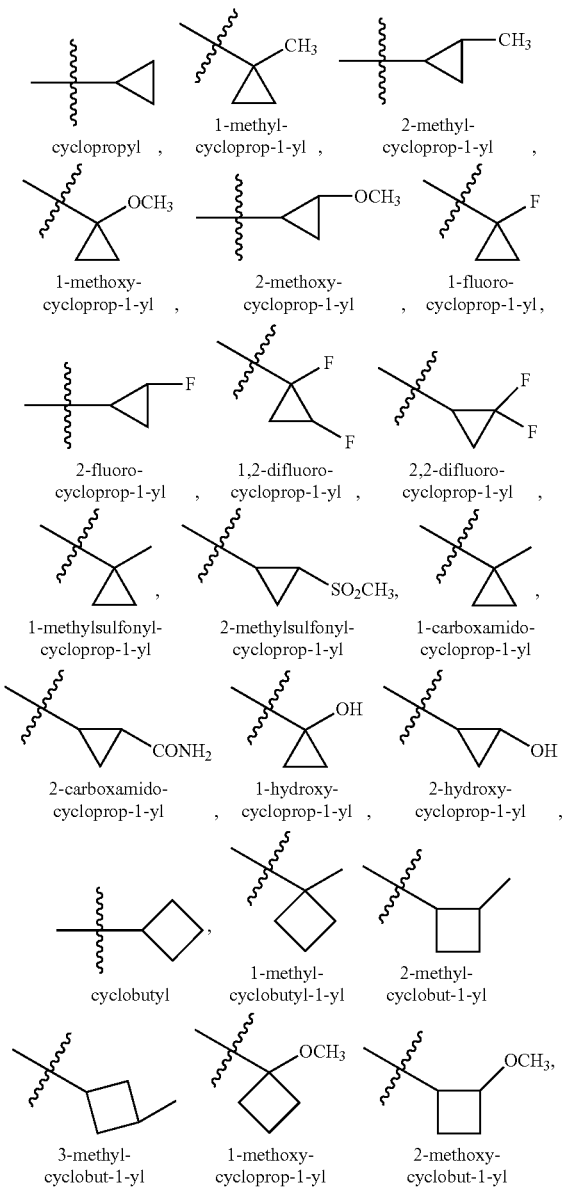

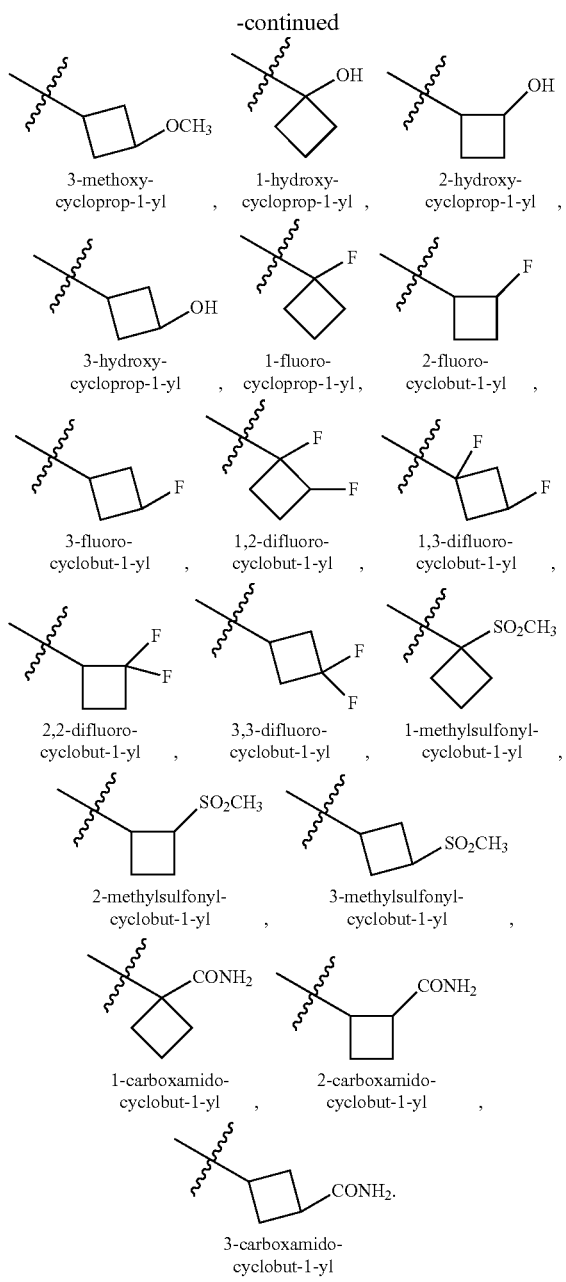

In yet another embodiment of the first aspect of the invention, the compound according to general formula (I) or (II) is characterized in that $R^5$ is 3 to 7 membered heterocyclyl, wherein said 3 to 7 membered heterocyclyl is characterized that it contains one heteroatom or heteroatom group, selected from O, NH, N(CH$_3$), S(=O) and S(=O)$_2$;

and wherein said 3 to 7 membered heterocyclyl is unsubstituted or substituted by one or two or three or four substituents independently selected from the group consisting of F, Cl, CN, CH$_3$, CFH$_2$, CHF$_2$, CF$_3$, =O, OH, OCH$_3$, CH$_2$OH, CH$_2$OCH$_3$, OCFH$_2$, OCHF$_2$, OCF$_3$, S(=O)$_2$CH$_3$, S(=O)$_2$CHF$_2$, S(=O)$_2$CF$_3$, S(=O)$_2$CH(CH$_3$)$_2$, S(=O)$_2$(c-propyl), NH$_2$, NH(CH$_3$), N(CH$_3$)$_2$, C(=O)NH$_2$, C(=O)NH(CH$_3$) and C(=O)N(CH$_3$)$_2$.

Preferably, $R^5$ is 3 to 7 membered heterocyclyl, wherein said 3 to 7 membered heterocyclyl is selected from the group consisting of oxetanyl, tetrahydrofuranyl, tetrahydropyranyl, azetidinyl, pyrrolidinyl, piperidinyl, piperazinyl, N-methylpiperazinyl or morpholinyl, wherein said 3 to 7 membered heterocyclyl is unsubstituted or substituted by one or two or three or four substituents independently selected from the group consisting of F, Cl, CN, CH$_3$, CFH$_2$, CHF$_2$, CF$_3$, =O, OH, OCH$_3$, OCFH$_2$, OCHF$_2$, OCF$_3$, S(=O)$_2$CH$_3$, S(=O)$_2$CHF$_2$, S(=O)$_2$CF$_3$, S(=O)$_2$CH(CH$_3$)$_2$, S(=O)$_2$(c-propyl), NH$_2$, NH(CH$_3$), N(CH$_3$)$_2$, C(=O)NH$_2$, C(=O)NH(CH$_3$) and C(=O)N(CH$_3$)$_2$.

Preferably,

L is selected from bond, CH$_2$, C(CH$_3$)$_2$, O or S(=O)$_2$ and $R^5$ is selected from the group consisting of

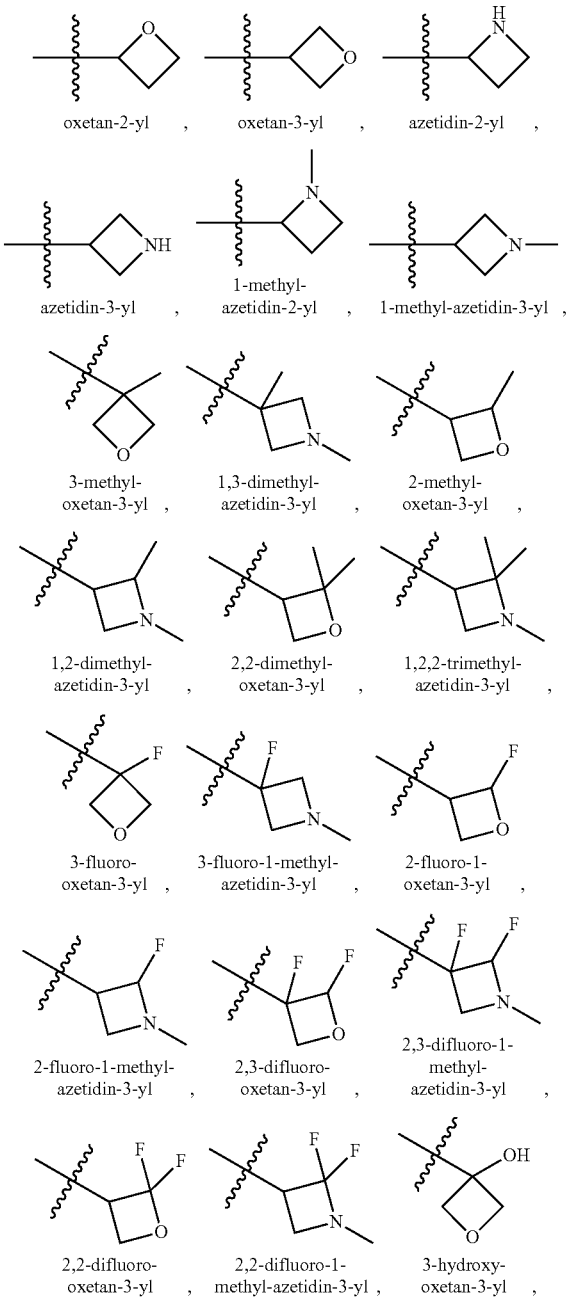

-continued

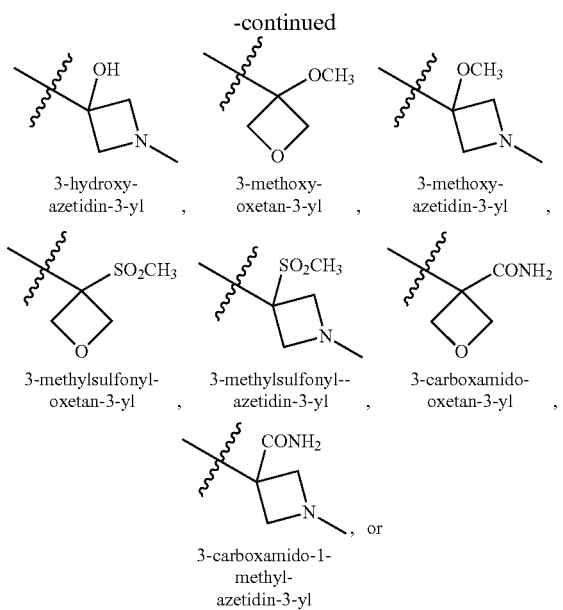

L is selected from bond, CH$_2$ and C(CH$_3$)$_2$ and R$^5$ is selected from the group consisting of

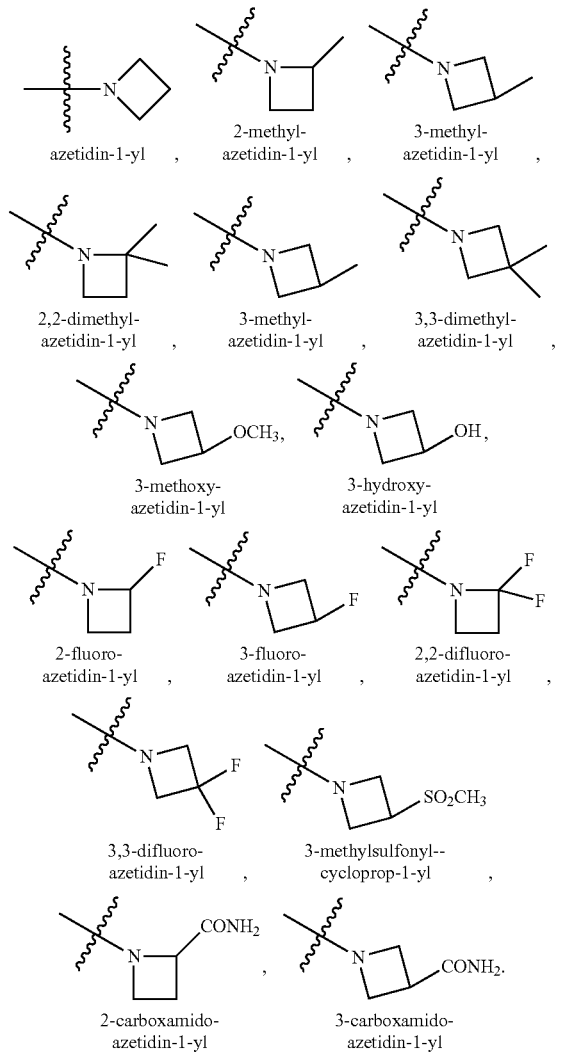

In yet another embodiment of the first aspect of the invention, the compound according to general formula (I) or (II) is characterized in that L is bond and R$^5$ is selected from the group consisting of CH$_3$, CH(CH$_3$)$_2$, C(CH$_3$)$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CFH$_2$, CHF$_2$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$CN, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl or oxetanyl, wherein said cyclopropyl, cyclobuytyl or oxetanyl are unsubstituted or substituted with OH, OCH$_3$ or S(O)$_2$CH$_3$; or L is CH$_2$ and R$^5$ is selected from the group consisting of CH$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CH(CH$_3$)$_2$, C(CH$_3$)$_3$, CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$S(=O)$_2$CH(CH$_3$)$_2$, C(CH$_3$)$_2$S(=O)$_2$(c-propyl), C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl or oxetanyl, wherein said cyclopropyl, cyclobuytyl or oxetanyl are unsubstituted or substituted with CH$_3$, OH, NH$_2$, NH(CH$_3$), N(CH$_3$)$_2$, OCH$_3$ or S(O)$_2$CH$_3$; or L is C(CH$_3$)$_2$ and R$^5$ is selected from the group consisting of CH(CH$_3$)$_2$, C(CH$_3$)$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$S(=O)$_2$CH(CH$_3$)$_2$, C(CH$_3$)$_2$S(=O)$_2$(c-propyl), C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl or oxetanyl, wherein said cyclopropyl, cyclobuytyl or oxetanyl are unsubstituted or substituted with CH$_3$, OH, NH$_2$, NH(CH$_3$), N(CH$_3$)$_2$, OCH$_3$ or S(O)$_2$CH$_3$;

or

L is O and

R⁵ is selected from the group consisting of CH₃, CH(CH₃)₂, C(CH₃)₃, CFH₂, CHF₂, CF₃, CH₂CF₃, CF₂CH₃, CH₂CFH₂, CH₂CHF₂, CH₂CH₂CF₃, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH(CH₃), CH₂C(=O)N (CH₃)₂, CH₂CH₂C(=O)NH₂CH₂CH₂C(=O)NH(CH₃), CH₂CH₂C(=O)N(CH₃)₂, C(CH₃)₂OCH₃, C(CH₃)₂N(CH₃)₂, C(CH₃)₂C(=O)NH₂C(CH₃)₂C(=O)NH(CH₃), C(CH₃)₂C(=O)N(CH₃)₂, cyclopropyl, cyclobuytyl or oxetanyl, wherein said cyclopropyl, cyclobuytyl or oxetanyl are unsubstituted or substituted with CH₃, OCH₃ or S(O)₂CH₃; or L is S(=O)₂ and R⁵ is selected from the group consisting of CH₃, CH₂CH₃, CH(CH₃)₂, CH₂CH(CH₃)₂, CH₂C(CH₃)₃, C(CH₃)₃, CFH₂, CHF₂, CF₃, CH₂CF₃, CF₂CH₃, CH₂CFH₂, CH₂CHF₂, CH₂CH₂CF₃, C(CH₃)₂CF₃, CH₂CH₂OCH₃, CH₂CH₂OH, C(CH₃)₂CH₂OCH₃, C(CH₃)₂CH₂OH, CH₂CH₂S(=O)₂CH₃, CH₂CH₂N(CH₃)₂, CH₂C(=O)NH₂, CH₂C(=O)NH (CH₃), CH₂C(=O)N(CH₃)₂, CH₂CH₂C(=O)NH₂CH₂CH₂C(=O)NH(CH₃), CH₂CH₂C(=O)N(CH₃)₂, cyclopropyl, cyclobuytyl or oxetanyl, wherein said cyclopropyl, cyclobuytyl or oxetanyl are unsubstituted or substituted with CH₃, OCH₃ or S(O)₂CH₃.

In yet another embodiment of the first aspect of the invention, the compound according to general formula (I) or (II) is characterized in that R⁴ is selected from the group consisting of CHF₂, CF₂CH₃, CH₂CHF₂, CH₂CF₃, CH(CH₃)₂, C(CH₃)₃, OCF₃, OCHF₂, OCH₂CF₃, OCH₂CHF₂, OCH₂CH₂F, O-c-propyl (cycloprop-1-yl-oxy), CH₂OCF₃, C(CH₃)₂OH, C(CH₃)₂CH₂OH, C(CH₃)₂CH₂OCH₃, C(CH₃)₂CN, C(CH₃)₂C(=O)NH₂, S(=O)₂CH₃, S(=O)₂CH₂CH(CH₃)₂, S(=O)₂CH₂C(CH₃)₃, S(=O)₂CHF₂, S(=O)₂CF₃, S(=O)₂C(CH₃)₂CF₃, S(=O)₂CH₂CH₂OCH₃, S(=O)₂CH₂CH₂OH, S(=O)₂CH₂CF₃, S(=O)₂CF₂CH₃, S(=O)₂CH₂CHF₂, S(=O)₂—CH(CH₂)₂O (S(=O)₂-oxetan-3-yl), CH₂S(=O)₂CHF₂, CH₂S(=O)₂CF₃, CH₂CH₂S(=O)₂CH₃, C(CH₃)₂S(=O)₂CH₃, cyclopropyl, C(CH₂)₂(CH₃) (1-methyl-cycloprop-1-yl), C(CH₂)₂S(=O)₂CH₃ (1-methyl sulfonyl-cycloprop-1-yl), C(OH)(CH₂)₂O (3-hydroxy-oxetan-3-yl), cyclobutyl.

Yet another embodiment of the first aspect of the invention, is characterized in that the compound of general formula (I) has general formula (III),

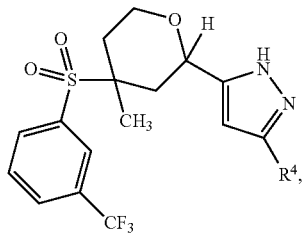

(III)

wherein R⁴ is defined as above, with the proviso that R⁴ is not CF₃, optionally in the form of a single stereoisomer or a mixture of stereoisomers, in the form of the free compound and/or a physiologically acceptable salt and/or a physiologically acceptable solvate thereof.

In a particularly preferred embodiment, the compound according to the present invention is according to general formula (III), wherein R⁴ represents L-R⁵, wherein L is bond, CH₂, C(CH₃)₂, O or S(=O)₂; and R⁵ is C₁₋₆-alkyl, wherein said C₁₋₆-alkyl is unsubstituted or substituted by one or two or three or four substituents independently selected from the group consisting of F, Cl, CN, OH, OCH₃, OCFH₂, OCHF₂, OCF₃, S(=O)₂CH₃, S(=O)₂CHF₂, S(=O)₂CF₃, S(=O)₂CH(CH₃)₂, S(=O)₂(c-propyl), NH₂, NH(CH₃), N(CH₃)₂, C(=O)NH₂, C(=O)NH(CH₃) and C(=O)N(CH₃)₂.

Particularly preferred compounds according to the invention are selected from the group consisting of 1  3-(Difluoro-methylsulfonyl)-5-[4-methyl-4-[[3-(trifluoromethyl)phenyl]sulfonyl]-tetrahydro-pyran-2-yl]-1H-pyrazole 2  3-(1,1-Difluoro-ethylsulfonyl)-5-[4-methyl-4-[[3-(trifluoromethyl)phenyl]sulfonyl]-tetrahydro-pyran-2-yl]-1H-pyrazole 3  3-(2,2-Difluoro-ethylsulfonyl)-5-[4-methyl-4-[[3-(trifluoromethyl)phenyl]sulfonyl]-tetrahydro-pyran-2-yl]-1H-pyrazole 4  5-[4-Methyl-4-[[3-(trifluoromethyl)phenyl]sulfonyl]-tetrahydro-pyran-2-yl]-3-(oxetan-3-ylsulfonyl)-1H-pyrazole 5  3-(2-M ethoxy-ethylsulfonyl)-5-[4-methyl-4-[[3-(trifluoromethyl)phenyl]sulfonyl]-tetrahydro-pyran-2-yl]-1H-pyrazole 6  2-[[5-[4-Methyl-4-[[3-(trifluoromethyl)phenyl]sulfonyl]-tetrahydro-pyran-2-yl]-1H-pyrazol-3-yl]sulfonyl]-ethanol 7  3-(1-Methyl-1-methylsulfonyl-ethyl)-5-[4-methyl-4-[[3-(trifluoromethyl)phenyl]sulfonyl]-tetrahydro-pyran-2-yl]-1H-pyrazole 8  3-(1-Methylsulfonyl-cyclopropyl)-5-[4-methyl-4-[[3-(trifluoromethyl)phenyl]sulfonyl]-tetrahydro-pyran-2-yl]-1H-pyrazole 9  3-(2-M ethylsulfonyl-ethyl)-5-[4-methyl-4-[[3-(trifluoromethyl)phenyl]sulfonyl]-tetrahydro-pyran-2-yl]-1H-pyrazole 12  (1,1-(Difluoro-methyl)-5-[4-methyl-4-[[3-(trifluoromethyl)phenyl]sulfonyl]-tetrahydro-pyran-2-yl]-1H-pyrazole 13  3-(1,1-Difluoro-ethyl)-5-[4-methyl-4-[[3-(trifluoromethyl)phenyl]sulfonyl]-tetrahydro-pyran-2-yl]-1H-pyrazole 14  3-(2,2-Difluoro-ethyl)-5-[4-methyl-4-[[3-(trifluoromethyl)phenyl]sulfonyl]-tetrahydro-pyran-2-yl]-1H-pyrazole 15  3-(2,2-Difluoro-ethyl)-5-[4-methyl-4-[[3-(trifluoromethyl)phenyl]sulfonyl]-tetrahydro-pyran-2-yl]-1H-pyrazole 16  5-[4-M ethyl-4-[[3-(trifluoromethyl)phenyl]sulfonyl]-tetrahydro-pyran-2-yl]-3-(2,2,2-trifluoro-ethyl)-1H-pyrazole 17  5-[4-Methyl-4-[[3-(trifluoromethyl)phenyl]sulfonyl]-tetrahydro-pyran-2-yl]-3-(2,2,2-trifluoro-ethoxy)-1H-pyrazole 18  3-[5-[4-Methyl-4-[[3-(trifluoromethyl)phenyl]sulfonyl]-tetrahydro-pyran-2-yl]-1H-pyrazol-3-yl]-oxetan-3-ol 19  2-[5-[4-Methyl-4-[[3-(trifluoromethyl)phenyl]sulfonyl]-tetrahydro-pyran-2-yl]-1H-pyrazol-3-yl]-propan-2-ol 20  3-Cyclopropyl-5-[4-methyl-4-[[3-(trifluoromethyl)phenyl]sulfonyl]-tetrahydro-pyran-2-yl]-1H-pyrazole 21  3-Cyclobutyl-5-[4-methyl-4-[[3-(trifluoromethyl)phenyl]sulfonyl]-tetrahydro-pyran-2-yl]-1H-pyrazole 22 3-tert-Butyl-5-[4-methyl-4-[[3-(trifluoromethyl)phenyl]sulfonyl]-tetrahydro-pyran-2-yl]-1H-pyrazole
23 3-(1-Methyl-cyclopropyl)-5-[4-methyl-4-[[3-(trifluoromethyl)phenyl]sulfonyl]-tetrahydro-pyran-2-yl]-1H-pyrazole
24 3-Cyclopropyloxy-5-[4-methyl-4-[[3-(trifluoromethyl)phenyl]sulfonyl]-tetrahydro-pyran-2-yl]-1H-pyrazole
25 3-(Difluoro-methoxy)-5-[4-methyl-4-[[3-(trifluoromethyl)phenyl]sulfonyl]-tetrahydro-pyran-2-yl]-1H-pyrazole
26 5-[4-Methyl-4-[[3-(trifluoromethyl)phenyl]sulfonyl]-tetrahydro-pyran-2-yl]-3-(trifluoromethyloxy)-1H-pyrazole
27 5-[4-Methyl-4-[[3-(trifluoromethyl)phenyl]sulfonyl]-tetrahydro-pyran-2-yl]-3-(trifluoromethylsulfonyl)-1H-pyrazole
28 3-[(Difluoro-methylsulfonyl)-methyl]-5-[4-methyl-4-[[3-(trifluoromethyl)phenyl]sulfonyl]-tetrahydro-pyran-2-yl]-1H-pyrazole
29 5-[4-Methyl-4-[[3-(trifluoromethyl)phenyl]sulfonyl]-tetrahydro-pyran-2-yl]-3-(2,2,2-trifluoro-ethylsulfonyl)-1H-pyrazole
30 2-Methyl-2-[5-[4-methyl-4-[[3-(trifluoromethyl)phenyl]sulfonyl]-tetrahydro-pyran-2-yl]-1H-pyrazol-3-yl]-propionamide
31 2-Methyl-2-[5-[4-methyl-4-[[3-(trifluoromethyl)phenyl]sulfonyl]-tetrahydro-pyran-2-yl]-1 H-pyrazol-3-yl]-propionitrile
32 5-(2,2-Difluoro-ethoxy)-3-[4-methyl-4-[[3-(trifluoromethyl)phenyl]sulfonyl]-tetrahydro-pyran-2-yl]-1H-pyrazole
33 3-(2-Methoxy-1,1-dimethyl-ethyl)-5-[4-methyl-4-[[3-(trifluoromethyl)phenyl]sulfonyl]-tetrahydro-pyran-2-yl]-1H-pyrazole
34 2-Methyl-2-[5-[4-methyl-4-[[3-(trifluoromethyl)phenyl]sulfonyl]-tetrahydro-pyran-2-yl]-1H-pyrazol-3-yl]-propan-1-ol
35 3-(2-Methyl-propylsulfonyl)-5-[4-methyl-4-[[3-(trifluoromethyl)phenyl]sulfonyl]-tetrahydro-pyran-2-yl]-1H-pyrazole
36 3-(2,2-Dimethyl-propylsulfonyl)-5-[4-methyl-4-[[3-(trifluoromethyl)phenyl]sulfonyl]-tetrahydro-pyran-2-yl]-1H-pyrazole
37 5-Methylsulfonyl-3-[4-methyl-4-[[3-(trifluoromethyl)phenyl]sulfonyl]-tetrahydro-pyran-2-yl]-1H-pyrazole
38 2-Methyl-2-[5-[4-methyl-4-[[6-(trifluoromethyl)-pyridin-2-yl]sulfonyl]-tetrahydro-pyran-2-yl]-1H-pyrazol-3-yl]-propionitrile
39 5-[4-Methyl-4-[[3-(trifluoromethyl)phenyl]sulfonyl]-tetrahydro-pyran-2-yl]-3-[(2,2,2-trifluoro-1,1-dimethyl-ethyl)sulfonyl]-1H-pyrazole
40 3-(2-Fluoro-1,1-dimethyl-ethyl)-5-[4-methyl-4-[[3-(trifluoromethyl)phenyl]sulfonyl]-tetrahydro-pyran-2-yl]-1H-pyrazole optionally in the form of a single stereoisomer or a mixture of stereoisomers, in the form of the free compound and/or a physiologically acceptable salt or solvate thereof.

Within the scope of the invention, it is understood that the compounds according the aforesaid list may be in the form of a single stereoisomer or any mixture of stereoisomers.

For instance, the given compound 3-(difluoro-methylsulfonyl)-5-[4-methyl-4-[[3-(trifluoromethyl)phenyl]sulfonyl]-tetrahydro-pyran-2-yl]-1H-pyrazole (Example 1),

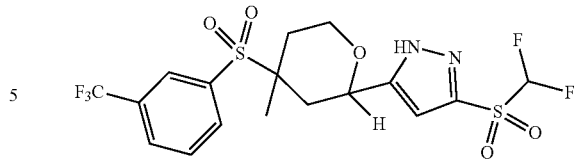

represents cis-rac-3-(difluoro-methylsulfonyl)-5-[4-methyl-4-[[3-(trifluoromethyl)phenyl]sulfonyl]-tetrahydro-pyran-2-yl]-1H-pyrazole,

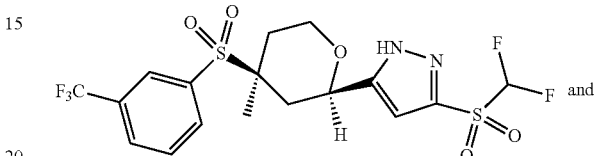

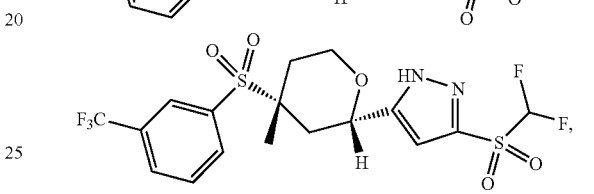

[(2R, 4S) and (2S, 4R)-3-(difluoro-methylsulfonyl)-5-[4-methyl-4-[[3-(trifluoromethyl)phenyl]-sulfonyl]-tetrahydro-pyran-2-yl]-1H-pyrazole,
and
trans-rac-3-(difluoro-methylsulfonyl)-5-[4-methyl-4-[[3-(trifluoromethyl)phenyl]sulfonyl]-tetrahydro-pyran-2-yl]-1H-pyrazole,

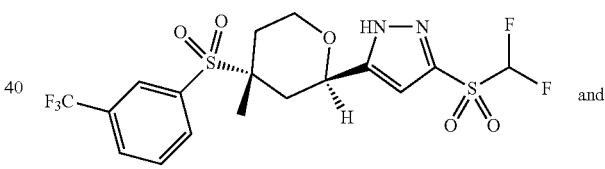

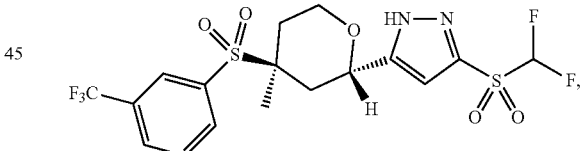

[(2S, 4S) and (2R, 4R)-3-(difluoro-methylsulfonyl)-5-[4-methyl-4-[[3-(trifluoromethyl)phenyl]-sulfonyl]-tetrahydro-pyran-2-yl]-1H-pyrazole, as well as each individual stereoisomer or any other mixture thereof.

Furthermore, preference may be given to compounds according to the invention that cause at least a 50% inhibition, which is present at a concentration of 3 µM, in a fluorescent assay for CaV2.2 channels with HEK293 cells in which human CaV2.2 channels were stably expressed at a concentration of less 3 µM, preferably less than 1000 nM, particularly preferably less than 300 nM, most particularly preferably less than 100 nM, even more preferably less than 75 nM, additionally preferably less than 50 nM, most preferably less than 10 nM.

In the process, the $Ca^{2+}$ influx is quantified in the FLIPR assay with the aid of a $Ca^{2+}$-sensitive dye (type Fluo-4, Molecular Probes Europe BV, Leiden, the Netherlands) in a fluorescent imaging plate reader (FLIPR 3, Molecular Devices, Sunnyvale, USA), as described hereinafter.

The present invention further relates to a compound according to the present invention for CaV2.2 calcium channel regulation, preferably for use in CaV2.2 calcium channel blockage. The present invention therefore further relates to a compound according to the present invention for use in the treatment and/or prophylaxis of disorders and/or diseases which are mediated, at least in part, at least in part, by CaV2.2 channels. The term "disorders and/or diseases which are mediated, at least in part, by CaV2.2 channels", is intended to include each of or all of the disease states.

In another aspect of the present invention, the invention therefore also provides pharmaceutical compositions, containing at least one compound according to the invention and optionally one or more suitable, pharmaceutically compatible auxiliaries and/or, if appropriate, one or more further pharmacologically active compounds.

The pharmaceutical composition according to the invention may be found as a liquid, semisolid or solid pharmaceutical form, for example in the form of injection solutions, drops, juices, syrups, sprays, suspensions, tablets, patches, capsules, plasters, suppositories, ointments, creams, lotions, gels, emulsions, aerosols or in multiparticulate form, for example in the form of pellets or granules, if appropriate pressed into tablets, decanted in capsules or suspended in a liquid, and also be administered as much.

In addition to at least one compound according to the invention, if appropriate in the form of one of its pure stereoisomers, in particular enantiomers or diastereomers, its racemate or in the form of mixtures of the stereoisomers, in particular the enantiomers or diastereomers, in any desired mixing ratio, or if appropriate in the form of a corresponding salt or respectively in the form of a corresponding solvate, the pharmaceutical composition according to the invention conventionally contains further physiologically compatible pharmaceutical auxiliaries which can for example be selected from the group consisting of excipients, fillers, solvents, diluents, surface-active substances, dyes, preservatives, blasting agents, slip additives, lubricants, aromas and binders.

The selection of the physiologically compatible auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The compounds according to the invention used in the pharmaceutical composition according to the invention in a repository in dissolved form or in a plaster, agents promoting skin penetration being added if appropriate, are suitable percutaneous application preparations. Orally or percutaneously applicable preparation forms can release the respective compound according to the invention also in a delayed manner.

The pharmaceutical compositions according to the invention are prepared with the aid of conventional means, devices, methods and process known in the art. The amount to be administered to the patient of the respective compounds according to the invention of the above-indicated general formula I may vary and is for example dependent on the patient's weight or age and also on the type of application, the indication and the severity of the disorder. Conventionally 0.001 to 100 mg/kg, preferably 0.05 to 75 mg/kg, particularly preferably 0.05 to 50 mg of at least one such compound according to the invention are applied per kg of the patient's body weight.

CaV2.2 channels are believed to be involved in a variety of diseases or disorders in mammals such as humans. These include pain (e.g.; acute pain, chronic pain, visceral pain, headache pain, inflammatory pain, mixed pain), stroke (the neuronal damage resulting from head trauma), epilepsy, mood disorders, schizophrenia, neurodegenerative disorders.

Another embodiment of the present invention is at least one compound according the present invention for use in the treatment and/or prophylaxis of one or more disorders selected from the group consisting of pain, preferably pain selected from the group consisting of acute pain, chronic pain, visceral pain, headache pain, inflammatory pain and mixed pain; stroke (the neuronal damage resulting from head trauma); mood disorders; epilepsy; schizophrenia, and neurodegenerative disorders.

Another embodiment of the present invention is at least one compound according to the present invention for use in the treatment and/or prophylaxis of pain, in particular acute pain and/or chronic pain and/or visceral pain and/or headache pain and/or inflammatory pain and/or mixed pain. Acute pain according to the invention might include nociceptive pain and post-operative or surgical pain. Chronic pain according to the invention might include peripheral neuropathic pain such as post-herpetic neuralgia, traumatic nerve injury, nerve compression or entrapment, small fibre neuropathy, diabetic neuropathy, neuropathic cancer pain, failed back surgery Syndrome, trigeminal neuralgia, phantom limb pain; neuroma pain, complex regional pain syndrome, chronic arthritic pain and related neuralgias, and pain associated with cancer, chemotherapy, HIV and HIV treatment-induced neuropathy; central neuropathic pain such as multiple sclerosis related pain, Parkinson disease related pain, post-stroke pain, post-traumatic spinal cord injury pain, and pain in dementia; musculoskeletal pain such as osteoarthritic pain and fibromyalgia syndrome. In treating osteoarthritic pain, joint mobility will also improve as the underlying chronic pain is reduced. Thus, at least one compound for treatment of osteoarthritic pain inherently will also improve joint mobility in patients suffering from osteoarthritis. Visceral pain according to the invention might include interstitial cystitis, irritable bowel syndrome, Crohn's disease and chronic pelvic pain syndrome. Inflammatory pain according to the invention might include rheumatoid arthritis and endometriosis. Headachepain according to the invention might include migraine, cluster headache, tension headache syndrome, facial pain and headache caused by other diseases. Mixed pain according to the invention might include lower back pain, neck and shoulder pain, burning mouth syndrome and complex regional pain syndrome.

In another embodiment of the invention, at least one compound according to the present invention is particularly suitable for use in the treatment and/or prophylaxis of mood disorders. Mood disorders according to the invention might include anxiety disorder, social anxiety disorder, panic disorder, specific phobias, for example, specific animal phobias, social phobias, obsessive-compulsive disorder, agoraphobia, post-traumatic stress syndrome, addiction (including dependence, withdrawal and/or relapse of medication, including opioids, but also drugs such as cocaine, opioids, alcohol and nicotine), generalised anxiety disorders, single episodic or recurrent major depressive disorders and dysthymic disorders, or bipolar disorders, for example, bipolar I disorder, bipolar II disorder and cyclothymic disorder.

In another embodiment of the invention, at least one compound according to the present invention is particularly suitable for use in the treatment and/or prophylaxis of epilepsy. Epilepsy according to the invention might include partial seizures such as temporal lobe epilepsy, absence seizures generalized seizures, and tonic/clonic seizures.

In yet another embodiment of the invention, at least one compound according to the present invention is particularly suitable for use in the treatment and/or prophylaxis of neurodegenerative disorders. Neurodegenerative disorders according to the invention might include Parkinson's disease, Alzheimer's disease, multiple sclerosis, neuropathies, Huntington's disease, presbycusis and amyotrophic lateral sclerosis (ALS).

Particularly preferably, at least one compound according to the present invention is suitable for use in the treatment and/or prophylaxis of one or more disorders and/or diseases selected from the group consisting of pain, preferably of pain selected from the group consisting of acute pain, chronic pain, visceral pain, headache pain, inflammatory pain and mixed pain; migraine; depression; neurodegenerative diseases, preferably selected from the group consisting of multiple sclerosis, Alzheimer's disease, Parkinson's disease and Huntington's disease; cognitive dysfunctions, preferably cognitive deficiency states, particularly preferably memory disorders; medication dependency; misuse of medication; withdrawal symptoms in medication dependency; development of tolerance to medication, preferably development of tolerance to natural or synthetic opioids; drug dependency; misuse of drugs; withdrawal symptoms in drug dependency; alcohol dependency; misuse of alcohol and withdrawal symptoms in alcohol dependency.

Another embodiment of the present invention therefore relates to use of at least one compound according to the present invention for the preparation of a pharmaceutical composition for the treatment and/or prophylaxis of one or more disorders or diseases, particularly selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders.

Another aspect of the present invention is a method of treatment and/or prophylaxis of disorders and/or diseases in a mammal, preferably of disorders and/or diseases selected from the group consisting of pain, preferably pain selected from the group consisting of acute pain, chronic pain, visceral pain, headache pain, inflammatory pain and mixed pain; stroke; mood disorders; epilepsy; schizophrenia, and neurodegenerative disorders, which comprises administering an effective amount of at least one compound according to the present invention to the mammal.

All preferred embodiments of the first aspect of the invention are preferred vice versa for the other aspects and embodiments.

The effectiveness against pain can be shown, for example, in the Bennett or Chung model (Bennett, G. J. and Xie, Y. K., A peripheral mononeuropathy in rat that produces disorders of pain sensation like those seen in man, Pain 1988, 33(1), 87-107; Kim, S. H. and Chung, J. M., An experimental model for peripheral neuropathy produced by segmental spinal nerve ligation in the rat, Pain 1992, 50(3), 355-363), by tail flick experiments (e.g. according to D'Amour and Smith (J. Pharm. Exp. Ther. 72, 74-79 (1941)) or by the formalin test (e.g. according to D. Dubuisson et al., Pain 1977, 4, 161-174).

EXAMPLES

The compounds according to the invention can be prepared in the manner described below. The following examples further illustrate the invention but are not to be construed as limiting its scope.

All starting materials which are not explicitly described were either commercially available (the details of suppliers such as for example Acros, Avocado, Aldrich, Apollo, Bachem, Fluka, FluoroChem, Lancaster, Manchester Organics, MatrixScientific, Maybridge, Merck, Rovathin, Sigma, TCI, Oakwood, etc. can be found in the Symyx® Available Chemicals Database of MDL, San Ramon, US or the SciFinder® Database of the ACS, Washington D.C., US, respectively, for example) or the synthesis thereof has already been described precisely in the specialist literature (experimental guidelines can be found in the Reaxys® Database of Elsevier, Amsterdam, NL or the SciFinder® Database of the ACS, Washington D.C., US, respectively, for example) or can be prepared using the conventional methods known to the person skilled in the art.

The reactions were, if necessary, carried out under an inert atmosphere (mostly $N_2$). The number of equivalents of reagents and the amounts of solvents employed as well as the reaction temperatures and times can vary slightly between different reactions carried out by analogous methods. The work-up and purification methods were adapted according to the characteristic properties of each compound and can vary slightly for analogous methods. The yields of the compounds prepared are not optimized.

All the intermediate products and exemplary compounds were analytically characterized by means of $^1$H-NMR spectroscopy. In addition, mass spectrometry tests (MS, m/z for [M+H]$^+$) were carried out for all the exemplary compounds and selected intermediate products.

The indication "equivalents" ("eq." or "eq" or "equiv.") means molar equivalents, "RT" or "rt" means room temperature T (23±7° C.), "M" are indications of concentration in mol/l, "aq." means aq., "sat." means sat., "sol." means solution, "conc." means concentrated and "anhydr." means anhydr. The mixing ratios of solvents are usually stated in the volume/volume ratio.

FURTHER ABBREVIATIONS

DCM=dichloromethane; DAST=diethylamino sulfur trifluoride; dba=dibenzylideneacetone; DIPEA=N,N-diisopropylethylamine; DMF=N,N-dimethylformamide; EtOAc=ethyl acetate; EtOH=ethanol; h=hour(s); iPrOH=iso-propanol; KOtBu=potassium tert-butoxide; LDA=Lithiumdiisopropylamid; m-CPBA=3-Chloroperoxybenzoic acid; min=minute(s); MeOH=methanol; MS=methanesulfonyl; MOM=methoxymethyl acetal; MsOH=methanesulfonic acid; NMP=N-methyl-2-pyrrolidone; NOE=Nuclear Overhauser Effect; NOESY=Nuclear Overhauser effect spectroscopy; PdCl$_2$(dppf)$_2$=[1,1'-Bis(diphenylphosphino)-ferrocene]dichloropalladium(II); PE=petroleum ether; PMB=para-methoxybenzyl; SEM=[2-(trimethylsilyl)ethoxy]methyl acetal; RM=reaction mixture; TBAF=tetrabutylammonium fluorid; TEA=triethylamine; TFA=trifluoroacetic acid; THF=tetrahydrofuran; Xantphos=4,5-bis(diphenylphosphino)-9,9-dimethylxanthene.

Instruments:

Analytical SFC were performed on Thar SFC analytical, or HPLC was performed on a Waters 2695 separation module Detector 2996 & Agilent 1200 series with G 1315B detector. Preparative SFC were performed THAR-SFC 80 or 200, or a Waters SFC Prep 100 q. $^1$H-NMR-spectra (including NOESYs) were recorded on an Agilent 300 MHz or 400 MHz, or a Bruker 400 MHz or 500 MHz spectrometer.

LCMS analytics were carried out on the following instruments:

1) Instrument-1 Agilent-1290 Infinity 6150 Quadra pole 1 cms Source: ESI (Agilent jet spray source)

2) Instrument-2 Agilent-1200 series 6130 Quadra pole 1 cms Source: Multi mode (ESI+APCI)

Cis/Trans Assignment

The cis racemic [cis-rac] and trans racemic [trans-rac] compounds were mostly separated after the methylation step using column chromatography or prep-HPLC. The assignment of cis racemic [cis-rac] versus trans racemic [trans-rac] was carried out by NOE studies. In case of reactive cis stereochemistry NOE was observed between OCH and SCCH$_3$ protons. For the corresponding trans isomers no NOE was observed between OCH and SCCH$_3$ protons. Formation of the cis racemic [cis-rac] isomer is generally favoured over formation of the trans racemic [trans-rac] isomer.

Regiochemistry Assignment

The regiochemistry of N-substituted pyrazole intermediates was assigned by NOE studies.

Synthesis of Example Compounds

General Reaction Scheme for compounds with R$^4$ = —SO$_2$—R$^5$:

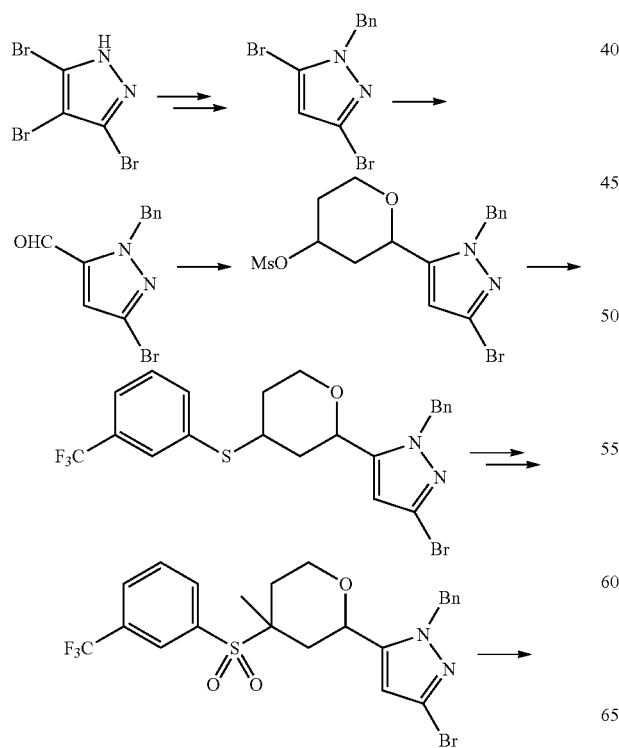

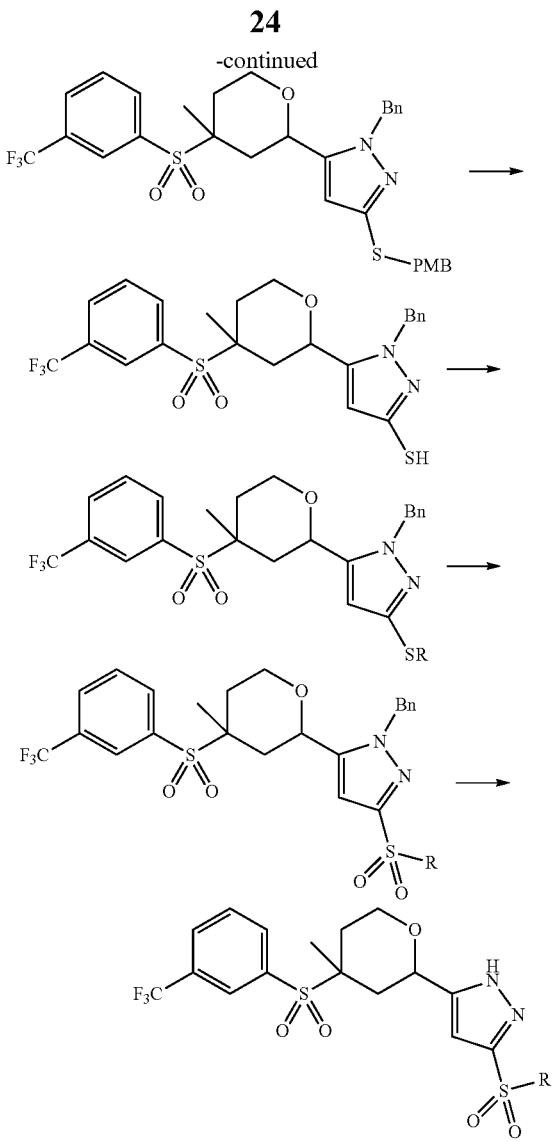

3-(Difluoro-methylsulfonyl)-5-[4-methyl-4-[[3-(trifluoromethyl)phenyl]sulfonyl]-tetrahydro-pyran-2-yl]-1H-pyrazole (Example 1)

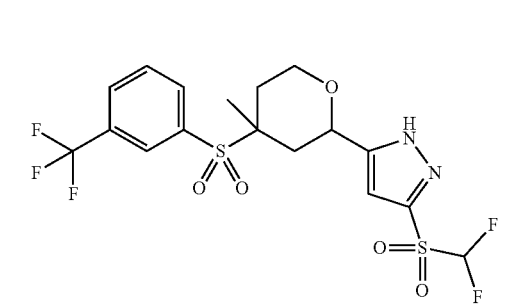 [SMILES: CC1(S(=O)(=O)c2cccc(C(F)(F)F)c2)CCOC(c2cc(S(=O)(=O)C(F)F)n[nH]2)C1]

Step 1: 3,5-Dibromo-1H-pyrazole

To a solution of 3,4,5-tribromo-1H-pyrazole (25 g, 81.96 mmol, 1.0 eq) in THF (300 ml), was added n-BuLi (2.5 M in hexanes, 65.6 ml, 164 mmol, 2.0 eq) over 30 min at −78° C. and the RM was stirred at this temperature for 30 min.

The RM was quenched by the dropwise addition of MeOH-THF (2:3; 125 ml) at −78° C., and stirred for an additional 1.5 h while gradually allowing it to warm to RT. The solvent was removed under reduced pressure. The residue was diluted with diethyl ether (600 ml), washed with aq. HCl (0.5 N, 60 ml) and brine (75 ml), dried ($Na_2SO_4$), filtered and concentrated under reduced pressure to afford the title product (16 g, 86%)

Step 2: 1-Benzyl-3,5-dibromo-1H-pyrazole

A solution of 3,5-dibromo-1H-pyrazole (16 g, 111.70 mmol, 1.0 eq) in DMF (100 ml) was added 60% NaH (7.1 g, 176.99 mmol, 2.5 eq) and benzyl bromide at 0° C. The mixture was then allowed to warm to RT and stirred for 12 h. The RM was quenched with sat $NH_4Cl$ solution at 0° C. and extracted with EtOAc (2×300 ml). The combined organic layers were washed with water (2×200 ml) and brine (200 ml), dried over ($Na_2SO_4$), filtered and concentrated under reduced pressure to afford the title product (14 g).

Step 3: 1-Benzyl-3-bromo-1H-pyrazole-5-carbaldehyde

A stirred solution of 1-benzyl-3,5-dibromo-1H-pyrazole (20 g, 63.69 mmol, 1.0 eq) in THF (300 ml) was treated with iPrMgCl (1.0 M, 76.43 ml, 76.43 mmol, 1.2 eq) at −78° C. The RM was stirred for 30 min, then DMF (35 ml, 445.83 mmol, 7.0 eq) was added and the RM was gradually allowed to RT and stir for 4.5 h. The RM was quenched with aq. $NH_4Cl$ and extracted with EtOAc (2×400 ml). The combined organic layers were washed with water (300 ml) and brine (150 ml), dried ($Na_2SO_4$), filtered and concentrated under reduced pressure to afford the title compound (16 g, 95%).

Step 4: 2-(1-Benzyl-3-bromo-1H-pyrazol-5-yl)tetrahydro-2H-pyran-4-yl methanesulfonate A stirred solution of 1-benzyl-3-bromo-1H-pyrazole-5-carbaldehyde (10 g, 37.73 mmol, 1.0 eq) in DCM (100 ml) was treated with MsOH (24 ml, 377.3 mmol, 10.0 eq) at 0° C., stirred for 10 min and but-3-en-1-ol (2.9 ml, 37.73 mmol, 1.0 eq) was added. The RM was allowed warm to RT and stir for 16 h. The RM was quenched with sat. aq. $Na_2CO_3$ and extracted with DCM (2×200 ml). The combined organic layers were washed with water (150 ml) and brine (150 ml), dried ($Na_2SO_4$), filtered and concentrated under reduced pressure to afford the title compound (8 g, 36%).

Step 5: 1-Benzyl-3-bromo-5-(4-((3-(trifluoromethyl)phenyl)thio)tetrahydro-2H-pyran-2-yl)-1H-pyrazole A stirred solution of 3-(trifluoromethyl)benzenethiol (12 g, 57.94 mmol, 1.2 eq) in DMF (200 ml) was treated with $K_2CO_3$ (13 g, 96.56 mmol, 2.0 eq), stirred for 20 min at RT before a solution of 2-(1-benzyl-3-bromo-1H-pyrazol-5-yl)tetrahydro-2H-pyran-4-yl methanesulfonate (20 g, 48.28 mmol, 1.0 eq) in DMF (50 ml) was added. The resulting RM was heated to 50° C., stirred for 6 h, then brought to RT and stirred for additional 10 h. The RM was concentrated under reduced pressure and the residue was diluted with water (500 ml) and extracted with EtOAc (2×400 ml). The combined organic layers were washed with water (2×300 ml) and brine (200 ml), dried ($Na_2SO_4$), filtered and concentrated under reduced pressure. The crude compound upon purification by flash chromatography (silica-gel; 20% EtOAc in PE) afforded the title product (20 g).

Step 6: 1-Benzyl-3-bromo-5-(4-((3-(trifluoromethyl)phenyl)sulfonyl)tetrahydro-2H-pyran-2-yl)-1H-pyrazole Oxone (7.3 g, 302.2 mmol, 2.5 eq) in water (15 ml) was added to a solution of 1-benzyl-3-bromo-5-(4-((3-(trifluoromethyl)phenyl)thio)tetrahydro-2H-pyran-2-yl)-1H-pyrazole (4.8 g, 9.65 mmol, 1.0 eq) in MeOH (48 ml) at RT and stirred for 18 h. After completion of the reaction, MeOH was distilled off under reduced pressure. The residue was made alkaline by addition of sat. aq. $NaHCO_3$ (100 ml) and extracted with EtOAc (3×150 ml). The organic layer was washed with water (150 ml) and brine (100 ml), dried over $Na_2SO_4$, filtered and concentrated under reduced pressure. The crude residue upon purification by flash chromatography (silica-gel; 18% EtOAc in PE) afforded the title product (3.2 g, 63%).

Step 7: 1-Benzyl-3-bromo-5-(4-methyl-4-((3-(trifluoromethyl)phenyl)sulfonyl)tetrahydro-2H-pyran-2-yl)-1H-pyrazole A solution of 1-benzyl-3-bromo-5-(4-((3-(trifluoromethyl)phenyl)sulfonyl)tetrahydro-2H-pyran-2-yl)-1H-pyrazole (10 g, 18.903 mmol, 1.0 eq) in THF (100 ml) was cooled to −78° C. and KOtBu (1M in THF, 26.9 ml, 26.9 mmol, 2.0 eq) was added dropwise. The mixture was stirred for 30 min, and then MeI (2.0 ml, 33.7 mmol, 2.5 eq) was added. The resulting RM was allowed to warm to RT and stirred for 18 h. The mixture was quenched with sat. aq. $NH_4Cl$ (200 ml) and water (200 ml), and extracted with EtOAc (3×200 ml). The combined organic layers were washed with water (2×200 ml) and brine (200 ml), dried ($Na_2SO_4$), filtered and concentrated under reduced pressure. The residue upon purification by flash chromatography (silica gel; 25-30% EtOAc in PE) afforded the title cis and trans racemates.

[cis-rac] 1-Benzyl-3-bromo-5-(4-methyl-4-((3-(trifluoromethyl)phenyl)sulfonyl)tetrahydro-2H-pyran-2-yl)-1H-pyrazole: 6 g (58%); TLC system: EtOAc-PE; 4:6; Rf: 0.24

[trans-rac] 1-Benzyl-3-bromo-5-(4-methyl-4-((3-(trifluoromethyl)phenyl)sulfonyl)tetrahydro-2H-pyran-2-yl)-1H-pyrazole: 1.32 g; TLC system: EtOAc-PE; 4:6; Rf: 0.32.

Step 8: [cis-rac]1-Benzyl-3-((4-methoxybenzyl)thio)-5-(4-methyl-4-((3-(trifluoromethyl)phenyl)sulfonyl)tetrahydro-2H-pyran-2-yl)-1H-pyrazole To a stirred solution of [cis-rac] 1-benzyl-3-bromo-5-(4-methyl-4-((3-(trifluoromethyl)phenyl)sulfonyl)tetrahydro-2H-pyran-2-yl)-1H-pyrazole (16 g, 29.46 mmol, 1.0 eq) in 1,4-dioxane (300 ml) was added DIPEA (37 ml, 206.26 mml, 7.0 eq), PMB-SH (6.2 ml, 44.19 mmol, 1.5 eq) and the mixture was degassed for 20 min with Ar. Then $Pd_2(dba)_3$ (1.9 g, 2.062 mmol, 0.07 eq) was added, followed by Xantphos (1.2 g, 2.062 mmol, 0.07 eq) and it was degassed again for 20 min. The resulting RM was heated to 100° C. and stirred for 18 h. The residue upon purification by flash chromatography (silica gel, 25% EtOAc in PE) afforded the title compound (12 g, 66%).

Step 9: [cis-rac]1-Benzyl-5-(4-methyl-4-((3-(trifluoromethyl)phenyl)sulfonyl)tetrahydro-2H-pyran-2-yl)-1H-pyrazole-3-thiol A stirred solution of [cis-rac] 1-benzyl-3-((4-methoxybenzyl)thio)-5-(4-methyl-4-((3-(trifluoromethyl)phenyl)sulfonyl)tetrahydro-2H-pyran-2-yl)-1H-pyrazole (1.3 g, 2.106 mmol, 1.0 eq) in TFA (3 ml) was added anisole (1.3 ml) at RT. The resulting RM was heated to 100° C. and stirred for 18 h. The reaction was monitored by LCMS, and the solvent was distilled off by downward distillation to afford the title compound (1.3 g).

Step 10: [cis-rac]1-Benzyl-3-((difluoromethyl)thio)-5-(4-methyl-4-((3-(trifluoromethyl)phenyl)sulfonyl) tetrahydro-2H-pyran-2-yl)-1H-pyrazole A stirred solution of [cis-rac] 1-benzyl-5-(4-methyl-4-((3-(trifluoromethyl)phenyl)sulfonyl)tetrahydro-2H-pyran-2-yl)-1H-pyrazole-3-thiol (1.3 g, 2.620 mmol, 1.0 eq), in DMF (15 ml) was cooled to 0° C. and $K_2CO_3$ (1.5 g, pH=9) was added. The mixture was then purged with Freon gas at 100° C. for 18 h. The RM was diluted with water (100 ml) and extracted with EtOAc (2×100 ml). The combined organic layers were washed with water (2×50 ml) and brine (50 ml), dried over anhydrous $Na_2SO_4$, filtered and concentrated under reduced pressure. The residue upon purification by flash chromatography (silica gel, 15% EtOAc in PE), afforded the title product (600 mg, 52% over 2 steps).

Step 11: [cis-rac] 1-Benzyl-3-((difluoromethyl)sulfonyl)-5-(4-methyl-4-((3-(trifluoromethyl)-phenyl)sulfonyl)tetrahydro-2H-pyran-2-yl)-1H-pyrazole To a stirred solution of [cis-rac] 1-benzyl-3-((difluoromethyl)thio)-5-(4-methyl-4-((3-(trifluoromethyl)phenyl)sulfonyl)tetrahydro-2H-pyran-2-yl)-1H-pyrazole (1 g, 1.828 mmol, 1.0 eq), in $CHCl_3$ (30 ml), was added m-CPBA (955 mg, 5.484 mmol, 3 eq) at 0° C. and the mixture was stirred for 48 h at RT. The RM was quenched with sat. aq. $NaHCO_3$ (40 ml), and extracted with DCM (2×100 ml). The combined organic layers were washed with water (30 ml) and brine (30 ml), dried over anhydrous $Na_2SO_4$, filtered and concentrated under reduced pressure. The residue upon purification by flash chromatography (basic alumina, 30% EtOAc in PE) afforded the title compound (740 mg, 70%).

Step 12: [cis-rac] 3-(Difluoro-methylsulfonyl)-5-[4-methyl-4-[[3-(trifluoromethyl)phenyl]sulfonyl]-tetrahydro-pyran-2-yl]-1H-pyrazole (Example 1)

A mixture of 5% Palladium on carbon (1.6 g) and [cis-rac] 1-benzyl-3-((difluoromethyl)sulfonyl)-5-(4-methyl-4-((3-(trifluoromethyl)phenyl)sulfonyl)tetrahydro-2H-pyran-2-yl)-1H-pyrazole (0.8 g, 1.384 mmol, 1.0 eq), in TFA (30 ml) was hydrogenated at 80° C. and 100 psi for 18 h. After completion of the reaction, the RM was filtered over a bed of Celite with EtOAc (150 ml), quenched with sat. aq. $NaHCO_3$ (pH ~10) and extracted with EtOAc (30 ml). The combined organic layers were washed with water (30 ml) and brine (30 ml), dried over anhydrous $Na_2SO_4$, filtered and concentrated under reduced pressure. The residue upon purification by flash chromatography (silica gel, 40% EtOAc in PE), afforded the title product (700 mg, 64%). TLC system: EtOAc-PE; 1:1; Rf: 0.17. NOE: On irradiating OCH proton NOE was observed with $SCCH_3$.

[Cis-rac] 3-(difluoro-methylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give 160 mg of [cis-EN1] Example 1 and 110 mg of [cis-EN2] Example 1.

[cis-EN1] Example 1—analytical SFC: Chiralpak AD-H (250×4.6 mm 5 μm) 30° C., 3 g/min, 100 bar, 30% MeOH, Ret. Time 3.56 min; m/z=489.0 [M+H]$^+$

[cis-EN2] Example 1—analytical SFC: Chiralpak AD-H (250×4.6 mm 5 μm), 26° C., 3 g/min, 100 bar, 30% MeOH, Ret. Time 6.96 min; m/z=488.9 [M+H]$^+$

[trans-rac] 3-(Difluoro-methylsulfonyl)-5-[4-methyl-4-[[3-(trifluoromethyl)phenyl]sulfonyl]-tetrahydro-pyran-2-yl]-1H-pyrazole (Example 1)

The corresponding [trans rac] isomer was prepared in analogy to steps 8 to 10 starting from [trans rac] 1-benzyl-3-bromo-5-(4-methyl-4-((3-(trifluoromethyl)phenyl)sulfonyl)tetrahydro-2H-pyran-2-yl)-1H-pyrazole (1.3 g, see step 7), followed by step 11 & 12 as described below.

Step 11: [trans-rac] 1-Benzyl-3-((difluoromethyl)sulfonyl)-5-(4-methyl-4-((3-(trifluoromethyl)-phenyl) sulfonyl)tetrahydro-2H-pyran-2-yl)-1H-pyrazole Oxone (1.12 g, 3.65 mmol, 10 eq) in water (5 ml) was added to a solution of [trans-rac] 1-benzyl-3-((difluoromethyl)thio)-5-(4-methyl-4-((3-(trifluoromethyl)phenyl)sulfonyl)tetrahydro-2H-pyran-2-yl)-1H-pyrazole (200 mg, 0.365 mmol, 1.0 eq) in MeOH (50 ml) and acetic acid (3 ml) at RT and the mixture was stirred for 18 h. After completion of the reaction, MeOH was distilled off under reduced pressure, the residue made alkaline by addition of sat. aq. $NaHCO_3$ (10 ml) and extracted with DCM (3×30 ml). The organic layer was washed with water (10 ml) and brine (10 ml), dried over $Na_2SO_4$, filtered and concentrated under reduced pressure. The crude residue upon purification by flash chromatography (silica-gel; 26% EtOAc in PE) afforded the title compound (150 mg, 71%).

Step 12: [trans-rac] 3-(Difluoro-methylsulfonyl)-5-[4-methyl-4-[[3-(trifluoromethyl)phenyl]sulfonyl]-tetrahydro-pyran-2-yl]-1H-pyrazole (Example 1)

A mixture of 5% Palladium on carbon (300 mg) [trans-rac] 1-benzyl-3-((difluoromethyl)sulfonyl)-5-(4-methyl-4-((3-(trifluoromethyl)phenyl)sulfonyl)tetrahydro-2H-pyran-2-yl)-1H-pyrazole (0.15 g, 0.2595 mmol, 1.0 eq) in TFA (10 ml) was hydrogenated at 80° C. and 100 psi for 18 h. After completion of the reaction, the RM was filtered over Celite with EtOAc (100 ml) then quenched with sat. aq. $NaHCO_3$ (pH~10) and extracted with EtOAc (20 ml). The combined organic layers were washed with water (20 ml) and brine (20 ml), dried over anhydrous $Na_2SO_4$, filtered and concentrated under reduced pressure. The residue upon purification by flash chromatography (silica gel, 40% EtOAc in PE), afforded the title product (40 mg, 32%).

[trans-rac] Example 1—m/z=487.0 [M−H]$^-$; TLC system: EtOAc-PE; 3:7; Rf: 0.15. NOE: On irradiating OCH proton no NOE was observed with $SCCH_3$.

Alternative Preparation of [cis-rac] 1-Benzyl-3-((difluoromethyl)thio)-5-(4-methyl-4-((3-(trifluoromethyl)-phenyl)sulfonyl)tetrahydro-2H-pyran-2-yl)-1H-pyrazole (Step 10)

Alternatively [cis-rac] 1-Benzyl-3-((difluoromethyl)thio)-5-(4-methyl-4-((3-(trifluoromethyl)phenyl)sulfonyl) tetrahydro-2H-pyran-2-yl)-1H-pyrazole (step 10) can be prepared as follows:

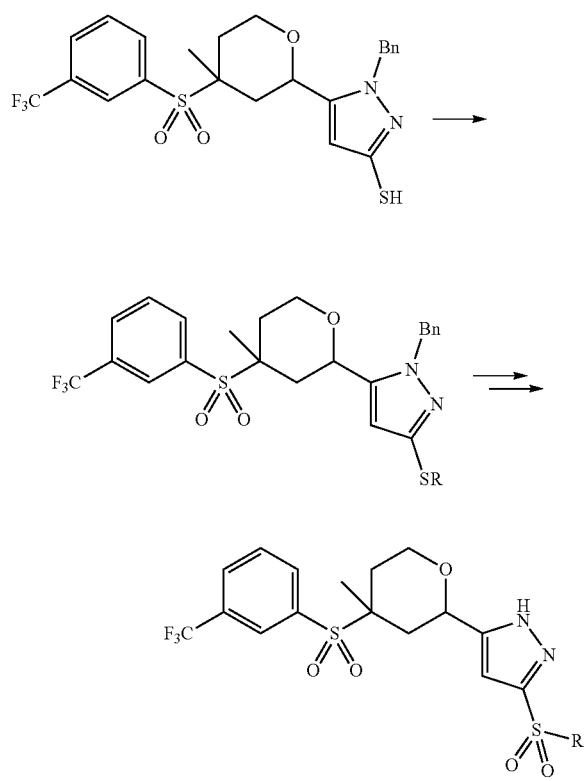

Step 10: [cis-rac] 1-Benzyl-3-((difluoromethyl) thio)-5-(4-methyl-4-((3-(trifluoromethyl)phenyl) sulfonyl)tetrahydro-2H-pyran-2-yl)-1H-pyrazole

[Cis-rac] 1-benzyl-5-(4-methyl-4-((3-(trifluoromethyl) phenyl)sulfonyl)tetrahydro-2H-pyran-2-yl)-1H-pyrazole-3-thiol (2 g, 3.24 mmol) was dissolved in a nitrogen flushed and degassed mixture of anisole (14.92 mmol, 1.630 ml), TfOH (0.6 ml, 6.76 mmol) and TFA (7.5 ml, 98 mmol). The solution was stirred at RT for 2 h. Then the reaction was alkalized with a degassed solution of K2CO3 (16.14 g, 117 mmol) in H2O (15 ml), followed by the addition of a degassed solution of chlorodifluoroacetic acid sodium salt (1.978 g, 12.97 mmol) in DMF (30 ml). The resulting solution was stirred at 150° C. (bath) for 1.5 h and the RM was cooled down to RT. The mixture was carefully diluted with sat. aq. NH4Cl (100 ml), brine (100 ml) and DCM (100 ml) respectively. The layers were separated and the aqueous layer was extracted with DCM (3×50 ml). The combined organic layers were washed with brine, dried over Na2SO4 (s) and concentrated in vacuo to obtain 2.6 g of crude product. Purification by flash column chromatography (80 g silica, EtOAc/heptane, 1:9→2:3) gave the title compound (1.4 g 2.56 mmol, 79%) LCMS: calculated for [M+H]+=547.58. found 547.1.

Steps 11 and 12 were carried out in analogy to the procedures described above to give [cis-rac] 3-(difluoro-methylsulfonyl)-5-[4-methyl-4-[[3-(trifluoromethyl)phenyl] sulfonyl]-tetrahydro-pyran-2-yl]-1H-pyrazole (Example 1) (930 mg, 1.847 mmol, 71%).

[Cis-rac] 3-(difluoro-methylsulfonyl)-5-[4-methyl-4-[[3-(trifluoromethyl)phenyl]sulfonyl]-tetrahydro-pyran-2-yl]-1H-pyrazole was subjected to chiral prep-SFC purification (Column: Phenomenex Amylose-1 (250×21.2 mm, 5 μm), Flow: 100 ml/min; Column temp: 40° C.; BPR: 120 bar, Eluent A: CO2, Eluent B: Isopropanol) to give 385 mg of [cis-EN1] Example 1 and 382 mg of [cis-EN2] Example 1.

[cis-EN1] Example 1—LCMS: calculated for [M+H]+=489.44. found 489.1. $^1$H NMR (400 MHz, CDCl$_3$) δ 11.23 (s, 1H), 8.14 (s, 1H), 8.08 (d, J=7.9 Hz, 1H), 7.99 (d, J=7.8 Hz, 1H), 7.79 (t, J=7.8 Hz, 1H), 6.76 (s, 1H), 6.28 (t, J=53.3 Hz, 1H), 4.72 (dd, J=11.7, 2.2 Hz, 1H), 4.20 (dd, J=12.1, 4.2 Hz, 1H), 3.74 (td, J=12.4, 2.1 Hz, 1H), 2.37 (td, J=13.0, 5.4 Hz, 1H), 2.25 (t, J=12.4 Hz, 1H), 1.95 (dt, J=13.0, 2.2 Hz, 1H), 1.60-1.56 (m, 1H), 1.55 (s, 3H).

[cis-EN2] Example 1—LCMS: calculated for [M+H]+=489.44. found 489.1. $^1$H NMR (400 MHz, CDCl$_3$) δ 11.16 (s, 1H), 8.14 (s, 1H), 8.08 (d, J=7.9 Hz, 1H), 7.99 (d, J=7.8 Hz, 1H), 7.79 (t, J=7.8 Hz, 1H), 6.76 (s, 1H), 6.28 (t, J=53.3 Hz, 1H), 4.72 (dd, J=11.7, 2.2 Hz, 1H), 4.30-4.12 (m, 1H), 3.74 (td, J=12.4, 2.1 Hz, 1H), 2.37 (td, J=12.8, 5.3 Hz, 1H), 2.25 (t, J=12.4 Hz, 1H), 1.95 (dt, J=13.0, 2.3 Hz, 1H), 1.60-1.56 (m, 1H), 1.56 (s, 3H).

The following compounds can be obtained in analogy to above-described procedures:

3-(2,2-Difluoro-ethylsulfonyl)-5-[4-methyl-4-[[3-(trifluoromethyl)phenyl]sulfonyl]-tetrahydro-pyran-2-yl]-1H-pyrazole (Example 3)

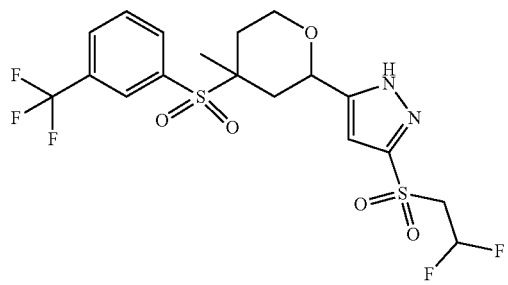 [SMILES: CC1(S(=O)(=O)c2cccc(C(F)(F)F)c2)CCOC(c2cc(S(=O)(=O)CC(F)F)n[nH]2)C1]

Synthesis of Example 3 was carried out as follows:

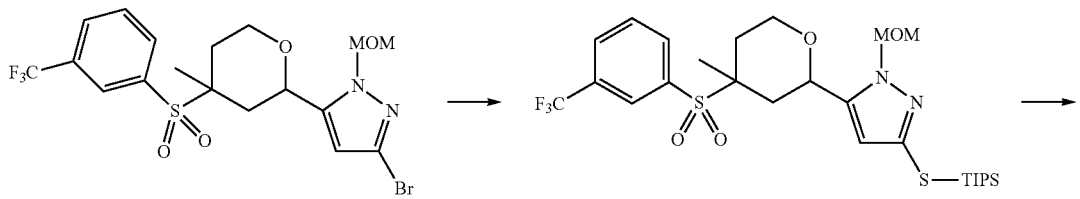

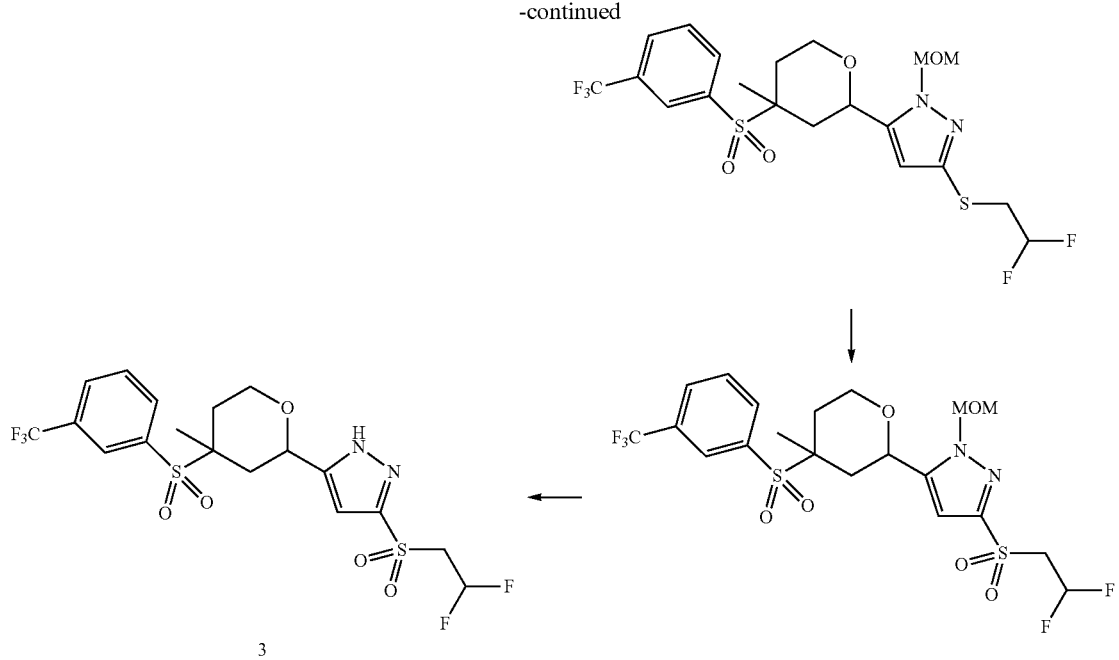

Step 1: [cis-rac] 1-(Methoxymethyl)-5-(4-methyl-4-((3-(trifluoromethyl)phenyl)sulfonyl)tetrahydro-2H-pyran-2-yl)-3-((triisopropylsilyl)thio)-1H-pyrazole A solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (1.0 g, 2.016 mmol) and DIPEA (0.72 ml, 4.02 mmol) in toluene (20 ml) was degassed for 10 min. To the RM were added Xantphos (0.08 g, 0.14 mmol), followed by $Pd_2(dba)_3$ (0.12 g, 0.14 mmol) and the mixture was degassed again for 10 min. Triisopropylsilanethiol (1.0 ml, 4.02 mmol) was added to the RM and it was further degassed for 5 min. The RM was heated at 120° C. for 12 h under argon. It was then filtered through a celite bed and the filtrate was concentrated under reduced pressure (bath temp 40° C.) to give the title compound (0.6 g).

Step 2: [cis-rac] 3-((2,2-Difluoroethyl)thio)-1-(methoxymethyl)-5-(4-methyl-4-((3-(trifluoromethyl)phenyl)sulfonyl)tetrahydro-2H-pyran-2-yl)-1H-pyrazole TBAF (1 M in THF) (1.70 ml, 1.65 mmol) was added to a solution of [cis-rac] 1-(methoxymethyl)-5-(4-methyl-4-((3-(trifluoromethyl)phenyl)sulfonyl)tetrahydro-2H-pyran-2-yl)-3-((triisopropylsilyl)thio)-1H-pyrazole (0.6 g, 0.99 mmol) in THF at 0° C. and the RM was stirred at 0° C. for 30 min. To the mixture was added potassium carbonate (0.40 mg, 2.97 mmol) and 1,1-difluoro-2-iodoethane (0.2 ml, 1.98 mmol) at 0° C. The RM was allowed to warm to RT and stirred for 16 h. The RM was quenched with water and the product was extracted with DCM (3×20 ml). The combined organic extracts were washed with water, followed by brine, dried over anhydrous $Na_2SO_4$, filtered and the solvent was evaporated in vacuo to give the crude product which was purified by flash column chromatography (silica gel 230-400 mesh, 0-35% EtOAc in PE) to give the title compound.

Step 3: [cis-rac] 3-((2,2-Difluoroethyl)sulfonyl)-1-(methoxymethyl)-5-(4-methyl-4-((3-(trifluoromethyl)phenyl)sulfonyl)tetrahydro-2H-pyran-2-yl)-1H-pyrazole A solution of oxone (0.95 g, 1.55 mmol) in water (12.5 ml) was added to a stirred solution of [cis-rac] 3-((2,2-difluoroethyl)thio)-1-(methoxymethyl)-5-(4-methyl-4-((3-(trifluoromethyl)phenyl)sulfonyl)tetrahydro-2H-pyran-2-yl)-1H-pyrazole (0.40 g, 0.77 mmol) in MeOH (18 ml) and the mixture was stirred for 16 h at RT. The RM was diluted with water (150 ml) and extracted with DCM (3×150 ml). The combined organic extracts were washed with brine (2×200 ml) and dried over anhydrous $Na_2SO_4$. The organic layer was filtered and the solvent was concentrated under reduced pressure to afford the crude product which was purified by column chromatography (silica gel 100-200 mesh, 0-50% EtOAc in PE) to give the title compound (0.35 g, 82%).

Step 4: [cis-rac] 3-(2,2-Difluoro-ethylsulfonyl)-5-[4-methyl-4-[[3-(trifluoromethyl)phenyl]sulfonyl]-tetrahydro-pyran-2-yl]-1H-pyrazole (Example 3)

4N HCl in dioxane (10.0 ml) was added to a solution of [cis-rac] 3-((2,2-difluoroethyl)sulfonyl)-1-(methoxymethyl)-5-(4-methyl-4-((3-(trifluoro methyl)phenyl)sulfonyl)tetrahydro-2H-pyran-2-yl)-1H-pyrazole (0.40 g, 0.73 mmol) in EtOH (5 ml) and the resulting RM was heated to 60° C. whilst stirring for 4 h. The RM was concentrated under reduced pressure and the residue was diluted with water. The resulting mixture was cooled to 0° C. and sat. aq. $NaHCO_3$ solution (100 ml) was added. The product was extracted with EtOAc (2×100 ml). The combined organic layers were washed with water (2×100 ml) and brine (100 ml), and dried over anhydrous $Na_2SO_4$. The organic layer was filtered and the solvent was concentrated under reduced pressure to afford the crude product which was purified by column chromatography (silica gel 100-200 mesh, 0-70% EtOAc in PE) to give the title compound (0.30 g, 93%). TLC system: EtOAc-PE; 3:7; Rf: 0.26).

[Cis-rac] 3-(2,2-difluoro-ethylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give 37 mg of [cis-EN1] Example 3 and 68 mg of [cis-EN2] Example 3.

[cis-EN1] Example 3—analytical SFC: Chiralpak IC (250×4.6 mm 5 µm) 29.9° C., 3 g/min, 100 bar, 20% MeOH, Ret. Time 3.00 min; m/z=503.0 [M+H]$^+$; $^1$H NMR (CDCl$_3$): 10.94 (br s, 1H), 8.13 (s, 1H), 8.07 (d, 1H), 7.98 (d, 1H), 7.78 (t, 1H), 6.64 (s, 1H), 6.40-6.10 (m, 1H), 4.70-4.68 (m, 1H), 4.21-4.17 (m, 1H), 3.86-3.70 (m, 3H), 2.39-2.31 (m, 1H), 2.25-2.17 (m, 1H), 1.93-1.90 (m, 1H), 1.61-1.55 (m, 4H).

[cis-EN2] Example 3—analytical SFC: Chiralpak IC (250×4.6 mm 5 µm), 30.1° C., 3 g/min, 100 bar, 20% MeOH, Ret. Time 4.07 min; m/z=503.0 [M+H]$^+$; $^1$H NMR (CDCl$_3$): 10.94 (br s, 1H), 8.13 (s, 1H), 8.07 (d, 1H), 7.98 (d, 1H), 7.78 (t, 1H), 6.64 (s, 1H), 6.40-6.10 (m, 1H), 4.71-4.68 (m, 1H), 4.21-4.17 (m, 1H), 3.86-3.70 (m, 3H), 2.39-2.31 (m, 1H), 2.25-2.17 (m, 1H), 1.93-1.90 (m, 1H), 1.62-1.55 (m, 4H).

5-[4-Methyl-4-[[3-(trifluoromethyl)phenyl]sulfonyl]-tetrahydro-pyran-2-yl]-3-(oxetan-3-ylsulfonyl)-1H-pyrazole (Example 4)

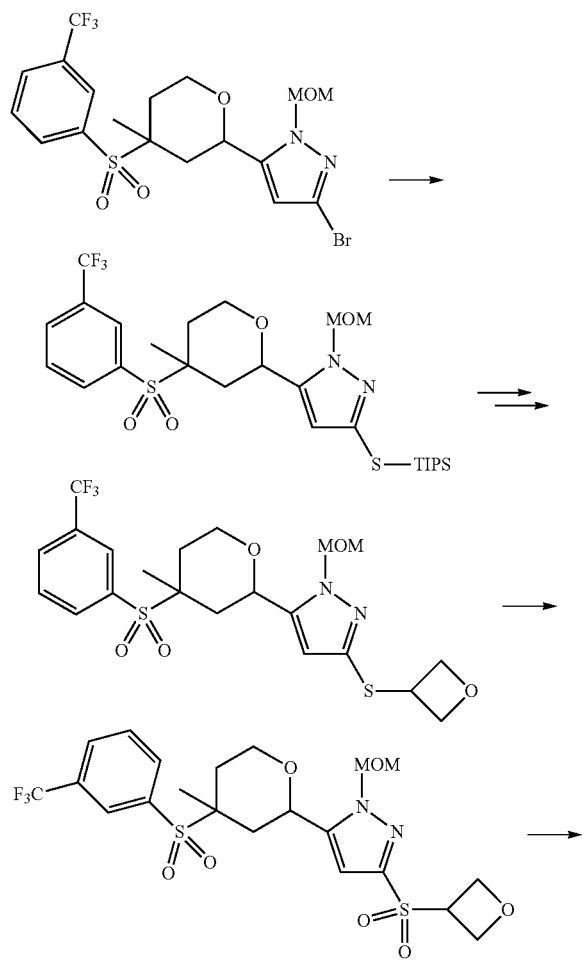

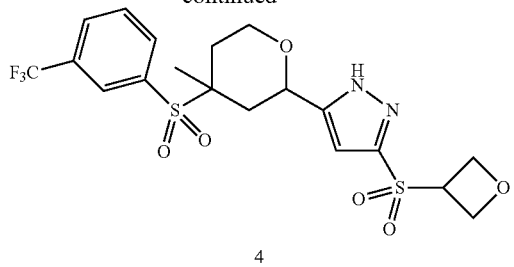

4

Step 1: 1-(methoxymethyl)-5-(4-methyl-4-(3-(trifluoromethyl)phenylsulfonyl)tetrahydro-2H-pyran-2-yl)-3-(triisopropylsilylthio)-1H-pyrazole A solution of 3-Bromo-1-(methoxymethyl)-5-(4-((3-(trifluoromethyl)phenyl)sulfonyl)tetrahydro-2H-pyran-2-yl-1H-pyrazole (1.0 g, 2.01 mmol) and DIPEA (0.73 mL, 4.03 mmol) in toluene (20 mL) was degassed for 10 min. To the reaction mixture were added Xantphos (174 mg, 0.30 mmol) followed by Pd$_2$(dba)$_3$ (91 mg, 0.10 mmol) and degassed again for 10 min. Triisopropylsilanethiol (767 mg, 4.03 mmol) was added to the reaction mixture and further degassed for 5 min. The resulting mixture was heated at 120° C. for 6 h under Ar. Reaction mixture was filtered through a neutral alumina bed and the filtrate was concentrated under reduced pressure (bath temp 35° C.) to get 1-(methoxymethyl)-5-(4-methyl-4-(3-(trifluoromethyl)phenyl)sulfonyl)tetrahydro-2H-pyran-2-yl-3-(triisopropylsilylthio)-1H-pyrazole (1.0 g, crude) as semi solid and used immediately for the next step.

Step 2&3: 1-(methoxymethyl)-5-(4-methyl-4-(3-(trifluoromethyl)phenylsulfonyl)tetrahydro-2H-pyran-2-yl)-3-(oxetan-3-ylthio)-1H-pyrazole TBAF (1M in THF) (3.30 mL, 3.30 mmol) was added to a solution of 1-(methoxymethyl)-5-(4-methyl-4-(3-(trifluoromethyl)phenyl)sulfonyl)tetrahydro-2H-pyran-2-yl-3-(triisopropylsilylthio)-1H-pyrazole (1.0 g, 1.65 mmol) in THF at 0° C. and stirred at 0° C. for 30 min to get the intermediate 1-(methoxymethyl)-5-(4-methyl-4-(3-(trifluoromethyl)phenylsulfonyl)tetrahydro-2H-pyran-2-yl)-3-thio-1H-pyrazole. The reaction mixture containing 1-(methoxymethyl)-5-(4-methyl-4-(3-(trifluoromethyl)phenylsulfonyl)tetrahydro-2H-pyran-2-yl)-3-thio-1H-pyrazole was added to a suspension of 3-iodooxetane (654 mg, 3.55 mmol) and K$_2$CO$_3$ (489 mg, 3.55 mmol) in THF at 0° C. The reaction mixture was allowed to come to rt and stirred for 16 h. The reaction mixture was quenched with water and the organic product was extracted with DCM (3×20 mL). The combined organic extracts were washed with water, followed by brine, dried over anhydrous Na$_2$SO$_4$, filtered and solvent was evaporated under vacuo to get crude, which was purified by flash column chromatography (silica gel 230-400 mesh, 0-75% EtOAc in PE as eluent) to get 1-(methoxymethyl)-5-(4-methyl-4-(3-(trifluoromethyl)phenyl sulfonyltetrahydro-2H-pyran-2-yl)-3-(oxetan-3-ylthio)-1H-pyrazole (250 mg, 24% over 3 steps) as off white solid.

Step 4: 1-(methoxymethyl)-5-(4-methyl-4-(3-(trifluoromethyl)-phenylsulfonyl)-tetrahydro-2H-pyran-2-yl)-3-(oxetan-3-ylsulfonyl)-1H-pyrazole A solution of oxone (606 mg, 0.98 mmol) in water (2 mL) was added to a stirred solution of 1-(methoxyrtmethyl)-5-

(4-methyl-4-(3-(trifluoromethyl)-phenyl)sulfonyl)tetrahydro-2H-pyran-2-yl)-3-(oxetan-3-ylthio)-1H-pyrazole (250 mg, 0.49 mmol) in MeOH (3 mL) and stirred at RT for 16 h. The reaction mixture was diluted with water (10 mL), the organic product was extracted with DCM (3×20 mL). The combined organic extracts were washed with brine (2×10 mL), dried over anhydrous Na$_2$SO$_4$. The organic layer was filtered and solvent was concentrated under reduced pressure to get 1-(methoxymethyl)-5-(4-methyl-4-(3-(trifluoromethyl)-phenylsulfonyl)-tetrahydro-2H-pyran-2-yl)-3-(oxetan-3-ylsulfonyl)-1H-pyrazole (220 mg, 83%) as white solid.

Step 5: 3-Bromo-5-(4-((3-(trifluoromethyl)phenyl) thio)tetrahydro-2H-pyran-2-yl)-1H-pyrazole and 3-Bromo-1-(methoxymethyl)-5-(4-((3-(trifluoromethyl)phenyl)thio)tetrahydro-2H-pyran-2-yl)-1H-pyrazole TFA (10 mL) was added to a solution of 1-(methoxymethyl)-5-(4-methyl-4-(3-(trifluoromethyl)-phenyl sulfonyl)-tetrahydro-2H-pyran-2-yl)-3-(oxetan-3-yl sulfonyl)-1H-pyrazole (220 mg, 0.408 mmol) and the resulting reaction mixture was heated to 60° C. under stirring condition for 8 h. The reaction mixture was concentrated under reduced pressure and the residue was diluted with water. The reaction mixture was cooled to 0° C., added sat. aq. NaHCO$_3$ solution (10 mL) and the organic product was extracted with EtOAc (2×25 mL). The combined organic layer was washed with water (2×10 mL), brine (10 mL), dried over anhydrous Na$_2$SO$_4$, The organic layer was filtered and solvent was concentrated under reduced pressure to afford crude product. The crude compound was purified by preparative TLC to obtain 5-(4-methyl-4-(3-(trifluoromethyl)phenyl)sulfonyl) tetrahydro-2H-pyran-2-yl)-3-(oxetan-3-ylsulfonyl)-1H-pyrazole (0.1 g, 49%) as a solid.

[Cis-rac] 5-[4-Methyl-4-[[3-(trifluoromethyl)phenyl]sulfonyl]-tetrahydro-pyran-2-yl]-3-(oxetan-3-ylsulfonyl)-1H-pyrazole was subjected to chiral prep-SFC purification to give [cis-EN1] Example 4 and [cis-EN2] Example 4.

[cis-EN1] Example 4—analytical SFC: Chiralpak IC (250×4.6 mm 5 µm) 29.7° C., 3 g/min, 100 bar, 35% MeOH, Ret. Time 3.25 min; m/z=495.0 [M+H]$^+$; $^1$H NMR (CDCl$_3$): δ 10.80 (br s, 1H), 8.13 (s, 1H), 8.06 (d, 1H), 7.98 (d, 1H), 7.80-7.78 (t, 1H), 6.65 (s, 1H), 5.02 (t, 2H), 4.89-4.85 (m, 2H), 4.69-4.62 (m, 2H), 4.21-4.17 (m, 1H), 3.76-3.69 (m, 1H), 2.36-2.35 (m, 1H), 2.25-2.19 (m, 1H), 1.92-1.89 (m, 1H), 1.58 (m, 4H).

[cis-EN2] Example 4—analytical SFC: Chiralpak IC (250×4.6 mm 5 µm), 30.4° C., 3 g/min, 100 bar, 35% MeOH, Ret. Time 4.07 min; m/z=495.0 [M+H]$^+$; $^1$H NMR (CDCl$_3$): δ 10.80 (br s, 1H), 8.13 (m, 1H), 8.06 (d, 1H), 7.98 (d, 1H), 7.78 (t, 1H), 6.65 (s, 1H), 5.02 (t, 2H), 4.89-4.85 (m, 2H), 4.69-4.62 (m, 2H), 4.21-4.17 (m, 1H), 3.76-3.69 (m, 1H), 2.36-2.35 (m, 1H), 2.25-2.19 (m, 1H), 1.92-1.89 (m, 1H), 1.58 (m, 4H).

3-(2-Methoxy-ethylsulfonyl)-5-[4-[[3-(trifluoromethyl)phenyl]sulfonyl]-tetrahydro-pyran-2-yl]-1H-pyrazole (Example 5)

Prepared in analogy to Example 4:

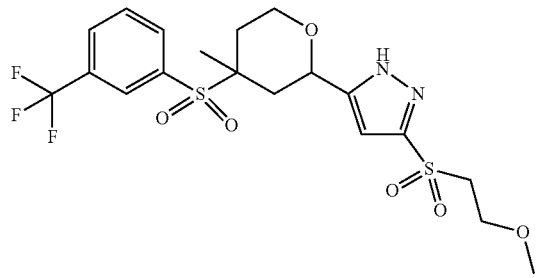 [SMILES: COCCS(=O)(=O)c1cc(C2CC(C)(S(=O)(=O)c3cccc(C(F)(F)F)c3)CCO2)[nH]n1]

[Cis-rac] 3-(2-Methoxy-ethylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give [cis-EN1] Example 5 and [cis-EN2] Example 5.

[cis-EN1] Example 5—analytical SFC: Chiralpak AD-H (250×4.6 mm 5 µm), 26° C., 3 g/min, 100 bar, 45% iPrOH, Ret. Time 4.57 min; m/z=497.1 [M+H]$^+$; $^1$H NMR (CDCl$_3$): δ 11.00 (br s, 1H), 8.11 (s, 1H), 8.05-8.03 (d, 1H), 7.95-7.94 (d, 1H), 7.75 (t, 1H), 6.62 (s, 1H), 4.68-4.65 (m, 1H), 4.16-4.13 (m, 1H), 3.81-3.67 (m, 3H), 3.50 (t, 2H), 3.28 (s, 3H), 2.36-2.29 (m, 1H), 2.21 (t, 1H), 1.90-1.86 (m, 1H), 1.55-1.52 (m, 4H). On irradiating SCCH$_3$ proton NOE was observed with OCH proton.

[cis-EN2] Example 5—analytical SFC: Chiralpak AD-H (250×4.6 mm 5 µm), 26° C., 3 g/min, 100 bar, 45% iPrOH, Ret. Time 6.56 min; m/z=497.1 [M+H]$^+$; $^1$H NMR (CDCl$_3$): δ 10.80 (br s, 1H), 8.13 (s, 1H), 8.07-8.05 (d, 1H), 7.98-7.96 (d, 1H), 7.77 (t, 1H), 6.63 (s, 1H), 4.68-4.65 (m, 1H), 4.20-4.16 (m, 1H), 3.83-3.69 (m, 3H), 3.51 (t, 2H), 3.30 (s, 3H), 2.39-2.29 (m, 1H), 2.22 (t, 1H), 1.91-1.88 (m, 1H), 1.59-1.52 (m, 4H).

2-[[5-[4-Methyl-4-[[3-(trifluoromethyl)phenyl]sulfonyl]-tetrahydro-pyran-2-yl]-1H-pyrazol-3-yl]sulfonyl]ethanol (Example 6)

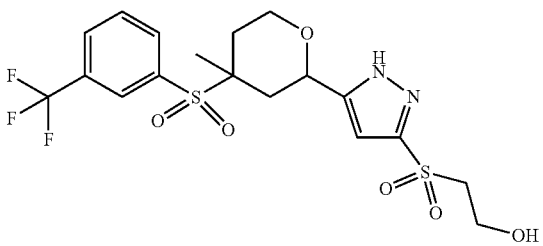 [SMILES: CC1(S(=O)(=O)c2cccc(C(F)(F)F)c2)CCOC(c2cc(S(=O)(=O)CCO)n[nH]2)C1]

Prepared in analogy to Example 4:
[Cis-rac] 2-[[5-[4-Methyl-4-[[3-(trifluoromethyl)phenyl] sulfonyl]-tetrahydro-pyran-2-yl]-1H-pyrazol-3-yl]sulfonyl] ethanol was subjected to chiral prep-SFC purification to give [cis-EN1] Example 5 and [cis-EN2] Example 6.

On irradiating SCCH$_3$ proton NOE was observed with OCH proton.

[cis-EN1] Example 6—analytical SFC: Chiralpak IC (250×4.6 mm 5 µm), 26° C., 3 g/min, 100 bar, 45% iPrOH, Ret. Time 5.09 min; m/z=483.1 [M+H]$^+$; $^1$H NMR (CDCl$_3$):

δ 11.20 (br s, 1H), 8.13 (s, 1H), 8.07-8.06 (d, 1H), 7.98-7.96 (d, 1H), 7.78 (t, 1H), 6.66 (s, 1H), 4.70-4.67 (m, 1H), 4.19-4.16 (m, 1H), 4.09-4.01 (m, 2H), 3.75-3.69 (m, 1H), 3.50 (t, 2H), 2.39-2.31 (m, 1H), 2.24 (t, 1H), 1.93-1.90 (d, 1H), 1.57-1.54 (m, 4H).

[cis-EN2] Example 6—analytical SFC: Chiralpak IC (250×4.6 mm 5 μm), 26° C., 3 g/min, 100 bar, 45% iPrOH, Ret. Time 8.94 min; m/z=483.1 [M+H]$^+$; $^1$H NMR (CDCl$_3$): δ 11.20 (br s, 1H), 8.13 (s, 1H), 8.07-8.06 (d, 1H), 7.98-7.96 (d, 1H), 7.78 (t, 1H), 6.66 (s, 1H), 4.69-4.67 (m, 1H), 4.20-4.17 (m, 1H), 4.09-4.07 (m, 2H), 3.75-3.69 (m, 1H), 3.50 (t, 2H), 3.0 (brs, 1H), 2.39-2.20 (m, 2H), 1.93-1.89 (d, 1H), 1.57-1.54 (m, 4H).

3-(1-Methyl-1-methylsulfonyl-ethyl)-5-[4-methyl-4-[[3-(trifluoromethyl)phenyl]sulfonyl]-tetrahydro-pyran-2-yl]-1H-pyrazole (Example 7)

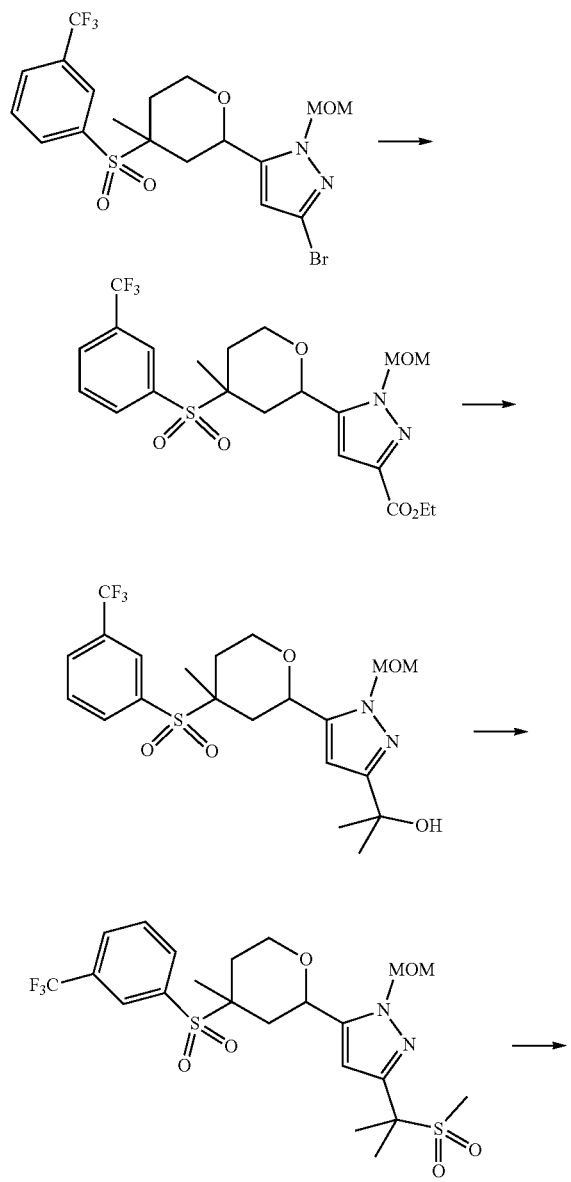

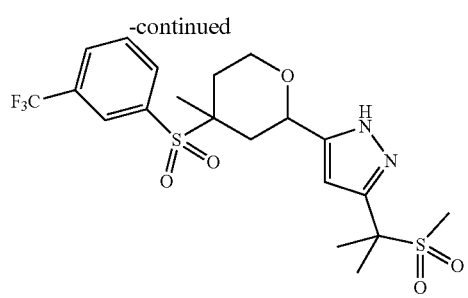

Step 1: ethyl 1-(methoxymethyl)-5-(4-methyl-4-(3-(trifluoromethyl)phenylsulfonyl)tetrahydro-2H-pyran-2-yl)-1H-pyrazole-3-carboxylate To a stirred solution of 3-bromo-1-(methoxymethyl)-5-(4-methyl-4-(3-(trifluoromethyl) phenylsulfonyl) tetrahydro-2H-pyran-2-yl)-1H-pyrazole (1.0 g, 2.01 mmol) and TEA (0.85 mL 6.04 mmol) in EtOH (10 mL) in a steel bomb, added catalytic PdCl$_2$(dppO.CH$_2$Cl$_2$ (0.145 g, 0.26 mmol) and palladium acetate (60 mg, 0.22 mmol) and filled with CO (gas; ~300 psi). The reaction mixture was heated at 120° C. under stirring condition for 19 h. The reaction mixture was cooled to rt and concentrated under reduced pressure. The residue was diluted with water and the organic product was extracted with EtOAc (2×50 ml). The combined organic extracts were washed with water (2×20 mL), brine (50 mL), dried over anhydrous Na$_2$SO$_4$ and solvent was concentrated under reduced pressure to get the crude. The crude was purified by column chromatography (silica gel 60-120 mesh, 0-15% EtOAc in PE) afforded ethyl 1-(methoxymethyl)-5-(4-methyl-4-(3-(trifluoromethyl)phenyl)sulfonyl)tetrahydro-2H-pyran-2-yl)-1H-pyrazole-3-carboxylate (0.70 g, 71%).

Step 2: 2-(1-(methoxymethyl)-5-(4-methyl-4-(3-(trifluoromethyl)phenylsulfonyl)tetrahydro-2H-pyran-2-yl)-1H-pyrazol-3-yl)propan-2-ol To a stirred solution of ethyl 1-(methoxymethyl)-5-(4-methyl-4-(3-(trifluoromethyl)phenyl)sulfonyl)tetrahydro-2H-pyran-2-yl)-1H-pyrazole-3-carboxylate (0.70 g, 1.42 mmol) in THF (10 mL) at 0° C. was added drop wise MeMgBr (1.45 mL, 4.28 mmol, 3.0 M in Et$_2$O). The resulting reaction mixture was stirred at 0° C.-10° C. for 1 h and then quenched with sat. aq. NH$_4$Cl (60 mL). The organic product was extracted with EtOAc (2×20 mL). The combined organic extracts were washed with water (2×20 mL), brine (20 mL), dried over anhydrous Na$_2$SO$_4$, organic layer was filtered and solvent was concentrated under reduced pressure to get the crude. Trituration with Et$_2$O (5 mL) afforded 490 mg of crude 2-(1-(methoxymethyl)-5-(4-methyl-4-(3-(trifluoromethyl)phenyl)sulfonyl)tetrahydro-2H-pyran-2-yl)-1H-pyrazol-3-ylpropan-2-ol Step 3: 1-(methoxymethyl)-5-(4-methyl-4-(3-(trifluoromethyl)phenylsulfonyl)tetrahydro-2H-pyran-2-yl)-3-(2-(methylsulfonyl)propan-2-yl)-1H-pyrazole TFA (2.00 mL) was added to a solution of 2-(1-(methoxymethyl)-5-(4-methyl-4-(3-(trifluoromethyl)phenyl)sulfonyl)tetrahydro-2H-pyran-2-yl)-1H-pyrazol-3-yl-propan-2-ol (450 mg, 0.94 mmol), sodium methane sulfinate (0.375 mg, 3.78 mmol) in CHCl₃ (10 mL) at 0° C. The reaction mixture was slowly warmed to RT, stirred for 27 h. The reaction mixture was quenched with water and the organic product was extracted with CHCl₃ (2×20 mL). The combined organic extracts were washed with water (2×20 mL), brine (20 mL), dried over anhydrous Na₂SO₄, organic layer was filtered and solvent was concentrated under reduced pressure to get the crude. The compound was purified by Prep TLC using EtOAc: PE (1:1 v/v) as eluent to get 8 mg of pure 1-(methoxymethyl)-5-(4-methyl-4-(3-(trifluoromethyl)-phenyl)sulfonyl)tetrahydro-2H-pyran-2-yl)-3-(2-(methyl sulfonyl)propan-2-yl)-1H-pyrazole and 280 mg of mixture of 1-(methoxymethyl)-5-(4-methyl-4-(3-(trifluoromethyl)phenyl)sulfonyl)tetrahydro-2H-pyran-2-yl)-3-(2-(methylsulfonyl)propan-2-yl)-1H-pyrazole and 5-(4-methyl-4-(3-(trifluoromethyl)phenylsulfonyl)tetrahydro-2H-pyran-2-yl)-3-(2-(methylsulfonyl) propan-2-yl)-1H-pyrazole.

Step 4: 3-(1-Methyl-1-methylsulfonyl-ethyl)-5-[4-methyl-4-[[3-(trifluoromethyl)phenyl]sulfonyl]-tetrahydro-pyran-2-yl]-1H-pyrazole Dioxane.HCl solution (5.0 mL, 4 M solution) was added to a solution of 1-(methoxymethyl)-5-(4-methyl-4-(3-(trifluoromethyl)phenyl)sulfonyl)tetrahydro-2H-pyran-2-yl)-3-(2-(methyl sulfonyl)propan-2-yl)-1H-pyrazole and 5-(4-methyl-4-(3-(trifluoromethyl)phenylsulfonyl) tetrahydro-2H-pyran-2-yl)-3-(2-(methylsulfonyl)propan-2-yl)-1H-pyrazole (altogether 280 mg) in EtOH (10 mL) and the resulting reaction mixture was heated to 60° C. under stirring condition for 5 h. The reaction mixture was concentrated under reduced pressure and the residue was diluted with water. The reaction mixture was cooled to 0° C., added sat. aq. NaHCO₃ solution (10 mL) and the organic product was extracted with EtOAc (2×25 mL). The combined organic extracts were washed with water (2×10 mL), brine (25 mL), dried over anhydrous Na₂SO₄, The organic layer was filtered and solvent was concentrated under reduced pressure to afford crude 5-(4-methyl-4-(3-(trifluoromethyl) phenylsulfonyl)tetrahydro-2H-pyran-2-yl)-3-(2-(methylsulfonyl) propan-2-yl)-1H-pyrazole as pale brown solid (110 mg).

[cis-rac] Example 7—m/z=495.0

[Cis-rac] 5-(4-methyl-4-(3-(trifluoromethyl)phenylsulfonyl)tetrahydro-2H-pyran-2-yl)-3-(2-(methylsulfonyl) propan-2-yl)-1H-pyrazole was subjected to chiral prep-SFC purification to give of [cis-EN1] Example 7 and [cis-EN2] Example 7.

[cis-EN1] Example 7—analytical SFC: Chiralpak IC (250×4.6 mm 5 μm), 30° C., 3 g/min, 100 bar, 20% MeOH, Ret. Time 7.05 min; m/z=495.1 [M+H]⁺; ¹H NMR (CDCl₃): δ 10.36 (br s, 1H), 8.14 (s, 1H), 8.09-8.07 (d, 1H), 7.96-7.94 (d, 1H), 7.76 (t, 1H), 6.31 (s, 1H), 4.63-4.60 (m, 1H), 4.16-4.12 (m, 1H), 3.73-3.66 (m, 1H), 2.65 (s, 3H), 2.39-2.25 (m, 2H), 1.93-1.88 (m, 1H), 1.79 (m, 3H), 1.78 (s, 3H), 1.55-1.50 (m, 4H)

[cis-EN2] Example 7—analytical SFC: Chiralpak IC (250×4.6 mm 5 μm), 30.2° C., 3 g/min, 100 bar, 20% MeOH, Ret. Time 10.97 min; m/z=495.1 [M+H]⁺; ¹H NMR (CDCl₃): δ 10.36 (br s, 1H), 8.14 (s, 1H), 8.09-8.07 (d, 1H), 7.96-7.94 (d, 1H), 7.76 (t, 1H), 6.31 (s, 1H), 4.63-4.60 (m, 1H), 4.16-4.12 (m, 1H), 3.73-3.66 (m, 1H), 2.65 (s, 3H), 2.39-2.25 (m, 2H), 1.93-1.88 (m, 1H), 1.79 (m, 3H), 1.78 (s, 3H), 1.55-1.50 (m, 4H)

3-(2-Methylsulfonyl-ethyl)-5-[4-methyl-4-[[3-(trifluoromethyl)phenyl]sulfonyl]-tetrahydro-pyran-2-yl]-1H-pyrazole (Example 9)

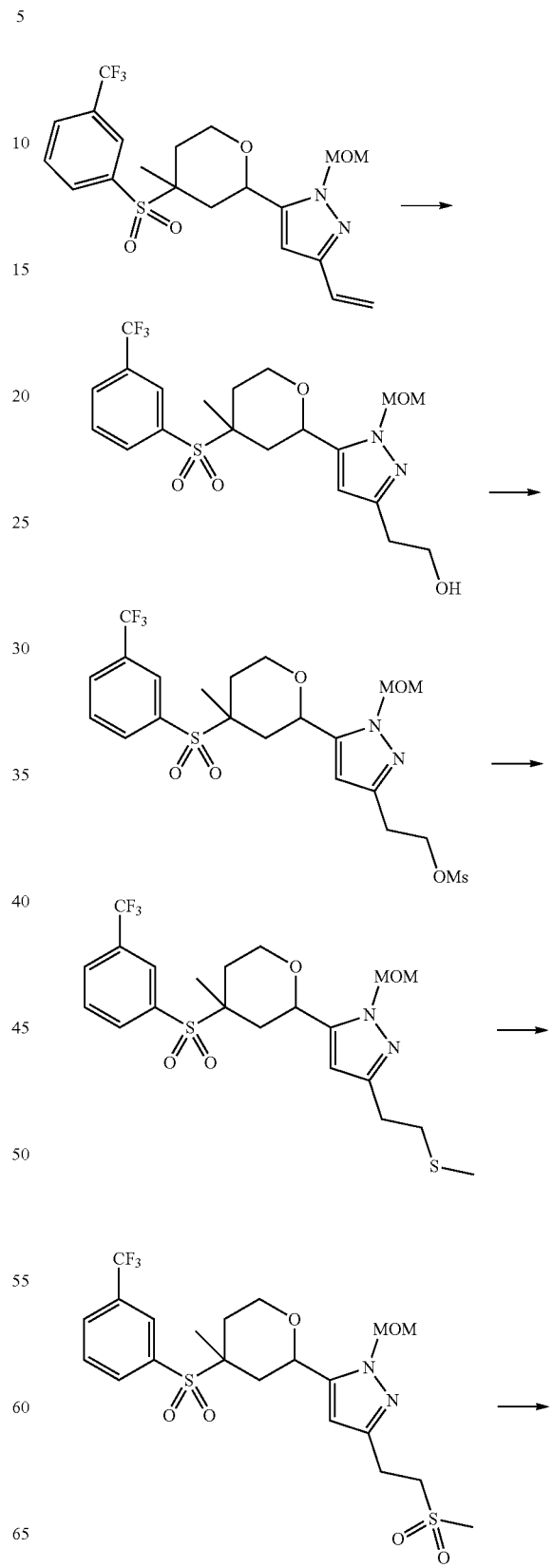

-continued

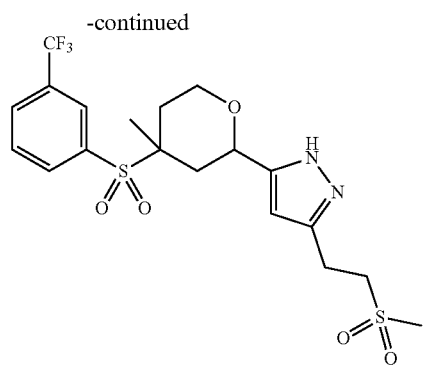

9

Step 1: 2-(1-(methoxymethyl)-5-(4-methyl-4-(3-(trifluoromethyl)phenylsulfonyl)tetrahydro-2H-pyran-2-yl)-1H-pyrazol-3-yl)ethanol BH$_3$.THF (1.0 M, 7.20 mL, 7.20 mmol) was added drop wise to a stirred solution of 1-(methoxymethyl)-5-(4-methyl-4-(3-(trifluoromethyl)phenyl)sulfonyl)tetrahydro-2H-pyran-2-yl)-3-vinyl-1H-pyrazole (1.60 g, 3.60 mmol) in THF (16 mL) at 0° C. Then reaction mixture was stirred at the same temperature for 45 min. To the reaction mixture were added dropwise 10% NaOH solution (7.2 mL) at 0° C. and followed by 30% H$_2$O$_2$ (7.2 mL). The reaction mixture was stirred at RT for 2 h. The reaction mixture was diluted with water (35 mL) and the organic product was extracted with EtOAc (3×50 mL). The organic layer was washed with brine (70 mL), dried over anhydrous Na$_2$SO$_4$, then filtered and solvent was concentrated under reduced pressure to get crude, which was purified by column chromatography (silica gel 100-200 mesh, 0-50% EtOAc in PE as eluent) followed by by prep TLC to get 2-(1-(methoxymethyl)-5-(4-methyl-4-(3-(trifluoromethyl)phenylsulfonyl)tetrahydro-2H-pyran-2-yl)-1H-pyrazol-3-yl)ethanol (0.3 g, 18%), as a thick solid.

Step 2: 2-(1-(methoxymethyl)-5-(4-methyl-4-(3-(trifluoromethyl)phenylsulfonyl)tetrahydro-2H-pyran-2-yl)-1H-pyrazol-3-yl)ethyl methanesulfonate TEA (0.27 ml, 1.94 mmol) was added to a stirred solution of 2-(1-(methoxymethyl)-5-(4-methyl-4-(3-(trifluoromethyl)phenyl)sulfonyl)tetrahydro-2H-pyran-2-yl)-1H-pyrazol-3-yl)ethanol (0.30 g, 0.64 mmol) in DCM (6 mL) at 0° C. To the reaction mixture was added methanesulfonyl chloride (0.075 mL, 0.97 mmol) at the same temperature and stirred for 1 h at 0° C. The reaction mixture was poured in ice water (15 mL) and separated the organic layer. The aq. layer was extracted again with DCM (2×20 mL). The organic layer was successively washed with sat. NaHCO$_3$ solution (10 mL), water (10 mL) and brine (20 mL), The organic layer was dried over Na$_2$SO$_4$, filtered and solvent was evaporated under reduced pressure to give 2-(1-(methoxymethyl)-5-(4-methyl-4-(3-(trifluoromethyl)phenyl sulfonyltetrahydro-2H-pyran-2-yl)-1H-pyrazol-3-yl)ethyl methanesulfonate (0.35 g, crude) as a thick liquid. This product was used as such for the next step without further purification.

Step 3: 1-(methoxymethyl)-5-(4-methyl-4-(3-(trifluoromethyl)phenylsulfonyl)tetrahydro-2H-pyran-2-yl)-3-(2-(methylthio)ethyl)-1H-pyrazole Sodium thiomethoxide (90 mg, 1.29 mmol) was added to a stirred solution of 2-(1-(methoxymethyl)-5-(4-methyl-4-(3-(trifluoromethyl)phenyl)sulfonyl)tetrahydro-2H-pyran-2-yl)-1H-pyrazol-3-yl)ethyl methanesulfonate (0.35 g, 0.64 mmol) in DMF (5 mL) at 0° C. The resulting reaction mixture was heated to 60° C. under stirring condition for 6 h. The reaction mixture was diluted with water (20 mL) and the organic product was extracted with EtOAc (2×25 mL). The combined organic layer was washed with water (2×10 mL), brine (2×20 mL), dried over anhydrous Na$_2$SO$_4$, The organic layer was filtered and solvent was concentrated under reduced pressure to afford crude product, which was purified by Prep-TLC to give 0.25 g (64%) of 1-(methoxymethyl)-5-(4-methyl-4-(3-(trifluoromethyl)phenylsulfonyl)tetrahydro-2H-pyran-2-yl)-3-(2-(methylthio)ethyl)-1H-pyrazole as thick liquid.

Step 4: 1-(methoxymethyl)-5-(4-methyl-4-(3-(trifluoromethyl)phenylsulfonyl)tetrahydro-2H-pyran-2-yl)-3-(2-(methylsulfonyl)ethyl)-1H-pyrazole A solution of oxone (0.62 g, 1.01 mmol) in water (6.25 mL) was added to a stirred solution of 1-(methoxymethyl)-5-(4-methyl-4-(3-(trifluoromethyl)phenylsulfonyl)tetrahydro-2H-pyran-2-yl)-3-(2-(methylthio)ethyl)-1H-pyrazole (0.25 g, 0.50 mmol) in MeOH (7.5 mL) and stirred for 16 h at RT. The reaction mixture was diluted with water (30 mL), the organic product was extracted with DCM (3×15 mL). The combined organic extracts were washed with brine (20 mL), dried over anhydrous Na$_2$SO$_4$. The organic layer was filtered and solvent was concentrated under reduced pressure to give 1-(methoxymethyl)-5-(4-methyl-4-(3-(trifluoromethyl)phenyl)sulfonyl)tetrahydro-2H-pyran-2-yl)-3-(2-(methylsulfonyl)ethyl)-1H-pyrazole (0.17 g, 65%) as thick liquid.

Step 5: 5-(4-methyl-4-(3-(trifluoromethyl)phenylsulfonyl)tetrahydro-2H-pyran-2-yl)-3-(2-(methylsulfonyl)ethyl)-1H-pyrazole Dioxane.HCl solution (10.0 mL, 4 M) was added to a solution of 1-(methoxymethyl)-5-(4-methyl-4-(3-(trifluoromethyl)phenyl)sulfonyl)tetrahydro-2H-pyran-2-yl)-3-(2-(methylsulfonyl)ethyl)-1H-pyrazole (0.17 g, 0.32 mmol) in EtOH (5 mL) and the resulting reaction mixture was heated to 60° C. under stirring condition for 4 h. The reaction mixture was concentrated under reduced pressure and the residue was diluted with water. The reaction mixture was cooled to 0° C., added sat. aq. NaHCO$_3$ (15 mL) and the organic product was extracted with DCM (2×15 mL). The combined organic layer was washed with water (2×10 mL), brine (20 mL), dried over anhydrous Na$_2$SO$_4$, The organic layer was filtered and solvent was concentrated under reduced pressure to give 60 mg of 5-(4-methyl-4-(3-(trifluoromethyl)-phenyl)sulfonyl)tetrahydro-2H-pyran-2-yl)-3-(2-(methylsulfonyl)ethyl)-1H-pyrazole as off white solid.

[cis-rac] Example 9—m/z=481.0

[Cis-rac] 3-(2-Methylsulfonyl-ethyl)-5-[4-methyl-4-[[3-(trifluoromethyl)phenyl]sulfonyl]-tetrahydro-pyran-2-yl]-1H-pyrazole was subjected to chiral prep-SFC purification to give of [cis-EN1] Example 9 and [cis-EN2] Example 9.

[cis-EN1] Example 9—analytical SFC: Chiralpak IC (250×4.6 mm 5 μm), 30° C., 3 g/min, 100 bar, 35% MeOH, Ret. Time 6.82 min; m/z=481.0 [M+H]$^+$; $^1$H NMR (CDCl$_3$): δ 10.28 (br s, 1H), 8.13 (s, 1H), 8.07 (d, 1H), 7.95 (d, 1H), 7.75 (t, 1H), 6.06 (s, 1H), 4.59 (d, 1H), 4.15-4.11 (m, 1H), 3.70 (t, 1H), 3.39-3.36 (m, 2H), 3.22-3.18 (m, 2H), 2.86 (s, 3H), 2.37-2.23 (m, 2H), 1.86 (d, 1H), 1.53 (s, 4H).

[cis-EN2] Example 9—analytical SFC: Chiralpak IC (250×4.6 mm 5 μm), 29.9° C., 3 g/min, 100 bar, 35% MeOH, Ret. Time 11.04 min; m/z=481.0 [M+H]⁺; ¹H NMR (CDCl₃): δ 10.20 (br s, 1H), 8.13 (s, 1H), 8.07 (d, 1H), 7.95 (d, 1H), 7.75 (t, 1H), 6.05 (s, 1H), 4.59 (d, 1H), 4.15-4.11 (m, 1H), 3.69 (t, 1H), 3.39-3.35 (m, 2H), 3.22-3.18 (m, 2H), 2.86 (s, 3H), 2.37-2.23 (m, 2H), 1.86 (d, 1H), 1.53 (s, 4H).

5-(Difluoro-methyl)-3-[4-methyl-4-[[3-(trifluoromethyl)phenyl]sulfonyl]-tetrahydro-pyran-2-yl]-1H-pyrazole (Example 12)

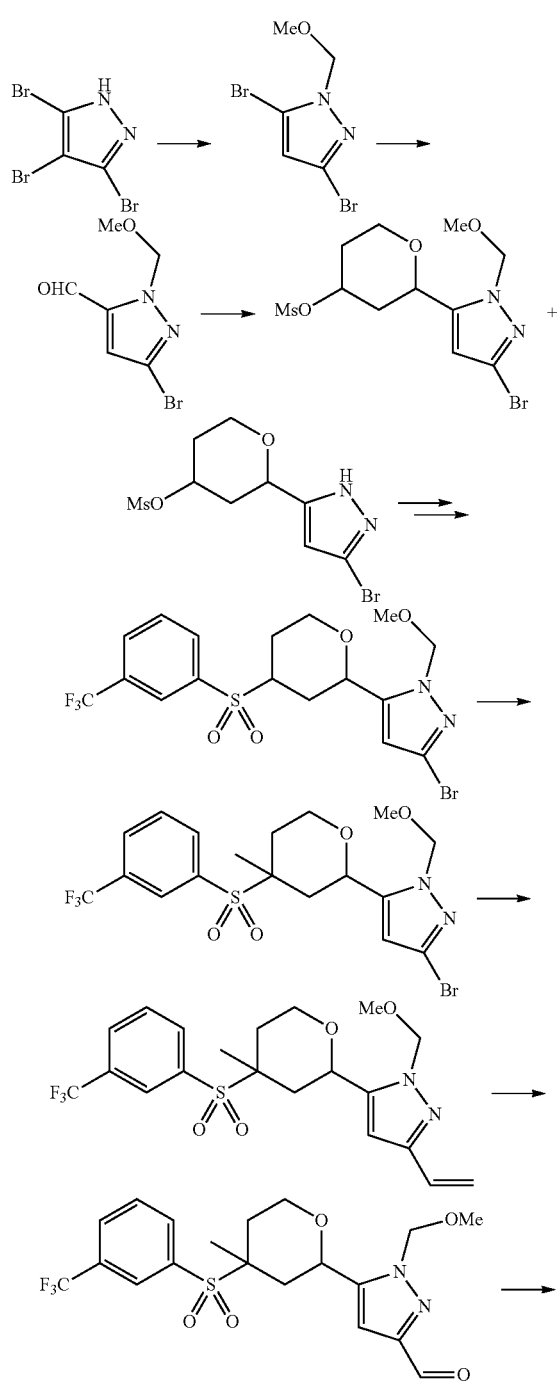

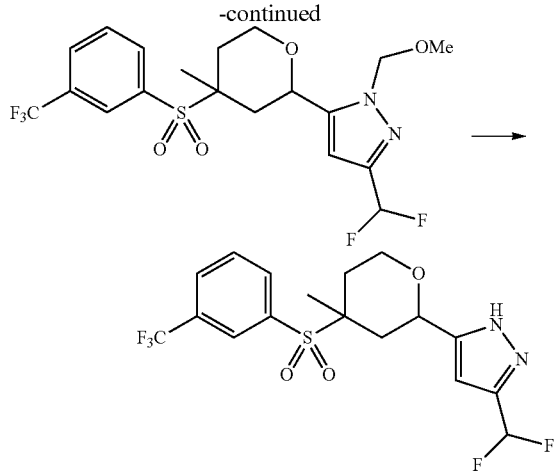

Step 1: 3,5-Dibromo-1-(methoxymethyl)-1H-pyrazole

A solution of 3,5-dibromo-1H-pyrazole (25 g, 111.70 mmol, 1.0 eq) in THF (200 ml) was added to a suspension of NaH (60%; 5.89 g, 245 mmol, 2.2 eq) in THF (100 ml) at 0° C. The mixture was stirred for 1 h before chloromethyl methyl ether (13.57 ml, 167.5 mmol, 1.5 eq) was added. The RM was stirred at 0° C. for 2 h and then allowed to warm to RT and stir for 12 h. The mixture was quenched with cold water (500 mL), and extracted with EtOAc (3×200 ml). The combined organic layers were washed with water (2×200 ml) and brine (200 ml), dried (Na₂SO₄), filtered and concentrated under reduced pressure to afford the title compound (15 g, 51%).

Step 2: 3-Bromo-1-(methoxymethyl)-1H-pyrazole-5-carbaldehyde

A stirred solution of 3,5-dibromo-1-(methoxymethyl)-1H-pyrazole (15 g, 56.01 mmol, 1.0 eq) in THF (150 ml) was treated with iPrMgCl (1.0 M, 67.2 ml, 67.2 mmol, 1.2 eq) at −78° C. The mixture was stirred for 30 min, before adding DMF (30.9 ml, 397 mmol, 7.0 eq) and gradually allowing it to warm to rt and stir for 14 h. The RM was quenched with aq NH₄Cl (300 ml) and extracted with EtOAc (3×150 ml). The combined organic layer was washed with water (2×150 ml) and brine (150 ml), dried (Na₂SO₄), filtered and concentrated under reduced pressure to afford the title compound (16.0 g).

Step 3: 2-(3-Bromo-1-(methoxymethyl)-1H-pyrazol-5-yl)tetrahydro-2H-pyran-4-yl methanesulfonate and 2-(3-Bromo-1H-pyrazol-5-yl)tetrahydro-2H-pyran-4-yl methanesulfonate A stirred solution of 3-bromo-1-(methoxymethyl)-1H-pyrazole-5-carbaldehyde (16.0 g, crude, 58.5 mmol, 1.0 eq) in DCM (250 ml) was treated with MsOH (36.4 ml, 585.1 mmol, 10.0 eq) at 0° C. The mixture was stirred for 10 min and but-3-en-1-ol (4.8 ml, 58.5 mmol, 1.0 eq) was added. The RM was allowed to warm to RT and stir for 18 h. The RM was quenched with sat. aq. Na₂CO₃ (150 ml) and extracted with DCM (2×200 ml). The combined organic layers were washed with water (2×150 ml) and brine (150 ml), dried (Na$_2$SO$_4$), filtered and concentrated under reduced pressure to afford the title compounds (18 g).

Step 4: 3-Bromo-5-(4-((3-(trifluoromethyl)phenyl) thio)tetrahydro-2H-pyran-2-yl)-1H-pyrazole and 3-Bromo-1-(methoxymethyl)-5-(4-((3-(trifluoromethyl)phenyl)thio)tetrahydro-2H-pyran-2-yl)-1H-pyrazole A stirred solution of 3-(trifluoromethyl)benzenethiol (17.3 g, 97.56 mmol, 2.0 eq) in DMF (250 ml) was treated with K$_2$CO$_3$ (20.19 g, 146.3 mmol, 3.0 eq), stirred for 10 min at RT. A solution of 2-(3-bromo-1-(methoxymethyl)-1H-pyrazol-5-yl)tetrahydro-2H-pyran-4-yl methanesulfonate and 2-(3-bromo-1H-pyrazol-5-yl)tetrahydro-2H-pyran-4-yl methanesulfonate (18 g, 48.78 mmol, 1.0 eq) in DMF (150 ml) was added. The resulting RM was heated to 50° C., stirred for 6 h, then brought to RT and stirred for additional 10 h. The RM was concentrated under reduced pressure and the residue was diluted with water (500 ml) and extracted with EtOAc (3×200 ml). The combined organic layers were washed with water (2×200 ml) and brine (200 ml), dried (Na$_2$SO$_4$) filtered and concentrated under reduced pressure. The crude compound upon purification by flash chromatography (silica-gel; EtOAc-PE; 20:80→30:70) afforded the title compounds (9 g, 2 g, over 3 steps).

Note: 3-Bromo-5-(4-((3-(trifluoromethyl)phenyl)thio)tetrahydro-2H-pyran-2-yl)-1H-pyrazole was converted to 3-bromo-1-(methoxymethyl)-5-(4-((3-(trifluoromethyl)phenyl)thio)tetrahydro-2H-pyran-2-yl)-1H-pyrazole (10 g, 60%) employing the method described in step 1.

Step 5: 3-Bromo-1-(methoxymethyl)-5-(4-((3-(trifluoromethyl)phenyl)sulfonyl)tetrahydro-2H-pyran-2-yl)-1H-pyrazole Oxone (27.2 g, 88.8 mmol, 5.0 eq) in water (50 ml,) was added to a solution of 3-bromo-1-(methoxymethyl)-5-(4-((3-(trifluoromethyl)phenyl)thio)tetrahydro-2H-pyran-2-yl)-1H-pyrazole (8 g, 17.7 mmol, 1.0 eq) in MeOH (150 ml) at RT and the mixture was stirred for 18 h. After completion of the reaction, MeOH was distilled off under reduced pressure. The residue was made alkaline by addition of sat. aq. NaHCO$_3$ (200 ml) and extracted with EtOAc (3×150 ml). The organic layer was washed with water (2×150 ml) and brine (100 ml), dried (Na$_2$SO$_4$), filtered and concentrated under reduced pressure. The crude residue upon purification by flash chromatography (silica-gel; EtOAc-PE; 10:90→30:70) afforded the title compound (6.5 g, 76%).

Step 6: 3-Bromo-1-(methoxymethyl)-5-(4-methyl-4-((3-(trifluoromethyl)phenyl)sulfonyl)tetrahydro-2H-pyran-2-yl)-1H-pyrazole A solution of 3-bromo-1-(methoxymethyl)-5-(4-((3-(trifluoromethyl)phenyl)sulfonyl)tetrahydro-2H-pyran-2-yl)-1H-pyrazole (6.5 g, 13.48 mmol 1.0 eq) in THF (100 ml) was cooled to −78° C. and KOtBu (1M in THF, 26.9 ml, 26.9 mmol, 2.0 eq) was added dropwise. The mixture was stirred for 30 min and MeI (2.0 ml, 33.7 mmol, 2.5 eq) was added. The resulting RM was allowed to RT and stir for 18 h. It was then quenched with sat. aq. NH$_4$Cl (200 ml) and water (200 ml), and extracted with EtOAc (3×200 ml). The combined organic layers were washed with water (2×200 ml) and brine (200 ml), dried (Na$_2$SO$_4$), filtered and concentrated under reduced pressure. The residue upon purification flash chromatography (silica gel; EtOAc-PE; 15:85→30:70) afforded the title cis and trans racemates.

[cis-rac] 3-Bromo-1-(methoxymethyl)-5-(4-methyl-4-((3-(trifluoromethyl)phenyl)sulfonyl)tetrahydro-2H-pyran-2-yl)-1H-pyrazole: 3.5 g (52%); TLC system: EtOAc-PE; 1:1; Rf: 0.50

[trans-rac] 3-Bromo-1-(methoxymethyl)-5-(4-methyl-4-((3-(trifluoromethyl)phenyl)sulfonyl)tetrahydro-2H-pyran-2-yl)-1H-pyrazole: 1.5 g; TLC system: EtOAc-PE; 1:1; Rf: 0.60.

Step 7: [cis-rac] 1-(Methoxymethyl)-5-(4-methyl-4-((3-(trifluoromethyl)phenyl)sulfonyl)tetrahydro-2H-pyran-2-yl)-3-vinyl-1H-pyrazole A stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole (3.5 g, 7.05 mmol, 1.0 eq), potassium vinyl trifluoroborate (3.7 g, 28.22 mmol, 4.0 eq) and Cs$_2$CO$_3$ (6.89 g, 21.15 mmol, 3.0 eq) in DMF-H$_2$O (150 ml & 20 ml) was degassed for 20 min with Ar. Then PdCl$_2$(dppf)$_2$.DCM (575 mg, 0.705 mmol, 0.1 eq) was added and the mixture degassed for 10 min. The resulting RM was heated to 120° C. and stirred for 16 h. The RM was concentrated under reduced pressure, and the residue was diluted with water (150 ml) and extracted with EtOAc (2×150 ml). The combined organic extract was washed with water (2×100 ml) and brine (100 ml), dried (Na$_2$SO$_4$) and concentrated under reduced pressure. The residue upon purification by flash chromatography (silica gel, EtOAc:PE; 30:70→60:40) afforded the title compound (2.5 g, 80%).

Step 8: [cis-rac] 1-(Methoxymethyl)-5-(4-methyl-4-((3-(trifluoromethyl)phenyl)sulfonyl)tetrahydro-2H-pyran-2-yl)-1H-pyrazole-3-carbaldehyde Ozone gas was bubbled through a solution of [cis-rac] 1-methoxymethyl)-5-(4-methyl-4-((3-(trifluoromethyl)phenyl)sulfonyl)tetrahydro-2H-pyran-2-yl)-3-vinyl-1H-pyrazole (2.5 g, 6.03 mmol, 1.0 eq) in acetone-H$_2$O (60 ml & 4 ml) at −20 to 0° C. for 30 min. The RM was diluted with water (100 ml), and extracted with EtOAc (3×70 ml). The combined organic layers were washed with water (2×100 ml) and brine (100 ml), dried over anhydrous Na$_2$SO$_4$, filtered and concentrated under reduced pressure to afford the title compound (1.5 g).

Step 9: [cis-rac] 3-(Difluoromethyl)-1-(methoxymethyl)-5-(4-methyl-4-((3-(trifluoromethyl)phenyl) sulfonyl)tetrahydro-2H-pyran-2-yl)-1H-pyrazole A stirred solution of [cis-rac] 1-(methoxymethyl)-5-(4-methyl-4-((3-(trifluoromethyl)phenyl)-sulfonyl)tetrahydro-2H-pyran-2-yl)-1H-pyrazole-3-carbaldehyde (1.5 g, 3.36 mmol, 1.0 eq), in DCM (25 ml) was cooled to −78° C. and treated with DAST (1.7 ml, 13.4 mml, 4.0 eq). The resulting RM was allowed to warm to RT and stir for 16 h. The mixture was cooled to 0° C., quenched with sat. aq. NaHCO$_3$ (30 mL) and extracted with EtOAc (2×20 mL). The combined organic layers were washed with water (2×20 ml) and brine (75 ml), dried over anhydrous Na$_2$SO$_4$, filtered and concentrated under reduced pressure. The residue upon purification by flash chromatography silica gel, EtOAc-PE; 30:70→60:40), afforded the title compound (700 mg, 30% over 2 steps).

Step 10: [cis-rac] 3-(Difluoromethyl)-5-(4-methyl-4-((3-(trifluoromethyl)phenyl)sulfonyl)tetrahydro-2H-pyran-2-yl)-1H-pyrazole (Example 12)

To a stirred solution of [cis-rac] 3-(difluoromethyl)-1-(methoxymethyl)-5-(4-methyl-4-((3-(trifluoromethyl)phenyl)sulfonyl)tetrahydro-2H-pyran-2-yl)-1H-pyrazole (0.7 g, 4.08 mmol, 1.0 eq), in EtOH (10 ml) was added 4 M HCl (20 ml) and the resulting RM was heated to 60° C. and stirred for 14 h. The RM was concentrated under reduced pressure and the residue was diluted with water. The mixture was cooled to 0° C. then quenched with sat. aq. NaHCO$_3$ (100 ml), and extracted with EtOAc (2×20 ml). The combined organic layers were washed with water (2×20 ml) and brine (20 ml), dried over anhydrous Na$_2$SO$_4$, filtered and concentrated under reduced pressure. The residue upon purification by flash chromatography (silica gel, EtOAc-PE; 35:70→70:30), afforded the title product (430 mg, 68%). TLC system: EtOAc-PE; 1:1; Rf: 0.40. NOE: On irradiating OCH proton NOE was observed with SCCH$_3$.

[Cis-rac] 3-(difluoromethyl)-5-(4-methyl-4-((3-(trifluoromethyl)phenyl)sulfonyl)tetrahydro-2H-pyran-2-yl)-1H-pyrazole was subjected to chiral prep-SFC purification to give 83 mg of [cis-EN1] Example 12 and 85 mg of [cis-EN2] Example 12.

[cis-EN1] Example 12—analytical SFC: Chiralpak-ID (250×4.6 mm 5 μm) 29.9° C., 3 g/min, 100 bar, 25% MeOH, Ret. Time 2.61 min; m/z=425.21 [M+H]$^+$

[cis-EN2] Example 12—analytical SFC: Chiralpak-ID (250×4.6 mm 5 μm) 29.9° C., 3 g/min, 100 bar, 25% MeOH, Ret. Time 4.87 min; m/z=425.21 [M+H]$^+$

[trans-rac] 3-(Difluoromethyl)-5-(4-methyl-4-((3-(trifluoromethyl)phenylsulfonyl)tetrahydro-2H-pyran-2-yl)-1H-pyrazole (Example 12)

The corresponding [trans rac] 1-methoxymethyl)-5-(4-methyl-4-((3-(trifluoromethyl)phenyl)sulfonyl)tetrahydro-2H-pyran-2-yl)-3-vinyl-1H-pyrazole isomer was prepared in analogy to step 7 starting from [trans rac] 3-bromo-1-(methoxymethyl)-5-(4-methyl-4-((3-(trifluoromethyl)phenyl)sulfonyl)tetrahydro-2H-pyran-2-yl)-1H-pyrazole (1.5 g, see step 6).

The corresponding [trans rac] isomer of example 12 was prepared in analogy to steps 8 to 10 starting from [trans rac] 1-methoxymethyl)-5-(4-methyl-4-((3-(trifluoromethyl)phenyl)sulfonyl)tetrahydro-2H-pyran-2-yl)-3-vinyl-1H-pyrazole (see step 7).

[trans-rac] Example 12—m/z=425.21 [M+H]$^+$; TLC system: EtOAc-PE; 1:1; Rf: 0.45; NOE: On irradiating OCH proton no NOE was observed with SCCH$_3$.

3-(1,1-Difluoro-ethyl)-5-[4-methyl-4-[[3-(trifluoromethyl)phenyl]sulfonyl]-tetrahydro-pyran-2-yl]-1H-pyrazole (Example 13)

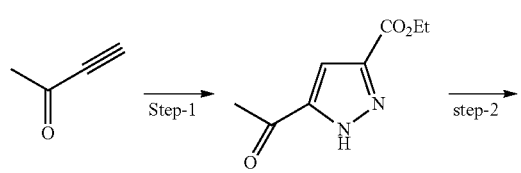

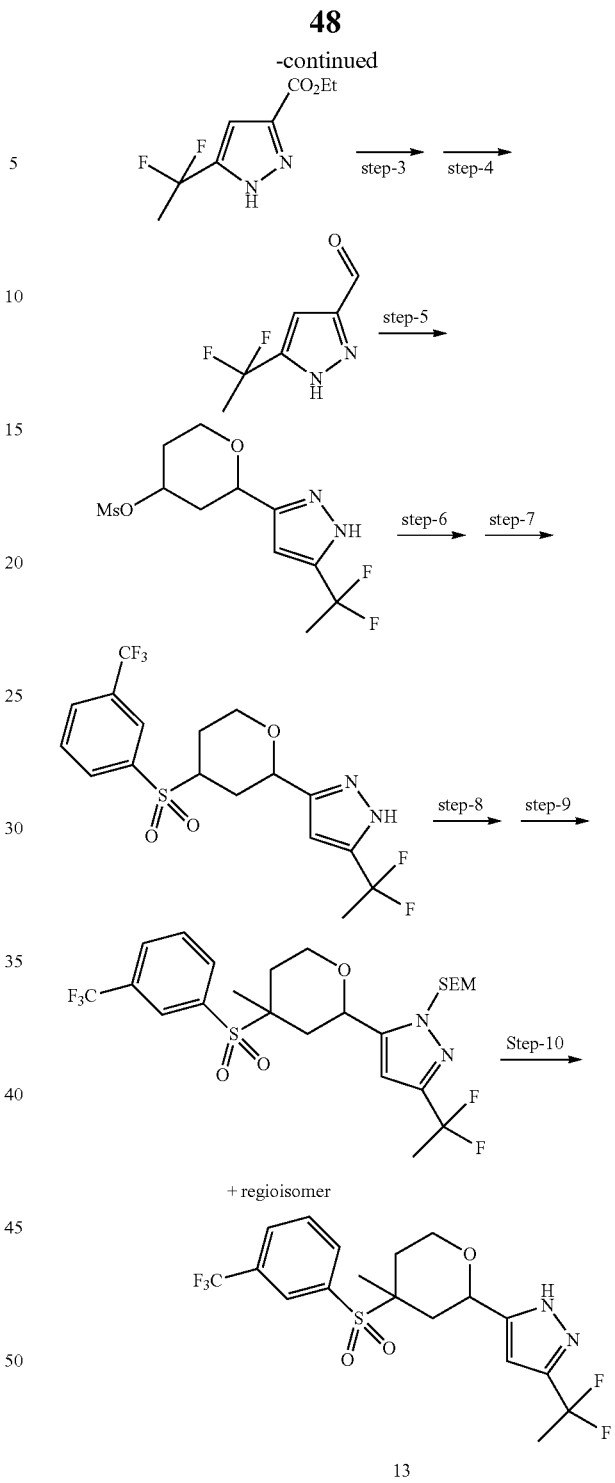

Step 1: Ethyl 5-acetyl-1H-pyrazole-3-carboxylate

To a solution of InCl$_3$ (6.50 g, 29.37 mmol) in water (300 mL) was added ethyldiazoacetate (18.5 mL, 176.26 mmol) and but-3yne-2-one (10.0 g, 146.88 mmol). The reaction mixture was stirred at rt for 4 h. Solid was precipitated out which was filtered and washed with water. The product was kept for drying under suction for 8 h to give ethyl 5-acetyl-1H-pyrazole-3-carboxylate (18.50 g, 70%) as yellow solid.

Step 2: Ethyl 5-(1,1-difluoroethyl)-1H-pyrazole-3-carboxylate

DAST (51.49 mL, 393.44 mmol) was added to a clear solution of ethyl 5-acetyl-1H-pyrazole-3-carboxylate (18.0 g, 98.36 mmol) in DCM (200 mL) at 0° C. The reaction mixture was warmed to rt and stirred further for 12 h. The reaction mixture was slowly quenched with ice-water and the organic product was extracted with DCM. The organic extracts were washed with sat. $NaHCO_3$ solution followed by water and brine. The organic layer was dried over anhydrous $Na_2SO_4$, filtered and evaporated the solvent under reduced pressure to get the crude which was purified by column chromatography (silica gel 100-200 mesh, 0-10% EtOAc in PE as eluent) to give product ethyl 5-(1,1-difluoroethyl)-1H-pyrazole-3-carboxylate (9.0 g, 40%) as light yellow oily liquid. (TLC system EtOAc-PE, 1:9; Rf: 0.52).

Step 3: (5-(1,1-difluoroethyl)-1H-pyrazol-3-yl)methanol

To a suspension of $LiAlH_4$ (1.84 g, 48.52 mmol) in dry THF (90 mL) at 0° C. was added a solution of ethyl 5-(1,1-difluoroethyl)-1H-pyrazole-3-carboxylate (9.0 g, 44.12 mmol) in dry THF (90 mL) dropwise at 0° C. The reaction mixture was warmed to rt and stirred further for 1 h. The reaction mixture was slowly quenched with aq. $Na_2SO_4$ solution (500 mL) at 0° C., the suspension was filtered and filtrate was washed with THF (200 mL). The THF solution of the product was directly used for the next step without isolation of the compound.

Step 4: 5-(1,1-difluoroethyl)-1H-pyrazole-3-carbaldehyde

Activated $MnO_2$ (30.0 g, 333.33 mmol) was added to a stirred solution of (5-(1,1-difluoroethyl)-1H-pyrazol-3-yl-methanol in THF (approx. 9.0 g, 55.55 mmol) at RT and refluxed for 16 h. The reaction mixture was cooled to rt, filtered through celite bed and washed with EtOAc (3×200 mL). The clear filtrate was concentrated under reduced pressure to get crude which was purified by column chromatography (silica gel 100-200 mesh, 0-20% EtOAc in PE as eluent) to give 5-(1,1-difluoroethyl)-1H-pyrazole-3-carbaldehyde (2.5 g, 29% after 2 steps) as white solid.

Step 5: 2-(5-(1,1-difluoroethyl)-1H-pyrazol-3-yl) tetrahydro-2H-pyran-4-yl methanesulfonate Methanesulfonic acid (24.30 mL, 375 mmol) was added to a stirred solution of 5-(1,1-difluoroethyl)-1H-pyrazole-3-carbaldehyde (6.0 g, 37.5 mmol) in DCM (120 mL) at 0° C. and 3-buten-1-ol (5.62 mL, 56.25 mmol) was added drop wise to the reaction mixture at the same temperature. The reaction mixture was allowed to come to rt and stirred for 16 h. The reaction mixture was diluted with DCM (200 mL). The organic layer was separated and washed with water (200 mL), aq. $NaHCO_3$ solution (100 mL) and brine (100 mL) then dried over anhydrous $Na_2SO_4$. The organic layer was filtered and solvent was concentrated under reduced pressure to give 2-(5-(1,1-difluoroethyl)-1H-pyrazol-3-yl)-tetrahydro-2H-pyran-4-yl methanesulfonate (12.0 g, crude) as a thick liquid. (TLC system: EtOAc-PE; 5:5 Rf: 0.25). The crude was taken as such for the next step.

Step 6: 5-(1,1-difluoroethyl)-3-(4-((3-(trifluoromethyl)phenyl)thio)tetrahydro-2H-pyran-2-yl)-1H-pyrazole 3-(trifluoromethyl)benzenethiol (10.60 mL, 77.41 mmol) was added to a suspension of $K_2CO_3$ (10.60 g, 77.41 mmol), 2-(5-(1,1-difluoroethyl)-1H-pyrazol-3-yl)tetrahydro-2H-pyran-4-yl methanesulfonate (12.0 g, 38.70 mmol) in DMF (200 mL) and stirred at 55° C. for 6 h and at rt for 6 h. The reaction mixture was diluted with water (200 ml) and the organic product was extracted with EtOAc (3×100 mL). The organic layer was washed with brine (2×100 mL), then dried over anhydrous $Na_2SO_4$. The organic layer was filtered and evaporated the solvent under reduced pressure to get crude which was purified by column chromatography (silica gel 100-200 mesh, 0-20% EtOAc in PE as eluent) to give 5-(1,1-difluoroethyl)-3-(4-((3-(trifluoromethyl)phenylthio) tetrahydro-2H-pyran-2-yl)-1H-pyrazole (10.0 g, 68%) as a thick liquid.

Step 7: 5-(1,1-difluoroethyl)-3-(4-((3-(trifluoromethyl)phenyl)sulfonyl)tetrahydro-2H-pyran-2-yl)-1H-pyrazole A solution of oxone (31.32 g, 51.02 mmol) in water (250 mL) was added to a stirred solution of 5-(1,1-difluoroethyl)-3-(4-((3-(trifluoromethyl) phenyl)thio)tetrahydro-2H-pyran-2-yl)-1H-pyrazole (10.0 g, 25.51 mmol) in MeOH (350 mL) and stirred for 16 h at RT. The reaction mixture was diluted with water (200 mL). The organic product was extracted with DCM (3×200 mL). The combined organic extracts were washed with brine (200 mL), dried over anhydrous $Na_2SO_4$. The organic layer was filtered and evaporated the solvent under reduced pressure to give crude, which was purified by column chromatography (silica gel 60-120 mesh, 0-30% EtOAc in PE as eluent) to give 5-(1,1-difluoroethyl)-3-(4-((3-(trifluoro-methyl)phenyl)sulfonyl)tetrahydro-2H-pyran-2-yl)-1H-pyrazole (9.0 g, 88%) as off white solid.

Step 8: 5-(1,1-difluoroethyl)-3-(4-(3-(trifluoromethyl)phenylsulfonyl)tetrahydro-2H-pyran-2-yl)-1-((2-(trimethylsilyl)ethoxy)methyl)-1H-pyrazole and 3-(1,1-difluoroethyl)-5-(4-((3-(trifluoromethyl) phenyl) sulfonyl) tetrahydro-2H-pyran-2-yl)-1((2-(trimethylsilyl) ethoxy) methyl)-1H-pyrazole NaH (60% in mineral oil) (1.52 g, 63.67 mmol) was added to a stirred solution of 5-(1,1-difluoroethyl)-3-(4-((3-(trifluoromethyl)phenyl)sulfonyl)tetrahydro-2H-pyran-2-yl)-1H-pyrazole (9.0 g, 21.22 mmol) in THF (100 mL) at 0° C. and stirred for 30 min. 2-(trimethylsilyl)ethoxymethylchloride (4.51 mL, 25.47 mmol) was added to the reaction mixture at 0° C. and slowly warmed to rt and stirred for 12 h. The RM was diluted with water (100 mL); the organic product was extracted with EtOAc (3×100 mL). The combined organic extracts were washed with brine, dried over anhydrous $Na_2SO_4$; the organic layer was filtered and evaporated the solvent under reduced pressure to give crude which was purified by column chromatography (silica gel 100-200 mesh, 15-17% EtOAc in PE as eluent to get Fraction-1 and 17-20% EtOAc in PE as eluent to get Fraction-2). After the solvent evaporation of Fraction-1 and Fraction-2 we have isolated 5-(1,1-difluoroethyl)-3-(4-(3-(trifluoromethyl)phenyl)sulfonyl)tetrahydro-2H-pyran-2-yl)-1-((2-(trimethylsilyl)ethoxy)methyl)-1H-pyrazole and 3-(1,1-difluoroethyl)-5-(4-((3-(trifluoromethyl) phenyl) sulfonyl)tetrahydro-2H-pyran-2-yl)-1-((2-(trimethylsilyl)

ethoxy)methyl)-1H-pyrazole (total 2.5 g+5.5 g, overall 68%) as yellow gummy solid.

Step 9: 5-(1,1-difluoroethyl)-3-(4-methyl-4-(3-(trifluoromethyl)phenylsulfonyl)tetrahydro-2H-pyran-2-yl)-1-((2-(trimethylsilyl)ethoxy)methyl)-1H-pyrazole and 3-(1,1-difluoroethyl)-5-(4-methyl-4-((3-(trifluoromethyl)phenyl)sulfonyl)tetrahydro-2H-pyran-2-yl)-1-((2-(trimethylsilyl)ethoxy)methyl)-1H-pyrazole KOtBu (20.0 mL, 19.85 mmol, 1.0 M in THF) was added to a stirred solution of 3-(1,1-difluoroethyl)-5-(4-((3-(trifluoromethyl)phenyl)sulfonyl)tetrahydro-2H-pyran-2-yl)-1-((2-(trimethylsilyl)ethoxy)methyl)-1H-pyrazole (5.50 g, 9.92 mmol) in THF (120 mL) at −78° C. and stirred for 30 min. MeI (1.56 mL, 24.81 mmol) was added to the reaction mixture and it was slowly warmed to rt and stirred for 16 h. The reaction mixture was diluted with water (200 mL); the organic product was extracted with EtOAc (3×150 mL). The combined organic layer was washed with brine, dried over anhydrous $Na_2SO_4$, filtered and evaporated the solvent under reduced pressure to give crude which was purified by column chromatography silica gel 100-200 mesh, 15-30% EtOAc in PE as eluent to give 3-(1,1-difluoroethyl)-5-(4-methyl-4-((3-(trifluoromethyl)phenyl)sulfonyl)tetrahydro-2H-pyran-2-yl)-1-((2-(trimethylsilyl)ethoxy)-methyl)-1H-pyrazole (4.4 g, 78%) as an off white solid. (TLC system: 3:7% EtOAc in PE; Rf: 0.58).

Step 10: 3-(1,1-Difluoro-ethyl)-5-[4-methyl-4-[[3-(trifluoromethyl)phenyl]sulfonyl]-tetrahydro-pyran-2-yl]-1H-pyrazole TFA (8.8 mL) was added to a clear solution of 3-(1,1-difluoroethyl)-5-(4-methyl-4-((3-(trifluoromethyl)phenyl)sulfonyl)tetrahydro-2H-pyran-2-yl)-1-((2-(trimethylsilyl)ethoxy)methyl)-1H-pyrazole (4.40 g, 7.74 mmol) dissolved in DCM (44 mL) at 0° C. The reaction mixture was stirred at RT for 4 h. Reaction mass was concentrated under reduced pressure; the residue was diluted with aq. $NaHCO_3$ (pH ~8) and the organic product was extracted with DCM (3×50 mL). The combined organic extract was washed with brine (50 mL), dried over anhydrous $Na_2SO_4$ and concentrated under reduced pressure to get crude. The crude compound was purified by column chromatography (silica gel 100-200 mesh, 50-60% EtOAc in PE) to obtain 3-(1,1-difluoroethyl)-5-(4-methyl-4-((3-(trifluoromethyl)phenylsulfonyl)-tetrahydro-2H-pyran-2-yl)-1H-pyrazole (3.1 g, 91%) as a solid. (TLC system: EtOAc-PE; 3:7; Rf: 0.30)

TFA (4.0 mL) was added to a clear solution of 5-(1,1-difluoroethyl)-3-(4-methyl-4-(3-(trifluoromethyl)phenyl)sulfonyl)tetrahydro-2H-pyran-2-yl)-1-((2-(trimethylsilyl)ethoxy)methyl)-1H-pyrazole (2.0 g, 3.52 mmol) dissolved in DCM (20 mL) at 0° C. The reaction mixture was stirred at RT for 4 h. Reaction mixture was concentrated under reduced pressure; the residue was diluted with aq. $NaHCO_3$ (pH ~8) and the organic product was extracted with DCM (3×50 mL). The combined organic extract was washed with brine (50 mL), dried over anhydrous $Na_2SO_4$ and solvent was concentrated under reduced pressure to get crude. The crude compound was purified by column chromatography (silica gel 100-200 mesh, 50-60% EtOAc in PE) to obtain 3-(1,1-difluoroethyl)-5-(4-methyl-4-((3-(trifluoromethyl) phenylsulfonyl) tetrahydro-2H-pyran-2-yl)-1H-pyrazole (1.0 g, 73%) as a solid. (TLC system: EtOAc-PE; 3:7; Rf: 0.30).

[cis-rac] Example 13—m/z=439.1

On irradiating $SCCH_3$ proton NOE was observed with OCH proton.

[Cis-rac] 3-(1,1-Difluoro-ethyl)-5-[4-methyl-4-[[3-(trifluoromethyl)phenyl]sulfonyl]-tetrahydro-pyran-2-yl]-1H-pyrazole was subjected to chiral prep-SFC purification to give of [cis-EN1] Example 13 and [cis-EN2] Example 13.

[cis-EN1] Example 13—analytical SFC: Chiralpak-AD-H (250×4.6 mm 5 μm) 29.9° C., 3 g/min, 100 bar, 15% EtOH, Ret. Time 6.58 min; m/z=439.1 [M+H]$^+$

[cis-EN2] Example 13—analytical SFC: Chiralpak-AD-H (250×4.6 mm 5 μm) 29.9° C., 3 g/min, 100 bar, 15% EtOH, Ret. Time 8.84 min; m/z=439.1 [M+H]$^+$ Synthesis of Aldehydes:

Reaction scheme for the synthesis of 3-cyclopropoxy-1H-pyrazole-5-carbaldehyde:

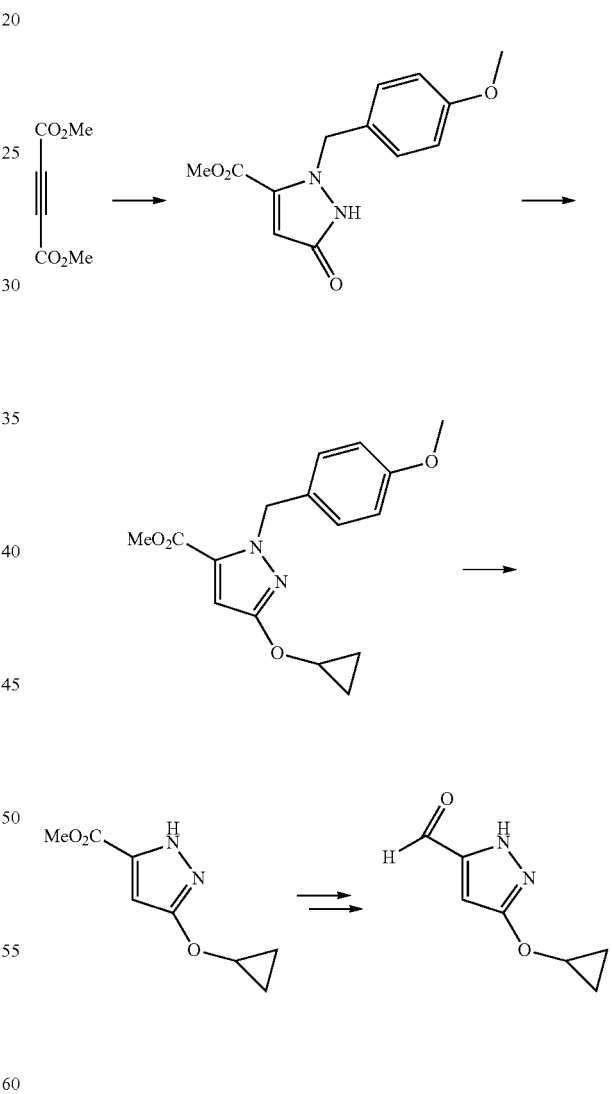

In analogy to above-described aldehyde synthesis, the following aldehydes can be obtained:

3-(difluoromethoxy)-1H-pyrazole-5-carbaldehyde 3-(trifluoromethoxy)-1H-pyrazole-5-carbaldehyde 3-(2,2,2-trifluoroethoxy)-1H-pyrazole-5-carbaldehyde 3-(2,2-Difluoro-ethyl)-5-[4-methyl-4-[[3-(trifluoromethyl)phenyl]sulfonyl]-tetrahydro-pyran-2-yl]-1H-pyrazole (Example 14)

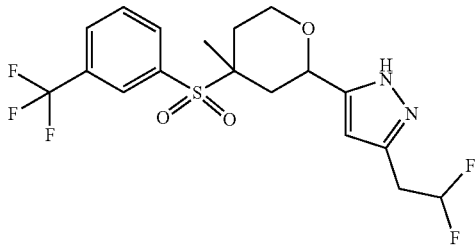 [SMILES: CC1(S(=O)(=O)c2cccc(C(F)(F)F)c2)CCOC(c2cc(CC(F)F)n[nH]2)C1]

Synthesis of Example 14 was carried out as follows:

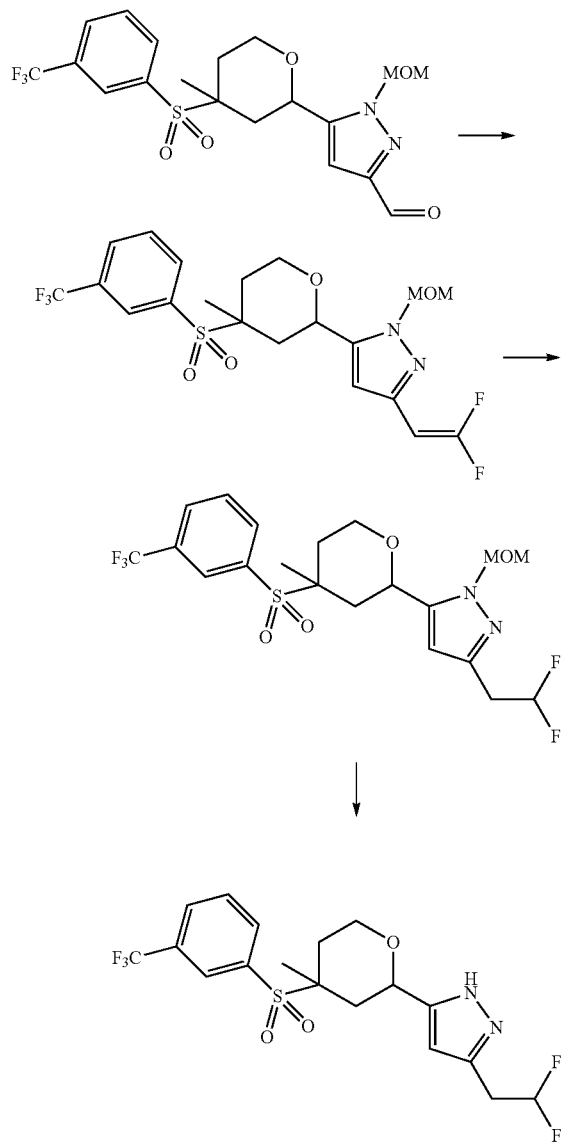

Preparation of 2,2-difluoro-2-(triphenylphosphonio)acetate

Triphenylphosphine (3.69 g, 14.08 mmol) was added to a stirred solution of potassium bromodifluoroacetate (3.00 g, 14.08 mmol) in DMF (15 ml) at RT. The resulting solution was stirred for 15 h. The crude product was precipitated from the solution. After filtration, the solid product was washed with DMF (2×2 ml), water (2×2 ml) and diethyl ether (3×3 ml), then dried under reduced pressure to give the desired product (2.50 g, 51%).

Step 1: [cis-rac] 3-(2,2-Difluorovinyl)-1-(methoxymethyl)-5-(4-methyl-4-((3-(trifluoromethyl)phenyl)sulfonyl)tetrahydro-2H-pyran-2-yl)-1H-pyrazole (Triphenylphosphino)difluoroacetate (1.90 g, 5.40 mmol) was added to a stirred solution of [cis-rac] 1-(methoxymethyl)-5-(4-methyl-4-((3-(trifluoromethyl)phenyl)sulfonyl)tetrahydro-2H-pyran-2-yl)-1H-pyrazole-3-carbaldehyde [example 12, step 8] (1.20 g, 2.70 mmol) in NMP (10 ml) and degassed under nitrogen for 15 min. The solution was stirred at 80° C. for 4 h. Similarly another 800 mg batch was repeated and both batches were combined for work-up and purification. The RM was concentrated under reduced pressure and the residue was diluted with water. The organic product was extracted with EtOAc (2×100 ml). The combined organic extracts were washed with water (2×50 ml) and brine (50 ml), and dried over anhydrous $Na_2SO_4$. The organic layer was filtered and the solvent was concentrated under reduced pressure to afford the crude product. The residue was purified by column chromatography (silica gel 60-120 mesh, 15% EtOAc in PE) to give the title compound (0.70 g, 33%, 63% purity).

Step 2: [cis-rac] 3-(2,2-Difluoroethyl)-1-(methoxymethyl)-5-(4-methyl-4-((3-(trifluoromethyl)phenyl)sulfonyl)tetrahydro-2H-pyran-2-yl)-1H-pyrazole 10% Palladium on carbon (0.10 g) was added to a stirred solution of [cis-rac] 3-(2,2-difluorovinyl)-1-(methoxymethyl)-5-(4-methyl-4-((3-(trifluoromethyl)phenyl)sulfonyl)tetrahydro-2H-pyran-2-yl)-1H-pyrazole (0.40 g, 0.833 mmol) in MeOH (5.0 ml) under $H_2$ balloon atmosphere at RT for 4 h. Similarly another 0.30 g batch was repeated and both were combined for work-up and purification. The RM was filtered through a celite pad and washed with DCM (3×50 ml). The clear filtrate was concentrated under reduced pressure to give the title compound (0.10 g, 19%).

Step 3: [cis-rac] 3-(2,2-Difluoro-ethyl)-5-[4-methyl-4-[[3-(trifluoromethyl)phenyl]sulfonyl]-tetrahydro-pyran-2-yl]-1H-pyrazole (Example 14)

4N HCl in dioxane solution (5.0 ml) was added to a solution of [cis-rac] 3-(2,2-difluoroethyl)-1-(methoxymethyl)-5-(4-methyl-4-((3-(trifluoromethyl)phenyl)sulfonyl)tetrahydro-2H-pyran-2-yl)-1H-pyrazole (0.10 g, 0.26 mmol) in EtOH (5 ml) and the resulting RM was heated to 60° C. under stirring conditions for 4 h. The RM was concentrated under reduced pressure and the residue was diluted with water. The RM was cooled to 0° C., added to sat. aq. $NaHCO_3$ solution (50 ml), and the organic product was extracted with EtOAc (2×30 ml). The combined organic layers were washed with water (2×50 ml) and brine (50 ml), and dried over anhydrous Na$_2$SO$_4$. The organic layer was filtered and the solvent was concentrated under reduced pressure to afford the crude product, which was purified by preparative thin layer chromatography (40% EtOAc in PE) to give the title compound (0.09 g). (TLC system: EtOAc-PE; 3:7; Rf: 0.26). [Cis-rac] 3-(2,2-difluoro-ethyl)-5-[4-methyl-4-[[3-(trifluoromethyl)phenyl]sulfonyl]-tetrahydro-pyran-2-yl]-1H-pyrazole was subjected to chiral prep-SFC purification to give 25 mg of [cis-EN1] Example 14 and 34 mg of [cis-EN2] Example 14.

[cis-EN1] Example 14—analytical SFC: Chiralpak IC (250×4.6 mm 5 μm) 29.9° C., 3 g/min, 100 bar, 15% MeOH, Ret. Time 3.36 min; m/z=439.0 [M+H]$^+$; $^1$H NMR (CDCl$_3$): δ 9.91 (br s, 1H) 8.13 (s, 1H), 8.07 (d, 1H), 7.95-7.93 (m, 1H), 7.76-7.72 (t, 1H), 6.12-5.81 (m, 2H), 4.60-4.57 (m, 1H), 4.15-4.11 (m, 1H), 3.73-3.67 (m, 1H), 3.25-3.15 (m, 2H), 2.36-2.23 (m, 2H), 1.89-1.86 (d, 1H), 1.55-1.54 (m, 4H). NOE: On irradiating OCH proton NOE was observed with SCCH$_3$.

[cis-EN2] Example 14—analytical SFC: Chiralpak IC (250×4.6 mm 5 μm), 29.9° C., 3 g/min, 100 bar, 15% MeOH, Ret. Time 7.1 min; m/z=439.0 [M+H]$^+$; $^1$H NMR (CDCl$_3$): δ 9.91 (br s, 1H), 8.14 (s, 1H), 8.07 (d, 1H), 7.95-7.93 (m, 1H), 7.77-7.73 (t, 1H), 6.13-5.81 (m, 2H), 4.60-4.57 (m, 1H), 4.15-4.11 (m, 1H), 3.73-3.67 (m, 1H), 3.25-3.15 (m, 2H), 2.36-2.23 (m, 2H), 1.89-1.86 (d, 1H), 1.55-1.54 (m, 4H).

5-[4-Methyl-4-[[3-(trifluoromethyl)phenyl]sulfonyl]-tetrahydro-pyran-2-yl]-3-(2,2,2-trifluoro-ethyl)-1H-pyrazole (Example 15)

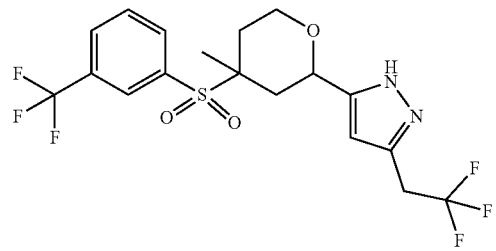 [SMILES: CC1(S(=O)(=O)c2cccc(C(F)(F)F)c2)CCOC(c2cc(CC(F)(F)F)n[nH]2)C1]

Synthesis of Example 15 was carried out as follows:

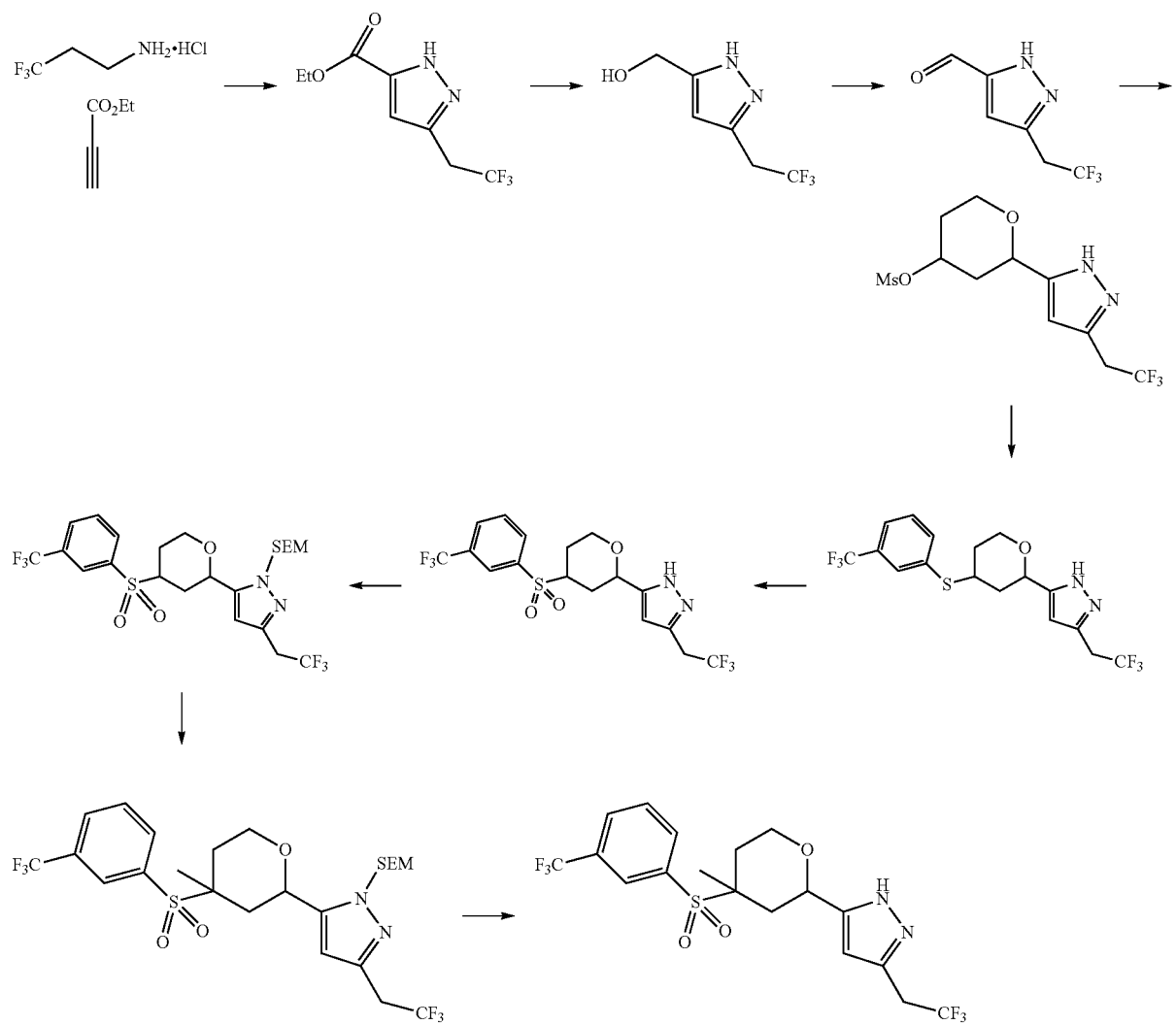

Step 1: Ethyl 3-(2,2,2-trifluoroethyl)-1H-pyrazole-5-carboxylate

To a solution of 3,3,3-trifluoropropan-1-amine hydrochloride (9.15 g, 61.22 mmol) in DCM (400 ml) at 0° C. were added aq. $NaNO_2$ solution (7.04 g, 102.04 mmol, in 20 ml of water) followed by ethyl propiolate (2.0 g, 20.40 mmol). The RM was slowly allowed to warm to RT and stirred for 72 h. Reaction conversion was monitored by LC-MS. Nitrogen gas was purged through the reaction mixture for 30 min. The RM was diluted with DCM (100 ml). The organic layer was washed with brine (200 ml), dried over anhydrous $Na_2SO_4$, filtered and the solvent evaporated under reduced pressure to give the title compound (2.1 g).

Step 2: (3-(2,2,2-Trifluoroethyl)-1H-pyrazol-5-yl)methanol

To a suspension of $LiAlH_4$ (1.74 g, 45.94 mmol) in dry THF (80 ml) at 0° C. was added dropwise a solution of ethyl 3-(2,2,2-trifluoroethyl)-1H-pyrazole-5-carboxylate (3.40 g, 15.31 mmol) in dry THF (30 ml). The RM was warmed to RT and stirred for 2 h. The RM was slowly quenched with aq. $Na_2SO_4$ solution (20 ml). The suspension was filtered and the filtrate was washed with EtOAc (100 ml). The organic layer was dried over anhydrous $Na_2SO_4$, filtered and the solvent evaporated under reduced pressure to give the crude product which was purified by column chromatography (silica-gel 100-200 mesh, 50% EtOAc in PE) to give the title compound (1.25 g, 21% over 2 steps).

Step 3: 3-(2,2,2-Trifluoroethyl)-1H-pyrazole-5-carbaldehyde

Activated $MnO_2$ (2.89 g, 33.33 mmol) was added to a stirred solution of (3-(2,2,2-trifluoroethyl)-1H-pyrazol-5-yl)methanol (1.0 g, 5.55 mmol) in 1,2-dimethoxyethane (40 ml) at RT and the mixture was refluxed for 16 h. The RM was filtered through celite and washed with DCM (100 ml). The filtrate was concentrated under reduced pressure to give the title compound (0.60 g).

Step 4: 2-(3-(2,2,2-Trifluoroethyl)-1H-pyrazol-5-yl)tetrahydro-2H-pyran-4-yl methanesulfonate Methanesulfonic acid (2.18 ml, 33.70 mmol) was added to a stirred solution of 3-(2,2,2-trifluoroethyl)-1H-pyrazole-5-carbaldehyde (0.60 g, 3.37 mmol) in DCM (20 ml) at 0° C. 3-Buten-1-ol (0.43 ml, 5.05 mmol) was added dropwise to the RM maintaining the same temperature. The RM was allowed to warm to RT and stirred for 16 h. The RM was diluted with DCM (50 ml). The organic layer was separated and washed with water (50 ml), aq. $NaHCO_3$ (50 ml) and brine (50 ml), then dried over anhydrous $Na_2SO_4$ and filtered. The organic layer was concentrated under reduced pressure to give the title compound (0.60 g).

Step 5: 3-(2,2,2-Trifluoroethyl)-5-(4-((3-(trifluoromethyl)phenyl)thio)tetrahydro-2H-pyran-2-yl)-1H-pyrazole 3-Trifloromethylthiophenol (0.49 ml, 3.65 mmol) was added to a suspension of $K_2CO_3$ (0.50 g, 3.65 mmol) and 2-(3-(2,2,2-trifluoroethyl)-1H-pyrazol-5-yl)tetrahydro-2H-pyran-4-yl methanesulfonate (0.60 g, 1.82 mmol) in DMF (10 ml). The RM was stirred at 55° C. for 6 h and further at RT for additional 6 h. The RM was allowed to cool to RT, diluted with water (50 ml) and the organic product was extracted with EtOAc (3×50 ml). The organic layer was washed with brine (50 ml), dried over anhydrous $Na_2SO_4$, filtered and the solvent evaporated under reduced pressure to give the crude product which was purified by column chromatography (silica gel 230-400 mesh, 30% EtOAc in PE) to give the title compound (0.48 g, 35% over 2 steps).

Step 6: 3-(2,2,2-Trifluoroethyl)-5-(4-((3-(trifluoromethyl)phenyl)sulfonyl)tetrahydro-2H-pyran-2-yl)-1H-pyrazole A solution of oxone (1.79 g, 2.92 mmol) in water (10 ml) was added to a stirred solution of 3-(2,2,2-trifluoroethyl)-5-(4-((3-(trifluoromethyl)phenylthio)tetrahydro-2H-pyran-2-yl)-1H-pyrazole (0.60 g, 1.46 mmol) in MeOH (20 ml) and the mixture was stirred at RT for 16 h. The RM was diluted with water (50 ml), and the organic product was extracted with EtOAc (2×50 ml). The combined organic layers were washed with brine (100 ml), dried over anhydrous $Na_2SO_4$, filtered and the solvent evaporated under reduced pressure to give the crude product, which was purified by column chromatography (silica gel 230-400 mesh, 40% EtOAc in PE) to give the title compound (0.50 g, 78%).

Step 7: 3-(2,2,2-Trifluoroethyl)-5-(4-((3-(trifluoromethyl)phenyl)sulfonyl)tetrahydro-2H-pyran-2-yl)-1-((2-(trimethylsilyl)ethoxy)methyl)-1H-pyrazole Sodium hydride (60% in mineral oil) (0.13 g, 3.39 mmol) was added to a stirred solution of 3-(2,2,2-trifluoroethyl)-5-(4-((3-(trifluoromethyl)phenyl)sulfonyl)tetrahydro-2H-pyran-2-yl)-1H-pyrazole (0.50 g, 1.13 mmol) in THF (10 ml) at 0° C. and the mixture was then stirred for 30 min. 2-(Trimethylsilyl)ethoxymethyl chloride (0.23 ml, 1.35 mmol) was added to the RM at 0° C. The mixture was slowly warmed to RT and stirred for 16 h. The RM was diluted with water (50 ml); and the organic product was extracted with EtOAc (2×50 ml). The combined organic layers were washed with brine, dried over anhydrous $Na_2SO_4$, filtered and the solvent evaporated under reduced pressure to give the crude product which was purified by column chromatography (silica gel 230-400 mesh, 15-20% EtOAc in PE) to give the title compound (0.50 g).

Step 8: 5-(4-Methyl-4-((3-(trifluoromethyl)phenyl)sulfonyl)tetrahydro-2H-pyran-2-yl)-3-(2,2,2-trifluoroethyl)-1-((2-(trimethylsilyl)ethoxy)methyl)-1H-pyrazole Potassium tert-butoxide (1.74 ml, 1.74 mmol, 1M in THF) was added to a stirred solution of 3-(2,2,2-trifluoroethyl)-5-(4-((3-(trifluoromethyl)phenyl)sulfonyl)tetrahydro-2H-pyran-2-yl)-1-((2-(trimethylsilyl)ethoxy)methyl)-1H-pyrazole (0.50 g, 0.87 mmol) in THF (10 ml) at −78° C. The mixture was then stirred for 30 min. Methyl iodide (0.13 ml, 2.18 mmol) was added to the RM and it was slowly warmed to RT and stirred for 16 h. The RM was diluted with water (50 ml). The organic product was extracted with EtOAc (2×50 ml). The combined organic layers were washed with brine, dried over anhydrous $Na_2SO_4$, filtered and the solvent evaporated under reduced pressure to give the crude product which was purified by column chromatography (silica gel 230-400 mesh, 20% EtOAc in PE) to give the title compound (0.35 g).

Step 9: [cis-rac] 5-[4-Methyl-4-[[3-(trifluoromethyl) phenyl]sulfonyl]-tetrahydro-pyran-2-yl]-3-(2,2,2-trifluoro-ethyl)-1H-pyrazole (Example 15)

5-(4-Methyl-4-((3-(trifluoro methyl)phenyl)sulfonyl)tetrahydro-2H-pyran-2-yl)-3-(2,2,2-trifluoroethyl)-1-((2-(trimethylsilyl)ethoxy)methyl)-1H-pyrazole (0.35 g, 0.59 mmol) was dissolved in TFA-DCM (1:1 v/v) (5:5 ml) at 0° C. The RM was stirred at RT for 2 h. The mixture was cooled to 0° C., diluted with aq. NaHCO₃ (pH ~8) and extracted with DCM (3×30 ml). The combined organic extract was washed with brine (30 ml), dried over anhydrous Na₂SO₄ and the solvent was concentrated under reduced pressure. The crude product was purified by prep-HPLC (LUNA-PHENYL-HEXYL-C18, 0.01M Ammonium bicarbonate in water:acetonitrile; 0/50→12/50) to obtain the title compound (0.036 g, 7% over 3 steps). TLC system: EtOAc-PE; 7:3; $R_f$: 0.3.

[cis-rac] Example 15—m/z=457.1 [M+H]⁺; ¹H NMR (CDCl₃): δ 9.98 (br s, 1H), 8.14 (s, 1H), 8.07 (d, 1H), 7.95 (d, 1H), 7.75 (t, 1H), 6.15 (s, 1H), 4.63-4.59 (m, 1H), 4.16-4.12 (m, 1H), 3.73-3.67 (m, 1H), 3.50-3.42 (m, 2H), 2.36-2.22 (m, 2H), 1.90 (d, 1H), 1.56-1.52 (m, 4H). NOE: On irradiating OCH proton NOE was observed with SCCH₃.

5-[4-Methyl-4-[[3-(trifluoromethyl)phenyl]sulfonyl]-tetrahydro-pyran-2-yl]-3-(2,2,2-trifluoro-ethoxy)-1H-pyrazole (Example 16)

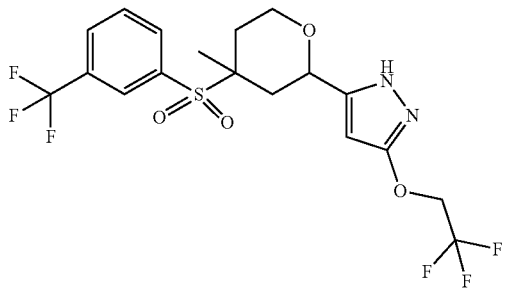 [SMILES: CC1(S(=O)(=O)c2cccc(C(F)(F)F)c2)CCOC(c2cc(OCC(F)(F)F)n[nH]2)C1]

Synthesis of Example 16 was carried out as follows:

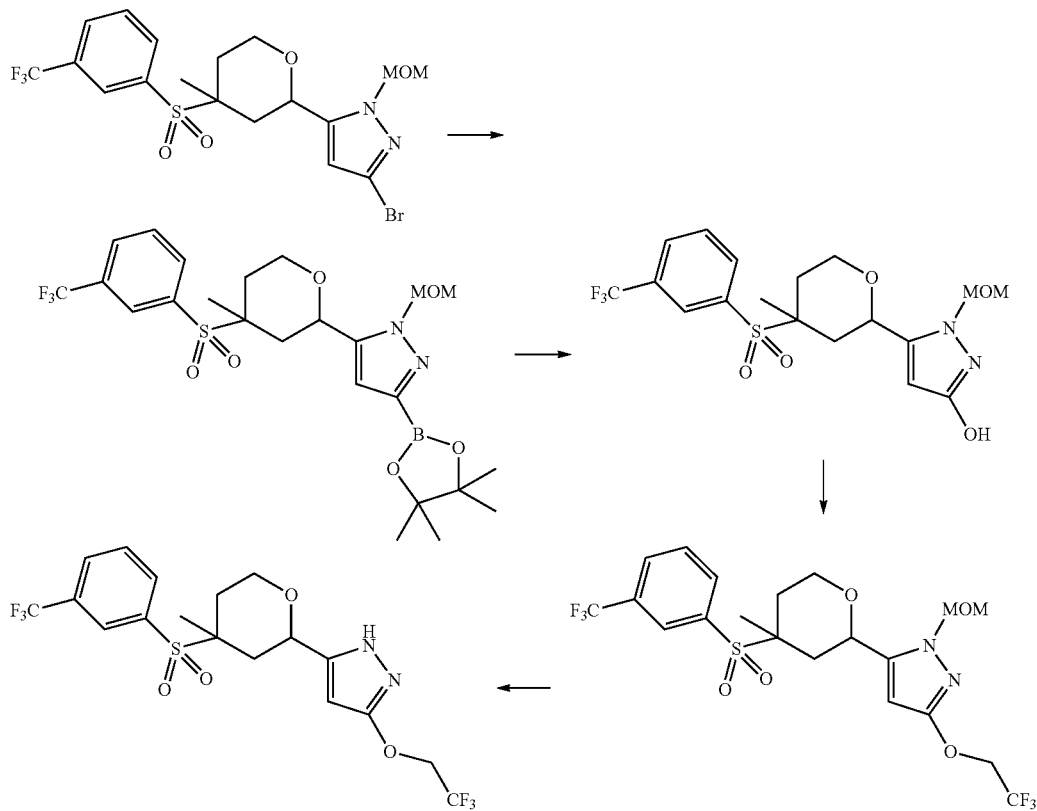

Step 1: [cis-rac] 1-(Methoxymethyl)-5-(4-methyl-4-((3-(trifluoromethyl)phenyl)sulfonyl)tetrahydro-2H-pyran-2-yl)-3-(4,4,5,5-tetramethyl-1,3,2-dioxaborolan-2-yl)-1H-pyrazole A solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (2.0 g, 4.03 mmol), potassium acetate (1.18 g, 12.09 mmol) and bis(pinacolato)diboron (5.09 g, 20.15 mmol) in DMF (40 ml) was degassed for 10 min. To the RM was added Pd₂(dppf)Cl₂ (0.49 mg, 0.60 mmol) and it was degassed again for 10 min. The resulting mixture was heated at 120°

C. for 48 h under argon. The RM was cooled to RT and filtered through a celite bed. The filtrate was concentrated under reduced pressure and the residue was diluted with water (100 ml). The organic product was extracted with EtOAc (2×100 ml). The combined organic extracts were washed with water (2×100 ml) and brine (100 ml), and dried over anhydrous Na₂SO₄. The organic layer was filtered and the solvent was concentrated under reduced pressure to afford the title compound (3.0 g).

Step 2: [cis-rac] 1-(Methoxymethyl)-5-(4-methyl-4-((3-(trifluoromethyl)phenyl)sulfonyl)tetrahydro-2H-pyran-2-yl)-1H-pyrazol-3-ol To a stirred solution of [cis-rac] 1-(methoxymethyl)-5-(4-methyl-4-((3-(trifluoromethyl)phenyl)sulfonyl)tetrahydro-2H-pyran-2-yl)-3-(4,4,5,5-tetramethyl-1,3,2-dioxaborolan-2-yl)-1H-pyrazole (3.0 g, 5.51 mmol), in THF (75 ml) at 10° C. were added aq. sodium hydroxide (1.10 g, 27.57 mmol in 12.5 m water), followed by dropwise addition of 30% aq. hydrogen peroxide solution (3.12 ml, 27.57 mmol). The mixture was then stirred at RT for another 16 h. The RM was diluted with water (50 ml) and acidified to pH ~3-4 with 1N aq. HCl. The organic product was extracted with EtOAc (3×75 ml). The combined organic extracts were washed with water (2×50 ml) and brine (100 ml), and dried over anhydrous Na₂SO₄. The organic layer was filtered and the solvent was concentrated under reduced pressure. The crude product was purified by short column chromatography (silica gel 100-200 mesh, 0-5% MeOH in DCM) to give the title compound (0.85 g).

Step 3: [cis-rac] 1-(Methoxymethyl)-5-(4-methyl-4-((3-(trifluoromethyl)phenyl)sulfonyl)tetrahydro-2H-pyran-2-yl)-3-(2,2,2-trifluoroethoxy)-1H-pyrazole To a stirred solution of [cis-rac] 1-(methoxymethyl)-5-(4-methyl-4-((3-(trifluoromethyl)phenyl)sulfonyl)tetrahydro-2H-pyran-2-yl)-1H-pyrazol-3-ol (0.40 g, 0.921 mmol) in DMF (20 ml) were added K₂CO₃ (0.38 g, 2.76 mmol), followed by 2,2,2-trifluoroethyl trifluoromethanesulfonate (0.26 ml, 1.84 mmol). The RM was heated to 70° C. under stirring conditions for 6 h. The RM was concentrated under reduced pressure and the residue was diluted with water (70 ml). The organic product was extracted with EtOAc (3×50 ml). The combined organic layers were washed with water (2×50 ml) and brine (3×50 ml), and dried over anhydrous Na₂SO₄. The organic layer was filtered and the solvent was concentrated under reduced pressure. The crude product was purified by column chromatography (silica gel 100-200 mesh, 0-50% EtOAc in PE) to give the title compound (0.20 g, 42%).

Step 4: [cis-rac] 5-[4-Methyl-4-[[3-(trifluoromethyl)phenyl]sulfonyl]-tetrahydro-pyran-2-yl]-3-(2,2,2-trifluoro-ethoxy)-1H-pyrazole (Example 16)

4N HCl in dioxane (10.0 ml) was added to a solution of [cis-rac] 1-(methoxymethyl)-5-(4-methyl-4-((3-(trifluoromethyl)phenyl)sulfonyltetrahydro-2H-pyran-2-yl)-3-(2,2,2-trifluoroethoxy)-1H-pyrazole (0.20 g, 0.38 mmol) in EtOH (5 ml) and the resulting RM was heated to 60° C. under stirring conditions for 16 h. The RM was concentrated under reduced pressure and the residue was diluted with water. The RM was cooled to 0° C. and sat. aq. NaHCO₃ solution (15 ml) was added. The organic product was extracted with EtOAc (2×25 ml). The combined organic layers were washed with water (2×10 ml) and brine (20 ml), and dried over anhydrous Na₂SO₄. The organic layer was filtered and the solvent was concentrated under reduced pressure to afford the crude product, which was purified by column chromatography (silica gel 60-120 mesh, 0-5% MeOH in DCM) to give the title compound (0.15 g, 82%). TLC system: EtOAc-pet ether; 5:5; Rf: 0.2.

[cis-rac] Example 16—NOE was observed between OCH and SCCH₃ proton.

[Cis-rac] 5-[4-Methyl-4-[[3-(trifluoromethyl)phenyl]sulfonyl]-tetrahydro-pyran-2-yl]-3-(2,2,2-trifluoro-ethoxy)-1H-pyrazole was subjected to chiral prep-SFC purification to give 50 mg of [cis-EN1] Example 16 and 52 mg of [cis-EN2] Example 16.

[cis-EN1] Example 16—analytical SFC: Lux Amylose-2 (250×4.6 mm 5 μm) 30.1° C., 3 g/min, 100 bar, 35% MeOH, Ret. Time 2.05 min; m/z=473.0 [M+H]⁺; ¹H NMR (CDCl₃): δ 9.35 (br s, 1H), 8.13 (s, 1H), 8.07-8.05 (d, 1H), 7.97-7.95 (d, 1H), 7.75 (t, 1H), 5.58 (s, 1H), 4.59-4.52 (m, 3H), 4.16-4.12 (m, 1H), 3.71-3.65 (m, 1H), 2.35-2.27 (m, 1H), 2.19 (t, 1H), 1.85-1.82 (m, 1H), 1.56 (s, 4H).

[cis-EN2] Example 16—analytical SFC: Lux Amylose-2 (250×4.6 mm 5 μm), 30° C., 3 g/min, 100 bar, 35% MeOH, Ret. Time 3.62 min; m/z=473.0 [M+H]⁺; ¹H NMR (CDCl₃): δ 9.31 (br s, 1H), 8.13 (s, 1H), 8.07-8.05 (d, 1H), 7.97-7.95 (d, 1H), 7.75 (t, 1H), 5.58 (s, 1H), 4.59-4.52 (m, 3H), 4.16-4.12 (q, 1H), 3.71-3.65 (t, 1H), 2.35-2.27 (m, 1H), 2.19 (t, 1H), 1.85-1.82 (m, 1H), 1.57-1.53 (s, 4H).

3-[5-[4-Methyl-4-[[3-(trifluoromethyl)phenyl]sulfonyl]-tetrahydro-pyran-2-yl]-1H-pyrazol-3-yl]-oxetan-3-61 (Example 18)

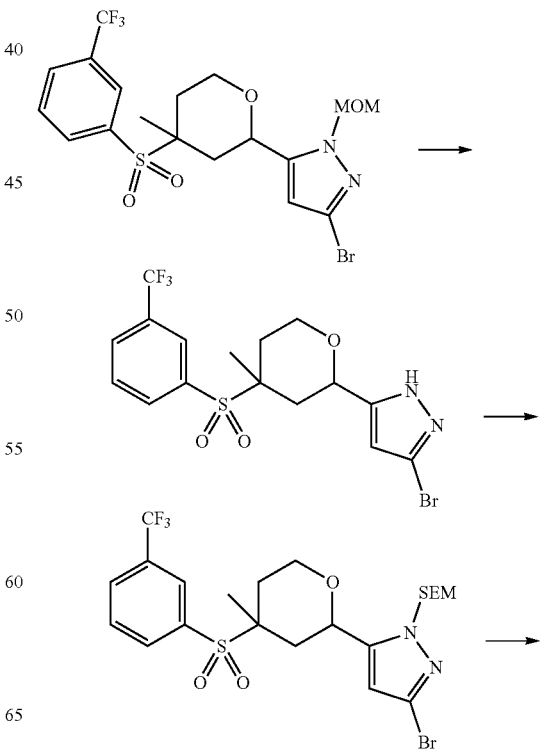

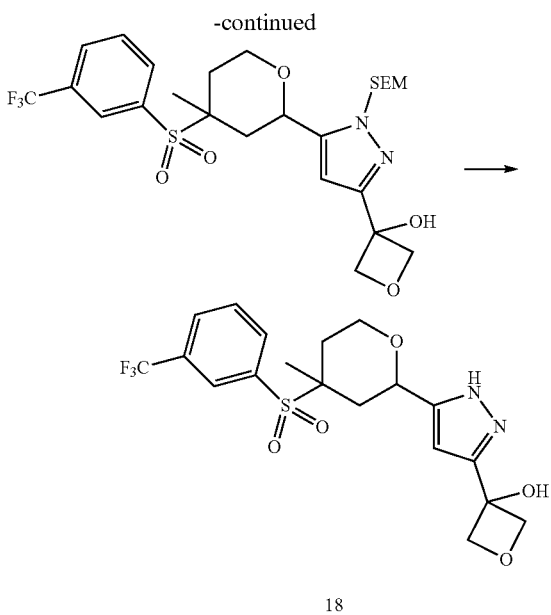

18

Step 1: 3-bromo-5-(4-methyl-4-(3-(trifluoromethyl) phenylsulfonyl)tetrahydro-2H-pyran-2-yl)-1H-pyrazole Dioxane.HCl solution (40.0 mL, 4 M solution in dioxane) was added to a solution of 3-bromo-1-(methoxymethyl)-5-(4-methyl-4-((3-(trifluoromethyl)phenyl)sulfonyl)tetrahydro-2H-pyran-2-yl)-1H-pyrazole (2.0 g, 4.03 mmol) in EtOH (20 mL) and the resulting reaction mixture was heated to 60° C. under stirring condition for 4 h. The reaction mixture was concentrated under reduced pressure and the residue was diluted with water. The reaction mixture was cooled to 0° C., added sat. aq. NaHCO$_3$ solution (100 mL) and the organic product was extracted with EtOAc (2×50 mL). The combined organic layer was washed with water (2×50 mL), brine (50 mL), dried over anhydrous Na$_2$SO$_4$, The organic layer was filtered and solvent was concentrated under reduced pressure to give 1.50 g (83%) of 3-bromo-5-(4-methyl-4-(3-(trifluoro-methyl)phenyl)sulfonyl)tetrahydro-2H-pyran-2-yl)-1H-pyrazole as yellowish gummy solid.

Step 2: 3-bromo-5-(4-methyl-4-(3-(trifluoromethyl) phenylsulfonyl)tetrahydro-2H-pyran-2-yl)-1-((2-(trimethylsilyl)ethoxy)methyl)-1H-pyrazole Sodium hydride (60% in mineral oil) (0.23 g, 9.95 mmol) was added to a stirred solution of 3-bromo-5-(4-methyl-4-(3-(trifluoromethyl)phenyl)sulfonyl)tetrahydro-2H-pyran-2-yl)-1H-pyrazole (1.50 g, 3.31 mmol) in THF (10 mL) at 0° C. and stirred for 30 min. 2-(trimethylsilyl)ethoxymethyl-chloride (0.70 mL, 3.98 mmol) was added to the reaction mixture at 0° C. and slowly warmed to rt and stirred for 16 h. The reaction mixture was diluted with water (20 mL); the organic product was extracted with EtOAc (3×20 mL). The combined organic layer was washed with brine, dried over anhydrous Na$_2$SO$_4$, filtered and evaporated the solvent under reduced pressure to give crude which was purified by column chromatography (silica gel 100-200 mesh, 15-20%) EtOAc in PE as eluent) to give 3-bromo-5-(4-methyl-4-(3-(trifluoromethyl)-phenylsulfonyl) tetrahydro-2H-pyran-2-yl)-1-((2-(trimethylsilyl)ethoxy)methyl)-1H-pyrazole (1.70 g, 88%) as white solid.

Step 3: 3-(5-(4-methyl-4-(3-(trifluoromethyl)phenylsulfonyl)tetrahydro-2H-pyran-2-yl)-1-((2-(trimethylsilyl)ethoxy)methyl)-1H-pyrazol-3-yl)oxetan-3-ol n-BuLi (2.5M in hexane) (0.82 mL, 2.06 mmol) was added to a solution of 3-bromo-5-(4-methyl-4-(3-(trifluoromethyl)phenyl)sulfonyl)tetrahydro-2H-pyran-2-yl)-1-((2-(trimethylsilyl)ethoxy)methyl)-1H-pyrazole (1.0 g, 1.71 mmol) in THF (10.0 mL) at −78° C. and stirred for 10 min. To the reaction mixture was added 3-oxetanone (2.0 mL, 34.36 mmol) at −78° C., slowly warmed to rt and stirred for 4 h. The reaction mixture was again cooled to 0° C. and quenched with sat. NH$_4$Cl solution and the organic product was extracted with EtOAc (2×20 mL). The combined organic layer was washed with water, followed by brine, dried over anhydrous Na$_2$SO$_4$, filtered and evaporated the solvent under vacuo to give crude, which was purified by column chromatography (silica gel 100-200 mesh, 0-60% EtOAc in PE as eluent) to get 3-(5-(4-methyl-4-(3-(trifluoromethyl) phenyl)sulfonyl)tetrahydro-2H-pyran-2-yl)-1-((2-(trimethylsilyl)ethoxy)methyl)-1H-pyrazol-3-yl)oxetan-3-ol (0.52 g, 52%) as yellow gummy solid (TLC system EtOAc-PE, 6:4; Rf: 0.28).

Step 4: 3-[5-[4-Methyl-4-[[3-(trifluoromethyl)phenyl]sulfonyl]-tetrahydro-pyran-2-yl]-1H-pyrazol-3-yl]-oxetan-3-ol TFA (1.0 mL) was added to a solution of 3-(5-(4-methyl-4-(3-(trifluoromethyl) phenylsulfonyl)tetrahydro-2H-pyran-2-yl)-1-((2-(trimethylsilyl)ethoxy)methyl)-1H-pyrazol-3-yl) oxetan-3-ol (0.52 g, 0.90 mmol) in DCM (10 mL) at 0° C. The reaction mixture was stirred at RT for 4 h. Reaction mixture was concentrated under reduced pressure; the residue was diluted with aq. NaHCO$_3$ (pH ~8) and the organic product was extracted with DCM (3×20 mL). The combined organic extracts were washed with brine (20 mL), dried over anhydrous Na$_2$SO$_4$, filtered and solvent was concentrated under reduced pressure to get crude. The crude compound was purified by preparative HPLC to obtain 3-(5-(4-methyl-4-(3-(trifluoromethyl)phenyl-sulfonyl)tetrahydro-2H-pyran-2-yl)-1H-pyrazol-3-yl)oxetan-3-ol (0.09 g, 22%) as a solid. (TLC system: EtOAc-PE; 3:7; Rf: 0.30)

[cis-rac] Example 18—m/z=447.1

[Cis-rac] 3-[5-[4-M ethyl-4-[[3-(trifluoro methyl)phenyl] sulfonyl]-tetrahydro-pyran-2-yl]-1H-pyrazol-3-yl]-oxetan-3-ol was subjected to chiral prep-SFC purification to give of [cis-EN1] Example 18 and [cis-EN2] Example 18.

[cis-EN1] Example 18—analytical SFC: Chiralpak IC (250×4.6 mm 5 μm) 29.9° C., 3 g/min, 100 bar, 30% MeOH, Ret. Time 2.83 min; m/z=447.0 [M+H]$^+$; $^1$H NMR (CDCl$_3$): δ 8.14 (s, 1H), 8.08 (d, 1H), 7.96 (d, 1H), 7.76 (t, 1H), 6.37 (s, 1H), 4.91-4.89 (m, 2H), 4.83-4.81 (m, 2H), 4.64 (d, 1H), 4.17-4.13 (m, 1H), 3.74-3.69 (m, 1H), 2.37-2.27 (m, 2H), 1.92 (m, 1H), 1.55 (m, 4H).

[cis-EN2] Example 18—analytical SFC: Chiralpak IC (250×4.6 mm 5 μm) 29.9° C., 3 g/min, 100 bar, 30% MeOH, Ret. Time 4.95 min; m/z=447.0 [M+H]$^+$; $^1$H NMR (CDCl$_3$): δ 8.14 (s, 1H), 8.08 (d, 1H), 7.96 (d, 1H), 7.76 (t, 1H), 6.37 (s, 1H), 4.91-4.89 (m, 2H), 4.83-4.81 (m, 2H), 4.64 (d, 1H), 4.16-4.13 (m, 1H), 3.75-3.69 (m, 1H), 2.37-2.27 (m, 2H), 1.92 (m, 1H), 1.55 (m, 4H).

2-[5-[4-Methyl-4-[[3-(trifluoromethyl)phenyl]sulfonyl]-tetrahydro-pyran-2-yl]-1H-pyrazol-3-yl]-propan-2-ol (Example 19)

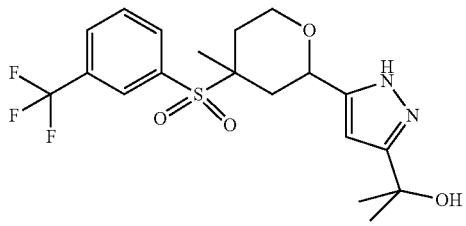 [SMILES: CC(C)(O)c1cc(C2CC(C)(S(=O)(=O)c3cccc(C(F)(F)F)c3)CCO2)[nH]n1]

Synthesis of Example 19 was carried out as follows:

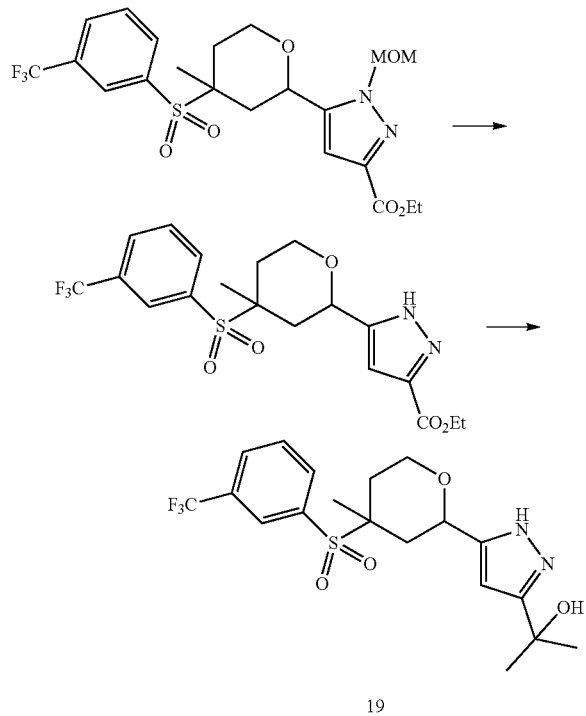

Step 1: [cis-rac] Ethyl 5-(4-methyl-4-((3-(trifluoromethyl)phenyl)sulfonyl)tetrahydro-2H-pyran-2-yl)-1H-pyrazole-3-carboxylate HCl in dioxane solution (5.0 ml, 4M solution) was added to a solution of ethyl 1-(methoxymethyl)-5-(4-methyl-4-(3-(trifluoromethyl)phenyl)sulfonyl)tetrahydro-2H-pyran-2-yl)-1H-pyrazole-3-carboxylate [Example 7, step 1] (400 mg, 0.89 mmol) in EtOH (15 ml) and the resulting RM was heated to 60° C. under stirring conditions for 3 h. The RM was concentrated under reduced pressure and the residue was diluted with water. The RM was cooled to 0° C., sat. aq. NaHCO$_3$ solution (10 ml) was added and the organic product was extracted with EtOAc (2×25 ml). The combined organic extracts were washed with water (2×10 ml) and brine (25 ml), and dried over anhydrous Na$_2$SO$_4$. The organic layer was filtered and the solvent was concentrated under reduced pressure to afford the title compound (320 mg, 88%).

Step 2: [cis-rac] 2-[5-[4-Methyl-4-[[3-(trifluoromethyl)phenyl]sulfonyl]-tetrahydro-pyran-2-yl]-1H-pyrazol-3-yl]-propan-2-ol (Example 19)

To a stirred solution of [cis-rac] ethyl 5-(4-methyl-4-((3-(trifluoromethyl)phenyl)sulfonyl)tetrahydro-2H-pyran-2-yl)-1H-pyrazole-3-carboxylate (0.32 g, 0.71 mmol) in THF (5 ml) at 0° C. was added dropwise methylmagnesium bromide (0.71 ml, 2.15 mmol, 3.0 M in Et$_2$O). The resulting RM was stirred at RT for 1 h and then additional methylmagnesium bromide (0.5 ml, 0.62 mmol, 3.0 M in Et$_2$O) was added. The RM was stirred for 17 h at RT. The RM was quenched with sat. aq. NH$_4$Cl (60 ml). The organic product was extracted with EtOAc (2×20 ml). The combined organic extracts were washed with water (2×20 ml) and brine (20 ml), and dried over anhydrous Na$_2$SO$_4$. The organic layer was filtered and the solvent was concentrated under reduced pressure to give the crude product, which was purified by prep TLC to afford the title compound (120 mg, 38%). TLC system: EtOAc-PE; 1:1; Rf: 0.2.

[cis-rac] Example 19—NOE was observed between OCH and SCCH$_3$ proton.

[Cis-rac] 2-[5-[4-methyl-4-[[3-(trifluoromethyl)phenyl]sulfonyl]-tetrahydro-pyran-2-yl]-1H-pyrazol-3-yl]-propan-2-ol was subjected to chiral prep-SFC purification to give 30 mg of [cis-EN1] Example 19 and 40 mg of [cis-EN2] Example 19.

[cis-EN1] Example 19—analytical SFC: Chiralpak AD-H (250×4.6 mm 5 μm) 29.9° C., 4 g/min, 100 bar, 40% MeOH, Ret. Time 3.27 min; m/z=433.1 [M+H]$^+$; $^1$H NMR (CDCl$_3$): δ 10.00 (br s, 1H), 8.14-8.07 (m, 2H), 7.95-7.93 (m, 1H), 7.75 (t, 1H), 6.08 (s, 1H), 4.59-4.57 (m, 1H), 4.15-4.10 (m, 1H), 3.74-3.68 (m, 1H), 2.37-2.28 (m, 2H), 2.03 (br s, 1H), 1.89-1.86 (m, 1H), 1.59-1.54 (m, 10H).

[cis-EN2] Example 19—analytical SFC: Chiralpak AD-H (250×4.6 mm 5 μm), 29.9° C., 4 g/min, 100 bar, 40% MeOH, Ret. Time 4.98 min; m/z=433.0 [M+H]$^+$; $^1$H NMR (CDCl$_3$): δ 10.00 (br s, 1H), 8.14-8.07 (m, 2H), 7.95-7.93 (m, 1H), 7.74 (t, 1H), 6.08 (s, 1H), 4.59-4.57 (m, 1H), 4.15-4.10 (m, 1H), 3.74-3.68 (m, 1H), 2.37-2.28 (m, 2H), 2.08 (br s, 1H), 1.89-1.86 (m, 1H), 1.59-1.54 (m, 10H).

3-(Trifluoro-methylsulfonyl)-5-[4-methyl-4-[[3-(trifluoromethyl)phenyl]sulfonyl]-tetrahydro-pyran-2-yl]-1H-pyrazole (Example 27)

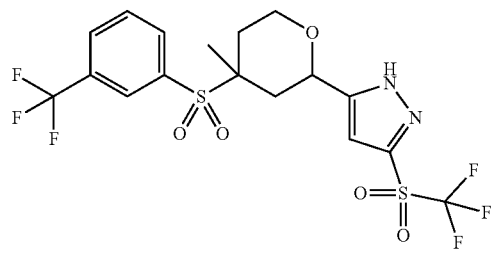 [SMILES: CC1(S(=O)(=O)c2cccc(C(F)(F)F)c2)CCOC(c2cc(S(=O)(=O)C(F)(F)F)n[nH]2)C1]

Step 10: [cis-rac] 1-Benzyl-5-(4-methyl-4-((3-(trifluoromethyl)phenyl)sulfonyl)tetrahydro-2H-pyran-2-yl)-3-((trifluoromethyl)thio)-1H-pyrazole To a solution of [cis-rac] 1-benzyl-5-(4-methyl-4-((3-(trifluoromethyl)phenyl)sulfonyl)tetrahydro-2H-pyran-2-yl)-1H-pyrazole-3-thiol [see step 9 above, Example 1] (1.8 g, 3.62 mmol, 1.0 eq) in DMF (18 ml), was added NaH (191 mg, 7.96 mmol, 2.2 eq) at 0° C. Then, CF$_3$I gas was bubbled through for 30 min. The RM was stirred under CF$_3$I gas atmosphere at RT for 12 h. The reaction was monitored by the TLC. It was quenched with water, extracted with EtOAc (50 ml), washed with brine (25 ml), dried (Na$_2$SO$_4$), filtered and concentrated under reduced pressure. The residue was purified by flash column chromatography (30% EtOAc in PE) to afford the title product (0.7 g, 45% over two steps).

Step 11: [cis-rac] 1-Benzyl-5-(4-methyl-4-((3-(trifluoromethyl)phenyl)sulfonyl)tetrahydro-2H-pyran-2-yl)-3-((trifluoromethyl)sulfonyl)-1H-pyrazole To a stirred solution of [cis-rac] 1-benzyl-5-(4-methyl-4-((3-(trifluoromethyl)phenyl)sulfonyl)tetrahydro-2H-pyran-2-yl)-3-((trifluoromethyl)thio)-1H-pyrazole (1.4 g, 2.48 mmol, 1.0 eq) in CHCl$_3$ (15 ml), was added mCPBA (1.72 g, 9.92 mmol, 4 eq) at 0° C. and stirred at RT for 18 h. The RM was quenched with sat. aq. NaHCO$_3$ (40 ml) at 0° C., and extracted with EtOAc (2×50 ml). The combined organic layers were washed with water (20 ml) and brine (30 ml), dried over anhydrous Na$_2$SO$_4$, filtered and concentrated under reduced pressure. The residue upon purification by flash chromatography (basic alumina, 30% EtOAc in PE) afforded the title product (1 g, 68%).

Step 12: [cis-rac] 3-(Trifluoro-methylsulfonyl)-5-[4-methyl-4-[[3-(trifluoromethyl)phenyl]sulfonyl]-tetrahydro-pyran-2-yl]-1H-pyrazole (Example 27)

A mixture of [cis-rac] 1-benzyl-5-(4-methyl-4-((3-(trifluoromethyl)phenyl)sulfonyl)tetrahydro-2H-pyran-2-yl)-3-((trifluoromethyl)sulfonyl)-1H-pyrazole (2 g, 3.37 mmol, 1.0 eq) and HBr in acetic acid (33%, 300 ml) was stirred at 120° C. for 96 h. The progress was monitored by the TLC. The RM was basified with aq. NaHCO$_3$ solution at 0° C., and extracted with EtOAc (2×100 ml). The combined organic layers were washed with water (50 ml) and brine (50 ml), dried (Na$_2$SO$_4$), filtered and concentrated under reduced pressure. The residue upon purification by flash chromatography (silica gel, 40% EtOAc in PE), afforded the title product (330 mg, 20%). TLC system: EtOAc-PE; 1:1; Rf: 0.2.

[Cis-rac] 3-(trifluoro-methylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give 82 mg of [cis-EN1] Example 27 and 86 mg of [cis-EN2] Example 27.

[cis-EN1] Example 27—analytical SFC: LuxCellulose-2 (250×4.6 mm 5 µm) 29.9° C., 3 g/min, 100 bar, 20% MeOH, Ret. Time 3.27 min; m/z=507.0 [M+H]$^+$; $^1$H NMR (500 MHz, DMSO-d$_6$): δ 1.46 (s, 3H), 1.52 (d, 1H), 1.90 (d, 1H), 2.09-2.14 (m, 2H), 3.75 (t, 1H), 4.04 (dd, 1H), 4.81 (d, 1H), 7.18 (s, 1H), 7.96 (t, 1H), 8.10 (s, 1H), 8.22 (d, 2H), 14.78 (b s, 1H)

[cis-EN2] Example 27—analytical SFC: LuxCellulose-2 (250×4.6 mm 5 µm) 29.9° C., 3 g/min, 100 bar, 20% MeOH, Ret. Time 4.36 min; m/z=507.0 [M+H]$^+$; $^1$H NMR (500 MHz, DMSO-d$_6$): δ 1.47 (s, 3H), 1.52 (d, 1H), 1.90 (d, 1H), 2.08-2.14 (m, 2H), 3.74 (t, 1H), 4.04 (dd, 1H), 4.81 (d, 1H), 7.19 (s, 1H), 7.96 (t, 1H), 8.10 (s, 1H), 8.22 (d, 2H), 14.81 (s, 1H). NOE: On irradiating OCH proton NOE was observed with SCCH$_3$.

3-[(Difluoro-methylsulfonyl)-methyl]-5-[4-methyl-4-[[3-(trifluoromethyl)phenyl]sulfonyl]-tetrahydropyran-2-yl]-1H-pyrazole (Example 28)

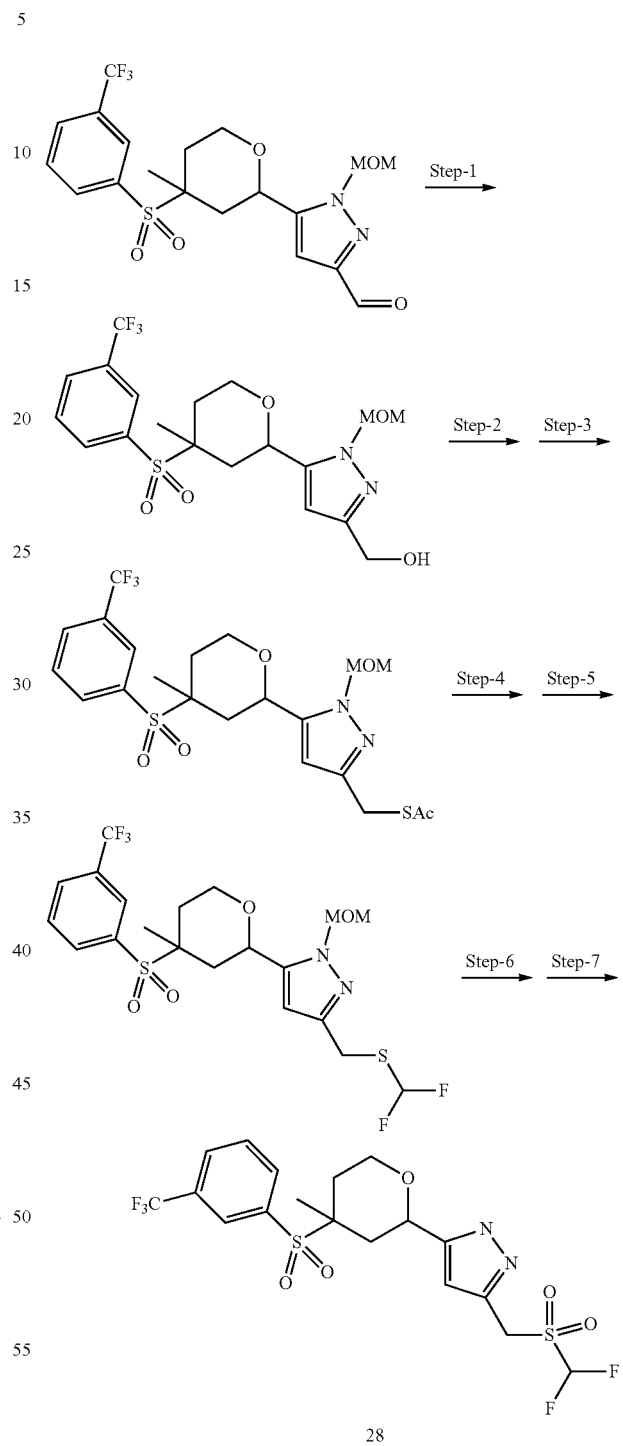

28

Step 1: (1-(methoxymethyl)-5-(4-methyl-4-(3-(trifluoromethyl) phenylsulfonyl)tetrahydro-2H-pyran-2-yl)-1H-pyrazol-3-yl) methanol Sodium borohydride (0.116 g, 3.13 mmol) was added portion wise at 0° C. to a solution of 1-(methoxymethyl)-

5-(4-methyl-4-((3-(trifluoromethyl)phenyl)sulfonyl)tetrahydro-2H-pyran-2-yl)-1H-pyrazole-3-carbaldehyde (1.4 g, 3.13 mmol) in MeOH (15 mL). The resulting mixture was stirred at rt for 1 h under Ar. Reaction was monitored by TLC. After completion of starting material, the reaction mixture was quenched with ice cold water and the organic product was extracted with EtOAc. The organic layer was dried over anhydrous $Na_2SO_4$ and solvent was concentrated under reduced pressure to obtain (1-(methoxymethyl)-5-(4-methyl-4-(3-(trifluoromethyl) phenylsulfonyl) tetrahydro-2H-pyran-2-yl)-1H-pyrazol-3-yl)methanol (1.0 g, 71.5%) as solid. (TLC system: EtOAc-PE; 7:3; Rf: 0.2).

Step 2: (1-(methoxymethyl)-5-(4-methyl-4-(3-(trifluoromethyl) phenylsulfonyl) tetrahydro-2H-pyran-2-yl)-1H-pyrazol-3-yl) methyl methanesulfonate TEA (0.75 mL, 5.357 mmol) was added to a stirred solution of (1-(methoxymethyl)-5-(4-methyl-4-(3-(trifluoromethyl) phenylsulfonyl)-tetrahydro-2H-pyran-2-yl)-1H-pyrazol-3-ylmethanol (0.80 g, 1.783 mmol) in DCM (10 mL) at 0° C. To the reaction mixture was added methanesulfonyl chloride (0.22 mL, 2.678 mmol) at the same temperature. The reaction mixture was slowly warmed to rt and stirred for 1 h. The reaction mixture was diluted with water (200 mL); the organic product was extracted with DCM (2×20 mL). The combined organic extracts were washed with brine, dried over anhydrous $Na_2SO_4$, filtered and evaporated the solvent under reduced pressure to give crude (1-(methoxymethyl)-5-(4-methyl-4-(3-(trifluoromethyl) phenylsulfonyl) tetrahydro-2H-pyran-2-yl)-1H-pyrazol-3-yl) methyl methanesulfonate (0.8 g, crude) as a sticky liquid. Crude product was taken immediately for the next step. (TLC system: 1:1 EtOAc in PE; Rf: 0.4).

Step 3: S-(1-(methoxymethyl)-5-(4-methyl-4-(3-(trifluoromethyl) phenylsulfonyl) tetrahydro-2H-pyran-2-yl)-1H-pyrazol-3-yl)methyl ethanethioate Potassium thioacetate (0.367 g, 2.737 mmol) was added to a solution (1-(methoxymethyl)-5-(4-methyl-4-(3-(trifluoromethyl) phenylsulfonyl) tetrahydro-2H-pyran-2-yl)-1H-pyrazol-3-yl) methyl methanesulfonate (0.8 g, 1.519 mmol) in DMF (10 mL) at 0° C. and slowly warmed to RT and stirred further for 2 h. The reaction mixture was diluted with water and the organic product was extracted with EtOAc. The organic layer was washed with brine (50 mL) and then dried over anhydrous $Na_2SO_4$. The organic layer was filtered and solvent was concentrated under reduced pressure to afford crude product, which was purified by flash column chromatography (silica gel 230-400 mesh, 20-40% EtOAc in PE as eluent) to get 0.5 g (65%) of S-(1-(methoxymethyl)-5-(4-methyl-4-(3-(trifluoromethyl) phenylsulfonyl)tetrahydro-2H-pyran-2-yl)-1H-pyrazol-3-yl) methyl ethanethioate (TLC system: EtOAc-PE; 4:6; Rf: 0.4).

Step 4&5: 3-((difluoromethylthio) methyl)-1-(methoxymethyl)-5-(4-methyl-4-(3-(trifluoromethyl) phenylsulfonyl)tetrahydro-2H-pyran-2-yl)-1H-pyrazole 25% NaOMe in MeOH (0.43 mL, 1.9762 mmol) was added to a solution of S-(1-(methoxymethyl)-5-(4-methyl-4-(3-(trifluoromethyl) phenylsulfonyl)tetrahydro-2H-pyran-2-yl)-1H-pyrazol-3-yl) methyl ethanethioate (0.50 g, 0.987 mmol) in DMF (10 mL) at 0° C. and stirred for 15 min. The reaction was monitored by TLC. After completion of starting material freon gas was purged into the reaction mixture at 0° C. for 30 min. After completion, $N_2$ gas was purged through the reaction mixture and diluted with water (50 mL). The organic product was extracted with EtOAc (2×50 mL). The combined organic extracts were washed with brine, dried over anhydrous $Na_2SO_4$. The organic layer was filtered and solvent was concentrated under reduced pressure to afford crude product, which was purified by flash column chromatography (silica gel 230-400 mesh, 20-40% EtOAc in PE as eluent) to get 0.25 g (50% over 2 steps) of 3-((difluoromethylthio) methyl)-1-(methoxymethyl)-5-(4-methyl-4-(3-(trifluoromethyl) phenylsulfonyl) tetrahydro-2H-pyran-2-yl)-1H-pyrazole. (TLC system: EtOAc-PE; 4:6; Rf: 0.5).

Step 6: 3-((difluoromethylsulfonyl) methyl)-1-(methoxymethyl)-5-(4-methyl-4-(3-(trifluoromethyl) phenylsulfonyl) tetrahydro-2H-pyran-2-yl)-1H-pyrazole 3-((difluoromethylthio) methyl)-1-(methoxymethyl)-5-(4-methyl-4-(3-(trifluoromethyl) phenylsulfonyl) tetrahydro-2H-pyran-2-yl)-1H-pyrazole (0.25 g, 0.486 mmol) was dissolved in MeOH (10 mL) and a solution of oxone (0.895 g, 1.459 mmol) in water (8 mL) was added. The reaction mixture was stirred at RT for 48 h. Reaction mixture was diluted with water (25 mL) and the organic product was extracted with EtOAc (2×50 mL). The combined organic extract was washed with brine (50 mL), dried over anhydrous $Na_2SO_4$ and solvent was concentrated to get crude product. The crude compound was purified by flash column chromatography (silica gel 230-400 mesh, 30-50% EtOAc in PE) to get 0.12 g (45%) of 3-((difluoromethylsulfonyl) methyl)-1-(methoxymethyl)-5-(4-methyl-4-(3-(trifluoromethyl) phenylsulfonyl) tetrahydro-2H-pyran-2-yl)-1H-pyrazole as white solid. (TLC system: EtOAc-PE; 4:6; Rf: 0.30).

Step 7: 3-((difluoromethylsulfonyl) methyl)-5-(4-methyl-4-(3-(trifluoromethyl) phenylsulfonyl) tetrahydro-2H-pyran-2-yl)-1H-pyrazole 4M HCl in 1,4-dioxane solution (8.0 mL) was added to a solution of 3-((difluoromethylsulfonyl) methyl)-1-(methoxymethyl)-5-(4-methyl-4-(3-(trifluoromethyl) phenylsulfonyl) tetrahydro-2H-pyran-2-yl)-1H-pyrazole (0.12 g, 0.219 mmol) in EtOH (4.0 mL) and the resulting reaction mixture was heated to 60° C. under stirring condition for 4 h. The reaction mixture was concentrated under reduced pressure and the residue was diluted with water. The reaction mixture was cooled to 0° C., added sat. aq. $NaHCO_3$ solution (20 mL) and the organic product was extracted with EtOAc (2×25 mL). The combined organic layer was washed with water (2×25 mL), brine (25 mL), dried over anhydrous $Na_2SO_4$. The organic layer was filtered and solvent was concentrated under reduced pressure to get 70 mg (63%) of 3-((difluoromethylsulfonyl) methyl)-5-(4-methyl-4-(3-(trifluoromethyl) phenylsulfonyl) tetrahydro-2H-pyran-2-yl)-1H-pyrazole.

[cis-rac] Example 28—m/z=503.0

[Cis-rac] 3-((difluoro methyl sulfonyl) methyl)-5-(4-methyl-4-(3-(trifluoromethyl) phenylsulfonyl) tetrahydro-2H-pyran-2-yl)-1H-pyrazole was subjected to chiral prep-SFC purification to give of [cis-EN1] Example 28 and [cis-EN2] Example 28.

[cis-EN1] Example 28—analytical SFC: Chiralpak OJ-H (250×4.6 mm 5 μm) 30.1° C., 3 g/min, 100 bar, 20% MeOH, Ret. Time 2.26 min; m/z=503.0 [M+H]$^+$; $^1$H NMR (CDCl$_3$): δ 13.05 (br s, 1H), 8.23-8.18 (m, 2H), 8.06 (s, 1H), 7.98-7.94

(t, 1H), 7.24-6.98 (t, 1H), 6.27 (s, 1H), 4.76 (s, 2H), 4.68-4.65 (d, 1H), 4.01-3.97 (m, 1H), 3.72-3.66 (t, 1H), 2.13-2.07 (t, 2H), 1.78-1.74 (d, 1H), 1.48-1.46 (m, 4H).

[cis-EN2] Example 28—analytical SFC: Chiralpak OJ-H (250×4.6 mm 5 μm), 29.9° C., 3 g/min, 100 bar, 20% MeOH, Ret. Time 2.78 min; m/z=503.0 [M+H]+; ¹H NMR (CDCl₃): δ 13.05 (br s, 1H), 8.23-8.18 (m, 2H), 8.06 (s, 1H), 7.98-7.94 (t, 1H), 7.24-6.98 (t, 1H), 6.27 (s, 1H), 4.76 (s, 2H), 4.68-4.65 (d, 1H), 4.01-3.97 (m, 1H), 3.72-3.66 (t, 1H), 2.13-2.07 (t, 2H), 1.78-1.74 (d, 1H), 1.48-1.46 (m, 4H).

5-[4-Methyl-4-[[3-(trifluoromethyl)phenyl]sulfonyl]-tetrahydro-pyran-2-yl]-3-(2,2,2-trifluoro-ethylsulfonyl)-1H-pyrazole (Example 29)

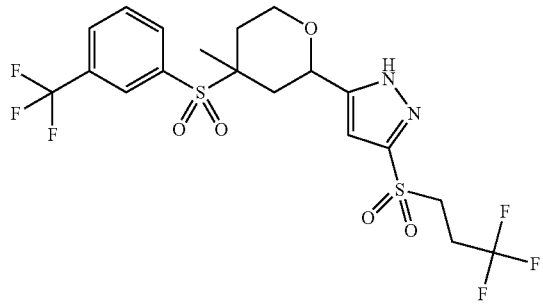 [SMILES: CC1(S(=O)(=O)c2cccc(C(F)(F)F)c2)CCOC(c2cc(S(=O)(=O)CCC(F)(F)F)n[nH]2)C1]

The compound 29 can be obtained in analogy to above described procedures or parts of above described procedures for example 1 and example 27.

Synthesis of Example 29 was carried out as follows:

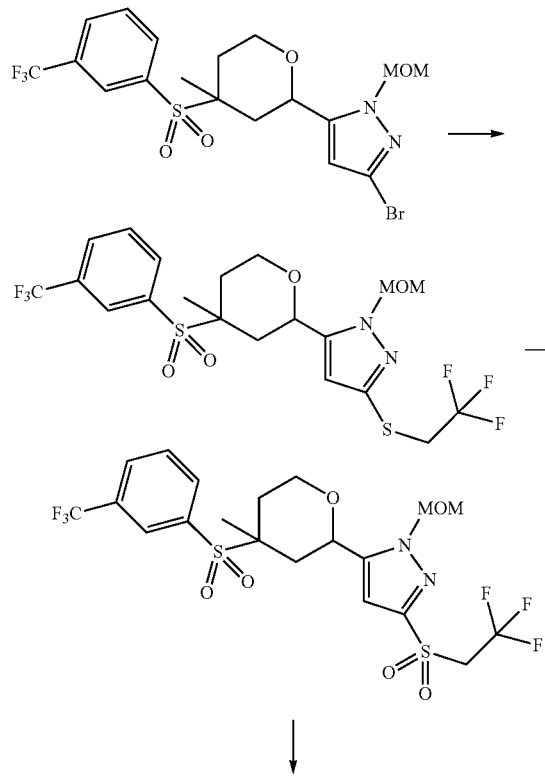

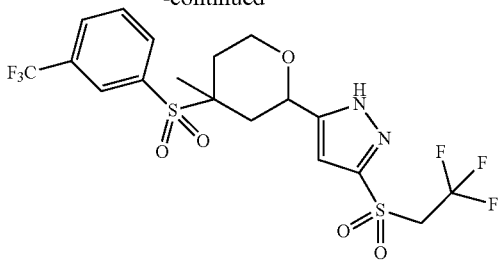

29

Step 1: [cis-rac] 1-(Methoxymethyl)-5-(4-methyl-4-((3-(trifluoromethyl)phenyl)sulfonyl)tetrahydro-2H-pyran-2-yl)-3-(2,2,2-trifluoroethyl)thio)-1H-pyrazole A solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (0.50 g, 1.00 mmol) and DIPEA (0.40 ml, 2.01 mmol) in toluene (10 ml) was degassed for 10 min. To the RM were added Xantphos (0.04 mg, 0.07 mmol) followed by Pd₂(dba)₃ (0.06 g, 0.07 mmol) and it was degassed again for 10 min. 2,2,2-Trifluoroethanethiol (0.2 ml, 2.01 mmol) was added to the RM in a sealed tube. The resulting RM was heated at 120° C. for 16 h under argon. The RM was filtered through a celite bed and the filtrate was concentrated under reduced pressure to give the crude product. The crude product was purified by column chromatography (silica gel 100-200 mesh, 0-30% EtOAc in PE) to obtain the title compound (0.50 g, 41% purity). The product was taken through to the next step without further purification. A second batch of starting material (0.70 g) was converted to the title compound (0.65 g) in analogy.

Step 2: [cis-rac] 1-(Methoxymethyl)-5-(4-methyl-4-((3-(trifluoromethyl)phenyl)sulfonyl)tetrahydro-2H-pyran-2-yl)-3-(2,2,2-trifluoroethyl)sulfonyl)-1H-pyrazole A solution of oxone (1.15 g, 1.87 mmol) in water (15 ml) was added to a stirred solution of [cis-rac] 1-(methoxymethyl)-5-(4-methyl-4-((3-(trifluoromethyl)phenyl)sulfonyl)tetrahydro-2H-pyran-2-yl)-3-((2,2,2-trifluoroethyl)thio)-1H-pyrazole (0.50 g, 0.93 mmol) in MeOH (21 ml) and the mixture was stirred for 16 h at RT. The RM was diluted with water (50 ml). The organic product was extracted with DCM (3×50 ml). The combined organic extracts were washed with brine (2×20 ml) and dried over anhydrous Na₂SO₄. The organic layer was filtered and the solvent was concentrated under reduced pressure to afford the crude product, which was purified by column chromatography (silica gel 60-120 mesh, 0-30% EtOAc in PE) to give the title compound (0.15 g, 26.4% over two steps). A second batch of starting material (0.65 g) was converted to the title compound (0.32 g) in analogy.

Step 3: [cis-rac] 5-[4-Methyl-4-[[3-(trifluoromethyl)phenyl]sulfonyl]-tetrahydro-pyran-2-yl]-3-(2,2,2-trifluoro-ethylsulfonyl)-1H-pyrazole (Example 29)

4N HCl in dioxane solution (10.0 ml) was added to a solution of [cis-rac] 1-(methoxymethyl)-5-(4-methyl-4-((3-(trifluoromethyl)phenyl)sulfonyl)tetrahydro-2H-pyran-2- yl)-3-((2,2,2-trifluoroethyl)sulfonyl)-1H-pyrazole (0.15 g, 0.26 mmol) in EtOH (5 ml) and the resulting RM was heated to 60° C. under stirring conditions for 4 h. The RM was concentrated under reduced pressure and the residue was diluted with water. The RM was cooled to 0° C., sat. aq. NaHCO₃ solution (100 ml) was added, and the organic product was extracted with EtOAc (2×25 ml). The combined organic layers were washed with water (2×50 ml) and brine (50 ml), and dried over anhydrous Na₂SO₄. The organic layer was filtered and the solvent was concentrated under reduced pressure to afford the crude product, which was purified by preparative thin layer chromatography (40% EtOAc in PE) to give the title compound (0.039 g). A second batch of starting material (0.32 g) was converted to the title compound (0.2 g) in analogy. TLC system: EtOAc-PE; 1:1; Rf: 0.26).

[Cis-rac] 5-[4-methyl-4-[[3-(trifluoromethyl)phenyl]sulfonyl]-tetrahydro-pyran-2-yl]-3-(2,2,2-trifluoro-ethylsulfonyl)-1H-pyrazole was subjected to chiral prep-SFC purification to give 80 mg of [cis-EN1] Example 29 and 81 mg of [cis-EN2] Example 29.

[cis-EN1] Example 29—analytical SFC: Chiralpak AD-H (250×4.6 mm 5 µm) 30.1° C., 3 g/min, 100 bar, 20% EtOH, Ret. Time 4.56 min; m/z=521.0 [M+H]⁺; ¹H NMR (CDCl₃): δ 10.91 (br s, 1H), 8.13 (s, 1H), 8.06 (d, 1H), 7.98 (d, 1H), 7.78 (t, 1H), 6.67 (s, 1H), 4.71-4.67 (m, 1H), 4.21-4.17 (m, 1H), 4.12-4.05 (m, 2H), 3.76-3.70 (m, 1H), 2.39-2.32 (m, 1H), 2.24-2.21 (m, 1H), 1.92-1.88 (m, 1H), 1.58 (m, 4H). NOE: On irradiating OCH proton NOE was observed with SCCH₃.

[cis-EN2] Example 29—analytical SFC: Chiralpak AD-H (250×4.6 mm 5 µm), 29.9° C., 3 g/min, 100 bar, 20% EtOH, Ret. Time 6.54 min; m/z=520.9 [M+H]⁺; ¹H NMR (CDCl₃): δ 10.97 (br s, 1H), 8.13 (s, 1H), 8.06 (d, 1H), 7.98 (d, 1H), 7.78 (t, 1H), 6.68 (s, 1H), 4.71-4.67 (m, 1H), 4.21-4.17 (m, 1H), 4.12-4.06 (m, 2H), 3.76-3.69 (m, 1H), 2.39-2.32 (m, 1H), 2.25-2.18 (m, 1H), 1.92-1.88 (m, 1H), 1.55 (m, 4H).

2-Methyl-2-[5-[4-methyl-4-[[3-(trifluoromethyl)phenyl]sulfonyl]-tetrahydro-pyran-2-yl]-1H-pyrazol-3-yl]-propionamide (Example 30) and 2-Methyl-2-[5-[4-methyl-4-[[3-(trifluoromethyl)phenyl]sulfonyl]-tetrahydro-pyran-2-yl]-1H-pyrazol-3-yl]-propionitrile (Example 31)

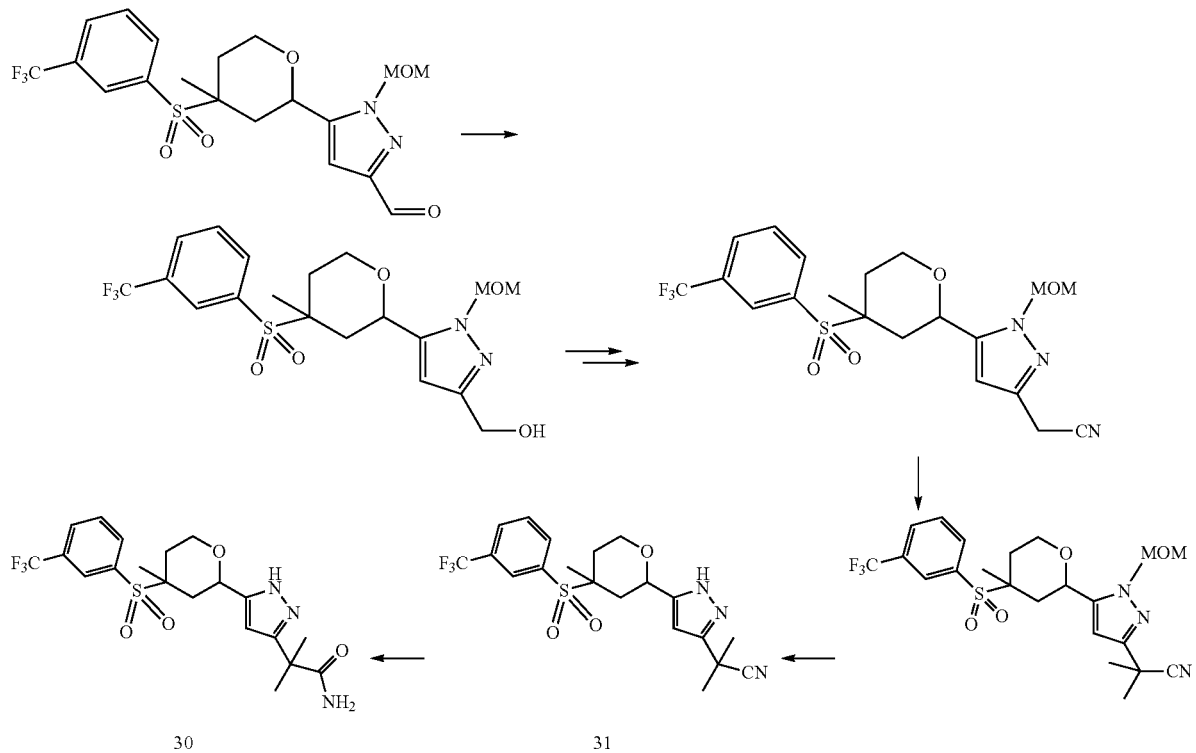

Step 1: [cis-rac] (1-(Methoxymethyl)-5-(4-methyl-4-((3-(trifluoromethyl)phenyl)sulfonyl)tetrahydro-2H-pyran-2-yl)-1H-pyrazol-3-yl)methanol Sodium borohydride (0.13 g, 3.69 mmol) was added portionwise at 0° C. to a solution of [cis-rac] 1-(methoxymethyl)-5-(4-methyl-4-((3-(trifluoromethyl)phenyl)sulfonyl)tetrahydro-2H-pyran-2-yl)-1H-pyrazole-3-carbaldehyde [example 12, step 8] (1.50 g, 3.36 mmol) in MeOH (15 ml). The resulting mixture was stirred at RT for 2 h under argon. The reaction was monitored by TLC. After completion, the RM was quenched with ice-cold water and the organic product was extracted with EtOAc. The organic layer was dried over anhydrous sodium sulfate and the solvent was concentrated under reduced pressure to obtain the title compound (1.0 g, 67%).

Step 2 & 3: [cis-rac] 2-(1-(Methoxymethyl)-5-(4-methyl-4-((3-(trifluoromethyl)phenyl)sulfonyl)tetrahydro-2H-pyran-2-yl)-1H-pyrazol-3-yl)acetonitrile Triethylamine (1.39 ml, 10.04 mmol) was added to a stirred solution of [cis-rac] (1-(methoxymethyl)-5-(4- methyl-4-((3-(trifluoromethyl)phenyl)sulfonyl)tetrahydro-2H-pyran-2-yl)-1H-pyrazol-3-ylmethanol (1.5 g, 3.34 mmol) in DCM (10 ml) at 0° C. To the RM was added methanesulfonyl chloride (0.388 ml, 5.02 mmol) at the same temperature. The RM was slowly warmed to RT and stirred for 1 h. The RM was diluted with water (50 ml) and the organic product was extracted with DCM (2×20 ml). The combined organic extracts were washed with brine, dried over anhydrous sodium sulfate, filtered and the solvent evaporated under reduced pressure to give the crude product (1.5 g), which was taken trough to the next reaction. Sodium cyanide (0.279 g, 5.7 mmol) was added to a solution 1-(methoxymethyl)-5-(4-methyl-4-((3-(trifluoromethyl)phenylsulfonyl)tetrahydro-2H-pyran-2-yl)-1H-pyrazol-3-yl)methyl methanesulfonate (1.50 g, 2.85 mmol) in DMF (15 ml) at RT and the mixture was heated to 80° C. for 16 h. The RM was diluted with water and the organic product was extracted with EtOAc. The organic layer was washed with brine (50 ml) and then dried over anhydrous $Na_2SO_4$. The organic layer was filtered and the solvent was concentrated under reduced pressure to afford the crude product, which was purified by flash column chromatography (silica gel 230-400 mesh, 20-40% EtOAc in PE) to give the title compound (0.7 g, 46% over two steps).

Step 4: [cis-rac] 2-(1-(Methoxymethyl)-5-(4-methyl-4-((3-(trifluoromethyl)phenyl)sulfonyl)tetrahydro-2H-pyran-2-yl)-1H-pyrazol-3-yl)-2-methylpropanenitrile 60% Sodium hydride in mineral oil (0.183 g, 4.59 mmol) was added to a solution of [cis-rac] 2-(1-(methoxymethyl)-5-(4-methyl-4-((3-(trifluoromethyl)phenyl)sulfonyl)tetrahydro-2H-pyran-2-yl)-1H-pyrazol-3-ylacetonitrile (0.7 g, 1.53 mmol) in DMF (8 ml) portionwise at 0° C. and the mixture was stirred for 10 min at the same temperature. Methyl iodide (0.24 ml, 3.82 mmol) was added to the RM, it was then slowly warmed to RT and stirred for 16 h. The RM was quenched with cold water (20 ml) and the organic product was extracted with EtOAc (2×50 ml). The combined organic layers were washed with water (2×40 ml) and brine (30 ml), and dried over anhydrous $Na_2SO_4$. The organic layer was filtered and the solvent was concentrated under reduced pressure to afford the title compound (0.6 g, 80%).

Step 5: [cis-rac] 2-Methyl-2-[5-[4-methyl-4-[[3-(trifluoromethyl)phenyl]sulfonyl]-tetrahydro-pyran-2-yl]-1H-pyrazol-3-yl]-propionitrile (Example 31)

Trifluoroaceticacid (10 ml) was added to [cis-rac] 2-(1-(methoxymethyl)-5-(4-methyl-4-((3-(trifluoromethyl)phenyl)sulfonyl)tetrahydro-2H-pyran-2-yl)-1H-pyrazol-3-yl)-2-methylpropanenitrile (0.6 g, 1.23 mmol) at RT and the resulting RM was heated to 60° C. for 2 h. The RM was concentrated under reduced pressure and the residue was diluted with water. The RM was cooled to 0° C. and sat. aq. NaHCO₃ solution (15 ml) was added. The organic product was extracted with EtOAc (2×25 ml). The combined organic layers were washed with water (2×10 ml) and brine (20 ml), and dried over anhydrous $Na_2SO_4$. The organic layer was filtered and the solvent was concentrated under reduced pressure to afford the crude product, which was purified by flash column chromatography (silica gel 230-400 mesh) to give the title compound (0.5 g, 90%). TLC system: EtOAc-PE; 5:5; Rf: 0.4.

[cis-rac] Example 31—NOE was observed between OCH and SCCH₃ proton.

[Cis-rac] 2-methyl-2-[5-[4-methyl-4-[[3-(trifluoromethyl)phenyl]sulfonyl]-tetrahydro-pyran-2-yl]-1H-pyrazol-3-yl]-propionitrile was subjected to chiral prep-SFC purification to give [cis-EN1] Example 31 and [cis-EN2] Example 31.

[cis-EN1] Example 31—analytical SFC: Chiralpak IC (250×4.6 mm 5 μm) 30.2° C., 4 g/min, 100 bar, 40% MeOH, Ret. Time 1.32 min; m/z=442.2 [M+H]⁺; ¹H NMR (DMSO-d₆): δ 12.89 (br s, 1H), 8.23-8.19 (t, 2H), 8.08 (s, 1H), 7.98-7.94 (t, 1H), 6.26 (s, 1H), 4.64-4.62 (d, 1H), 4.00-3.96 (m, 1H), 3.71-3.65 (m, 1H), 2.14-2.07 (m, 2H), 1.79-1.75 (m, 1H), 1.63 (s, 6H), 1.48-1.45 (m, 4H). NOE: On irradiating OCH proton NOE was observed with SCCH₃.

[cis-EN2] Example 31—analytical SFC: Chiralpak IC (250×4.6 mm 5 μm), 29.9° C., 4 g/min, 100 bar, 40% MeOH, Ret. Time 2.15 min; m/z=442.1 [M+H]⁺; ¹H NMR (DMSO-d₆): δ 12.89 (br s, 1H), 8.23-8.19 (m, 2H), 8.08 (s, 1H), 7.98-7.94 (t, 1H), 6.26 (s, 1H), 4.64-4.63 (m, 1H), 3.99-3.97 (m, 1H), 3.70-3.66 (m, 1H), 2.13-2.06 (m, 2H), 1.79-1.76 (m, 1H), 1.63 (s, 6H), 1.48-1.45 (m, 4H).

Step 6: [cis-rac] 2-Methyl-2-[5-[4-methyl-4-[[3-(trifluoromethyl)phenyl]sulfonyl]-tetrahydro-pyran-2-yl]-1H-pyrazol-3-yl]-propionamide (Example 30)

To a stirred solution of [cis-rac] 2-methyl-4-[[3-(trifluoromethyl)phenyl]sulfonyl]-tetrahydro-pyran-2-yl]-1H-pyrazol-3-yl]-propionitrile (Example 31) (0.25 g, 0.56 mmol) in DMSO (5 ml), KOH (0.317 g, 5.62 mmol) in water (2 ml) and H₂O₂ (30% aq) (1 ml) were added at 10° C. The RM was stirred for 1 h at 10° C. The RM was diluted with water and extracted with EtOAc (2×25 ml). The organic layer was dried over anhydrous Na₂SO₄ and the solvent was concentrated under reduced pressure. The product was purified by flash column chromatography (silica gel 230-400 mesh) to afford the title compound (0.15 g, 58%). TLC system: 80% EtOAc-PE; Rf: 0.1.

[cis-rac] Example 30—NOE was observed between OCH and SCCH₃ proton.

[Cis-rac] 2-Methyl-2-[5-[4-methyl-4-[[3-(trifluoromethyl)phenyl]sulfonyl]-tetrahydro-pyran-2-yl]-1H-pyrazol-3-yl]-propionamide was subjected to chiral prep-SFC purification to give 45 mg of [cis-EN1] Example 30 and 45 mg of [cis-EN2] Example 30.

[cis-EN1] Example 30—analytical SFC: Chiralpak IC (250×4.6 mm 5 μm) 30° C., 3 g/min, 100 bar, 30% MeOH, Ret. Time 5.81 min; m/z=460.2 [M+H]⁺

[cis-EN2] Example 30—analytical SFC: Chiralpak IC (250×4.6 mm 5 μm), 30.2° C., 3 g/min, 100 bar, 30% MeOH, Ret. Time 8.91 min; m/z=460.1 [M+H]⁺

5-(2,2-Difluoro-ethoxy)-3-[4-methyl-4-[[3-(trifluoromethyl)phenyl]sulfonyl]-tetrahydro-pyran-2-yl]-1H-pyrazole (Example 32)

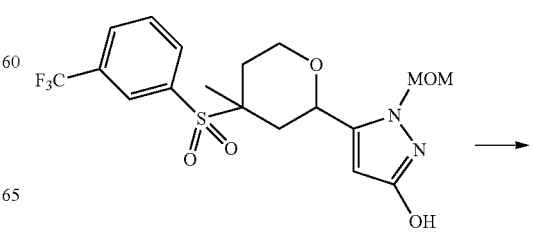

-continued

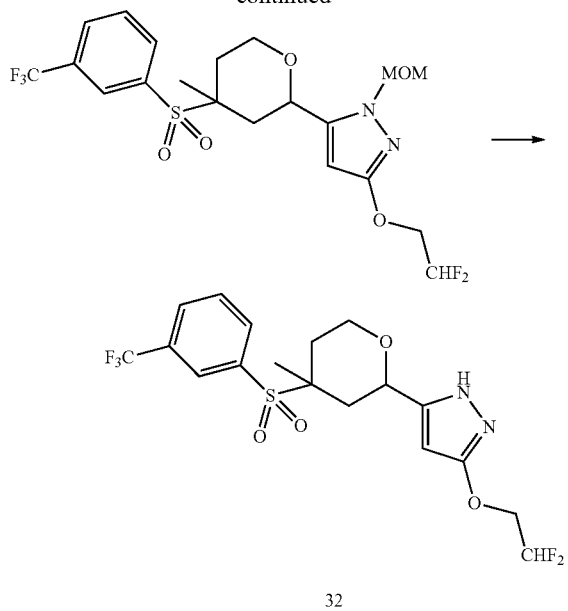

32

Step 1: [cis-rac] 3-(2,2-Difluoroethoxy)-1-(methoxymethyl)-5-(4-methyl-4-((3-(trifluoromethyl)phenyl)sulfonyl)tetrahydro-2H-pyran-2-yl)-1H-pyrazole To a stirred solution of [cis-rac] 1-(methoxymethyl)-5-(4-methyl-4-((3-(trifluoromethyl)phenyl)sulfonyl)tetrahydro-2H-pyran-2-yl)-1H-pyrazol-3-ol [Example 16, step 2] (0.8 g, 1.84 mmol) in DMF (24 ml) was added K₂CO₃ (0.76 g, 5.52 mmol) and 1,1-difluoro-2-iodoethane (0.32 ml, 3.68 mmol) at 0° C. The RM was heated to 60° C. for 16 h. The RM was diluted with water (70 ml) and the organic product was extracted with EtOAc (3×50 ml). The combined organic layers were washed with water (2×50 ml) and brine (3×50 ml), dried over anhydrous Na₂SO₄, filtered and the solvent was concentrated under reduced pressure. The crude product was purified by column chromatography (silica gel 100-200 mesh, 0-50% EtOAc in PE) to give the title compound (0.6 g, 65%).

Step 2: [cis-rac] 5-(2,2-Difluoro-ethoxy)-3-[4-methyl-4-[[3-(trifluoromethyl)phenyl]sulfonyl]-tetrahydro-pyran-2-yl]-1H-pyrazole (Example 32)

4N HCl in dioxane solution (16.0 ml) was added to a solution of [cis-rac] 3-(2,2-difluoroethoxy)-1-(methoxymethyl)-5-(4-methyl-4-((3-(trifluoromethyl)phenyl)sulfonyl) tetrahydro-2H-pyran-2-yl)-1H-pyrazole (0.5 g, 1.00 mmol) in EtOH (20 ml) and the resulting RM was heated to 60° C. under stirring conditions for 5 h. The RM was concentrated under reduced pressure and the residue was diluted with water and sat. aq. NaHCO₃ (35 ml). The organic product was extracted with EtOAc (2×35 ml). The combined organic layers were washed with water (2×30 ml) and brine (50 ml), and dried over anhydrous Na₂SO₄. The organic layer was filtered and the solvent was concentrated under reduced pressure to give the crude product, which was purified by column chromatography (silica gel 60-120 mesh, 0-5% MeOH in DCM) to afford the title compound (0.29 g, 64%). TLC system: EtOAc-PE; 5:5; Rf: 0.25.

[Cis-rac] 5-(2,2-Difluoro-ethoxy)-3-[4-methyl-4-[[3-(trifluoromethyl)phenyl]sulfonyl]-tetrahydro-pyran-2-yl]-1H-pyrazole was subjected to chiral prep-SFC purification to give 60 mg of [cis-EN1] Example 32 and 58 mg of [cis-EN2] Example 32.

[cis-rac] Example 32—NOE was observed between OCH and SCCH₃ proton.

[cis-EN1] Example 32—analytical SFC: Lux Amylose-2 (250×4.6 mm 5 µm) 30.2° C., 3 g/min, 100 bar, 40% MeOH, Ret. Time 1.95 min; m/z=455.1 [M+H]⁺; ¹H NMR (CDCl₃): δ 9.28 (br s, 1H), 8.13 (s, 1H), 8.07-8.05 (d, 1H), 7.96-7.95 (d, 1H), 7.75 (t, 1H), 6.24-5.94 (m, 1H), 5.55 (s, 1H), 4.55-4.52 (m, 1H), 4.40-4.32 (m, 2H), 4.15-4.11 (m, 1H), 3.71-3.64 (m, 1H), 2.34-2.26 (m, 1H), 2.19 (t, 1H), 1.85-1.82 (m, 1H), 1.56-1.53 (m, 4H).

[cis-EN2] Example 32—analytical SFC: Lux Amylose-2 (250×4.6 mm 5 µm), 30.1° C., 3 g/min, 100 bar, 40% MeOH, Ret. Time 3.78 min; m/z=455.1 [M+H]⁺; ¹H NMR (CDCl₃): δ 9.26 (br s, 1H), 8.13 (s, 1H), 8.07-8.05 (d, 1H), 7.96-7.95 (d, 1H), 7.75 (t, 1H), 6.23-5.95 (m, 1H), 5.55 (s, 1H), 4.55-4.52 (m, 1H), 4.40-4.32 (m, 2H), 4.15-4.11 (m, 1H), 3.71-3.64 (m, 1H), 2.34-2.26 (m, 1H), 2.19 (t, 1H), 1.85-1.82 (m, 1H), 1.56-1.53 (m, 4H).

3-(2-Methoxy-1,1-dimethyl-ethyl)-5-[4-methyl-4-[[3-(trifluoromethyl)phenyl]sulfonyl]-tetrahydro-pyran-2-yl]-1H-pyrazole (Example 33)

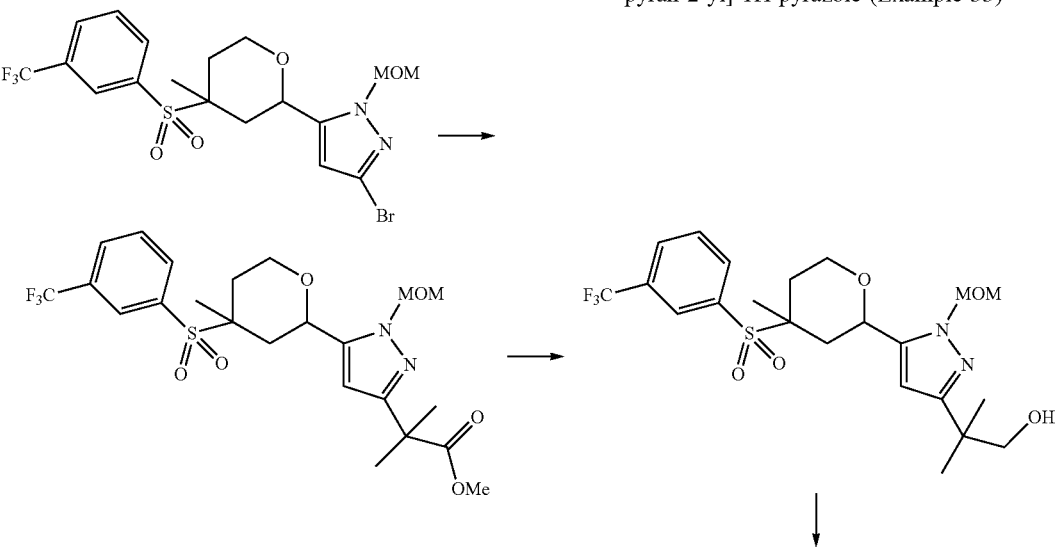

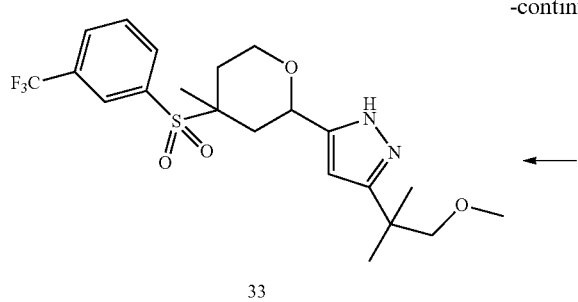

33

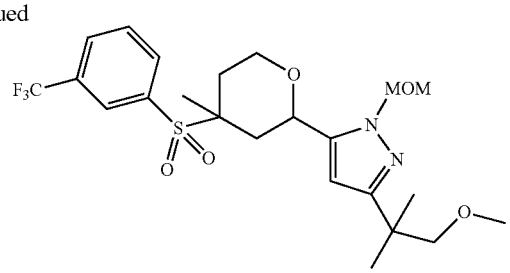

Step 1: [cis-rac] Methyl 2-(1-(methoxymethyl)-5-(4-methyl-4-((3-(trifluoromethyl)phenyl)sulfonyl)tetrahydro-2H-pyran-2-yl)-1H-pyrazol-3-yl)-2-methylpropanoate A stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (2.0 g, 4.03 mmol) in DMF (30 ml) was degassed for 30 min. The solution was added to a stirred solution of methyl trimethylsillyl dimethylketene acetal (4.12 ml, 20.15 mmol), Pd(dba)$_2$ (0.231 g, 0.403 mmol) and t-Bu$_3$PHBF$_4$ (0.072 g, 0.86 mmol) in DMF (20 ml) in a sealed tube. To the RM was added ZnF$_2$ (0.416 g, 4.03 mmol) at RT and the RM was stirred at 90° C. for 48 h. The RM was filtered through celite and the filtrate was concentrated under reduced pressure to give the crude product which was purified by column chromatography (silica gel 100-200 mesh, 0-35% EtOAc in PE) to give the title compound (1.2 g).

Step 2: [cis-rac] 2-(1-(Methoxymethyl)-5-(4-methyl-4-((3-(trifluoromethyl)phenyl)sulfonyl)tetrahydro-2H-pyran-2-yl)-1H-pyrazol-3-yl)-2-methylpropan-1-ol To a stirred solution of [cis-rac] methyl 2-(1-(methoxymethyl)-5-(4-methyl-4-((3-(trifluoromethyl)phenyl)sulfonyl)tetrahydro-2H-pyran-2-yl)-1H-pyrazol-3-yl)-2-methylpropanoate (1.2 g, 2.31 mmol) in THF (100 ml) at −30° C. was added dropwise LiAlH$_4$ (1.0 M solution in THF) (11.58 ml, 11.58 mmol). The RM was stirred at −30° to −5° C. for 3 h and was then quenched with saturated sodium sulphate solution. The RM was filtered through celite and washed with EtOAc (3×80 ml). The filtrate was concentrated under reduced pressure. The crude product was purified by column chromatography (silica gel 100-200 mesh 0-100% EtOAc in PE) to give the title compound (0.7 g, 72%).

Step 3: [cis-rac] 3-(1-Methoxy-2-methylpropan-2-yl)-1-(methoxymethyl)-5-(4-methyl-4-((3-(trifluoromethyl)phenyl)sulfonyl)tetrahydro-2H-pyran-2-yl)-1H-pyrazole NaH (0.12 g, 3.06 mmol, 60% suspension on mineral oil) was added portionwise to a clear solution of [cis-rac] 2-(1-(methoxymethyl)-5-(4-methyl-4-((3-(trifluoromethyl)phenyl)sulfonyl)tetrahydro-2H-pyran-2-yl)-1H-pyrazol-3-yl)-2-methylpropan-1-ol (0.5 g, 1.02 mmol) in THF (70 ml) at 0° C. The RM was stirred for 30 min at the same temperature. Methyl iodide (0.158 ml, 2.55 mmol) was added to the RM. It was then slowly warmed to RT and stirred for 16 h. The RM was quenched with cold water (100 ml) and the organic product was extracted with EtOAc (3×60 ml). The combined organic layers were washed with water (2×60 ml) and brine (100 ml). The organics were dried over anhydrous Na$_2$SO$_4$, filtered and the solvent was concentrated under reduced pressure. The crude product was purified by column chromatography (silica gel 100-200 mesh, 0-60% EtOAc in PE) to give the title compound (0.4 g, 98%).

Step 4: [cis-rac] 3-(2-Methoxy-1,1-dimethyl-ethyl)-5-[4-methyl-4-[[3-(trifluoromethyl)phenyl]sulfonyl]-tetrahydro-pyran-2-yl]-1H-pyrazole (Example 33)

4N HCl in dioxane solution (30.0 ml) was added to a solution of [cis-rac] 3-(1-methoxy-2-methylpropan-2-yl)-1-(methoxymethyl)-5-(4-methyl-4-((3-(trifluoromethyl)phenyl)sulfonyl)tetrahydro-2H-pyran-2-yl)-1H-pyrazole (0.5 g, 0.99 mmol) in EtOH (50 ml) and the resulting RM was heated to 60° C. for 6 h. The RM was concentrated under reduced pressure and the residue was diluted with water. The mixture was basified to pH ~8.0 by using sat. aq. NaHCO$_3$ (45 ml) and the organic product was extracted with EtOAc (2×50 ml). The combined organic extracts were washed with water (2×20 ml) and brine (40 ml), and dried over anhydrous Na$_2$SO$_4$. The organic layer was filtered and the solvent was concentrated under reduced pressure. The crude product was purified by column chromatography (silica gel 100-200 mesh, 0-60% EtOAc in PE) to give the title compound (0.4 g, 86%). TLC system: EtOAc-PE; 7:3; Rf: 0.3

[Cis-rac] 3-(2-methoxy-1,1-dimethyl-ethyl)-5-[4-methyl-4-[[3-(trifluoromethyl)phenyl]sulfonyl]-tetrahydro-pyran-2-yl]-1H-pyrazole was subjected to chiral prep-HPLC purification to give 56 mg of [cis-EN1] Example 33 and 60 mg of [cis-EN2] Example 33.

[cis-rac] Example 33—NOE was observed between OCH and SCCH$_3$ proton.

[cis-EN1] Example 33—analytical SFC: Chiralpak-IC (250×4.6 mm 5 μm) 29.9° C., 3 g/min, 100 bar, 35% MeOH, Ret. Time 1.92 min; m/z=461.2 [M+H]$^+$; $^1$H NMR (CDCl$_3$): 10.49 (br s, 1H), 8.15 (s, 1H), 8.09 (d, 1H), 7.93 (d, 1H), 7.73 (t, 1H), 6.05 (s, 1H), 4.58-4.54 (m, 1H), 0.4.13-4.09 (m, 1H), 3.75-3.68 (m, 1H), 3.39 (s, 3H), 3.33 (s, 2H), 2.37-2.29 (m, 2H), 1.88-1.84 (m, 1H), 1.56-1.54 (m, 4H), 1.27 (s, 6H).

[cis-EN2] Example 33—analytical SFC: Chiralpak-IC (250×4.6 mm 5 μm), 30° C., 3 g/min, 100 bar, 35% MeOH, Ret. Time 3.13 min; m/z=461.2 [M+H]$^+$; $^1$H NMR (CDCl$_3$): 10.49 (br s, 1H), 8.15 (s, 1H), 8.08 (d, 1H), 7.93 (d, 1H), 7.73 (t, 1H), 6.05 (s, 1H), 4.58-4.54 (m, 1H), 0.4.13-4.09 (m, 1H), 3.75-3.68 (m, 1H), 3.39 (s, 3H), 3.33 (s, 2H), 2.37-2.29 (m, 2H), 1.88-1.84 (m, 1H), 1.56-1.54 (m, 4H), 1.27 (s, 6H).

2-Methyl-2-[5-[4-methyl-4-[[3-(trifluoromethyl)phenyl]sulfonyl]-tetrahydro-pyran-2-yl]-1H-pyrazol-3-yl]-propan-1-ol (Example 34)

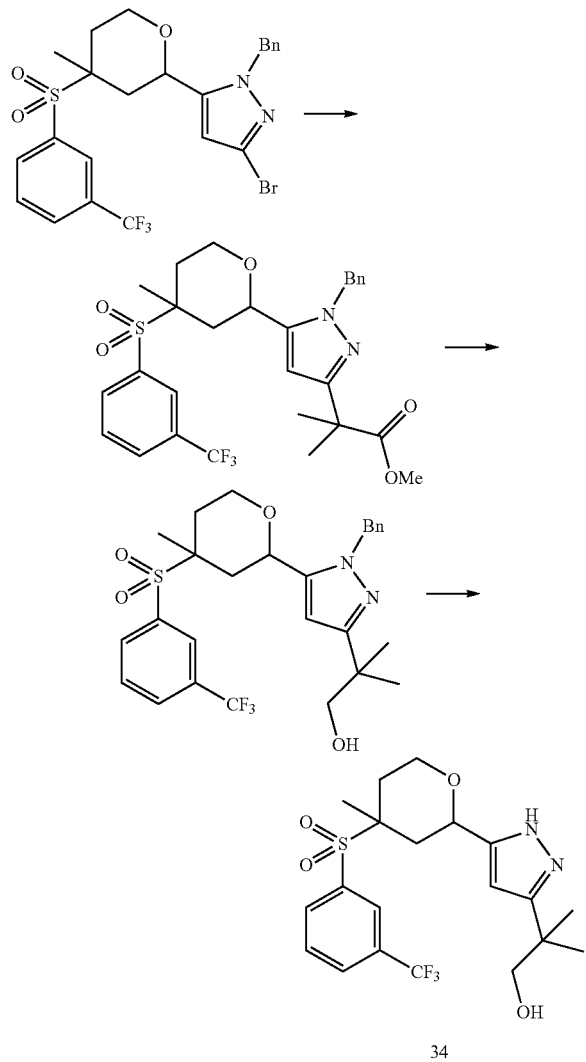

Step 1: [cis-rac] Methyl 2-(1-benzyl-5-(4-methyl-4-((3-(trifluoromethyl)phenyl)sulfonyl)tetrahydro-2H-pyran-2-yl)-1H-pyrazol-3-yl)-2-methylpropanoate The experiment was performed in a glovebox. To an oven dried vial containing LiNCy$_2$ (155 mg, 0.828 mmol) was added degassed and dry toluene (10 ml) followed by methyl isobutyrate (0.079 ml, 0.69 mmol). The mixture was stirred at RT for 10 min. Then a mixture of Pd(dba)$_2$ (13.23 mg, 0.023 mmol) and [cis-rac] 1-Benzyl-3-bromo-5-(4-methyl-4-((3-(trifluoromethyl)phenyl)sulfonyl)tetrahydro-2H-pyran-2-yl)-1H-pyrazole [Example 1, step 7] (250 mg, 0.46 mmol) were added. Finally, a 1M solution of P(tBu)$_3$ in toluene (0.046 ml, 0.046 mmol) was added and the mixture was stirred at RT for 15 min followed by stirring at 80° C. for 2 h. The RM was diluted with sat. aq. NH$_4$Cl (15 ml) and the organic layer was evaporated in vacuo. DCM (30 ml) was added, and the layers were separated using a phase separator. The aqueous layer was washed several times with DCM (10 ml). The combined organic layers were in vacuo concentrated. Using the same procedure, another batch (250 mg scale) was synthesised. The combined crude products were purified by flash column chromatography (40 g silica, EtOAc/heptane, 1:19→1:2) to obtain the title compound (350 mg (64% pure)).

Step 2: [cis-rac] 2-(1-Benzyl-5-(4-methyl-4-((3-(trifluoromethyl)phenyl)sulfonyl)tetrahydro-2H-pyran-2-yl)-1H-pyrazol-3-yl)-2-methylpropan-1-ol To an Ar(g)-flushed solution of [cis-rac] methyl 2-(1-benzyl-5-(4-methyl-4-((3-(trifluoromethyl)phenyl)sulfonyl)tetrahydro-2H-pyran-2-yl)-1H-pyrazol-3-yl)-2-methylpropanoate (339 mg (64% pure)) in absolute EtOH (20 ml) was added a solution of 2M LiBH$_4$ in THF (1.441 ml, 2.88 mmol) at RT. The mixture was heated to 70° C. for 30 min. Then, an additional solution of 2M LiBH$_4$ in THF (4.80 ml, 9.61 mmol) was added at 70° C. Stirring was continued for 30 min. Additional 2M LiBH$_4$ in THF (0.961 ml, 1.921 mmol) was added at 70° C. and the mixture was stirred for 30 min. Upon complete conversion by TLC, the reaction was quenched carefully with sat. aq. NH$_4$Cl (50 ml) and diluted with DCM (50 ml). The layers were separated and the aq. layer was extracted with DCM (3×30 ml). The water layer was in vacuo concentrated and twice extracted with DCM (20 ml). The combined organic layers were washed with brine, dried over Na$_2$SO$_4$ and concentrated to obtain the crude product which was purified by flash column chromatography (12 g silica, EtOAc/heptane 3:7→7:3) to give the title compound (179 mg, 87%).

Step 3: [cis-rac] 2-Methyl-2-[5-[4-methyl-4-[[3-(trifluoromethyl)phenyl]sulfonyl]-tetrahydro-pyran-2-yl]-1H-pyrazol-3-yl]-propan-1-ol (Example 34)

To an Ar(g)-flushed solution of [cis-rac] 2-(1-benzyl-5-(4-methyl-4-((3-(trifluoromethyl)phenyl)sulfonyl)tetrahydro-2H-pyran-2-yl)-1H-pyrazol-3-yl)-2-methylpropan-1-ol (50 mg, 0.093 mmol) in MeOH (9 ml) containing 4N aq. HCl solution (0.127 mmol, 0.032 ml) was added 10% Pd/C (23.80 mg, 0.022 mmol). The mixture was stirred under a H$_2$(g) atmosphere (balloon) for 2 h. Then, the mixture was flushed with Ar(g) and diluted with DCM (3 ml). It was then filtered over a 0.45 µm nylon LCMS filter and the filter was rinsed with DCM/MeOH (2×2 ml). The combined filtrates were concentrated to dryness. Purification by flash column chromatography (4 g silica, DCM/MeOH, 9:1→1:3) gave the title compound (28 mg, 67%).

[Cis-rac] 2-methyl-2-[5-[4-methyl-4-[[3-(trifluoromethyl)phenyl]sulfonyl]-tetrahydro-pyran-2-yl]-1H-pyrazol-3-yl]-propan-1-ol was subjected to chiral prep-SFC purification (Column: Phenomenex Amylose-1 (250×21.2 mm, 5 µm), Flow: 100 mL/min; Column temp: 40° C.; BPR: 120 bar, Eluent A: CO$_2$, Eluent B:Isopropanol) to give 4.8 mg of [cis-EN1] Example 34 and 4.0 mg of [cis-EN2] Example 34.

[cis-EN1] Example 34—LCMS: calculated for [M+H]$^+$=447.49. found 447.1 $^1$H NMR (400 MHz, CDCl$_3$) δ 8.15 (s, 1H), 8.09 (d, J=7.9 Hz, 1H), 7.95 (d, J=7.6 Hz, 1H), 7.75 (t, J=7.8 Hz, 1H), 6.07 (s, 1H), 4.59 (dd, J=11.6, 2.1 Hz, 1H), 4.13 (dd, J=12.1, 5.4 Hz, 1H), 3.78-3.66 (m, 1H), 3.61 (s, 2H), 2.33 (t, J=12.2 Hz, 2H), 1.88 (d, J=12.9 Hz, 1H), 1.55 (s+m, 3H+2H), 1.29 (s, 6H).

[cis-EN2] Example 34—LCMS: calculated for [M+H]$^+$=447.49. found 447.1 $^1$H NMR (400 MHz, CDCl$_3$) δ 8.15 (s, 1H), 8.09 (d, J=7.9 Hz, 1H), 7.95 (d, J=7.7 Hz, 1H), 7.75 (t, J=7.8 Hz, 1H), 6.07 (s, 1H), 4.63-4.55 (m, 1H), 4.13 (dd, J=11.6, 4.7 Hz, 1H), 3.72 (t, J=11.4 Hz, 1H), 3.60 (s, 2H), 2.33 (t, J=12.3 Hz, 2H), 1.88 (d, J=13.0 Hz, 1H), 1.55 (s+m, 3H+2H), 1.29 (s, 6H).

3-(2-Methyl-propylsulfonyl)-5-[4-methyl-4-[[3-(trifluoromethyl)phenyl]sulfonyl]-tetrahydro-pyran-2-yl]-1H-pyrazole (Example 35)

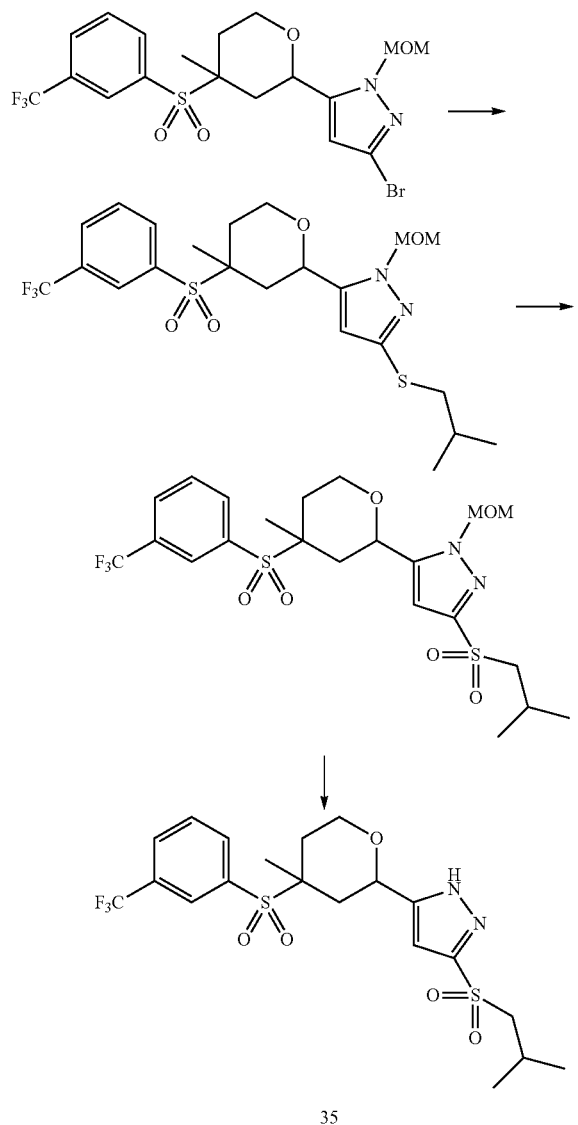

Step 1: [cis-rac] 3-(Isobutylthio)-1-(methoxymethyl)-5-(4-methyl-4-((3-(trifluoromethyl)phenyl)sulfonyl)tetrahydro-2H-pyran-2-yl)-1H-pyrazole To a stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (500 mg, 1.01 mmol, 1 eq) in toluene (15 ml), 2-methylpropane-1-thiol (0.3 ml, 3.03 mmol, 3 eq) and DIPEA (0.4 ml, 2.02 mmol, 2 eq) were added at RT in a sealed tube. The RM was purged with argon gas for 10 min and then Xantphos (117 mg, 0.20 mmol, 0.2 eq) and Pd$_2$(dba)$_3$ (92 mg, 0.10 mmol, 0.1 eq) were added at RT. The RM was again purged with argon gas for 5 min. The resulting RM was heated to 110° C. and stirred for 18 h at 110° C. After completion the RM was cooled to RT, filtered through celite and the celite bed was washed with EtOAc (150 ml). The filtrate was evaporated. The residue was purified by column chromatography (silica gel (100-200 mesh), eluent 45% EtOAc-PE) to afford the title compound (800 mg).

Step 2: [cis-rac] 3-(Isobutylsulfonyl)-1-(methoxymethyl)-5-(4-methyl-4-((3-(trifluoromethyl)phenyl)sulfonyl)tetrahydro-2H-pyran-2-yl)-1H-pyrazole To a stirred solution of [cis-rac] 3-(isobutylthio)-1-(methoxymethyl)-5-(4-methyl-4-((3-(trifluoromethyl)phenyl)sulfonyl)tetrahydro-2H-pyran-2-yl)-1H-pyrazole (800 mg, 1.58 mmol, 1 eq) in MeOH—H$_2$O (2:1) (15 ml), Oxone (1.45 g, 4.74 mmol, 3 eq) was added at RT. The RM was stirred for 18 h at RT. After completion of the reaction the solvent was evaporated. The residue was diluted with ice-water (100 ml) and basified to pH ~9 with sat. aq. NaHCO$_3$ (30 ml). The product was extracted with EtOAc (3×100 ml) and the combined organic layers were washed with brine (100 ml), dried (Na$_2$SO$_4$), filtered and concentrated. The residue was purified by reverse phase prep-HPLC to afford the title compound (210 mg, 39% over two steps).

Step 3: [cis-rac] 3-(2-Methyl-propylsulfonyl)-5-[4-methyl-4-[[3-(trifluoromethyl)phenyl]sulfonyl]-tetrahydro-pyran-2-yl]-1H-pyrazole (Example 35)

To a stirred solution of [cis-rac] 3-(isobutylsulfonyl)-1-(methoxymethyl)-5-(4-methyl-4-((3-(trifluoromethyl)phenyl)sulfonyl)tetrahydro-2H-pyran-2-yl)-1H-pyrazole (210 mg, 0.39 mmol, 1 eq) in EtOH (10 ml), 4M HCl in 1,4-dioxane (5 ml) was added at RT. The RM was heated to 80° C. and stirred for 18 h at 80° C. After completion of the reaction the RM was poured in to ice and basified to pH~9 using sat. aq. NaHCO$_3$ (25 ml). The product was extracted with EtOAc (3×100 ml) and the combined organic layers were washed with water (100 ml) and brine (100 ml), dried (Na$_2$SO$_4$), filtered and concentrated. The residue was purified by column chromatography (silica gel (100-200 mesh), eluent 4% MeOH-DCM) to afford the title compound (130 mg, 67%). TLC system: 5% MeOH-DCM; R$_f$: 0.14

[Cis-rac] 3-(2-methyl-propylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give 26 mg of [cis-EN1] Example 35 and 28 mg of [cis-EN2] Example 35.

[cis-EN1] Example 35—analytical SFC: Chiralpak-IC (250×4.6 mm 5 μm) 30° C., 3 g/min, 100 bar, 30% MeOH, Ret. Time 5.64 min; m/z=495.1 [M+H]$^+$; $^1$H NMR (400 MHz, DMSO-d$_6$): 0.95 (d, 6H), 1.46-1.51 (m, 4H), 1.81 (d, 1H), 1.99-2.13 (m, 3H), 3.16 (d, 2H), 3.71 (t, 1H), 4.01 (dd, 1H), 4.72 (d, 1H), 6.67 (s, 1H), 7.96 (t, 1H), 8.08 (s, 1H), 8.22 (t, 2H), 13.94 (brs, 1H, NH).

[cis-EN2] Example 35—analytical SFC: Chiralpak-IC (250×4.6 mm 5 μm), 30.1° C., 3 g/min, 100 bar, 30% MeOH, Ret. Time 9.74 min; m/z=495.1 [M+H]$^+$; $^1$H NMR (400 MHz, DMSO-d$_6$): 0.95 (d, 6H), 1.46-1.50 (m, 4H), 1.77 (d, 1H), 2.00-2.14 (m, 3H), 3.11 (d, 2H), 3.69 (t, 1H), 3.99 (dd, 1H), 4.68 (d, 1H), 6.59 (s, 1H), 7.96 (t, 1H), 8.07 (s, 1H), 8.21 (t, 2H), 13.94 (brs, 1H, NH).

3-(2,2-Dimethyl-propylsulfonyl)-5-[4-methyl-4-[[3-(trifluoromethyl)phenyl]sulfonyl]-tetrahydro-pyran-2-yl]-1H-pyrazole (Example 36)

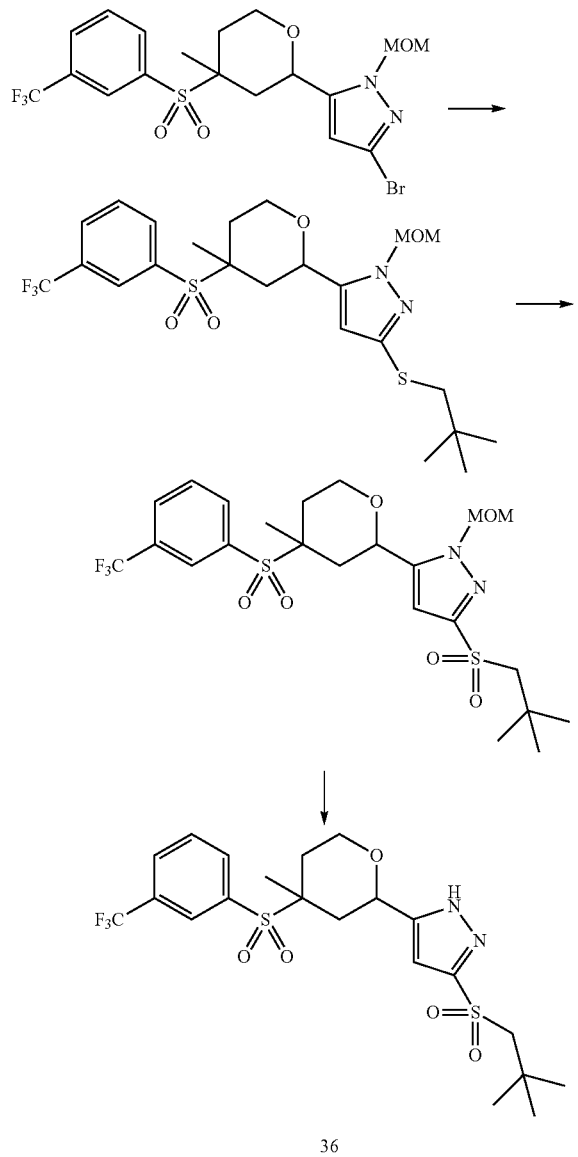

36

Step 1: [cis-rac] 1-(Methoxymethyl)-5-(4-methyl-4-((3-(trifluoromethyl)phenyl)sulfonyl)tetrahydro-2H-pyran-2-yl)-3-(neopentylthio)-1H-pyrazole To a stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (500 mg, 1.01 mmol, 1 eq) in toluene (15 ml), 2-methylpropane-1-thiol (750 mg, 1.51 mmol, 1 eq) in toluene (15 ml), 2,2-dimethylpropane-1-thiol (786 mg, 7.55 mmol, 5 eq) and DIPEA (0.5 ml, 3.02 mmol, 2 eq) were added at RT in a sealed tube. The RM was purged with argon gas for 10 min and then Xantphos (175 mg, 0.30 mmol, 0.2 eq) and Pd$_2$(dba)$_3$ (138 mg, 0.15 mmol, 0.1 eq) were added at RT. The RM was again purged with argon gas for 5 min. The resulting RM was heated to 110° C. and stirred for 18 h at 110° C. After completion of the reaction the RM was cooled to RT, filtered through celite and the celite bed was washed with EtOAc (150 ml). The filtrate was evaporated. The residue was purified by column chromatography (silica gel (100-200 mesh), eluent 42% EtOAc-PE) to afford the title compound (830 mg).

Step 2: [cis-rac] 1-(Methoxymethyl)-5-(4-methyl-4-((3-(trifluoromethyl)phenyl)sulfonyl)tetrahydro-2H-pyran-2-yl)-3-(neopentylsulfonyl)-1H-pyrazole To a stirred solution of [cis-rac] 1-(methoxymethyl)-5-(4-methyl-4-((3-(trifluoromethyl)phenyl)sulfonyl)tetrahydro-2H-pyran-2-yl)-3-(neopentylthio)-1H-pyrazole (830 mg, 1.59 mmol, 1 eq) in MeOH—H$_2$O (2:1) (15 ml), Oxone (1.47 g, 4.79 mmol, 3 eq) was added at RT. The RM was stirred for 18 h at RT. After completion of the reaction, the solvent was evaporated. The residue was diluted with ice-water (100 ml) and basified to pH ~9 with sat. aq. NaHCO$_3$ (30 ml). The product was extracted with EtOAc (3×100 ml). The combined organic layers were washed with brine (100 ml), dried (Na$_2$SO$_4$), filtered and concentrated. The residue was purified by flash column chromatography (65% EtOAc-PE) to afford the title compound (180 mg, 21% over two steps).

Step 3: [cis-rac] 3-(2,2-Dimethyl-propylsulfonyl)-5-[4-methyl-4-[[3-(trifluoromethyl)phenyl]sulfonyl]-tetrahydro-pyran-2-yl]-1H-pyrazole (Example 36)

To a stirred solution of [cis-rac] 1-(methoxymethyl)-5-(4-methyl-4-((3-(trifluoromethyl)phenyl)sulfonyl)tetrahydro-2H-pyran-2-yl)-3-(neopentylsulfonyl)-1H-pyrazole (180 mg, 0.32 mmol, 1 eq) in EtOH (10 ml), 4M HCl in 1,4-dioxane (5 ml) was added at RT. The RM was heated to 80° C. and stirred for 18 h at 80° C. After completion of the reaction the RM was poured in to ice and basified to pH~9 using sat. aq. NaHCO$_3$ (25 ml). The product was extracted with EtOAc (3×100 ml), and the combined organic layers were washed with water (100 ml) and brine (100 ml), dried (Na$_2$SO$_4$), filtered and concentrated. The residue was purified by column chromatography (silica gel (100-200 mesh), eluent 4% MeOH-DCM) to afford the title compound (110 mg, 66%). TLC system: 5% MeOH-DCM; R$_f$ 0.14.

[Cis-rac] 3-(2,2-dimethyl-propylsulfonyl)-5-[4-methyl-4-[[3-(trifluoromethyl)phenyl]sulfonyl]-tetrahydro-pyran-2-yl]-1H-pyrazole was subjected to chiral prep-SFC purification to give 28 mg of [cis-EN1] Example 35 and 23 mg of [cis-EN2] Example 36.

[cis-EN1] Example 36—analytical SFC: Chiralpak-IC (250×4.6 mm 5 µm) 30° C., 3 g/min, 100 bar, 35% MeOH, Ret. Time 5.25 min; m/z=509.2 [M+H]$^+$; $^1$H NMR (400 MHz, DMSO-d$_6$): 1.04 (s, 9H), 1.46-1.51 (m, 4H), 1.81 (d, 1H), 2.06-2.14 (m, 2H), 3.25 (s, 2H), 3.71 (t, 1H), 4.02 (dd, 1H), 4.72 (d, 1H), 6.68 (s, 1H), 7.96 (t, 1H), 8.08 (brs, 1H), 8.21 (t, 2H).

[cis-EN2] Example 36—analytical SFC: Chiralpak-IC (250×4.6 mm 5 µm) 30° C., 3 g/min, 100 bar, 30% MeOH, Ret. Time 8.58 min; m/z=509.2 [M+H]$^+$; $^1$H NMR (400 MHz, DMSO-d$_6$): 1.04 (s, 9H), 1.46-1.51 (m, 4H), 1.80 (d, 1H), 2.06-2.14 (m, 2H), 3.25 (s, 2H), 3.71 (t, 1H), 4.01 (dd, 1H), 4.72 (d, 1H), 6.66 (s, 1H), 7.96 (t, 1H), 8.07 (brs, 1H), 8.21 (t, 2H).

5-Methylsulfonyl-3-[4-methyl-4-[[3-(trifluoromethyl)phenyl]sulfonyl]-tetrahydro-pyran-2-yl]-1H-pyrazole (Example 37)

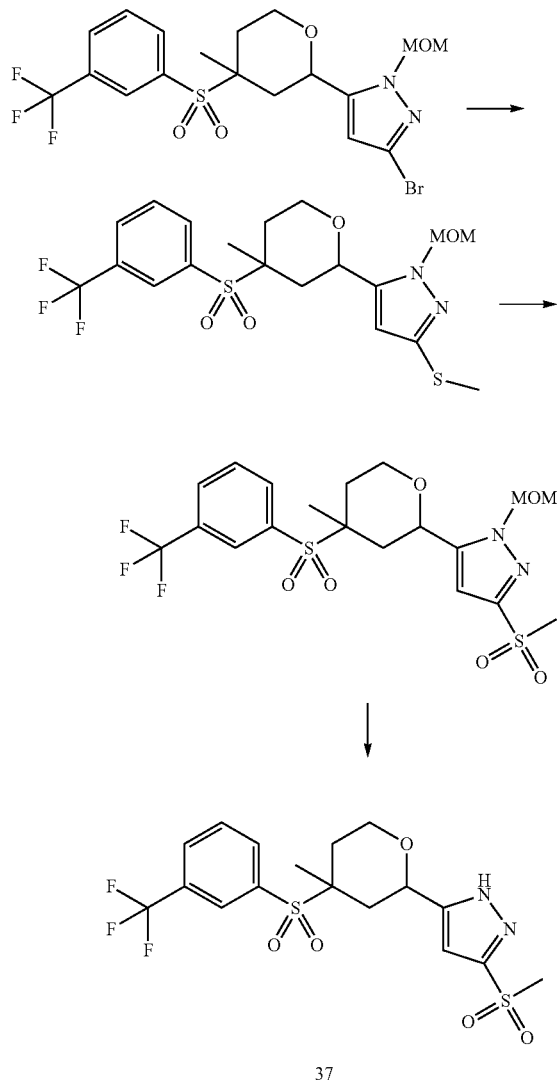

Step 1: [cis-rac] 1-(Methoxymethyl)-5-(4-methyl-4-((3-(trifluoromethyl)phenyl)sulfonyl)tetrahydro-2H-pyran-2-yl)-3-(methylthio)-1H-pyrazole To a stirred solution of [cis-rac] 3-bromo-1-(methoxymethyl)-5-(4-methyl-4-((3-(trifluoromethyl)phenyl)sulfonyl)tetrahydro-2H-pyran-2-yl)-1H-pyrazole [example 12, step 6] (500 mg, 1.01 mmol, 1 eq) in toluene (15 ml), NaSMe (176 mg, 2.52 mmol, 2.5 eq) and DIPEA (0.5 ml, 3.03 mmol, 3 eq) were added at RT in a sealed tube. The RM was purged with argon gas for 10 min and then Xantphos (117 mg, 0.20 mmol, 0.2 eq) and $Pd_2(dba)_3$ (92 mg, 0.10 mmol, 0.1 eq) were added at RT. The RM was again purged with argon gas for 5 min. The resulting RM was heated to 110° C. and stirred for 18 h at 110° C. After completion of the reaction, the RM was cooled to RT and diluted with EtOAc (200 ml). The organic layer was washed with water (3×80 ml) and brine (80 ml), dried over $Na_2SO_4$, filtered and concentrated. The residue was purified by column chromatography (silica gel (100-200 mesh), 39% EtOAc-PE) to afford the title compound (400 mg, crude). In another batch 500 mg starting material were transformed into the title compound (400 mg).

Step 2: [cis-rac] 1-(Methoxymethyl)-5-(4-methyl-4-((3-(trifluoromethyl)phenyl)sulfonyl)tetrahydro-2H-pyran-2-yl)-3-(methylsulfonyl)-1H-pyrazole To a stirred solution of [cis-rac] 1-(methoxymethyl)-5-(4-methyl-4-((3-(trifluoromethyl)phenyl)sulfonyl)tetrahydro-2H-pyran-2-yl)-3-(methylthio)-1H-pyrazole (400 mg, 0.86 mmol, 1 eq) in MeOH—$H_2O$ (2:1) (15 ml), Oxone (794 mg, 2.58 mmol, 3 eq) was added at RT. The RM was stirred for 18 h at RT. In another batch 400 mg of starting material were transformed in analogy. After completion of the reactions both batches were combined and the solvent was evaporated. The residue was diluted with ice-water (100 ml) and basified to pH ~9 with sat. aq. $NaHCO_3$ (30 ml). The product was extracted with EtOAc (3×100 ml) and the combined organic layers were washed with brine (100 ml), dried ($Na_2SO_4$), filtered and concentrated. The residue was purified by flash column chromatography (57% EtOAc-PE) to afford the title compound (250 mg, 25% over two steps).

Step 3: [cis-rac] 5-Methylsulfonyl-3-[4-methyl-4-[[3-(trifluoromethyl)phenyl]sulfonyl]-tetrahydro-pyran-2-yl]-1H-pyrazole (Example 37)

To a stirred solution of [cis-rac] 1-(methoxymethyl)-5-(4-methyl-4-((3-(trifluoromethyl)phenyl)sulfonyl)tetrahydro-2H-pyran-2-yl)-3-(methylsulfonyl)-1H-pyrazole (250 mg, 0.50 mmol, 1 eq) in EtOH (10 ml), 4M HCl in 1,4-dioxane (5 ml) was added at RT. The RM was heated to 80° C. and stirred for 18 h at 80° C. After completion, the RM was poured into ice and basified to pH~9 using sat. aq. $NaHCO_3$ (25 ml). The product was extracted with EtOAc (3×100 ml), the combined organic layers were washed with water (100 ml) and brine (100 ml), dried ($Na_2SO_4$), filtered and concentrated. The residue was purified by flash column chromatography (3% MeOH-DCM) to afford the title compound (160 mg). TLC system: 5% MeOH-DCM; $R_f$: 0.19.

[Cis-rac] 5-methylsulfonyl-3-[4-methyl-4-[[3-(trifluoromethyl)phenyl]sulfonyl]-tetrahydro-pyran-2-yl]-1H-pyrazole was subjected to chiral prep-SFC purification to give 32 mg of [cis-EN1] Example 37 and 37 mg of [cis-EN2] Example 37.

[cis-EN1] Example 37—analytical SFC: Chiralpak-IC (250×4.6 mm 5 µm) 29.9° C., 3 g/min, 100 bar, 30% MeOH, Ret. Time 4.27 min; m/z=453.1 [M+H]$^+$; $^1$H NMR (400 MHz, DMSO-$d_6$): 1.46-1.51 (m, 4H), 1.83 (d, 1H), 2.11 (t, 2H), 3.19 (s, 3H), 3.72 (t, 1H), 4.02 (dd, 1H), 4.73 (d, 1H), 6.71 (s, 1H), 7.96 (t, 1H), 8.08 (s, 1H), 8.22 (t, 2H), 13.91 (brs, 1H).

[cis-EN2] Example 37—analytical SFC: Chiralpak-IC (250×4.6 mm 5 µm), 30° C., 3 g/min, 100 bar, 30% MeOH, Ret. Time 6.31 min; m/z=453.1 [M+H]$^+$; $^1$H NMR (400 MHz, DMSO-$d_6$): 1.46-1.51 (m, 4H), 1.83 (d, 1H), 2.11 (t, 2H), 3.19 (s, 3H), 3.72 (t, 1H), 4.02 (dd, 1H), 4.73 (d, 1H), 6.71 (s, 1H), 7.96 (t, 1H), 8.08 (s, 1H), 8.22 (t, 2H), 13.92 (brs, 1H).

2-Methyl-2-[5-[4-methyl-4-[[6-(trifluoromethyl)-pyridin-2-yl]sulfonyl]-tetrahydro-pyran-2-yl]-1H-pyrazol-3-yl]-propionitrile (Example 38)

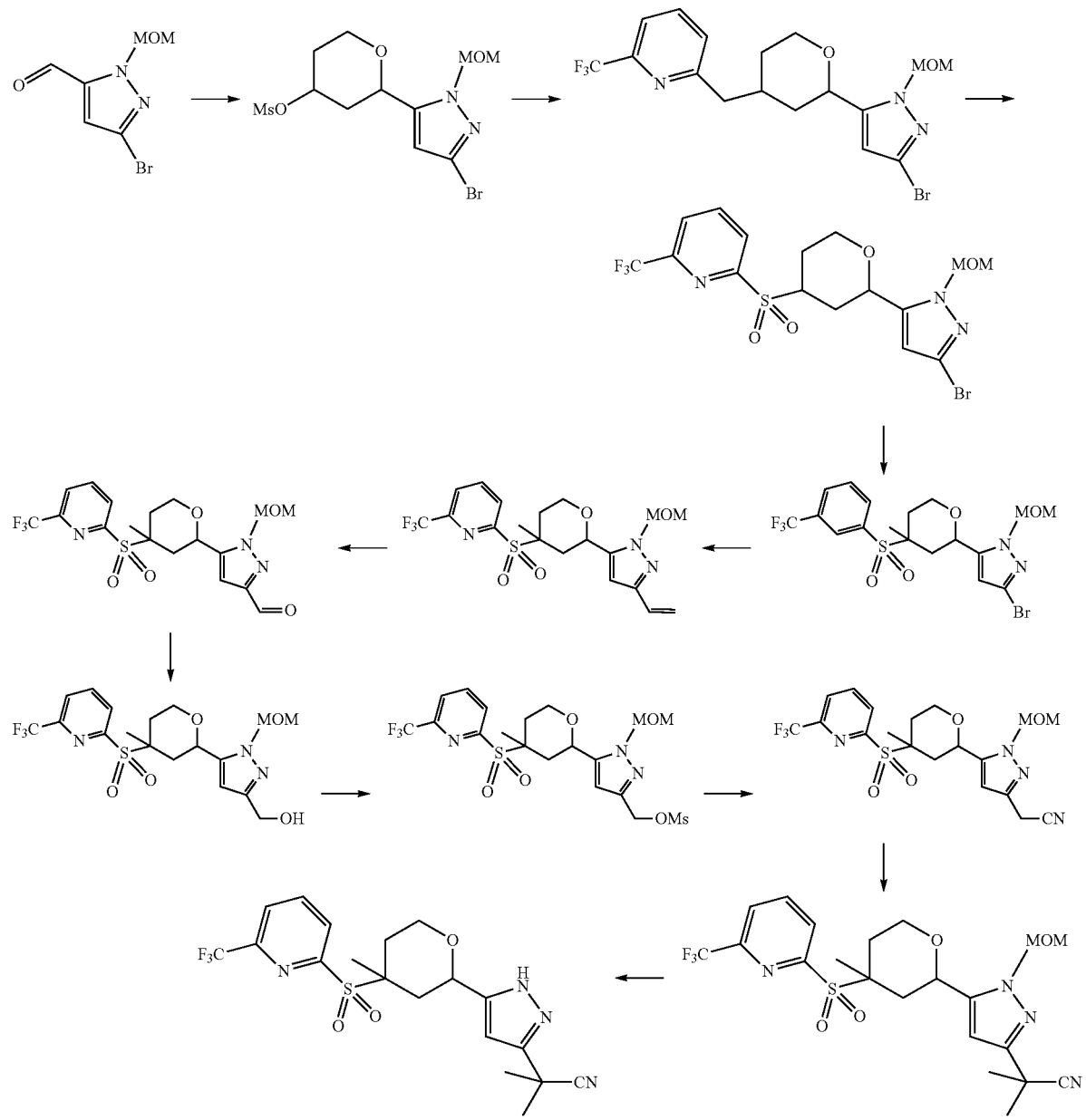

38

Step 1: 2-(3-Bromo-1-(methoxymethyl)-1H-pyrazol-5-yl)tetrahydro-2H-pyran-4-yl methanesulfonate Methanesulfonic acid (149.0 ml, 2.29 mol) was added to a stirred solution of 3-bromo-1-(methoxymethyl)-1H-pyrazole-5-carbaldehyde [example 12, step 2] (50.0 g, 229.35 mmol) and 3-buten-1-ol (34.0 ml, 344.03 mmol) in DCM (500 ml) at 0° C. over a period of 30 min and the mixture was stirred for 1 h at the same temperature. The RM was diluted with DCM (2×300 ml). The resulting mixture was washed with water (200 ml), aq. NaHCO₃ (2×200 ml) and brine (200 ml), and dried over anhydrous Na₂SO₄. The organic layer was filtered and the solvent was concentrated under reduced pressure to give the title compound (65 g).

Step 2: 2-((2-(Bromo-1-(methoxymethyl)-1H-pyrazol-5-yl)tetrahydro-2H-pyran-4-yl)thio)-6-(trifluoromethyl)pyridine 6-(Trifluoromethyl)pyridine-2-thiol (63.29 g, 264.94 mmol) was added to a suspension of K₂CO₃ (48.74 g, 353.26 mmol) and 2-(3-bromo-1-(methoxymethyl)-1H-pyrazol-5- yl)tetrahydro-2H-pyran-4-yl methanesulfonate (65.0 g, 176.63 mmol) in DMF (1000 ml) and the mixture was stirred at 80° C. for 4 h and 12 h at RT. The RM was diluted with water (1000 ml) and the organic product was extracted with EtOAc (3×200 ml). The organic layer was washed with brine (2×200 ml) and dried over anhydrous $Na_2SO_4$. The organic layer was filtered and the solvent was concentrated under reduced pressure to give the crude product which was purified by column chromatography (silica gel 100-200 mesh, 0-15% EtOAc in PE) to get the title compound (6.5 g, 5% over 5 steps).

Step 3: 2-((2-(3-Bromo-1-(methoxymethyl)-1H-pyrazol-5-yl)tetrahydro-2H-pyran-4-yl)sulfonyl)-6-(trifluoromethyl)pyridine A solution of oxone (17.68 g, 28.82 mmol) in water (163 ml) was added to a stirred solution of 2-((2-(3-bromo-1-(methoxymethyl)-1H-pyrazol-5-yl)tetrahydro-2H-pyran-4-yl)thio)-6-(trifluoromethyl)pyridine (6.50 g, 14.41 mmol) in MeOH (230 ml) and the mixture was stirred for 16 h at RT. The RM was diluted with water (200 ml) and the organic product was extracted with DCM (3×200 ml). The combined organic layers were washed with brine (2×100 ml) and dried over anhydrous $Na_2SO_4$. The organic layer was filtered and the solvent was concentrated under reduced pressure to give the crude product which was purified by column chromatography (silica gel 100-120 mesh, 0-20% EtOAc in PE) to give the title compound (5.0 g, 72%).

Step 4: 2-((2-(3-Bromo-1-(methoxymethyl)-1H-pyrazol-5-yl)-4-methyltetrahydro-2H-pyran-4-yl) sulfonyl)-6-(trifluoromethyl)pyridine KOtBu solution (21.0 ml, 20.66 mmol, 1M in THF) was added to a stirred solution of 2-((2-(3-bromo-1-(methoxymethyl)-1H-pyrazol-5-yl)tetrahydro-2H-pyran-4-ylsulfonyl)-6-(trifluoromethyl)pyridine (5.0 g, 10.33 mmol) in (THF-DMF) (2:1 v/v) (50 ml) at −78° C. and the mixture was stirred for 30 min. Methyl iodide (1.63 ml, 25.82 mmol) was added and the mixture was slowly warmed to RT and stirred for 16 h. The RM was diluted with water (50 ml) and the organic product was extracted with EtOAc (2×10 ml). The combined organic layers were washed with brine and dried over anhydrous $Na_2SO_4$. The organic layer was filtered and the solvent was concentrated under reduced pressure to give the crude product which was purified by column chromatography (silica gel 100-200 mesh, 0-25% EtOAc in PE) to give the title compound. [cis-rac] (1.0 g, 20%) and [trans-rac] (1.20 g, 24%).

Step 5: [cis-rac] 2-((2-(1-(Methoxymethyl)-3-vinyl-1H-pyrazol-5-yl)-4-methyltetrahydro-2H-pyran-4-yl) sulfonyl)-6-(trifluoromethyl)pyridine A stirred solution of compound [cis-rac] 2-((2-(3-bromo-1-(methoxymethyl)-1H-pyrazol-5-yl)-4-methyltetrahydro-2H-pyran-4-ylsulfonyl)-6-(trifluoromethyl)pyridine (1.0 g, 2.10 mmol), potassium vinyltrifluoroborate (1.70 g, 8.04 mmol) and $Cs_2CO_3$ (1.96 g, 6.03 mmol) in DMF-$H_2O$ (20 ml-5 ml) was degassed for 15 min with argon. To the RM was added $PdCl_2(dppf)_2.CH_2Cl_2$ (0.49 g, 0.60 mmol) and it was degassed again for 5 min. The resulting RM was heated to 120° C. and stirred for 3 h. The RM was concentrated under reduced pressure and the residue was diluted with water (50 ml). The organic product was extracted with EtOAc (2×100 ml). The combined organic extracts were washed with water (2×50 ml) and brine (2×50 ml) and dried over anhydrous $Na_2SO_4$. The organic layer was filtered and the solvent was concentrated under reduced pressure to give the crude product which was purified by flash chromatography (silica gel 100-200 mesh, 0-45% EtOAc in PE) to afford the title compound (0.75 g, 84%).

Step 6: [cis-rac] 1-(Methoxymethyl)-5-(4-methyl-4-((6-(trifluoromethyl)pyridin-2-yl)sulfonyl)tetrahydro-2H-pyran-2-yl)-1H-pyrazole-3-carbaldehyde Ozone gas was bubbled through a solution of [cis-rac] 2-((2-(1-(methoxymethyl)-3-vinyl-1H-pyrazol-5-yl)-4-methyltetrahydro-2H-pyran-4-ylsulfonyl)-6-(trifluoromethyl)pyridine (0.75 g, 1.68 mmol) in acetone-$H_2O$ (3:1 v/v) (15 ml-5 ml) at 0° C. for 15 min. The RM was diluted with water (30 ml), and the organic product was extracted with EtOAc (2×30 ml). The combined organic layers were washed with water (2×20 ml) and brine (20 ml), and dried over anhydrous $Na_2SO_4$. The organic layer was filtered and the solvent was concentrated under reduced pressure to give the title compound (0.7 g).

Step 7: [cis-rac] (1-(Methoxymethyl)-5-(4-methyl-4-((6-(trifluoromethyl)pyridin-2-yl)sulfonyl)tetrahydro-2H-pyran-2-yl)-1H-pyrazol-3-yl)methanol Sodium borohydride (0.119 g, 3.13 mmol) was added portionwise at 0° C. to a solution of [cis-rac] 1-(methoxymethyl)-5-(4-methyl-4-((6-(trifluoromethyl)pyridin-2-yl)sulfonyl)tetrahydro-2H-pyran-2-yl)-1H-pyrazole-3-carbaldehyde (0.7 g, 1.56 mmol) in MeOH (10 ml). The resulting RM was stirred at RT for 2 h under argon. The reaction was monitored by TLC. Upon consumption of starting material, the RM was quenched with ice-cold water and the organic product was extracted with EtOAc. The organic layer was dried over anhydrous sodium sulfate and the solvent was concentrated under reduced pressure to obtain the title compound (0.55 g, 73%).

Step 8: [cis-rac] (1-(Methoxymethyl)-5-(4-methyl-4-((6-(trifluoromethyl)pyridin-2-yl)sulfonyl)tetrahydro-2H-pyran-2-yl)-1H-pyrazol-3-yl)methyl methanesulfonate Triethylamine (0.5 ml, 3.67 mmol) was added to a stirred solution of [cis-rac] (1-(methoxymethyl)-5-(4-methyl-4-((6-(trifluoromethyl)pyridin-2-yl)sulfonyl)tetrahydro-2H-pyran-2-yl)-1H-pyrazol-3-yl)methanol (0.55 g, 1.22 mmol) in DCM (10 ml) at 0° C. To the RM was added methanesulfonyl chloride (0.15 ml, 1.83 mmol) at the same temperature. The RM was slowly warmed to RT and stirred for 1 h. The RM was diluted with water (25 ml); and the organic product was extracted with DCM (2×50 ml). The combined organic extracts were washed with brine, dried over anhydrous sodium sulfate, filtered and evaporated under reduced pressure to give the title compound (0.6 g).

Step 9: [cis-rac] 2-(1-(Methoxymethyl)-5-(4-methyl-4-((6-(trifluoromethyl)pyridin-2-yl)sulfonyl) tetrahydro-2H-pyran-2-yl)-1H-pyrazol-3-yl)acetonitrile Sodium cyanide (0.105 g, 2.15 mmol) was added to a solution of [cis-rac] (1-(methoxymethyl)-5-(4-methyl-4-((6-(trifluoromethyl)pyridin-2-yl)sulfonyl)tetrahydro-2H-pyran-2-yl)-1H-pyrazol-3-ylmethyl methanesulfonate (0.6 g, 1.07 mmol) in DMF (10 ml) and the mixture was stirred at RT for 2 h. The RM was diluted with water and the organic product was extracted with EtOAc. The organic layer was washed with brine (20 ml) and dried over anhydrous Na₂SO₄. The organic layer was filtered and the solvent was concentrated under reduced pressure to afford the title compound (0.45 g).

Step 10: [cis-rac] 2-(1-(Methoxymethyl)-5-(4-methyl-4-((6-(trifluoromethyl)pyridin-2-yl)sulfonyl)tetrahydro-2H-pyran-2-yl)-1H-pyrazol-3-yl)-2-methylpropanenitrile 60% sodium hydride (0.12 g, 2.94 mmol) was added portionwise to a solution of [cis-rac] 2-(1-(methoxymethyl)-5-(4-methyl-4-((6-(trifluoromethyl)pyridin-2-yl)sulfonyl)tetrahydro-2H-pyran-2-yl)-1H-pyrazol-3-ylacetonitrile (0.45 g, 0.98 mmol) in DMF (10 ml) at 0° C. and the mixture was stirred for 10 min at the same temperature. Methyl iodide (0.15 ml, 2.45 mmol) was added to the RM, and this was slowly warmed to RT and stirred for 16 h. The RM was quenched with cold water (20 ml), and the organic product was extracted with EtOAc (2×50 ml). The combined organic layers were washed with water (2×40 ml), and brine (30 ml), and dried over anhydrous Na₂SO₄. The organic layer was filtered and the solvent was concentrated under reduced pressure to afford the crude product which was purified by preparative TLC (45% EtOAc in PE) to give the title compound (0.2 g, 24% for 6 steps).

Step 11: [cis-rac] 2-Methyl-2-[5-[4-methyl-4-[[6-(trifluoromethyl)-pyridin-2-yl]sulfonyl]-tetrahydro-pyran-2-yl]-1H-pyrazol-3-yl]-propionitrile (Example 38)

Trifluoroacetic acid (5.0 ml) was added to [cis-rac] 2-(1-(methoxymethyl)-5-(4-methyl-4-((6-(trifluoromethyl)pyridin-2-yl)sulfonyl)tetrahydro-2H-pyran-2-yl)-1H-pyrazol-3-yl)-2-methylpropanenitrile (0.2 g, 0.41 mmol) at RT and the resulting RM was heated to 60° C. for 2 h. The RM was concentrated under reduced pressure and the residue was diluted with water. The RM was cooled to 0° C. and sat. aq. NaHCO₃ s (15 ml) was added. The organic product was extracted with EtOAc (2×25 ml). The combined organic layers were washed with water (2×10 ml) and brine (20 ml), and dried over anhydrous Na₂SO₄. The organic layer was filtered and the solvent was concentrated under reduced pressure to afford the title compound. TLC system: EtOAc-PE; 6:4; Rf: 0.3.

[Cis-rac] 2-methyl-2-[5-[4-methyl-4-[[6-(trifluoromethyl)-pyridin-2-yl]sulfonyl]-tetrahydro-pyran-2-yl]-1H-pyrazol-3-yl]-propionitrile was subjected to chiral prep-SFC purification to give 44 mg of [cis-EN1] Example 38 and 42 mg of [cis-EN2] Example 38.

[cis-EN1] Example 38—analytical SFC: Chiralpak AD-H (250×4.6 mm 5 μm) 30.1° C., 3 g/min, 100 bar, 35% MeOH, Ret. Time 2.42 min; m/z=443.2 [M+H]⁺

[cis-EN2] Example 38—analytical SFC: Chiralpak AD-H (250×4.6 mm 5 μm), 30° C., 3 g/min, 100 bar, 35% MeOH, Ret. Time 3.58 min; m/z=443.2 [M+H]⁺

[trans-rac] 2-Methyl-2-[5-[4-methyl-4-[[6-(trifluoromethyl)-pyridin-2-yl]sulfonyl]-tetrahydro-pyran-2-yl]-1H-pyrazol-3-yl]-propionitrile (Example 38)

The [trans-rac] isomer was prepared in analogy to the [cis-rac] isomer, starting from [trans-rac] product of step 4, and purified by reverse phase prep HPLC.

5-[4-Methyl-4-[[3-(trifluoromethyl)phenyl]sulfonyl]-tetrahydro-pyran-2-yl]-3-[(2,2,2-trifluoro-1,1-dimethyl-ethyl)sulfonyl]-1H-pyrazole (Example 39)

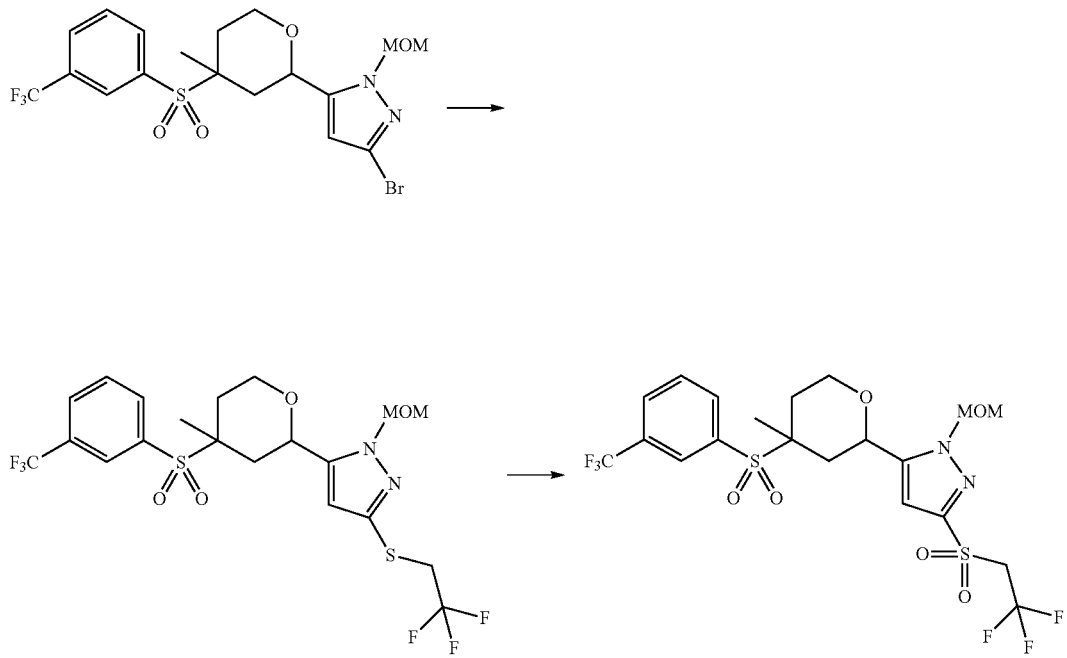

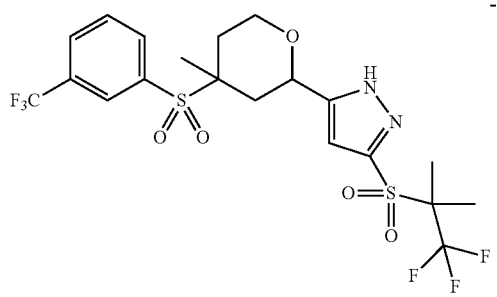

39

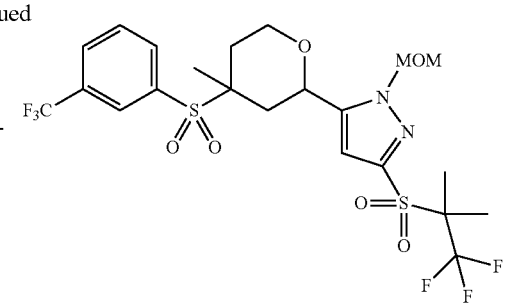

Step 2: [cis-rac] 1-(Methoxymethyl)-5-(4-methyl-4-((3-(trifluoromethyl)phenyl)sulfonyl)tetrahydro-2H-pyran-2-yl)-3-(2,2,2-trifluoroethyl)sulfonyl)-1H-pyrazole Steps 1 & step 2 were carried out in analogy to example 36.

Step 3: [cis-rac] 1-(Methoxymethyl)-5-(4-methyl-4-((3-(trifluoromethyl)phenyl)sulfonyl)tetrahydro-2H-pyran-2-yl)-3-((1,1,1-trifluoro-2-methylpropan-2-yl)sulfonyl)-1H-pyrazole To a stirred solution of [cis-rac] 1-(methoxymethyl)-5-(4-methyl-4-((3-(trifluoromethyl)phenyl)sulfonyl)tetrahydro-2H-pyran-2-yl)-3-((2,2,2-trifluoroethyl)sulfonyl)-1H-pyrazole (120 mg, 0.21 mmol, 1 eq) in THF (10 ml), HMPA (1 ml) and methyl iodide (2 ml) were added at −78° C. Then LDA (2 M in THF) (0.3 ml, 0.63 mmol, 3 eq) was added at −78° C. and the RM was stirred for 10 min at −78° C. After completion of the reaction, the RM was quenched with sat. aq. NH₄Cl (5 ml). The RM was diluted with EtOAc (200 ml), and the organic layer was washed with water (2×100 ml) and brine (100 ml), dried (Na₂SO₄), filtered and concentrated to afford the title compound (120 mg).

Step 4: [cis-rac] 5-[4-Methyl-4-[[3-(trifluoromethyl)phenyl]sulfonyl]-tetrahydro-pyran-2-yl]-3-[(2,2,2-trifluoro-1,1-dimethyl-ethyl)sulfonyl]-1H-pyrazole (Example 39)

Step 4 was carried out in analogy to step 3 example 36. [cis-rac] Example 39—m/z=549.1 [M+H]⁺

3-(2-Fluoro-1,1-dimethyl-ethyl)-5-[4-methyl-4-[[3-(trifluoromethyl)phenyl]sulfonyl]-tetrahydro-pyran-2-yl]-1H-pyrazole (Example 40)

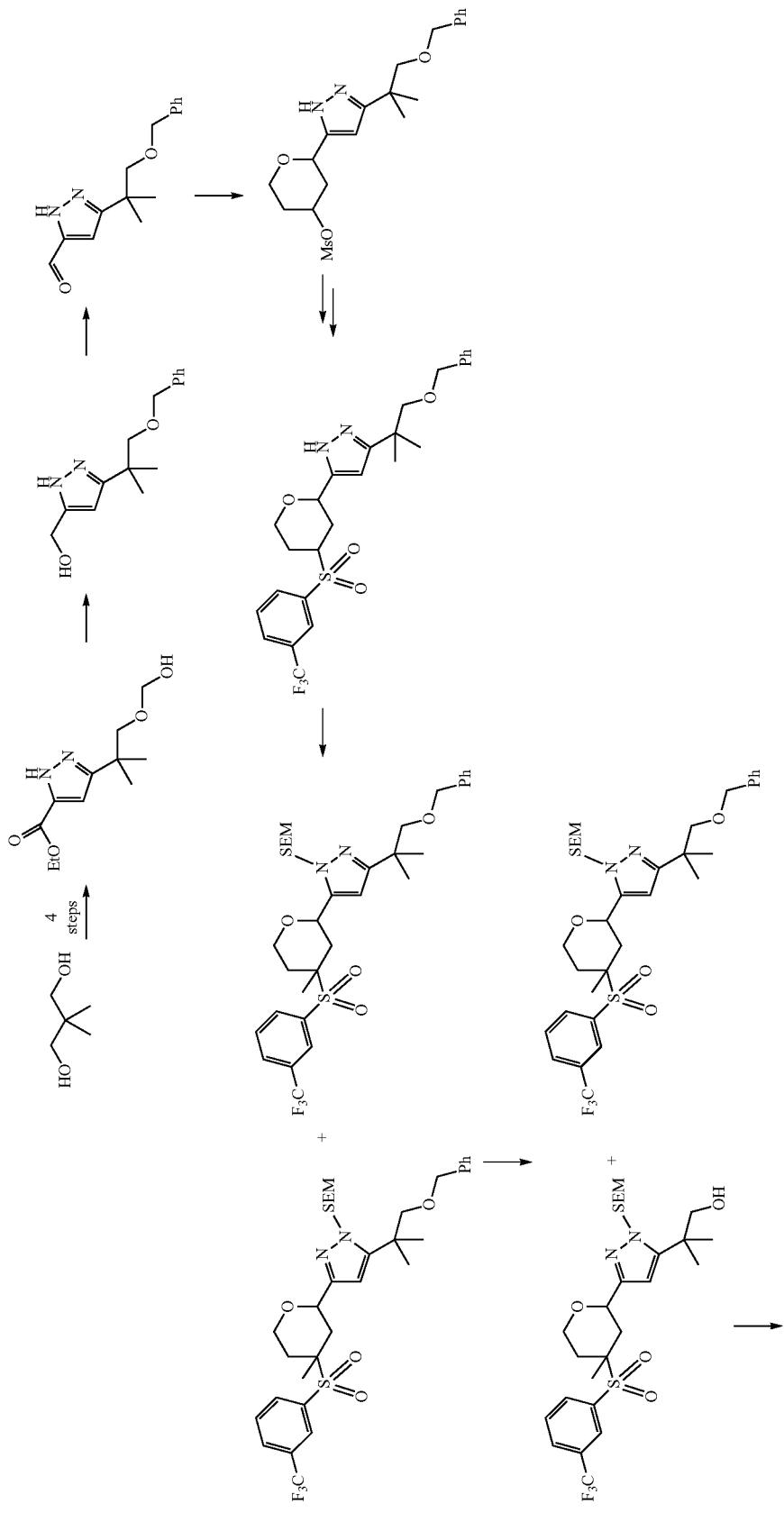

-continued
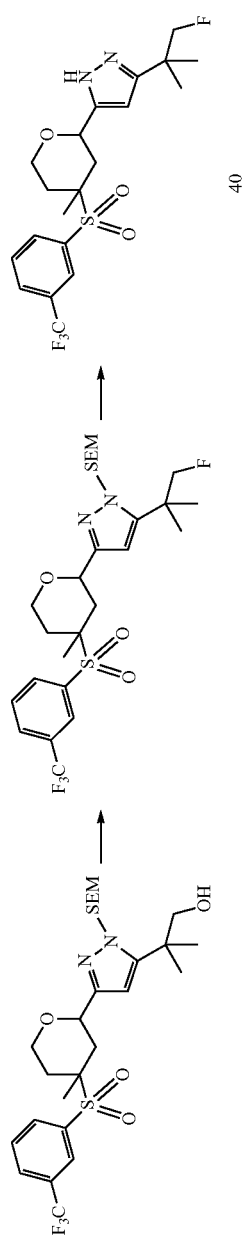
40

Step 1: 3-(Benzyloxy)-2,2-dimethylpropan-1-ol

Sodium hydride (2.50 g, 105.62 mmol, 60% in mineral oil) was suspended in dry DMF (150 ml) at 0° C. and a solution of 2,2-dimethylpropane-1,3-diol (10.0 g, 96.02 mmol) in DMF (50.0 ml) was added dropwise. The RM was stirred at 0° C. for 30 min. To the RM was added dropwise benzyl bromide (11.50 ml, 96.02 mmol) and the RM was allowed to warm to RT and stirred for 16 h. The RM was diluted with water (300 ml) and the organic product was extracted with EtOAc (3×200 ml). The organic layer was washed with brine (2×200 ml), dried over $Na_2SO_4$, filtered and the solvent evaporated in vacuo to give the crude product, which was purified by column chromatography (silica gel 60-120 mesh, 0-10% EtOAc in PE) to get the title compound (12.50 g).

Step 2: 3-(Benzyloxy)-2,2-dimethylpropanal

Dess-Martin periodinane (10.90 g, 25.77 mmol) was slowly added to a solution of 3-(benzyloxy)-2,2-dimethylpropan-1-ol (5.0 g, 25.77 mmol) in THF-DMSO (1:1 v/v, 200 ml) at 0° C., and the mixture was slowly warmed to RT and stirred for 16 h. The RM was filtered through a celite bed and washed with DCM. The organic layer was washed with sat. sodium bicarbonate solution (2×100 ml) and brine (2×100 ml), dried over anhydrous $Na_2SO_4$, filtered and the solvent evaporated in vacuo to give the crude product, which was purified by column chromatography (60-120 mesh silica gel, 0-10% EtOAc in PE) to give the title compound (3.3 g, 66%).

Step 3: (((2,2-Dimethylbut-3-yn-1-yl)oxy)methyl) benzene

Bestmann-Ohira reagent (4.50 g, 23.43 mmol) was added to a suspension of $K_2CO_3$ (2.15 g, 15.62 mmol) and 3-(benzyloxy)-2,2-dimethylpropanal (3.0 g, 15.62 mmol) in MeOH (30 ml) at 0° C. and the mixture was stirred at RT for 1 h. The RM was concentrated under reduced pressure to give the crude product, which was purified by column chromatography (silica gel 60-120 mesh, 0-10% EtOAc in PE) to give the title compound (1.30 g, 44%).

Step 4: Ethyl 5-(1-(benzyloxy)-2-methylpropan-2-yl)-1H-pyrazole-3-carboxylate Ethyl diazoacetate (0.6 ml, 5.31 mmol) was added to a suspension of (((2,2-dimethylbut-3-yn-1-yl)oxy)methyl) benzene (1.0 g, 5.31 mmol) in toluene (20 ml) at RT and the mixture was stirred at 120° C. for 16 h. The RM was concentrated under reduced pressure to give the crude product, which was purified by column chromatography (silica gel 60-120 mesh, 20% EtOAc in PE) to give the title compound (400 mg, 25%).

Step 5: (5-(1-(Benzyloxy)-2-methylpropan-2-yl)-1H-pyrazol-3-yl)methanol $LiAlH_4$ solution (1.98 ml, 1.98 mmol, 1 M in THF) was added to a solution of ethyl 5-(1-(benzyloxy)-2-methylpropan-2-yl)-1H-pyrazole-3-carboxylate (400 mg, 1.32 mmol) in THF (10 ml) at 0° C. and the mixture was stirred at RT for 16 h. The RM was quenched with sat. $Na_2SO_4$ solution, filtered through a celite bed, and washed with EtOAc. The filtrate was dried over anhydrous $Na_2SO_4$, filtered and the solvent evaporated in vacuo to give the crude product. The crude product was purified by column chromatography (60-120 mesh silica gel, 0-5% EtOAc in PE) to give the title compound (300 mg, 87%).

Step 6: 5-(1-(Benzyloxy)-2-methylpropan-2-yl)-1H-pyrazole-3-carbaldehyde

Activated $MnO_2$ (5.40 g, 62.50 mmol) was added to a stirred solution of (5-(1-(benzyloxy)-2-methylpropan-2-yl)-1H-pyrazol-3-yl)methanol (4.0 g, 15.62 mmol) in 1,2-dimethoxyethane (60 ml) at RT and the mixture was refluxed for 16 h. The RM was filtered through celite and washed with EtOAc (3×200 ml). The clear filtrate was concentrated under reduced pressure to give the title compound (4.30 g).

Step 7: 2-(5-(1-(Benzyloxy)-2-methylpropan-2-yl)-1H-pyrazol-3-yl)tetrahydro-2H-pyran-4-yl methanesulfonate Methanesulfonic acid (9.50 ml, 147.28 mol) was added to a stirred solution of 5-(1-(benzyloxy)-2-methylpropan-2-yl)-1H-pyrazole-3-carbaldehyde (4.30 g, 14.72 mmol) and 3-buten-1-ol (2.10 ml, 22.09 mmol) in DCM (50 ml) at 0° C. over a period of 30 min and the mixture was stirred for 16 h at RT. The RM was diluted with DCM (2×200 ml). The organic layer was washed with water (200 ml), aq. $NaHCO_3$ solution (2×100 ml) and brine (100 ml), dried over anhydrous $Na_2SO_4$, filtered, and the solvent was concentrated under reduced pressure to give the title compound (4.50 g).

Step 8: 5-(1-(Benzyloxy)-2-methylpropan-2-yl)-3-(trifluoromethyl)phenyl)thio)tetrahydro-2H-pyran-2-yl)-1H-pyrazole 3-Trifluoromethylthiophenol (5.40 ml, 22.16 mmol) was added to a suspension of $K_2CO_3$ (3.0 g, 22.16 mmol) and 2-(5-(1-(benzyloxy)-2-methylpropan-2-yl)-1H-pyrazol-3-yl)tetrahydro-2H-pyran-4-yl methanesulfonate (4.50 g, 11.08 mmol) in DMF (50 ml) and the mixture was stirred at 50° C. for 6 h and 6 h at RT. The RM was diluted with water (200 ml) and the organic product was extracted with EtOAc (3×200 ml). The organic layer was washed with brine (2×100 ml), dried over anhydrous $Na_2SO_4$, filtered and the solvent evaporated in vacuo to give the crude product, which was purified by column chromatography (silica gel 60-120 mesh, 0-10% EtOAc in PE) to give the title compound (3.0 g, 55%).

Step 9: 5-(1-(Benzyloxy)-2-methylpropan-2-yl)-3-(4-((3-(trifluoromethyl)phenyl)sulfonyl)tetrahydro-2H-pyran-2-yl)-1H-pyrazole A solution of Oxone (7.50 g, 12.24 mmol) in water (20.0 ml) was added to a stirred solution of 5-(1-(benzyloxy)-2-methylpropan-2-yl)-3-(4-((3-(trifluoromethyl)phenylthio) tetrahydro-2H-pyran-2-yl)-1H-pyrazole (3.0 g, 6.12 mmol) in MeOH (30 ml) at 0° C. and the mixture was stirred for 16 h at RT. The RM was diluted with water (100 ml) and the organic product was extracted with DCM (3×100 ml). The combined organic layers were washed with brine (2×100 ml), dried over anhydrous $Na_2SO_4$, filtered and the solvent evaporated in vacuo to give the crude product, which was purified by column chromatography (silica gel 60-120 mesh, 0-20% EtOAc in PE) to give the title compound (2.5 g, 78%).

Step 10: 3-(1-(Benzyloxy)-2-methylpropan-2-yl)-5-(4-((3-(trifluoromethyl)phenyl) sulfonyl)tetrahydro-2H-pyran-2-yl)-1-((2-(trimethylsilyl)ethoxy)methyl)-1H-pyrazole and 5-(1-(Benzyloxy)-2-methylpropan-2-yl)-3-(4-((3-(trifluoromethyl)phenyl)sulfonyl) tetrahydro-2H-pyran-2-yl)-1-((2-(trimethylsilyl) ethoxy)methyl)-1H-pyrazole A solution of 5-(1-(benzyloxy)-2-methylpropan-2-yl)-3-(4-((3-(trifluoromethyl)phenyl)sulfonyl)tetrahydro-2H-pyran-2-yl)-1H-pyrazole (500 mg, 0.957 mmol) in THF (10 ml) was added to a suspension of NaH (69.0 mg, 2.873 mmol, 60% dispersion in mineral oil) in THF (5.0 ml) at 0° C. over a period of 10 min and the mixture was stirred for 30 min at the same temperature. 2(Trimethylsilyl)ethoxymethyl chloride (0.16 ml, 0.957 mmol) was added to the RM. The mixture was slowly warmed to RT and stirred for 16 h. The RM was quenched with cold water (50 ml) and the organic product was extracted with EtOAc (2×50 ml). The combined organic layers were washed with water (2×20 ml) and brine (40 ml), and dried over anhydrous $Na_2SO_4$. The organic layer was filtered and the solvent was concentrated under reduced pressure to get the crude mixture of desired regioisomers (500 mg).

Step 11: [cis rac] 3-(1-(Benzyloxy)-2-methylpropan-2-yl)-5-(4-methyl-4-((3-(trifluoromethyl)phenyl) sulfonyl)tetrahydro-2H-pyran-2-yl)-1-((2-(trimethylsilyl)ethoxy)methyl)-1H-pyrazole and 5-(1-(Benzyloxy)-2-methylpropan-2-yl)-3-(4-methyl-4-((3-(trifluoromethyl)phenyl)sulfonyl)tetrahydro-2H-pyran-2-yl)-1-((2-(trimethylsilyl)ethoxy)methyl)-1H-pyrazole KOtBu solution (1.53 ml, 1.53 mmol, 1M in THF) was added to a stirred solution of a mixture of 3-(1-(benzyloxy)-2-methylpropan-2-yl)-5-(4-((3-(trifluoromethyl)phenyl)sulfonyl)tetrahydro-2H-pyran-2-yl)-1-((2-(trimethylsilyl) ethoxy)methyl)-1H-pyrazole and 5-(1-(benzyloxy)-2-methylpropan-2-yl)-3-(4-((3-(trifluoromethyl)phenyl) sulfonyl)tetrahydro-2H-pyran-2-yl)-1-((2-(trimethylsilyl) ethoxy)methyl)-1H-pyrazole (500 mg, 0.766 mmol) in dry THF (10 ml) at −78° C. and the mixture was stirred for 30 min. To the RM was added methyl iodide (0.11 ml, 1.917 mmol). It was slowly warmed to RT and stirred for 16 h. Similarly another batch was repeated starting from 1.5 g and the two batches worked up in a combined manner. The RM was diluted with water (100 ml) and the organic product was extracted with EtOAc (2×100 ml). The combined organic layers were washed with brine (100 ml), dried over anhydrous $Na_2SO_4$, filtered and the solvent evaporated in vacuo to give a mixture of the desired regioisomers. The regioisomers were separated by RP-HPLC (KROMOSIL-C18, 10 mM ammonium bicarbonate in water:acetonitrile; 0/80→14.5/80) followed by achiral SFC (Chiralpak IE, 90% CO2, 10% MeOH) to give 90 mg of [cis rac] 3-(1-(Benzyloxy)-2-methylpropan-2-yl)-5-(4-methyl-4-((3-(trifluoromethyl)phenyl)sulfonyl)tetrahydro-2H-pyran-2-yl)-1-((2-(trimethylsilyl)ethoxy)methyl)-1H-pyrazole [NOE: On irradiating OCH proton NOE was observed with $SCCH_3$.] and 410 mg of [cis rac] 5-(1-(Benzyloxy)-2-methylpropan-2-yl)-3-(4-methyl-4-((3-(trifluoromethyl)phenyl)sulfonyl) tetrahydro-2H-pyran-2-yl)-1-((2-(trimethylsilyl)ethoxy) methyl)-1H-pyrazole.

Step 12: [cis rac] 2-Methyl-2-(3-(4-methyl-4-((3-(trifluoromethyl)phenyl)sulfonyl)tetrahydro-2H-pyran-2-yl)-1-((2-(trimethylsilyl)ethoxy)methyl)-1H-pyrazol-5-yl)propan-1-ol 10% Palladium on carbon (50 mg) was added to a stirred solution of [cis rac] 5-(1-(benzyloxy)-2-methylpropan-2-yl)-3-(4-methyl-4-((3-(trifluoromethyl)phenyl)sulfonyl)tetrahydro-2H-pyran-2-yl)-1-((2-(trimethylsilyl)ethoxy) methyl)-1H-pyrazole (100 mg, 0.150 mmol) in MeOH (2.0 ml) under $H_2$ balloon pressure at RT for 4 h. Similarly another batch was repeated starting from 300 mg and both batches were worked-up in combined manner. The RM was filtered through a celite pad and washed with DCM (3×20 ml). The clear filtrate was concentrated under reduced pressure to the title compound (200 mg).

Step 13: [cis rac] 5-(1-Fluoro-2-methylpropan-2-yl)-3-(4-methyl-4-((3-(trifluoromethyl)phenyl)sulfonyl)tetrahydro-2H-pyran-2-yl)-1-((2-(trimethylsilyl)ethoxy)methyl)-1H-pyrazole DAST (0.18 ml, 1.38 mmol) was added to a solution of [cis rac] 2-methyl-2-(3-(4-methyl-4-((3-(trifluoromethyl) phenyl)sulfonyl)tetrahydro-2H-pyran-2-yl)-1-((2-(trimethylsilyl)ethoxy)methyl)-1H-pyrazol-5-yl)propan-1-ol (200 mg, 0.34 mol) in DCM (5 ml) at 0° C. and the mixture was slowly warmed to RT and stirred for 16 h. The RM was quenched with sat. $NaHCO_3$ solution (20 ml) and the organic product was extracted with EtOAc (2×30 ml). The organic layer was washed with brine (2×10 ml), dried over anhydrous $Na_2SO_4$, filtered and the solvent evaporated in vacuo to give the crude product, which was purified by column chromatography (silica gel 60-120 mesh, 0-30% EtOAc in PE) to give the title compound (170 mg).

Step 14: [cis rac] 3-(2-Fluoro-1,1-dimethyl-ethyl)-5-[4-methyl-4-[[3-(trifluoromethyl)phenyl]sulfonyl]-tetrahydro-pyran-2-yl]-1H-pyrazole (Example 40)

Trifluoroacetic acid (2.0 ml) was added to a solution of [cis rac] 5-(1-fluoro-2-methylpropan-2-yl)-3-(4-methyl-4-((3-(trifluoromethyl)phenyl)sulfonyl)tetrahydro-2H-pyran-2-yl)-1-((2-(trimethylsilyl)ethoxy)methyl)-1H-pyrazole (170 mg, 0.29 mmol) dissolved in DCM (2.0 ml) at 0° C. The RM was stirred at RT for 4 h. The RM was concentrated under reduced pressure to give a residue which was stirred with sat. NaHCO3 solution. The organic product was extracted with EtOAc (2×50 ml) and the solvent was concentrated under reduced pressure to give the title compound (150 mg). TLC system: EtOAc-PE; 5:5; Rf: 0.4.

[Cis-rac] 3-(2-fluoro-1,1-dimethyl-ethyl)-5-[4-methyl-4-[[3-(trifluoro methyl)phenyl] sulfonyl]-tetrahydro-pyran-2-yl]-1H-pyrazole was subjected to chiral prep-SFC purification to give 40 mg of [cis-EN1] Example 40 and 40 mg of [cis-EN2] Example 40. [cis-EN1] Example 40 was purified further by RP prep-HPLC (KROMOSIL-C18, 0.1% formic acid in water: acetonitrile; 0/40→11/40) to get 20 mg of pure desired product.

[cis-EN1] Example 40—analytical SFC: Chiralpak IC (250×4.6 mm 5 µm) 30.1° C., 3 g/min, 100 bar, 20% MeOH, Ret. Time 2.69 min; m/z=449.2 $[M+H]^+$; $^1H$ NMR (DMSO $d_6$): δ 12.45 (br m, 1H), 8.23-8.17 (m, 2H), 8.04 (s, 1H), 7.97-7.94 (t, 1H), 6.00 (s, 1H), 4.61-4.50 (m, 1H), 3.97-3.93 (m, 1H), 3.67-3.63 (m, 1H), 2.90-2.79 (m, 2H), 2.15-2.04 (m, 2H), 1.73-1.65 (m, 1H), 1.45 (m, 4H), 1.30 (s, 3H), 1.26 (s, 3H).

[cis-EN2] Example 40—analytical SFC: Chiralpak IC (250×4.6 mm 5 μm), 29.9° C., 3 g/min, 100 bar, 20% MeOH, Ret. Time 4.92 min; m/z=449.1 [M+H]+; ¹H NMR (DMSO d₆): δ 12.54-12.46 (br m, 1H), 8.23-8.18 (m, 2H), 8.04 (s, 1H), 7.96-7.94 (t, 1H), 6.00 (s, 1H), 4.52-4.50 (m, 1H), 3.94-3.93 (m, 1H), 3.65 (m, 1H), 2.90-2.79 (m, 2H), 2.15-2.07 (m, 2H), 1.67-1.65 (m, 1H), 1.45 (m, 4H), 1.30 (s, 3H), 1.26 (s, 3H).

Prophetic Examples

The following compounds can be obtained in analogy to above described procedure or parts of above described procedure. Required aldehydes can be in analogy to procedures described herein:

3-(1,1-Difluoro-ethylsulfonyl)-5-[4-methyl-4-[[3-(trifluoromethyl)phenyl]sulfonyl]-tetrahydro-pyran-2-yl]-1H-pyrazole (Example 2)

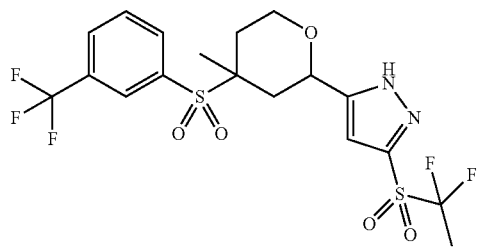 [SMILES: CC(F)(F)S(=O)(=O)c1cc(C2CC(C)(S(=O)(=O)c3cccc(C(F)(F)F)c3)CCO2)[nH]n1]

3-(1-Methylsulfonyl-cyclopropyl)-5-[4-methyl-4-[[3-(trifluoromethyl)phenyl]sulfonyl]-tetrahydro-pyran-2-yl]-1H-pyrazole (Example 8)

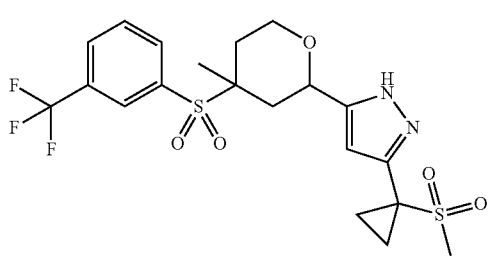 [SMILES: CC1(S(=O)(=O)c2cccc(C(F)(F)F)c2)CCOC(c2cc(C3(S(C)(=O)=O)CC3)n[nH]2)C1]

Synthesis of 5-[4-Methyl-4-[[3-(trifluoromethyl)phenyl]sulfonyl]-tetrahydro-pyran-2-yl]-3-(trifluoromethyloxy-methyl)-1H-pyrazole (Example 17)

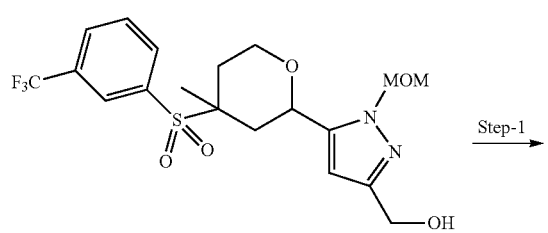

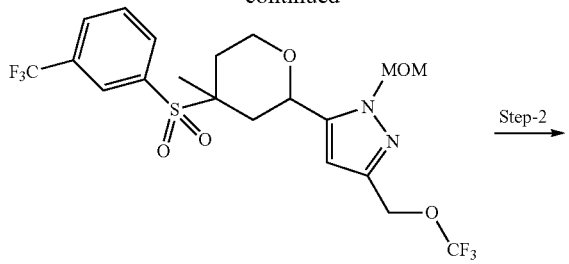

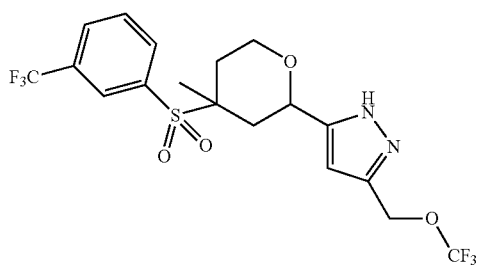

17

3-Cyclopropyl-5-[4-methyl-4-[[3-(trifluoromethyl)phenyl]sulfonyl]-tetrahydro-pyran-2-yl]-1H-pyrazole (Example 20)

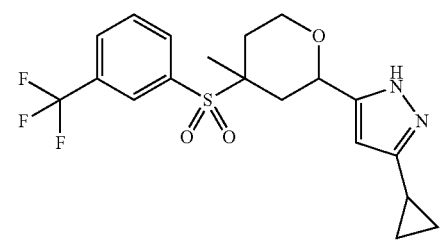 [SMILES: CC1(S(=O)(=O)c2cccc(C(F)(F)F)c2)CCOC(c2cc(C3CC3)n[nH]2)C1]

3-Cyclobutyl-5-[4-methyl-4-[[3-(trifluoromethyl)phenyl] sulfonyl]-tetrahydro-pyran-2-yl]-1H-pyrazole (Example 21)

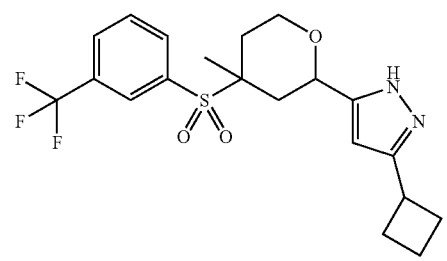 [SMILES: CC1(S(=O)(=O)c2cccc(C(F)(F)F)c2)CCOC(c2cc(C3CCC3)n[nH]2)C1]

3-tert-Butyl-5-[4-methyl-4-[[3-(trifluoromethyl)phenyl]sulfonyl]-tetrahydro-pyran-2-yl]-1H-pyrazole (Example 22)

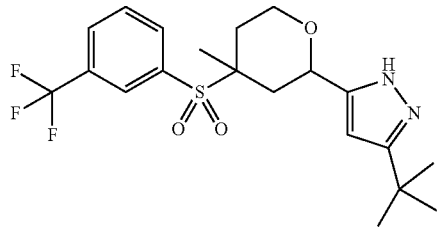 [SMILES: CC(C)(C)c1cc(C2CC(C)(S(=O)(=O)c3cccc(C(F)(F)F)c3)CCO2)[nH]n1]

3-(1-Methyl-cyclopropyl)-5-[4-methyl-4-[[3-(trifluoromethyl)phenyl]sulfonyl]-tetrahydro-pyran-2-yl]-1H-pyrazole (Example 23)

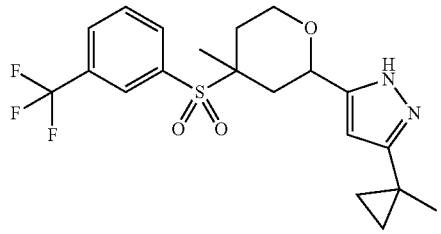 [SMILES: CC1(c2cc(C3CC(C)(S(=O)(=O)c4cccc(C(F)(F)F)c4)CCO3)[nH]n2)CC1]

3-Cyclopropyloxy-5-[4-methyl-4-[[3-(trifluoromethyl)phenyl]sulfonyl]-tetrahydro-pyran-2-yl]-1H-pyrazole (Example 24)

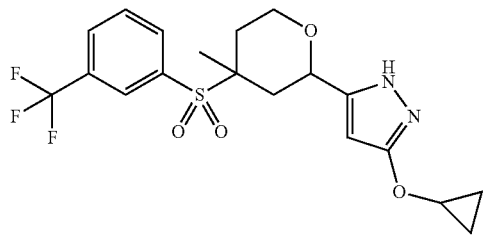 [SMILES: CC1(S(=O)(=O)c2cccc(C(F)(F)F)c2)CCOC(c2cc(OC3CC3)n[nH]2)C1]

3-(Difluoro-methoxy)-5-[4-methyl-4-[[3-(trifluoromethyl)phenyl]sulfonyl]-tetrahydro-pyran-2-yl]-1H-pyrazole (Example 25)

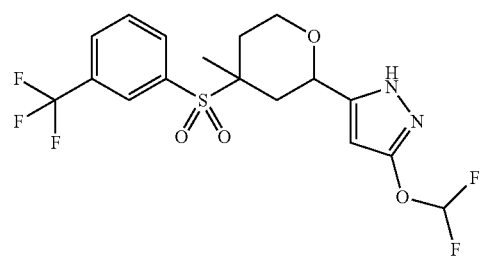 [SMILES: CC1(S(=O)(=O)c2cccc(C(F)(F)F)c2)CCOC(c2cc(OC(F)F)n[nH]2)C1]

5-[4-Methyl-4-[[3-(trifluoromethyl)phenyl]sulfonyl]-tetrahydro-pyran-2-yl]-3-(trifluoromethyloxy)-1H-pyrazole (Example 26)

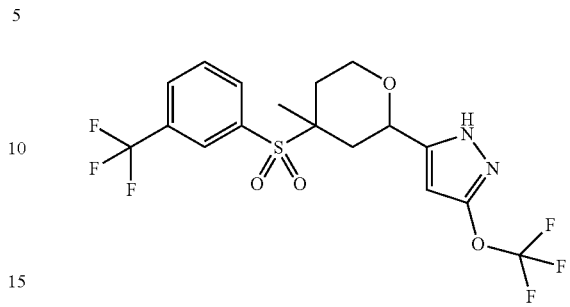

2. Assay Descriptions and Biological Data:
2.1 Fluorescence Assay for CaV2.2 Channels Using Potassium Depolarization to Induce Channel Opening Human CaV2.2 channels were stably expressed in HEK293 cells together with alpha2-delta and beta subunits of voltage gated calcium channels. In addition, an inwardly rectifying potassium channel (Kir2.3) was stably expressed in these cells to augment control of the cell membrane potential by the concentration of extracellular potassium ions. Raise of the extracellular potassium concentration leads to depolarization of the membrane potential and thus regulates the voltage dependent state of CaV2.2 channels. For preparation, cells were seeded in black poly-D-lysine coated 96-well plates (Becton Dickinson, Biocoat 4640) in 100 µL medium [500 mL DMEM/F-12 plus Glutamax (Invitrogen 31331-093) plus 5.5 mL MEM NEAA 100× (Invitrogen 11140-035) plus 50 mL FBS decomplemented (Invitrogen 10270-106) plus 200 µg/mL Geneticin (Invitrogen 10131-027) plus 50 µg/mL Hygromycin B (Invitrogen 10687-010) plus 2 µg/mL Blasticidin (anti-b15b InvivoGen) plus 0.2 µg/mL Puromycin (A 11138-03)] at a cell density of 30.000 cells per well. Plates were incubated at 37° C. (5% $CO_2$) for 20 to 23 h. On the day of experiment medium was discarded and cells were loaded with Fluo 4 by addition of 100 µL of basic assay buffer (10 mM HEPES, 1 mM KCl, 149 mM NaCl, 0.8 mM $CaCl_2$, 1.7 mM $MgCl_2$, 10 mM Glucose, 0.1% BSA, pH 7.4) containing 2 µM Fluo 4 (Molecular Probes; F-14201), 0.01% pluronic acid (Molecular Probes; P-6866) and 2.5 mM probenecid (Molecular Probes; P36400). Cells were incubated in the dark at 25° C. for 60 min. Then dye containing buffer was discarded and 100 µL basic (1 mM KCl) or alternative (30 mM KCl) assay buffer was added. The alternative assay buffer contained altered concentrations of KCl (30 mM) and NaCl (120 mM) and was used in order to promote the inactivated channel state. After that 25 µL of basic or alternative assay buffer with or without test compound were added and cells were incubated again in the dark at 25° C. for 15 min. Fluorescence intensity was measured on a FLIPR 3 instrument (Molecular Devices Corp., Sunnyvale, Calif.) with excitation at 480 nm and emission at 535 nm. After continuously reading fluorescence for 30 sec, 50 µL of basic assay buffer containing 210 mM KCl(NaCl omitted) were added for depolarization. Peak fluorescent signal intensity was determined and the amplitude of the peak signal, normalized to base line, was used to measure channel inhibition by test compounds.

The following tables summarize the inhibitory activity of exemplified compounds according to the present invention.

| Example [Isomer] | Activity Category | Example [Isomer] | Activity Category |
|---|---|---|---|
| [cis-EN1] Example 1 | B | [cis-EN1] Example 12 | B |
| [cis-EN2] Example 1 | B | [cis-EN2] Example 12 | A |
| [trans-rac] Example 1 | B | [trans-rac] Example 12 | B |

| Example | Isomer | Activity Category | Example | Isomer | Activity Category |
|---|---|---|---|---|---|
| 3 | cis-EN1 | D | 28 | cis-EN1 | B |
| 4 | cis-EN1 | C | 28 | cis-EN2 | B |
| 4 | cis-EN2 | B | 29 | cis-EN1 | B |
| 5 | cis-EN1 | B | 29 | cis-EN2 | B |
| 5 | cis-EN2 | C | 30 | cis-EN2 | C |
| 7 | cis-EN1 | B | 30 | cis-EN1 | C |
| 7 | cis-EN2 | B | 31 | cis-EN1 | A |
| 9 | cis-EN1 | C | 31 | cis-EN2 | A |
| 9 | cis-EN2 | C | 32 | cis-EN1 | A |
| 13 | cis-EN1 | A | 32 | cis-EN2 | B |
| 13 | cis-EN2 | A | 33 | cis-EN1 | A |
| 14 | cis-EN1 | B | 33 | cis-EN2 | A |
| 14 | cis-EN2 | A | 34 | cis-EN1 | B |
| 15 | cis-rac | A | 34 | cis-EN2 | B |
| 16 | cis-EN2 | A | 35 | cis-EN1 | B |
| 16 | cis-EN1 | A | 35 | cis-EN2 | A |
| 18 | cis-EN1 | C | 36 | cis-EN1 | B |
| 18 | cis-EN2 | C | 36 | cis-EN2 | A |
| 19 | cis-EN1 | B | 37 | cis-EN1 | C |
| 19 | cis-EN2 | C | 37 | cis-EN2 | B |
| 27 | cis-EN1 | A | 38 | cis-EN1 | C |
| 27 | cis-EN2 | B | 38 | cis-EN2 | B |

\* %-Inhib (CaV2.2) @3 µM @30 mM KCl: "A": %-Inhibition >95%; "B": %-Inhibition >75% up to ≤95%; "C": %-Inhibition >40% up to ≤75%, "D": %-Inhibition >30% up to ≤40%.

2.2 Electrophysiological Assessment of Calcium Channel Activity

Patch-clamp recordings were performed using HEK293 cells stably expressing human Cav2.2. Cells were plated in T150 flasks and grown a humidified incubator at 37° C. and under 5% $CO_2$ to approximately 50-60% confluency. Cells were maintained at 30° C. for 48 hrs prior to recording. On the day of the experiment, cells were harvested with TrypLE cell detachment solution (Invitrogen) diluted to 25% with phosphate buffered saline and maintained in 50% cell culture media, 50% NaCl based external saline (in mM, 140 NaCl, 4 KCl, 1 $MgCl_2$, 2 $CaCl_2$, 5 Glucose, 10 HEPES, pH 7.4) up to several hours prior to experiment.

Currents were recorded at RT (21-23° C.) using the Patchliner planar array technology (Nanion). Patchliner is a multi-well whole-cell automated patch clamp device that operates asynchronously with fully integrated fluidics. Capacitance and series resistance compensation was automated and no correction for liquid junction potential was employed. Leak was subtracted on-line. Whole-cell patch-clamp recordings were obtained using extracellular saline consisting of (mM): 145 TEA-Cl, 10 $BaCl_2$, 10 HEPES, 10 Glucose. The pH was adjusted to 7.35 with NaOH and the osmolarity was adjusted to 310 mOsm with sucrose. Intracellular solution consisted of (mM): 50 CsCl, 60 CsF, 10 NaCl, 20 EGTA, 5 BAPTA, 10 HEPES. Prior to an experiment, 5 mM MgATP and 0.3 NaGTP were added, the pH was adjusted to 7.2 with CsOH and the osmolarity was adjusted to 290 mOsm with sucrose.

A voltage pulse protocol was utilised to assess compound inhibition. Cells were held at a holding potential of −60 mV and channels were activated using a 10 ms test pulse to +30 mV activated every 10 seconds (0.1 Hz). Increasing concentrations of compound were applied to individual cells with 5 minutes at each test concentration. Compounds were prepared in DMSO as 10 mM stock solutions and subsequent 1:3 serial dilutions performed. Final dilution of 1:1000 in external solution resulted in a final DMSO concentration of 0.1%. For each cell, current responses were normalized to dimethyl sulfoxide vehicle control to generate concentration-response curves. When multiple doses were achieved per cell, $IC_{50}$ values were calculated from the fits of the Hill equation to the data. The form of the Hill equation used was: Relative current=$(100/(1+(IC_{50}/conc)^{Slope}))$. A selection of the foregoing exemplified compounds was tested under these conditions: Several compounds are potent inhibitors ($IC_{50}$<5 µM) or even very potent inhibitors ($IC_{50}$<2 µM).

The invention claimed is:

1. A compound of general formula (I):

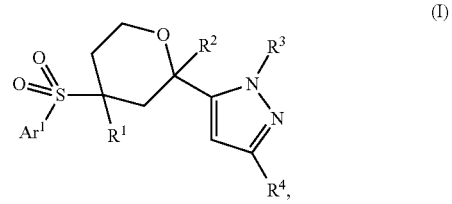

wherein
R$^1$ is selected from the group consisting of H and $C_{1-6}$-alkyl;
R$^2$ is selected from the group consisting of H and $C_{1-6}$-alkyl;
R$^3$ is H;
R$^4$ represents L-R$^5$,
wherein L is bond, $CH_2$, $C(CH_3)_2$, O or $S(=O)_2$ and
R$^5$ is selected from the group consisting of $C_{1-6}$-alkyl, $C_{3-6}$-cycloalkyl and 3 to 7 membered heterocyclyl,
wherein said 3 to 7 membered heterocyclyl contains one heteroatom or heteroatom group selected from O, NH, N(CH$_3$), S(=O) and S(=O)$_2$;

wherein said $C_{1-6}$-alkyl is unsubstituted or substituted by one or two or three or four substituents independently selected from the group consisting of F, Cl, CN, OH, $OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$; and wherein said $C_{3-6}$-cycloalkyl or said 3 to 7 membered heterocyclyl is unsubstituted or substituted by one or two or three or four substituents independently selected from the group consisting of F, Cl, CN, $CH_3$, $CFH_2$, $CHF_2$, $CF_3$, =O, OH, $OCH_3$, $CH_2OH$, $CH_2OCH_3$, $OCFH_2$, $OCHF_2$, $OCF_3$, $S(=O)_2CH_3$, $S(=O)_2CHF_2$, $S(=O)_2CF_3$, $S(=O)_2CH(CH_3)_2$, $S(=O)_2$(c-propyl), $NH_2$, $NH(CH_3)$, $N(CH_3)_2$, $C(=O)NH_2$, $C(=O)NH(CH_3)$ and $C(=O)N(CH_3)_2$;

$Ar^1$ represents aryl or heteroaryl, wherein said aryl or said heteroaryl is substituted by zero or one or two or three substituents $R^7$, wherein each $R^7$ is independently selected from the group consisting of F; Cl; Br; I; $NO_2$; CN; $C_{1-6}$-alkyl; $CF_3$; $CF_2H$; $CFH_2$; $CF_2Cl$; $CFCl_2$; C(O)—H; C(O)—$C_{1-6}$-alkyl; C(O)—OH; C(O)—O—$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; C(=N—OH)—H; C(=N—OH)—$C_{1-6}$-alkyl; C(=N—O—$C_{1-6}$-alkyl)-H; C(=N—O—$C_{1-6}$-alkyl)-$C_{1-6}$-alkyl; OH; $OCF_3$; $OCF_2H$; $OCFH_2$; $OCF_2Cl$; $OCFCl_2$; O—$C_{1-6}$-alkyl; O—C(O)—$C_{1-6}$-alkyl; O—C(O)—O—$C_{1-6}$-alkyl; O—(CO)—N(H)($C_{1-6}$-alkyl); O—C(O)—N($C_{1-6}$-alkyl)$_2$; O—$S(O)_2$—$C_{1-6}$-alkyl; O—$S(O)_2$—OH; O—$S(O)_2$—O—$C_{1-6}$-alkyl; O—$S(O)_2$—$NH_2$; O—$S(O)_2$—N(H)($C_{1-6}$-alkyl); O—$S(O)_2$—N($C_{1-6}$-alkyl)$_2$; $NH_2$; N(H)($C_{1-6}$-alkyl); N($C_{1-6}$-alkyl)$_2$; N($R^{13}$)—C(O)—$C_{1-6}$-alkyl; N($R^{13}$)—C(O)—O—$C_{1-6}$-alkyl; N($R^{13}$)—C(O)—$NH_2$; N($R^{13}$)—C(O)—N(H)($C_{1-6}$-alkyl); N($R^{13}$)—C(O)—N($C_{1-6}$-alkyl)$_2$; N($R^{13}$)—$S(O)_2$OH; N($R^{13}$)—$S(O)_2$—$C_{1-6}$-alkyl; N($R^{13}$)—$S(O)_2$—O—$C_{1-6}$-alkyl; N($R^{13}$)—$S(O)_2$—$NH_2$; N($R^{13}$)—$S(O)_2$—N(H)($C_{1-6}$-alkyl); N($R^{13}$)—$S(O)_2$N($C_{1-6}$-alkyl)$_2$; SH; $SCF_3$; $SCF_2H$; $SCFH_2$; $SCF_2Cl$; $SCFCl_2$; S—$C_{1-6}$-alkyl; S(O)—$C_{1-6}$-alkyl; $S(O)_2$—$C_{1-6}$-alkyl; $S(O)_2$—OH; $S(O)_2$—O—$C_{1-6}$-alkyl; $S(O)_2$—$NH_2$; $S(O)_2$—N(H)($C_{1-6}$-alkyl); $S(O)_2$—N($C_{1-6}$-alkyl)$_2$; $C_{3-6}$-cycloalkyl; 3 to 7 membered heterocyclyl; aryl; heteroaryl; O—$C_{3-6}$-cycloalkyl; O-(3 to 7 membered heterocyclyl); O-aryl; O-heteroaryl; N($R^{13}$)—$C_{3-6}$-cycloalkyl; N($R^{13}$)-(3 to 7 membered heterocyclyl); N($R^{13}$)-aryl; N($R^{13}$)-heteroaryl; C(O)—$C_{3-6}$-cycloalkyl; C(O)-(3 to 7 membered heterocyclyl); C(O)-aryl; C(O)-heteroaryl; $S(O)_2$—$C_{3-6}$-cycloalkyl; $S(O)_2$-(3 to 7 membered heterocyclyl); $S(O)_2$-aryl; $S(O)_2$-heteroaryl; S(O)N($R^{13}$)—$C_{3-6}$-cycloalkyl; S(O)N($R^{13}$)-(3 to 7 membered heterocyclyl); S(O)N($R^{13}$)-aryl and S(O)N($R^{13}$)-heteroaryl, wherein $R^{13}$ represents H or $C_{1-6}$-alkyl;

with the proviso that the compound of general formula (I) is not 5-(Trifluoro-methyl)-3-[4-methyl-4-[[3-(trifluoromethyl)phenyl]sulfonyl]-tetrahydro-pyran-2-yl]-1H-pyrazole; optionally in the form of a single stereoisomer or a mixture of stereoisomers, in form of the free compound and/or a physiologically acceptable salt and/or a physiologically acceptable solvate thereof.

2. A compound according to claim 1, wherein the compound of general formula (I) is a compound according to general formula (II):

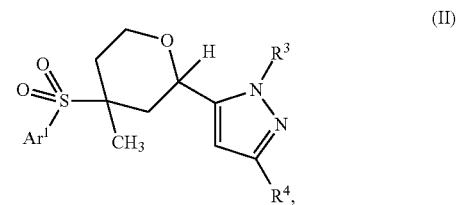

wherein $Ar^1$, $R^3$ and $R^4$ are defined as in claim 1.

3. A compound according to claim 1, wherein $Ar^1$ represents phenyl or pyridinyl, substituted by zero or one or two or three substituents $R^7$, wherein each $R^7$ is independently selected from the group consisting of F; Cl; CN; $C_{1-6}$-alkyl; $CF_3$; $CF_2H$; $CFH_2$; C(O)—$C_{1-6}$-alkyl; C(O) OH; C(O)—O—$C_{1-6}$-alkyl; C(O)—N(H)(OH); C(O)—$NH_2$; C(O)—N(H)($C_{1-6}$-alkyl); C(O)—N($C_{1-6}$-alkyl)$_2$; OH; $OCF_3$; $OCF_2H$; $OCFH_2$; $OCF_2Cl$; $OCFCl_2$; O—$C_{1-6}$-alkyl; $NH_2$; N(H)($C_{1-6}$-alkyl); N($C_{1-6}$-alkyl)$_2$; N(H)—C(=O)—$C_{1-6}$-alkyl; N($C_{1-6}$-alkyl)-C(O)—$C_{1-6}$-alkyl; N(H)—$S(O)_2$—$C_{1-6}$-alkyl; $SCF_3$; S—$C_{1-6}$-alkyl; S(O)—$C_{1-6}$-alkyl; $S(O)_2$—$C_{1-6}$-alkyl; $S(O)_2$—$NH_2$; $S(O)_2$—N(H)($C_{1-6}$-alkyl); $S(O)_2$—N($C_{1-6}$-alkyl)$_2$; $C_{3-6}$-cycloalkyl; 3 to 7 membered heterocyclyl; O—$C_{3-6}$-cycloalkyl and O-(3 to 7 membered heterocyclyl).

4. A compound according to claim 1, wherein $Ar^1$ is selected from the group consisting of 3-trifluoromethyl-phenyl; 3-difluoromethyl-phenyl; 3-fluoromethyl-phenyl; 3-trifluoromethoxy-phenyl; 3-difluoromethoxy-phenyl; 3-fluoromethoxy-phenyl; 3-fluoro-phenyl; 3-cyanophenyl; 6-trifluoromethyl-pyridin-2-yl; 3-difluoromethyl-pyridin-2-yl; 3-fluoromethyl-pyridin-2-yl; 3-trifluoromethoxy-pyridin-2-yl; 3-difluoromethoxy-pyridin-2-yl; 3-fluoromethoxy-pyridin-2-yl; 3-fluoro-pyridin-2-yl and 3-cyano-pyridin-2-yl.

5. A compound according to claim 1, wherein

L is bond; and $R^5$ is selected from the group consisting of $CH_3$, $CH(CH_3)_2$, $C(CH_3)_3$, $CH_2OH$, $CH_2OCH_3$, $CH_2OCFH_2$, $CH_2OCHF_2$, $CH_2OCF_3$, $CH_2S(=O)_2CH_3$, $CH_2S(=O)_2CHF_2$, $CH_2S(=O)_2CF_3$, $CH_2S(=O)_2CFH_2$, $CH_2S(=O)_2CH(CH_3)_2$, $CH_2S(=O)_2$(c-propyl), $CFH_2$, $CHF_2$, $CH_2CF_3$, $CF_2CH_3$, $CH_2CFH_2$, $CH_2CHF_2$, $CH_2CH_2CF_3$, $CH_2CH_2OCH_3$, $CH_2CH_2OH$, $C(CH_3)_2CH_2OCH_3$, $C(CH_3)_2CH_2OH$, $C(CH_3)_2CN$, $CH_2CH_2S(=O)_2CH_3$, $CH_2CH_2N(CH_3)_2$, $CH_2C(=O)NH_2$, $CH_2C(=O)NH(CH_3)$, $CH_2C(=O)N(CH_3)_2$, $CH_2CH_2C(=O)NH_2$, $CH_2CH_2C(=O)NH(CH_3)$, $CH_2CH_2C(=O)N(CH_3)_2$, $C(CH_3)_2OCH_3$, $C(CH_3)_2OH$, $C(CH_3)_2S(=O)_2CH_3$, $C(CH_3)_2S(=O)_2CHF_2$, $C(CH_3)_2S(=O)_2CF_3$, $C(CH_3)_2S(=O)_2CFH_2$, $C(CH_3)_2N(CH_3)_2$, $C(CH_3)_2C(=O)NH_2$, $C(CH_3)_2C(=O)NH(CH_3)$, $C(CH_3)_2C(=O)N(CH_3)_2$, cyclopropyl, cyclobuytyl and oxetanyl;

wherein said cyclopropyl, cyclobuytyl or oxetanyl are unsubstituted or substituted with OH, $OCH_3$ or $S(O)_2CH_3$;

or

L is CH$_2$; and

R$^5$ is selected from the group consisting of CH$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CH(CH$_3$)$_2$, C(CH$_3$)$_3$, CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$S(=O)$_2$CH(CH$_3$)$_2$, C(CH$_3$)$_2$S(=O)$_2$(c-propyl), C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl and oxetanyl;

wherein said cyclopropyl, cyclobuytyl or oxetanyl are unsubstituted or substituted with CH$_3$, OH, NH$_2$, NH(CH$_3$), N(CH$_3$)$_2$, OCH$_3$ or S(O)$_2$CH$_3$;

or

L is C(CH$_3$)$_2$; and

R$^5$ is selected from the group consisting of CH(CH$_3$)$_2$, C(CH$_3$)$_3$, CH$_2$OH, CH$_2$OCH$_3$, CH$_2$OCFH$_2$, CH$_2$OCHF$_2$, CH$_2$OCF$_3$, CH$_2$S(=O)$_2$CH$_3$, CH$_2$S(=O)$_2$CHF$_2$, CH$_2$S(=O)$_2$CF$_3$, CH$_2$S(=O)$_2$CFH$_2$, CH$_2$S(=O)$_2$CH(CH$_3$)$_2$, CH$_2$S(=O)$_2$(c-propyl), CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$, CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$OH, C(CH$_3$)$_2$S(=O)$_2$CH$_3$, C(CH$_3$)$_2$S(=O)$_2$CHF$_2$, C(CH$_3$)$_2$S(=O)$_2$CF$_3$, C(CH$_3$)$_2$S(=O)$_2$CFH$_2$, C(CH$_3$)$_2$S(=O)$_2$CH(CH$_3$)$_2$, C(CH$_3$)$_2$S(=O)$_2$(c-propyl), C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl and oxetanyl, wherein said cyclopropyl, cyclobuytyl or oxetanyl are unsubstituted or substituted with CH$_3$, OH, NH$_2$, NH(CH$_3$), N(CH$_3$)$_2$, OCH$_3$ or S(O)$_2$CH$_3$;

or

L is O; and

R$^5$ is selected from the group consisting of CH$_3$, CH(CH$_3$)$_2$, C(CH$_3$)$_3$, CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$CH$_2$CH$_2$C(=O)NH(CH$_3$), CH$_2$CH$_2$C(=O)N(CH$_3$)$_2$, C(CH$_3$)$_2$OCH$_3$, C(CH$_3$)$_2$N(CH$_3$)$_2$, C(CH$_3$)$_2$C(=O)NH$_2$C(CH$_3$)$_2$C(=O)NH(CH$_3$), C(CH$_3$)$_2$C(=O)N(CH$_3$)$_2$, cyclopropyl, cyclobuytyl and oxetanyl, wherein said cyclopropyl, cyclobuytyl or oxetanyl are unsubstituted or substituted with CH$_3$, OCH$_3$ or S(O)$_2$CH$_3$;

or

L is S(=O)$_2$; and

R$^5$ is selected from the group consisting of CH$_3$, CH$_2$CH$_3$, CH(CH$_3$)$_2$, CH$_2$CH(CH$_3$)$_2$, C(CH$_3$)$_3$, CH$_2$C(CH$_3$)$_3$, CFH$_2$, CHF$_2$, CF$_3$, CH$_2$CF$_3$, CF$_2$CH$_3$, CH$_2$CFH$_2$, CH$_2$CHF$_2$, CH$_2$CH$_2$CF$_3$, C(CH$_3$)$_2$CF$_3$, CH$_2$CH$_2$OCH$_3$, CH$_2$CH$_2$OH, C(CH$_3$)$_2$CH$_2$OCH$_3$, C(CH$_3$)$_2$CH$_2$OH, CH$_2$CH$_2$S(=O)$_2$CH$_3$, CH$_2$CH$_2$N(CH$_3$)$_2$, CH$_2$C(=O)NH$_2$, CH$_2$C(=O)NH(CH$_3$), CH$_2$C(=O)N(CH$_3$)$_2$, CH$_2$CH$_2$C(=O)NH$_2$CH$_2$CH$_2$C(=O)NH(CH$_3$), CH$_2$CH$_2$C(=O)N(CH$_3$)$_2$, cyclopropyl, cyclobuytyl and oxetanyl, wherein said cyclopropyl, cyclobuytyl or oxetanyl are unsubstituted or substituted with CH$_3$, OCH$_3$ or S(O)$_2$CH$_3$.

6. A compound according to claim 1, wherein

R$^4$ is selected from the group consisting of CHF$_2$, CF$_3$, CF$_2$CH$_3$, CH$_2$CHF$_2$, CH$_2$CF$_3$, CH(CH$_3$)$_2$, C(CH$_3$)$_3$, OCF$_3$, OCHF$_2$, OCH$_2$CF$_3$, OCH$_2$CHF$_2$, OCH$_2$CH$_2$F, O-c-propyl (cyclopropyl-oxy), CH$_2$OCF$_3$, C(CH$_3$)$_2$OH, C(CH$_3$)$_2$CH$_2$OH, C(CH$_3$)$_2$CH$_2$OCH$_3$, C(CH$_3$)$_2$CN, C(CH$_3$)$_2$C(=O)NH$_2$, S(=O)$_2$CH$_3$, S(=O)$_2$CH$_2$CH(CH$_3$)$_2$, S(=O)$_2$CH$_2$C(CH$_3$)$_3$, S(=O)$_2$CHF$_2$, S(=O)$_2$CF$_3$, S(=O)$_2$C(CH$_3$)$_2$CF$_3$, S(=O)$_2$CH$_2$CH$_2$OCH$_3$, S(=O)$_2$CH$_2$CH$_2$OH, S(=O)$_2$CH$_2$CF$_3$, S(=O)$_2$CF$_2$CH$_3$, S(=O)$_2$CH$_2$CHF$_2$, S(=O)$_2$—CH(CH$_2$)$_2$O (S(=O)$_2$-oxetan-3-yl), CH$_2$S(=O)$_2$CHF$_2$, CH$_2$S(=O)$_2$CF$_3$, CH$_2$CH$_2$S(=O)$_2$CH$_3$, C(CH$_3$)$_2$S(=O)$_2$CH$_3$, cyclopropyl, C(CH$_2$)$_2$(CH$_3$) (1-methyl-cycloprop-1-yl), C(CH$_2$)$_2$S(=O)$_2$CH$_3$ (1-methylsulfonyl-cycloprop-1-yl), C(OH)(CH$_2$)$_2$O (3-hydroxy-oxetan-3-yl) and cyclobutyl.

7. A compound according to claim 5, wherein the compound of general formula (I) has general formula (III):

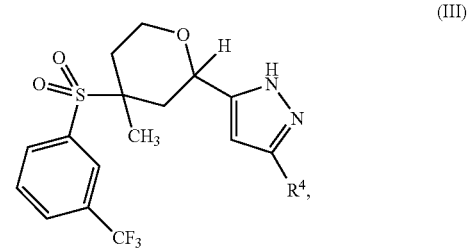

(III)

with the proviso that R$^4$ is not CF$_3$.

8. A compound according to claim 1, wherein the compound of general formula (I) is one diastereomer.

9. A compound according to claim 1, wherein the compound of general formula (I) is one enantiomer.

10. A compound according to claim 1, which is selected from the group consisting of:

1  3-(Difluoro-methylsulfonyl)-5-[4-methyl-4-[[3-(trifluoromethyl)phenyl]sulfonyl]-tetrahydro-pyran-2-yl]-1H-pyrazole;

2  3-(1,1-Difluoro-ethylsulfonyl)-5-[4-methyl-4-[[3-(trifluoromethyl)phenyl]sulfonyl]-tetrahydro-pyran-2-yl]-1H-pyrazole;

3  3-(2,2-Difluoro-ethylsulfonyl)-5-[4-methyl-4-[[3-(trifluoromethyl)phenyl]sulfonyl]-tetrahydro-pyran-2-yl]-1H-pyrazole;

4  5-[4-Methyl-4-[[3-(trifluoromethyl)phenyl]sulfonyl]-tetrahydro-pyran-2-yl]-3-(oxetan-3-ylsulfonyl)-1H-pyrazole;

5  3-(2-Methoxy-ethylsulfonyl)-5-[4-methyl-4-[[3-(trifluoromethyl)phenyl]sulfonyl]-tetrahydro-pyran-2-yl]-1H-pyrazole;

6  2-[[5-[4-Methyl-4-[[3-(trifluoromethyl)phenyl]sulfonyl]-tetrahydro-pyran-2-yl]-1H-pyrazol-3-yl]sulfonyl]-ethanol;

7 3-(1-Methyl-1-methyl sulfonyl-ethyl)-5-[4-methyl-4-[[3-(trifluoromethyl)phenyl]sulfonyl]-tetrahydro-pyran-2-yl]-1H-pyrazole;
8 3-(1-Methylsulfonyl-cyclopropyl)-5-[4-methyl-4-[[3-(trifluoromethyl)phenyl]sulfonyl]-tetrahydro-pyran-2-yl]-1H-pyrazole;
9 3-(2-Methylsulfonyl-ethyl)-5-[4-methyl-4-[[3-(trifluoromethyl)phenyl]sulfonyl]-tetrahydro-pyran-2-yl]-1H-pyrazole;
12 3-(Difluoro-methyl)-5-[4-methyl-4-[[3-(trifluoromethyl)phenyl]sulfonyl]-tetrahydro-pyran-2-yl]-1H-pyrazole;
13 3-(1,1-Difluoro-ethyl)-5-[4-methyl-4-[[3-(trifluoromethyl)phenyl]sulfonyl]-tetrahydro-pyran-2-yl]-1H-pyrazole;
14 3-(2,2-Difluoro-ethyl)-5-[4-methyl-4-[[3-(trifluoromethyl)phenyl]sulfonyl]-tetrahydro-pyran-2-yl]-1H-pyrazole;
15 3-(2,2-Difluoro-ethyl)-5-[4-methyl-4-[[3-(trifluoromethyl)phenyl]sulfonyl]-tetrahydro-pyran-2-yl]-1H-pyrazole;
16 5-[4-Methyl-4-[[3-(trifluoromethyl)phenyl]sulfonyl]-tetrahydro-pyran-2-yl]-3-(2,2,2-trifluoro-ethyl)-1H-pyrazole;
17 5-[4-Methyl-4-[[3-(trifluoromethyl)phenyl]sulfonyl]-tetrahydro-pyran-2-yl]-3-(2,2,2-trifluoro-ethoxy)-1H-pyrazole;
18 3-[5-[4-Methyl-4-[[3-(trifluoromethyl)phenyl]sulfonyl]-tetrahydro-pyran-2-yl]-1H-pyrazol-3-yl]-oxetan-3-ol;
19 2-[5-[4-Methyl-4-[[3-(trifluoromethyl)phenyl]sulfonyl]-tetrahydro-pyran-2-yl]-1H-pyrazol-3-yl]-propan-2-ol;
20 3-Cyclopropyl-5-[4-methyl-4-[[3-(trifluoromethyl)phenyl]sulfonyl]-tetrahydro-pyran-2-yl]-1H-pyrazole;
21 3-Cyclobutyl-5-[4-methyl-4-[[3-(trifluoromethyl)phenyl]sulfonyl]-tetrahydro-pyran-2-yl]-1H-pyrazole;
22 3-tert-Butyl-5-[4-methyl-4-[[3-(trifluoromethyl)phenyl]sulfonyl]-tetrahydro-pyran-2-yl]-1H-pyrazole;
23 3-(1-Methyl-cyclopropyl)-5-[4-methyl-4-[[3-(trifluoromethyl)phenyl]sulfonyl]-tetrahydro-pyran-2-yl]-1H-pyrazole;
24 3-Cyclopropyloxy-5-[4-methyl-4-[[3-(trifluoromethyl)phenyl]sulfonyl]-tetrahydro-pyran-2-yl]-1H-pyrazole;
25 3-(Difluoro-methoxy)-5-[4-methyl-4-[[3-(trifluoromethyl)phenyl]sulfonyl]-tetrahydro-pyran-2-yl]-1H-pyrazole;
26 5-[4-Methyl-4-[[3-(trifluoromethyl)phenyl]sulfonyl]-tetrahydro-pyran-2-yl]-3-(trifluoromethyloxy)-1H-pyrazole;
27 5-[4-Methyl-4-[[3-(trifluoromethyl)phenyl]sulfonyl]-tetrahydro-pyran-2-yl]-3-(trifluoromethylsulfonyl)-1H-pyrazole;
28 3-[(Difluoro-methylsulfonyl)-methyl]-5-[4-methyl-4-[[3-(trifluoromethyl)phenyl]sulfonyl]-tetrahydro-pyran-2-yl]-1H-pyrazole;
29 5-[4-Methyl-4-[[3-(trifluoromethyl)phenyl]sulfonyl]-tetrahydro-pyran-2-yl]-3-(2,2,2-trifluoro-ethylsulfonyl)-1H-pyrazole;
30 2-Methyl-2-[5-[4-methyl-4-[[3-(trifluoromethyl)phenyl]sulfonyl]-tetrahydro-pyran-2-yl]-1H-pyrazol-3-yl]-propionamide;
31 2-Methyl-2-[5-[4-methyl-4-[[3-(trifluoromethyl)phenyl]sulfonyl]-tetrahydro-pyran-2-yl]-1H-pyrazol-3-yl]-propionitrile;
32 5-(2,2-Difluoro-ethoxy)-3-[4-methyl-4-[[3-(trifluoromethyl)phenyl]sulfonyl]-tetrahydro-pyran-2-yl]-1H-pyrazole;
33 3-(2-Methoxy-1,1-dimethyl-ethyl)-5-[4-methyl-4-[[3-(trifluoromethyl)phenyl]sulfonyl]-tetrahydro-pyran-2-yl]-1H-pyrazole;
34 2-Methyl-2-[5-[4-methyl-4-[[3-(trifluoromethyl)phenyl]sulfonyl]-tetrahydro-pyran-2-yl]-1H-pyrazol-3-yl]-propan-1-ol;
35 3-(2-Methyl-propylsulfonyl)-5-[4-methyl-4-[[3-(trifluoromethyl)phenyl]sulfonyl]-tetrahydro-pyran-2-yl]-1H-pyrazole;
36 3-(2,2-Dimethyl-propylsulfonyl)-5-[4-methyl-4-[[3-(trifluoromethyl)phenyl]sulfonyl]-tetrahydro-pyran-2-yl]-1H-pyrazole;
37 5-Methylsulfonyl-3-[4-methyl-4-[[3-(trifluoromethyl)phenyl]sulfonyl]-tetrahydro-pyran-2-yl]-1H-pyrazole;
38 2-Methyl-2-[5-[4-methyl-4-[[6-(trifluoromethyl)-pyridin-2-yl]sulfonyl]-tetrahydro-pyran-2-yl]-1H-pyrazol-3-yl]-propionitrile;
39 5-[4-Methyl-4-[[3-(trifluoromethyl)phenyl]sulfonyl]-tetrahydro-pyran-2-yl]-3-[(2,2,2-trifluoro-1,1-dimethyl-ethyl)sulfonyl]-1H-pyrazole; and
40 3-(2-Fluoro-1,1-dimethyl-ethyl)-5-[4-methyl-4-[[3-(trifluoromethyl)phenyl]sulfonyl]-tetrahydro-pyran-2-yl]-1H-pyrazole;

optionally in the form of a single stereoisomer or a mixture of stereoisomers, in the form of the free compound and/or a physiologically acceptable salt or solvate thereof.

11. A pharmaceutical composition comprising at least one compound according to claim 1 and a pharmaceutically acceptable carrier.

12. A method for the treatment and/or prophylaxis of one or more disorders selected from the group consisting of pain, stroke, mood disorders, epilepsy, schizophrenia, and neurodegenerative disorders, said method comprising administering to a patient in need thereof an effective amount therefor of at least one compound according to claim 1.

13. A method for the treatment and/or prophylaxis of at least one form of pain selected from the group consisting of acute pain, chronic pain, visceral pain, headache pain, inflammatory pain and mixed pain, said method comprising administering to a patient in need thereof an effective amount therefor of at least one compound according to claim 1.

* * * * *